(12) United States Patent
Cha et al.

(10) Patent No.: US 10,800,969 B2
(45) Date of Patent: Oct. 13, 2020

(54) HETEROCYCLIC COMPOUND AND ORGANIC LIGHT EMITTING ELEMENT COMPRISING SAME

(71) Applicant: LG Chem, Ltd., Seoul (KR)

(72) Inventors: Yongbum Cha, Daejeon (KR); Seongmi Cho, Daejeon (KR); Sung Kil Hong, Daejeon (KR); Jungbum Kim, Daejeon (KR); Sung Jae Lee, Daejeon (KR)

(73) Assignee: LG Chem, Ltd. (KR)

( * ) Notice: Subject to any disclaimer, the term of this patent is extended or adjusted under 35 U.S.C. 154(b) by 333 days.

(21) Appl. No.: 15/579,366

(22) PCT Filed: Nov. 16, 2016

(86) PCT No.: PCT/KR2016/013221
§ 371 (c)(1),
(2) Date: Dec. 4, 2017

(87) PCT Pub. No.: WO2017/086696
PCT Pub. Date: May 26, 2017

(65) Prior Publication Data
US 2018/0148641 A1    May 31, 2018

(30) Foreign Application Priority Data
Nov. 17, 2015  (KR) .................. 10-2015-0161274

(51) Int. Cl.
*H01L 51/50* (2006.01)
*C09K 11/06* (2006.01)
(Continued)

(52) U.S. Cl.
CPC ............ *C09K 11/06* (2013.01); *C07C 211/54* (2013.01); *C07D 209/80* (2013.01); *C07D 209/82* (2013.01); *C07D 235/30* (2013.01); *C07D 401/10* (2013.01); *C07D 401/14* (2013.01); *C07D 403/04* (2013.01); *C07D 403/10* (2013.01); *C07D 403/14* (2013.01); *C07D 405/04* (2013.01); *C07D 405/14* (2013.01);
(Continued)

(58) Field of Classification Search
None
See application file for complete search history.

(56) References Cited

U.S. PATENT DOCUMENTS

| 2004/0251816 A1 | 12/2004 | Leo et al. |
| 2014/0117326 A1 | 5/2014 | Lee et al. |
| 2015/0263293 A1 | 9/2015 | Hwang et al. |

FOREIGN PATENT DOCUMENTS

| KR | 20100108924 A | 10/2010 |
| KR | 20110006915 A | 1/2011 |

(Continued)

OTHER PUBLICATIONS

Extended European Search Report including Written Opinion for Application No. 16866648.5 dated May 24, 2019, 7 pages.
(Continued)

*Primary Examiner* — Gregory D Clark
(74) *Attorney, Agent, or Firm* — Lerner, David, Littenberg, Krumholz & Mentlik, LLP

(57) ABSTRACT

The present specification relates to a hetero-cyclic compound and an organic light emitting device including the same.

20 Claims, 1 Drawing Sheet

(51) Int. Cl.
| | |
|---|---|
| C07C 211/54 | (2006.01) |
| C07D 401/10 | (2006.01) |
| C07D 405/14 | (2006.01) |
| C07D 401/14 | (2006.01) |
| C07D 403/14 | (2006.01) |
| C07D 417/10 | (2006.01) |
| C07D 409/14 | (2006.01) |
| C07D 405/04 | (2006.01) |
| C07F 9/572 | (2006.01) |
| C07D 209/80 | (2006.01) |
| C07D 403/04 | (2006.01) |
| C07D 413/10 | (2006.01) |
| C07D 409/04 | (2006.01) |
| C07F 7/30 | (2006.01) |
| C07D 403/10 | (2006.01) |
| H01L 51/00 | (2006.01) |
| C07D 209/82 | (2006.01) |
| C07D 235/30 | (2006.01) |

(52) U.S. Cl.
CPC ......... *C07D 409/04* (2013.01); *C07D 409/14* (2013.01); *C07D 413/10* (2013.01); *C07D 417/10* (2013.01); *C07F 7/30* (2013.01); *C07F 9/5728* (2013.01); *H01L 51/0054* (2013.01); *H01L 51/0059* (2013.01); *H01L 51/0067* (2013.01); *H01L 51/0072* (2013.01); *H01L 51/0073* (2013.01); *H01L 51/50* (2013.01); *H01L 51/006* (2013.01); *H01L 51/0058* (2013.01); *H01L 51/0081* (2013.01); *H01L 51/0085* (2013.01); *H01L 51/5016* (2013.01); *H01L 51/5056* (2013.01); *H01L 51/5096* (2013.01)

(56) References Cited

FOREIGN PATENT DOCUMENTS

| | | | |
|---|---|---|---|
| KR | 20110041726 A | 4/2011 | |
| KR | 20120081539 A | 7/2012 | |
| KR | 20150010016 A | 1/2015 | |
| KR | 20150098062 A | 8/2015 | |
| KR | 20150107940 A | 9/2015 | |
| WO | 2010114264 A2 | 10/2010 | |
| WO | WO 2010/114264 A2 * | 10/2010 | ............. C09K 11/06 |

OTHER PUBLICATIONS

Search report from International Application No. PCT/KR2016/013221, dated Feb. 17, 2017.

* cited by examiner

【FIG. 1】
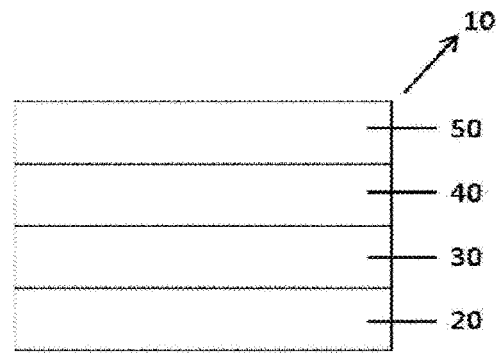
【FIG. 2】
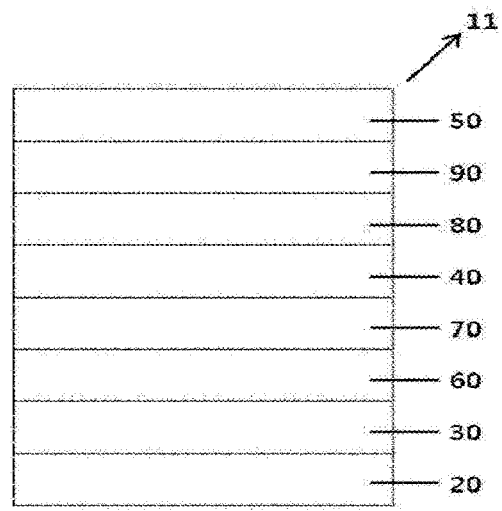

HETEROCYCLIC COMPOUND AND ORGANIC LIGHT EMITTING ELEMENT COMPRISING SAME

CROSS-REFERENCE TO RELATED APPLICATIONS

The present application is a national phase entry under 35 U.S.C. § 371 of International Application No. PCT/KR2016/013221 filed Nov. 16, 2016, which claims priority from Korean Patent Application No. 10-2015-0161274 filed Nov. 17, 2015, all of which are incorporated herein by reference.

TECHNICAL FIELD

The present specification relates to a hetero-cyclic compound and an organic light emitting device including the same.

BACKGROUND ART

An organic light emission phenomenon generally refers to a phenomenon converting electrical energy to light energy using an organic material. An organic light emitting device using an organic light emission phenomenon normally has a structure including an anode, a cathode, and an organic material layer therebetween. Herein, the organic material layer is often formed in a multilayer structure formed with different materials in order to increase efficiency and stability of the organic light emitting device, and for example, may be formed with a hole injection layer, a hole transfer layer, a light emitting layer, an electron transfer layer, an electron injection layer and the like. When a voltage is applied between the two electrodes in such an organic light emitting device structure, holes and electrons are injected to the organic material layer from the anode and the cathode, respectively, and when the injected holes and electrons meet, excitons are formed, and light emits when these excitons fall back to the ground state.

Development of new materials for such an organic light emitting device has been continuously required.

PRIOR ART DOCUMENTS

Patent Documents

US Patent Application Laid-Open Publication No. 2004-0251816

DISCLOSURE

Technical Problem

The present specification provides a hetero-cyclic compound and an organic light emitting device including the same.

Technical Solution

One embodiment of the present specification provides a hetero-cyclic compound represented by the following Chemical Formula 1.

[Chemical Formula 1]

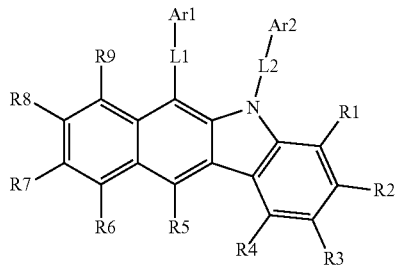

In Chemical Formula 1,

L1 and L2 are the same as or different from each other, and each independently a direct bond; a substituted or unsubstituted monocyclic or multicyclic arylene group; or a substituted or unsubstituted monocyclic or multicyclic heteroarylene group, Ar1 is a substituted or unsubstituted amine group; a substituted or unsubstituted silyl group; a substituted or unsubstituted phosphine oxide group; a substituted or unsubstituted phenyl group; a substituted or unsubstituted biphenyl group; a substituted or unsubstituted terphenyl group; a substituted or unsubstituted quaterphenyl group; a substituted or unsubstituted multicyclic aryl group; or a substituted or unsubstituted monocyclic or multicyclic heteroaryl group, Ar2 is a substituted or unsubstituted amine group; a substituted or unsubstituted silyl group; a substituted or unsubstituted phosphine oxide group; a substituted or unsubstituted monocyclic or multicyclic aryl group; or a substituted or unsubstituted monocyclic or multicyclic heteroaryl group, however, when L1 is a direct bond and Ar1 is an unsubstituted phenyl group, Ar2 is a substituted or unsubstituted amine group; a substituted or unsubstituted phosphine oxide group; a substituted or unsubstituted monocyclic or multicyclic aryl group; or a substituted or unsubstituted multicyclic heteroaryl group, and R1 to R9 are hydrogen, or adjacent groups bond to each other to form a substituted or unsubstituted ring.

Another embodiment of the present specification provides an organic light emitting device including a first electrode; a second electrode provided opposite to the first electrode; and one or more organic material layers provided between the first electrode and the second electrode, wherein one or more layers of the organic material layers include the hetero-cyclic compound represented by Chemical Formula 1.

Advantageous Effects

Hetero-cyclic compounds according to one embodiment of the present specification may be used as a material of an organic material layer of an organic light emitting device, and by using the hetero-cyclic compounds, efficiency enhancement, low driving voltage and/or lifespan property enhancement are capable of being accomplished in the organic light emitting device.

DESCRIPTION OF DRAWINGS

FIG. 1 illustrates an organic light emitting device (10) according to one embodiment of the present specification.

FIG. 2 illustrates an organic light emitting device (11) according to another embodiment of the present specification.

MODE FOR DISCLOSURE

Hereinafter, the present specification will be described in more detail.

The present specification provides a hetero-cyclic compound represented by Chemical Formula 1.

In the present specification, a description of a certain part "including" certain constituents means capable of further including other constituents, and does not exclude other constituents unless particularly stated on the contrary.

In the present specification, a description of one member being placed "on" another member includes not only a case of the one member adjoining the another member but a case of still another member being present between the two members.

Examples of the substituents in the present specification are described below, however, the substituents are not limited thereto.

The term "substitution" means a hydrogen atom bonding to a carbon atom of a compound is changed to another substituent, and the position of substitution is not limited as long as it is a position at which the hydrogen atom is substituted, that is, a position at which a substituent can substitute, and when two or more substituents substitute, the two or more substituents may be the same as or different from each other.

The term "substituted or unsubstituted" in the present specification means being substituted with one, two or more substituents selected from the group consisting of deuterium; a halogen group; a nitrile group; a nitro group; an imide group; an amide group; a carbonyl group; an ester group; a hydroxyl group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted amine group; a substituted or unsubstituted arylphosphine group; a substituted or unsubstituted phosphine oxide group; a substituted or unsubstituted aryl group; and a substituted or unsubstituted hetero-cyclic group, or being substituted with a substituent linking two or more substituents among the substituents illustrated above, or having no substituents. For example, "a substituent linking two or more substituents" may include a biphenyl group. In other words, a biphenyl group may be an aryl group, or interpreted as a substituent linking two phenyl groups.

In the present specification,

means a site bonding to other substituents or bonding sites.

In the present specification, the halogen group may include fluorine, chlorine, bromine or iodine.

In the present specification, the number of carbon atoms of the imide group is not particularly limited, but is preferably from 1 to 30. Specifically, compounds having structures as below may be included, but the imide group is not limited thereto.

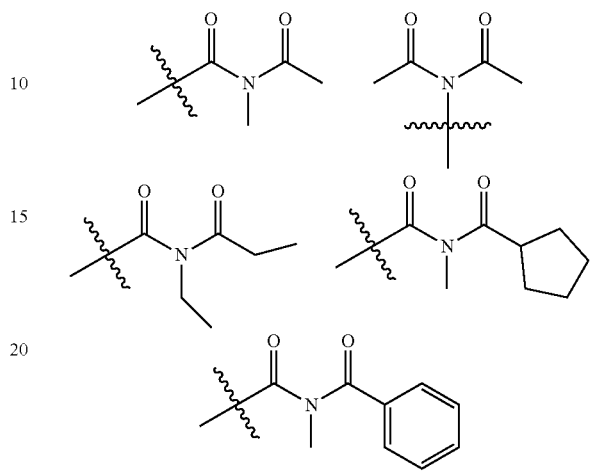

In the present specification, in the amide group, the nitrogen of the amide group may be substituted with a linear, branched or cyclic alkyl group having 1 to 30 carbon atoms or an aryl group having 6 to 30 carbon atoms. Specifically, compounds having the following structural formulae may be included, but the amide group is not limited thereto.

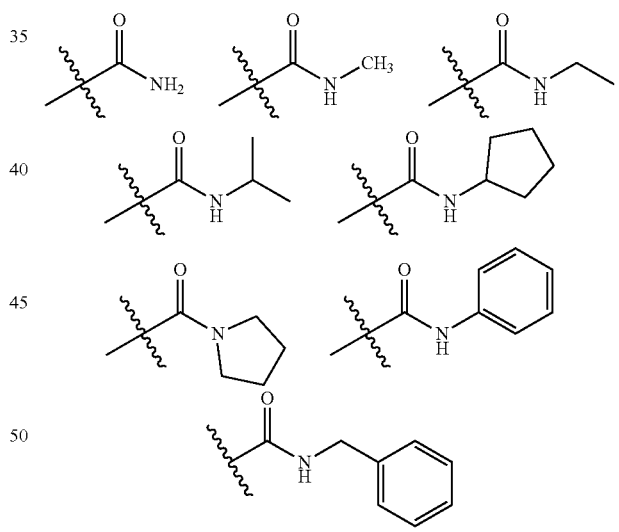

In the present specification, the number of carbon atoms of the carbonyl group is not particularly limited, but is preferably from 1 to 30. Specifically, compounds having structures as below may be included, but the carbonyl group is not limited thereto.

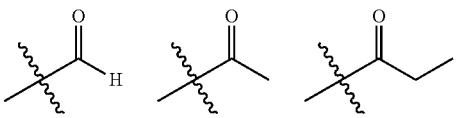

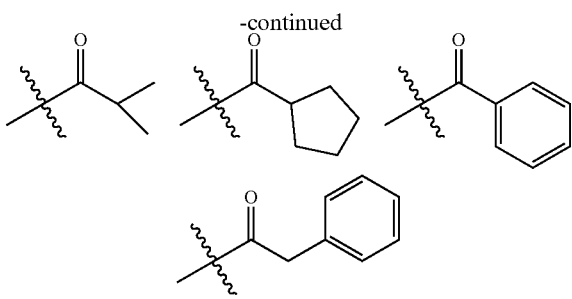

In the present specification, in the ester group, the oxygen of the ester group may be substituted with a linear, branched or cyclic alkyl group having 1 to 25 carbon atoms or an aryl group having 6 to 30 carbon atoms. Specifically, compounds having the following structural formulae may be included, but the ester group is not limited thereto.

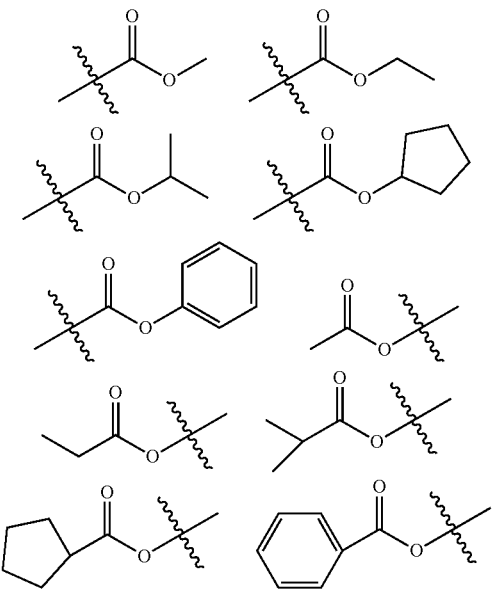

In the present specification, the alkyl group may be linear or branched, and the number of carbon atoms is not particularly limited, but is preferably from 1 to 30. Specific examples thereof may include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl and the like, but are not limited thereto.

In the present specification, the cycloalkyl group is not particularly limited, but preferably has 3 to 30 carbon atoms, and specific examples thereof may include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl and the like, but are not limited thereto.

In the present specification, the alkoxy group may be linear, branched or cyclic. The number of carbon atoms of the alkoxy group is not particularly limited, but is preferably from 1 to 30. Specific examples thereof may include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy and the like, but are not limited thereto.

In the present specification, the amine group may be selected from the group consisting of —$NH_2$; an alkylamine group; an N-alkylarylamine group; an arylamine group; an N-arylheteroarylamine group; an N-alkylheteroarylamine group and a heteroarylamine group, and the number of carbon atoms is, although not particularly limited thereto, preferably from 1 to 30. Specific examples of the amine group may include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, an N-phenylnaphthylamine group, a ditolylamine group, an N-phenyltolylamine group, a triphenylamine group, an N-phenylbiphenylamine group; an N-phenylnaphthylamine group; an N-biphenylnaphthylamine group; an N-naphthylfluorenylamine group; an N-phenylphenanthrenylamine group; an N-biphenylphenanthrenylamine group; an N-phenylfluorenylamine group; an N-phenylterphenylamine group; an N-phenanthrenylfluorenylamine group; an N-biphenylfluorenylamine group and the like, but are not limited thereto.

In the present specification, the N-alkylarylamine group means an amine group in which N of the amine group is substituted with an alkyl group and an aryl group.

In the present specification, the N-arylheteroarylamine group means an amine group in which N of the amine group is substituted with an aryl group and a heteroaryl group.

In the present specification, the N-alkylheteroarylamine group means an amine group in which N of the amine group is substituted with an alkyl group and a heteroaryl group.

In the present specification, the alkyl group in the alkylamine group, the N-arylalkylamine group, the alkylthioxy group, the alkylsulfoxy group and the N-alkylheteroarylamine group is the same as the examples of the alkyl group described above. Specifically, the alkylthioxy group may include a methylthioxy group, an ethylthioxy group, a tert-butylthioxy group, a hexylthioxy group, an octylthioxy group and the like, and the alkylsulfoxy group may include mesyl, an ethylsulfoxy group, a propylsulfoxy group, a butylsulfoxy group and the like, however, the examples are not limited thereto.

In the present specification, the alkenyl group may be linear or branched, and although not particularly limited thereto, the number of carbon atoms is preferably from 2 to 30. Specific examples thereof may include vinyl, 1-propenyl, isopropenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis(diphenyl-1-yl)vinyl-1-yl, a stilbenyl group, a styrenyl group and the like, but are not limited thereto.

In the present specification, specific examples of the silyl group may include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group and the like, but are not limited thereto.

In the present specification, the boron group may be —$BR_{100}R_{101}$, and herein, $R_{100}$ and $R_{101}$ are the same as or different from each other, and may be each independently selected from the group consisting of hydrogen; deuterium; a halogen group; a nitrile group; a substituted or unsubstituted monocyclic or multicyclic cycloalkyl group having 3 to 30 carbon atoms; a substituted or unsubstituted linear or branched alkyl group having 1 to 30 carbon atoms; a substituted or unsubstituted monocyclic or multicyclic aryl group having 6 to 30 carbon atoms; and a substituted or unsubstituted monocyclic or multicyclic heteroaryl group having 2 to 30 carbon atoms.

In the present specification, specific examples of the phosphine oxide group may include a diphenylphosphine oxide group, a dinaphthylphosphine oxide group and the like, but are not limited thereto.

In the present specification, the aryl group is not particularly limited, but preferably has 6 to 30 carbon atoms, and the aryl group may be monocyclic or multicyclic.

When the aryl group is a monocyclic aryl group, the number of carbon atoms is not particularly limited, but is preferably from 6 to 30. Specific examples of the monocyclic aryl group may include a phenyl group, a biphenyl group, a terphenyl group and the like, but are not limited thereto.

When the aryl group is a multicyclic aryl group, the number of carbon atoms is not particularly limited, but is preferably from 10 to 30. Specific examples of the multicyclic aryl group may include a naphthyl group, an anthracenyl group, a phenanthryl group, a triphenyl group, a pyrenyl group, a phenalenyl group, a perylenyl group, a chrysenyl group, a fluorenyl group and the like, but are not limited thereto.

In the present specification, the fluorenyl group may be substituted, and adjacent substituents may bond to each other to form a ring.

When the fluorenyl group is substituted,

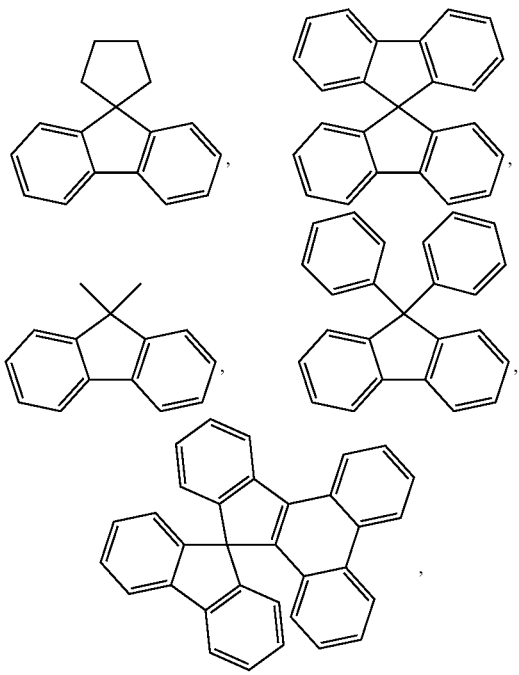

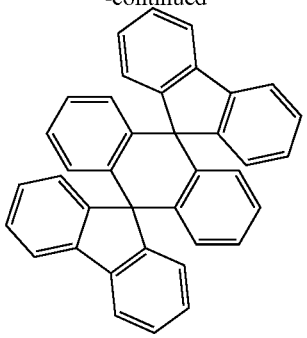

and the like may be included. However, the compound is not limited thereto.

In the present specification, an "adjacent" group may mean a substituent substituting an atom directly linked to an atom substituted by the corresponding substituent, a substituent sterically most closely positioned to the corresponding substituent, or another substituent substituting an atom substituted by the corresponding substituent. For example, two substituents substituting ortho positions in a benzene ring, and two substituents substituting the same carbon in an aliphatic ring may be interpreted as groups "adjacent" to each other.

In the present specification, the aryl group in the aryloxy group, the arylthioxy group, the arylsulfoxy group, the N-alkylarylamine group, the N-arylheteroarylamine group and the arylphosphine group is the same as the examples of the aryl group described above. Specific examples of the aryloxy group may include a phenoxy group, a p-tolyloxy group, a m-tolyloxy group, a 3,5-dimethyl-phenoxy group, a 2,4,6-trimethylphenoxy group, a p-tert-butylphenoxy group, a 3-biphenyloxy group, a 4-biphenyloxy group, a 1-naphthyloxy group, a 2-naphthyloxy group, a 4-methyl-1-naphthyloxy group, a 5-methyl-2-naphthyloxy group, a 1-anthryloxy group, a 2-anthryloxy group, a 9-anthryloxy group, a 1-phenanthryloxy group, a 3-phenanthryloxy group, a 9-phenanthryloxy group and the like, and specific examples of the arylthioxy group may include a phenylthioxy group, a 2-methylphenylthioxy group, a 4-tert-butylphenylthioxy group and the like, and specific examples of the arylsulfoxy group may include a benzenesulfoxy group, a p-toluenesulfoxy group and the like, however, the examples are not limited thereto.

In the present specification, examples of the arylamine group include a substituted or unsubstituted monoarylamine group, a substituted or unsubstituted diarylamine group, or a substituted or unsubstituted triarylamine group. The aryl group in the arylamine group may be a monocyclic aryl group or a multicyclic aryl group. The arylamine group including two or more aryl groups may include monocyclic aryl groups, multicyclic aryl groups, or both monocyclic aryl groups and multicyclic aryl groups. For example, the aryl group in the arylamine group may be selected from among the examples of the aryl group described above.

In the present specification, the heteroaryl group is a group including one or more atoms that are not carbon, that is, heteroatoms, and specifically, the heteroatom may include one or more atoms selected from the group consisting of O, N, Se, S and the like. The number of carbon atoms is not particularly limited, but is preferably from 2 to 30, and the heteroaryl group may be monocyclic or multicyclic. Examples of the hetero-cyclic group may include a thiophene group, a furanyl group, a pyrrole group, an imidazolyl group, a triazolyl group, an oxazolyl group, an oxadiazolyl group, a pyridyl group, a bipyridyl group, a pyrimidyl group, triazinyl group, a triazolyl group, an acridyl group, a pyridazinyl group, a pyrazinyl group, a qinolinyl group, a quinazolinyl group, a quinoxalinyl group, a phthalazinyl group, a pyridopyrimidyl group, a pyridopyrazinyl group, a pyrazinopyrazinyl group, an isoquinolinyl group, an indolyl group, a carbazolyl group, a benzoxazolyl group, a benzimidazolyl group, a benzothiazolyl group, a benzocarbazolyl group, a benzothiophene group, a dibenzothiophene group, a benzofuranyl group, a phenanthroline group, an isoxazolyl group, a thiadiazolyl group, a phenothiazinyl group and a dibenzofuranyl group and the like, but are not limited thereto.

In the present specification, examples of the heteroarylamine group include a substituted or unsubstituted monoheteroarylamine group, a substituted or unsubstituted diheteroarylamine group, or a substituted or unsubstituted triheteroarylamine group. The heteroarylamine group including two or more heteroaryl groups may include monocyclic heteroaryl groups, multicyclic heteroaryl groups, or both monocyclic heteroaryl groups and multicyclic heteroaryl groups. For example, the heteroaryl group in the heteroarylamine group may be selected from among the examples of the heteroaryl group described above.

In the present specification, examples of the heteroaryl group in the N-arylheteroarylamine group and the N-alkylheteroarylamine group are the same as the examples of the heteroaryl group described above.

In the present specification, the arylene group means an aryl group having two bonding sites, that is, a divalent group. Descriptions on the aryl group provided above may be applied thereto except for being each a divalent group.

In the present specification, the heteroarylene group means a heteroaryl group having two bonding sites, that is, a divalent group. Descriptions on the heteroaryl group provided above may be applied thereto except for being each a divalent group.

In the present specification, the "ring" in the substituted or unsubstituted ring formed by adjacent groups bonding to each other means a substituted or unsubstituted hydrocarbon ring; or a substituted or unsubstituted heteroring.

In the present specification, the ring means a substituted or unsubstituted hydrocarbon ring; or a substituted or unsubstituted heteroring.

In the present specification, the hydrocarbon ring may be aromatic, aliphatic or a fused ring of aromatic and aliphatic, and may be selected from among the examples of the cycloalkyl group or the aryl group except for those that are not monovalent.

In the present specification, the aromatic ring may be monocyclic or multicyclic, and may be selected from among the examples of the aryl group except for being not monovalent.

In the present specification, the heteroring is a group including one or more atoms that are not carbon, that is, heteroatoms, and specifically, the heteroatom may include one or more atoms selected from the group consisting of O, N, Se, S and the like. The heteroring may be monocyclic or multicyclic, may be aromatic, aliphatic or a fused ring of aromatic and aliphatic, and may be selected from among the examples of the heteroaryl group except for those that are not monovalent.

According to one embodiment of the present specification, in Chemical Formula 1, R1 to R4 are hydrogen, or adjacent groups bond to each other to form a substituted or unsubstituted ring.

According to one embodiment of the present specification, in Chemical Formula 1, R1 to R4 are hydrogen.

According to one embodiment of the present specification, in Chemical Formula 1, R1 to R9 are hydrogen.

According to one embodiment of the present specification, in Chemical Formula 1, adjacent groups in R1 to R4 bond to each other to form a substituted or unsubstituted ring.

According to one embodiment of the present specification, in Chemical Formula 1, R1 and R2 bond to each other to form a substituted or unsubstituted ring.

According to one embodiment of the present specification, in Chemical Formula 1, R1 and R2 bond to each other to form a substituted or unsubstituted aromatic ring.

According to one embodiment of the present specification, in Chemical Formula 1, R1 and R2 bond to each other to form a substituted or unsubstituted benzene ring.

According to one embodiment of the present specification, in Chemical Formula 1, R1 and R2 bond to each other to form a benzene ring.

According to one embodiment of the present specification, in Chemical Formula 1, R2 and R3 bond to each other to form a substituted or unsubstituted ring.

According to one embodiment of the present specification, in Chemical Formula 1, R2 and R3 bond to each other to form a substituted or unsubstituted aromatic ring.

According to one embodiment of the present specification, in Chemical Formula 1, R2 and R3 bond to each other to form a substituted or unsubstituted benzene ring.

According to one embodiment of the present specification, in Chemical Formula 1, R2 and R3 bond to each other to form a benzene ring.

According to one embodiment of the present specification, in Chemical Formula 1, R3 and R4 bond to each other to form a substituted or unsubstituted ring.

According to one embodiment of the present specification, in Chemical Formula 1, R3 and R4 bond to each other to form a substituted or unsubstituted aromatic ring.

According to one embodiment of the present specification, in Chemical Formula 1, R3 and R4 bond to each other to form a substituted or unsubstituted benzene ring.

According to one embodiment of the present specification, in Chemical Formula 1, R3 and R4 bond to each other to form a benzene ring.

According to one embodiment of the present specification, Chemical Formula 1 is represented by the following Chemical Formula 1-1.

[Chemical Formula 1-1]

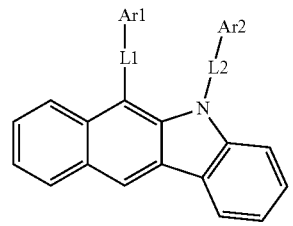

In Chemical Formula 1-1,
definitions of L1, L2, Ar1 and Ar2 are the same as in Chemical Formula 1.

According to one embodiment of the present specification, Chemical Formula 1 is represented by any one of the following Chemical Formulae 1-2 to 1-4.

[Chemical Formula 1-2]

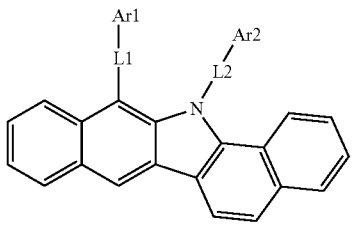

[Chemical Formula 1-3]

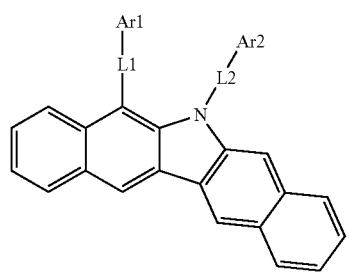

[Chemical Formula 1-4]

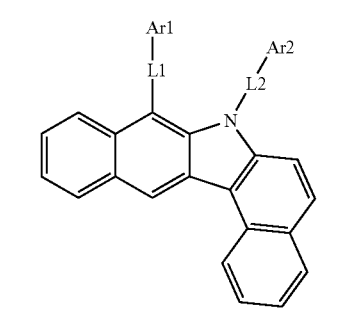

In Chemical Formulae 1-2 to 1-4, definitions of L1, L2, Ar1 and Ar2 are the same as in Chemical Formula 1.

According to one embodiment of the present specification, in Chemical Formula 1, L1 and L2 are the same as or different from each other, and each independently a direct bond; or a substituted or unsubstituted monocyclic or multicyclic arylene group.

According to one embodiment of the present specification, in Chemical Formula 1, L1 and L2 are the same as or different from each other, and each independently a direct bond; or a monocyclic or multicyclic arylene group unsubstituted or substituted with an alkyl group.

According to one embodiment of the present specification, in Chemical Formula 1, L1 and L2 are the same as or different from each other, and each independently a direct bond; a monocyclic arylene group; or a multicyclic arylene group substituted with an alkyl group.

According to one embodiment of the present specification, in Chemical Formula 1, L1 and L2 are the same as or different from each other, and each independently a direct bond; a phenylene group; a biphenylylene group; or a fluorenyl group substituted with an alkyl group.

According to one embodiment of the present specification, in Chemical Formula 1, L1 and L2 are the same as or different from each other, and each independently a direct bond; a phenylene group; a biphenylylene group; or a fluorenyl group substituted with a methyl group.

According to one embodiment of the present specification, in Chemical Formula 1, Ar1 and Ar2 are the same as or different from each other, and each independently selected from the group consisting of a substituted or unsubstituted diarylamine group; a substituted or unsubstituted diheteroarylamine group; a substituted or unsubstituted silyl group; a substituted or unsubstituted phosphine oxide group; a substituted or unsubstituted monocyclic or multicyclic aryl group having 6 to 30 carbon atoms; and a substituted or unsubstituted monocyclic or multicyclic heteroaryl group having 2 to 30 carbon atoms.

According to one embodiment of the present specification, in Chemical Formula 1, Ar1 and Ar2 are the same as or different from each other, and each independently selected from the group consisting of a substituted or unsubstituted phenyl group; a substituted or unsubstituted biphenyl group; a substituted or unsubstituted phenanthrenyl group; a substituted or unsubstituted naphthyl group; a substituted or unsubstituted terphenyl group; a substituted or unsubstituted fluorenyl group; a substituted or unsubstituted anthracenyl group; a substituted or unsubstituted chrysenyl group; a substituted or unsubstituted quaterphenyl group; a substituted or unsubstituted spirobifluorenyl group; a substituted or unsubstituted pyrenyl group; a substituted or unsubstituted triphenylenyl group; a substituted or unsubstituted perylenyl group; a substituted or unsubstituted triazinyl group; a substituted or unsubstituted pyrimidyl group; a substituted or unsubstituted pyridyl group; a substituted or unsubstituted quinolinyl group; a substituted or unsubstituted quinazolinyl group; a substituted or unsubstituted benzoquinolinyl group; a substituted or unsubstituted phenanthrolinyl group; a substituted or unsubstituted quinoxalinyl group; a substituted or unsubstituted dibenzofuranyl group; a substituted or unsubstituted dibenzothiophene group; a substituted or unsubstituted benzonaphthofuranyl group; a substituted or unsubstituted benzonaphthothiophene group; a substituted or unsubstituted dimethylphosphine oxide group; a substituted or unsubstituted diphenylphosphine oxide group; a substituted or unsubstituted dinaphthylphosphine oxide group; a substituted or unsubstituted benzoxazolyl group; a substituted or unsubstituted benzothiazolyl group; a substituted or unsubstituted benzimidazolyl group; a substituted or unsubstituted triphenylsilyl group; a substituted or unsubstituted phenothiazinyl group; a substituted or unsubstituted phenoxazinyl group; a substituted or unsubstituted thiophene group; a substituted or unsubstituted diphenylamine group; a substituted or unsubstituted N-phenylnaphthylamine group; a substituted or unsubstituted N-phenylbiphenylamine group; a substituted or unsubstituted N-phenylphenanthrenylamine group; a substituted or unsubstituted N-biphenylnaphthylamine group; a substituted or unsubstituted dibiphenylamine group; a substituted or unsubstituted N-biphenylphenanthrenylamine group; a substituted or unsubstituted dinaphthylamine group; a substituted or unsubstituted N-quaterphenylfluorenylamine group; a substituted or unsubstituted N-terphenylfluorenylamine group; a substituted or unsubstituted N-biphenylterphenylamine group; a substituted or unsubstituted N-biphenylfluorenylamine group; a substituted or unsubstituted N-phenylfluorenylamine group; a substituted or unsubstituted N-naphthylfluorenylamine group; a substituted or unsubstituted N-phenanthrenylfluorenylamine group; a substituted or unsubstituted difluorenylamine group; a substituted or unsubstituted N-phenylterphenylamine group; a substituted or unsubstituted N-phenylcarbazolylamine group; a substituted or unsubstituted N-biphenylcarbazolylamine group; a substituted or unsubstituted N-phenylbenzocarbazolylamine group; a substituted or unsubstituted N-biphenylbenzocarbazolylamine group; a substituted or unsubstituted N-fluorenylcarbazolylamine group; a substituted or unsubstituted benzocarbazolyl group; a substituted or unsubstituted dibenzocarbazolyl group; a substituted or unsubstituted carbazolyl group; substituted or unsubstituted

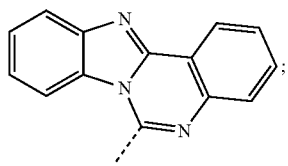

substituted or unsubstituted

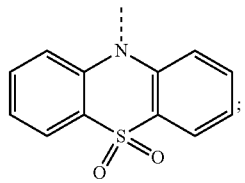

and a structure represented by the following Chemical Formula a, and

---- means a site bonding to Chemical Formula 1 through L1 or L2.

[Chemical Formula a]

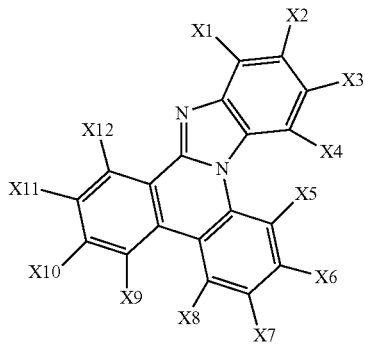

In Chemical Formula a, any one of X1 to X12 is a site bonding to Chemical Formula 1 through L1 or L2, and the rest are the same as or different from each other, and each independently hydrogen; a substituted or unsubstituted alkyl group; a substituted or unsubstituted aryl group; or a substituted or unsubstituted heteroaryl group, or adjacent groups bond to each other to form a substituted or unsubstituted ring.

According to one embodiment of the present specification, in Chemical Formula a, any one of X1 to X12 is a site bonding to Chemical Formula 1 through L1 or L2, and the rest are hydrogen.

According to one embodiment of the present specification, in Chemical Formula a, X11 and X12 bond to each other to form a substituted or unsubstituted monocyclic or multicyclic hydrocarbon ring having 6 to 20 carbon atoms.

According to one embodiment of the present specification, in Chemical Formula a, X11 and X12 bond to each other to form a substituted or unsubstituted monocyclic or multicyclic hydrocarbon ring having 6 to 10 carbon atoms.

According to one embodiment of the present specification, in Chemical Formula a, X11 and X12 bond to each other to form a substituted or unsubstituted benzene ring.

According to one embodiment of the present specification, in Chemical Formula a, X11 and X12 bond to each other to form a benzene ring.

According to one embodiment of the present specification, in Chemical Formula 1, Ar1 and Ar2 are the same as or different from each other, and each independently selected from the group consisting of a phenyl group; a biphenyl group; a phenanthrenyl group; a naphthyl group; a terphenyl group; a fluorenyl group; an anthracenyl group; a chrysenyl group; a quaterphenyl group; a spirobifluorenyl group; a pyrenyl group; a triphenylenyl group; a perylenyl group; a triazinyl group; a pyrimidyl group; a pyridyl group; a quinolinyl group; a quinazolinyl group; a benzoquinolinyl group; a phenanthrolinyl group; a quinoxalinyl group; a dibenzofuranyl group; a dibenzothiophene group; a benzonaphthofuranyl group; a benzonaphthothiophene group; a dimethylphosphine oxide group; a diphenylphosphine oxide group; a dinaphthylphosphine oxide group; a benzoxazolyl group; a benzothiazolyl group; a benzimidazolyl group; a triphenylsilyl group; a phenothiazinyl group; a phenoxazinyl group; a thiophene group; a diphenylamine group; an N-phenylnaphthylamine group; an N-phenylbiphenylamine group; an N-phenylphenanthrenylamine group; an N-biphenylnaphthylamine group; a dibiphenylamine group; an N-biphenylphenanthrenylamine group; a dinaphthylamine group; an N-quaterphenylfluorenylamine group; an N-terphenylfluorenylamine group; an N-biphenylterphenylamine group; an N-biphenylfluorenylamine group; a substituted or unsubstituted N-phenylfluorenylamine group; an N-naphthylfluorenylamine group; an N-phenanthrenylfluorenylamine group; a difluorenylamine group; an N-phenylterphenylamine group; an N-phenylcarbazolylamine group; an N-biphenylcarbazolylamine group; an N-phenylbenzocarbazolylamine group; an N-biphenylbenzocarbazolylamine group; an N-fluorenylcarbazolylamine group; a benzocarbazolyl group; a dibenzocarbazolyl group; a carbazolyl group;

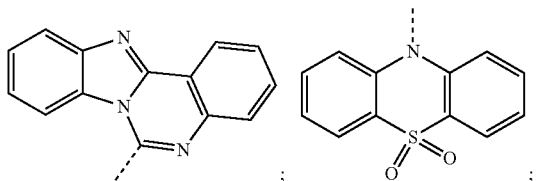

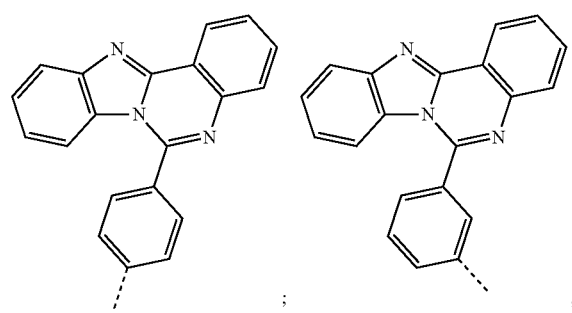

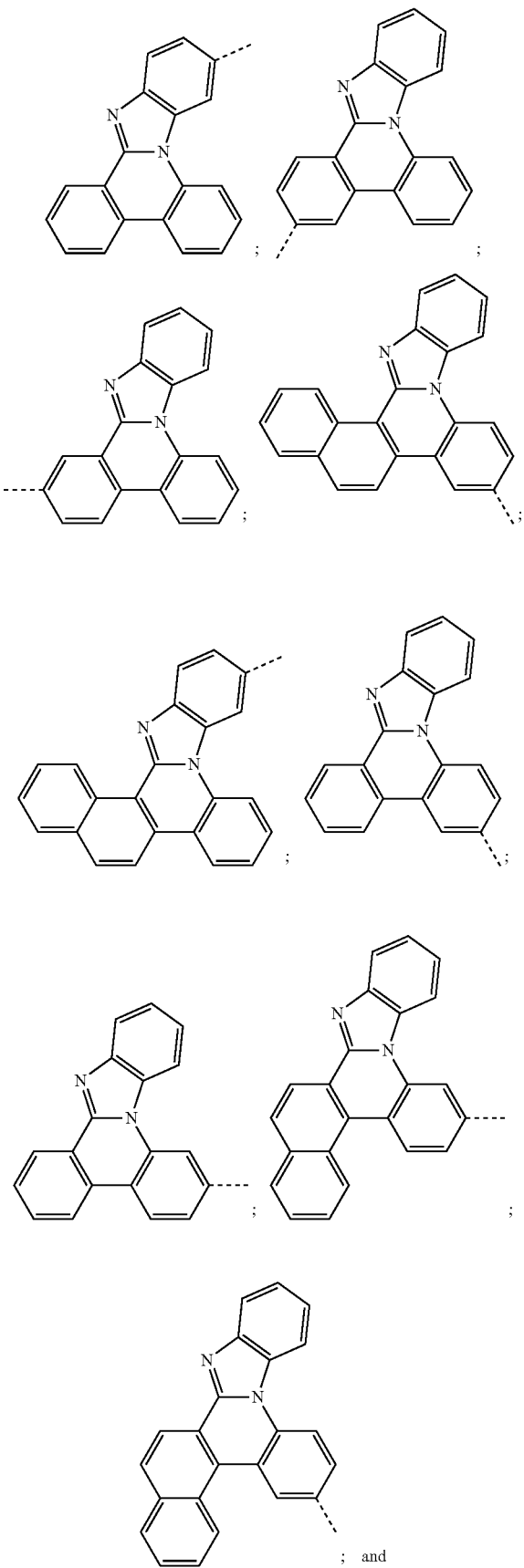

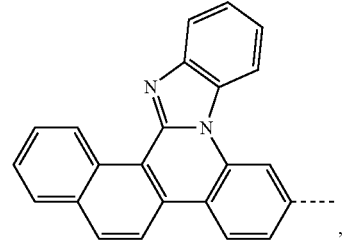

and

Ar1 and Ar2 may be unsubstituted or substituted with one or more selected from the group consisting of deuterium; a fluorine group; a nitrile group; a methyl group; a t-butyl group; a phenyl group; a biphenyl group; a naphthyl group; a fluorenyl group; a phenanthrenyl group; a carbazolyl group; a benzocarbazolyl group; a pyridyl group; a triazinyl group; a triphenylenyl group; a pyrimidyl group; a quinolinyl group; a dibenzofuranyl group; a dibenzothiophene group; a benzimidazolyl group; a benzothiazolyl group; a benzoxazolyl group; a thiophene group; a dimethylphosphine oxide group; a diphenylphosphine oxide group; a dinaphthylphosphine oxide group; a trimethylsilyl group; a triphenylsilyl group; a diphenylamine group; a dibiphenylamine group; an N-phenylbiphenylamine group; an N-phenylnaphthylamine group; an N-biphenylnaphthylamine group; an N-naphthylfluorenylamine group; an N-phenylphenanthrenylamine group; an N-biphenylphenanthrenylamine group; an N-phenylfluorenylamine group; an N-phenylterphenylamine group; an N-phenanthrenylfluorenylamine group; an N-biphenylfluorenylamine group; and

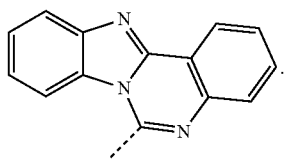

---- means a site bonding to Chemical Formula 1 through L1.

According to one embodiment of the present specification, in Chemical Formula 1, Ar1 and Ar2 are the same as or different from each other, and each independently represented by any one of the following structural formulae [A-1] to [A-5].

[A-1]

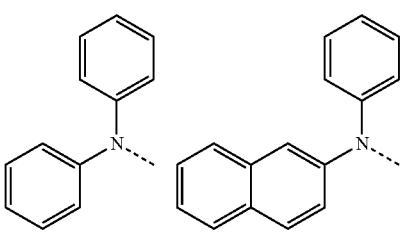

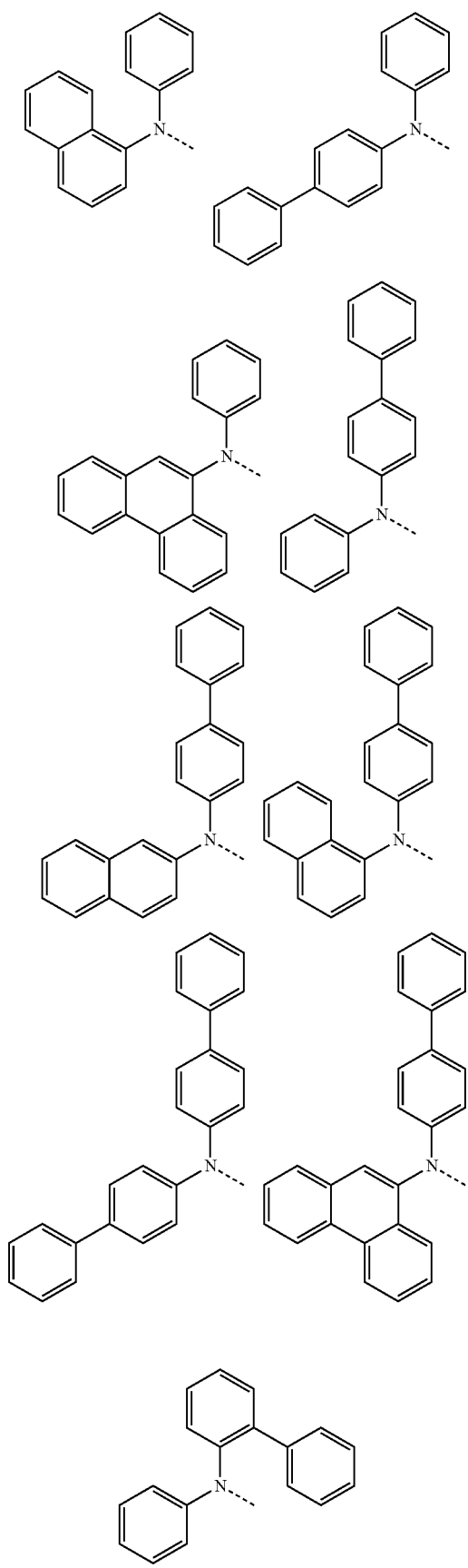
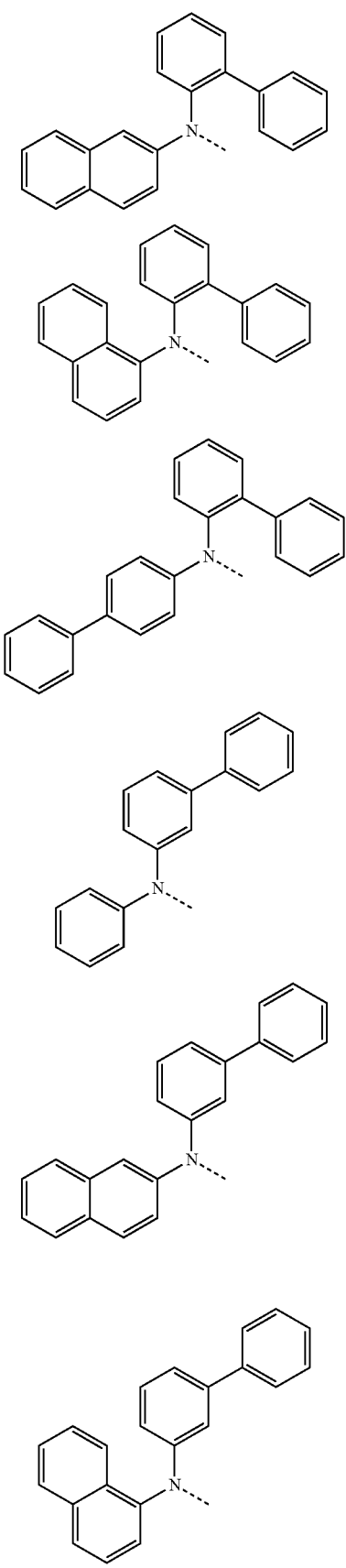

19
-continued
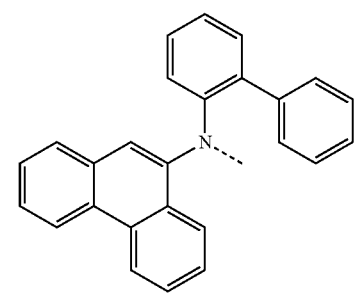
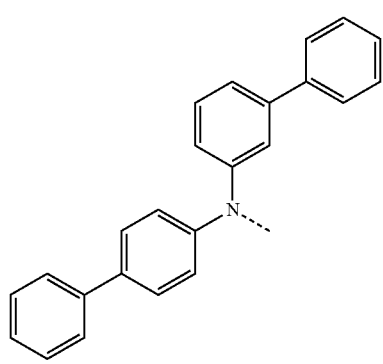
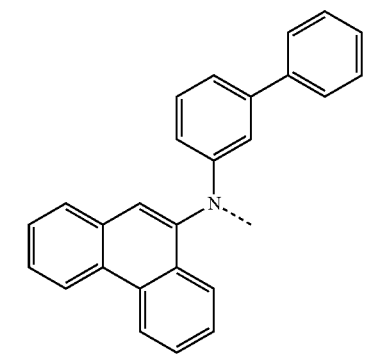
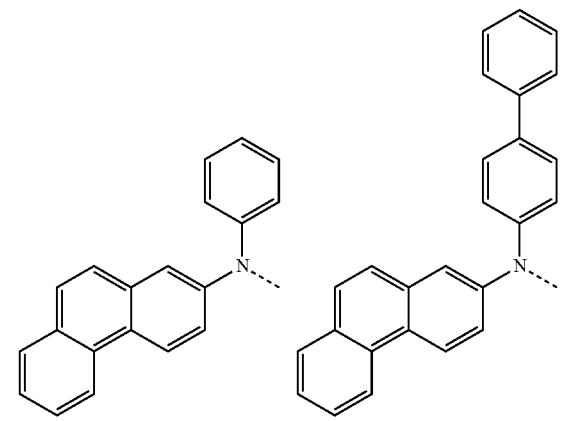
20
-continued
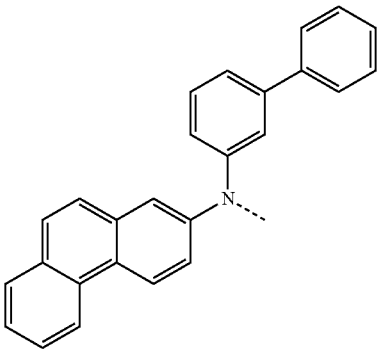
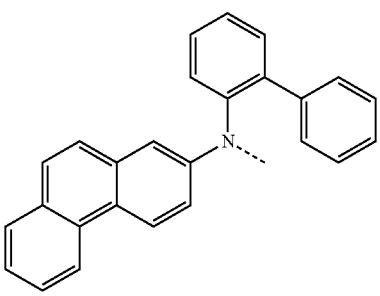
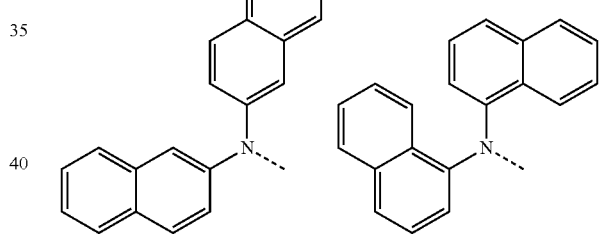
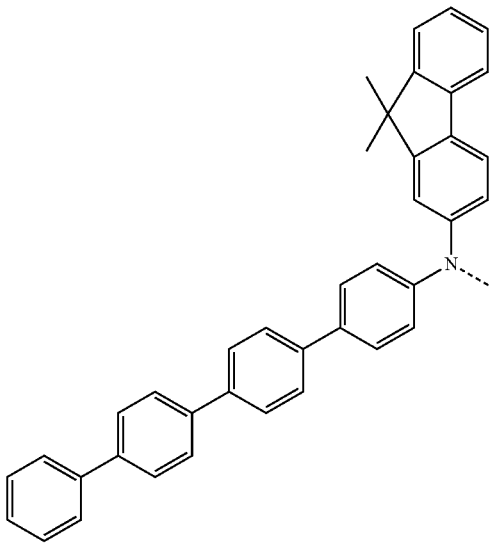

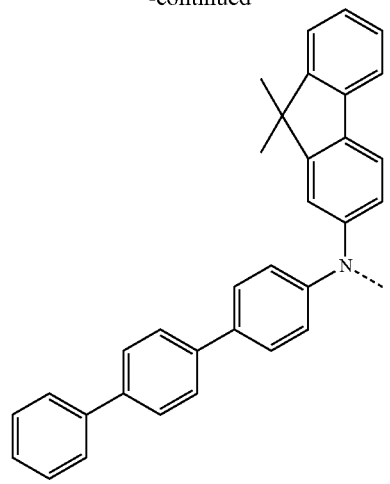
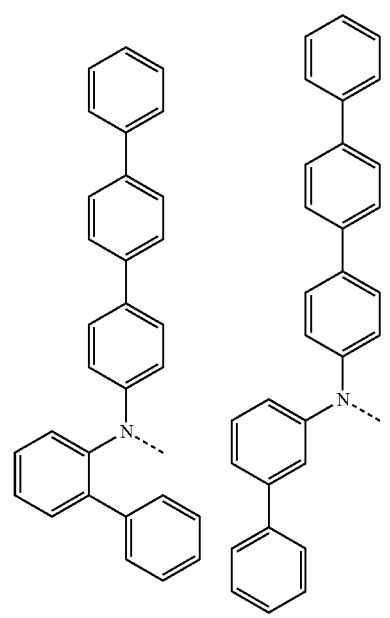
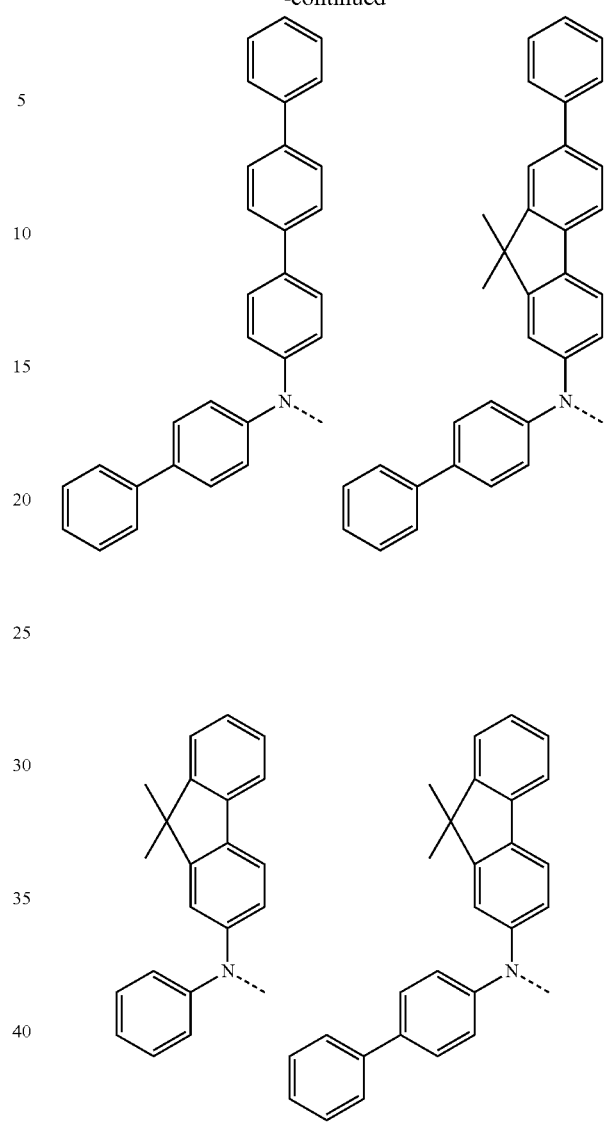
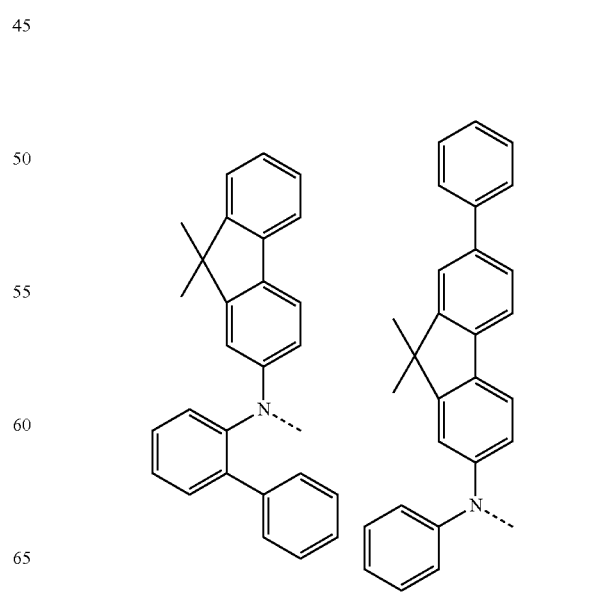

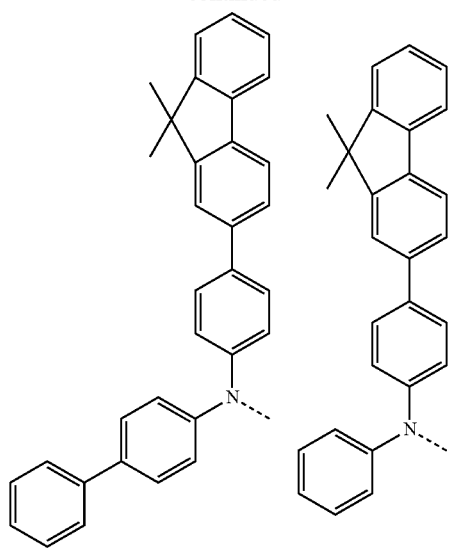
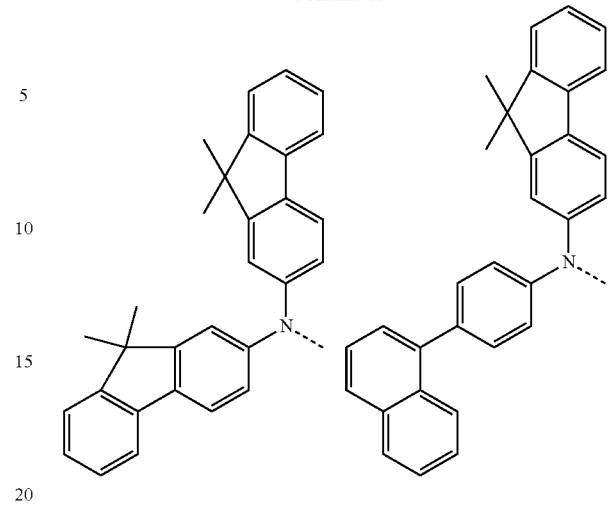
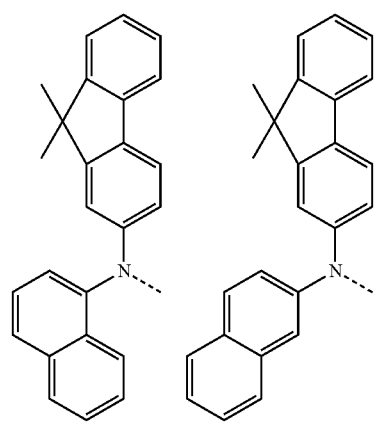
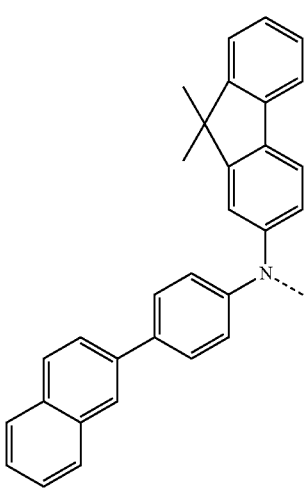
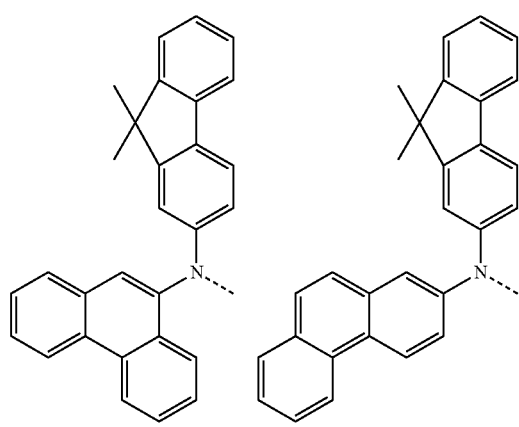
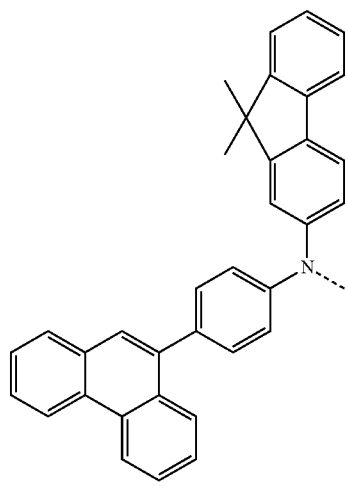

-continued
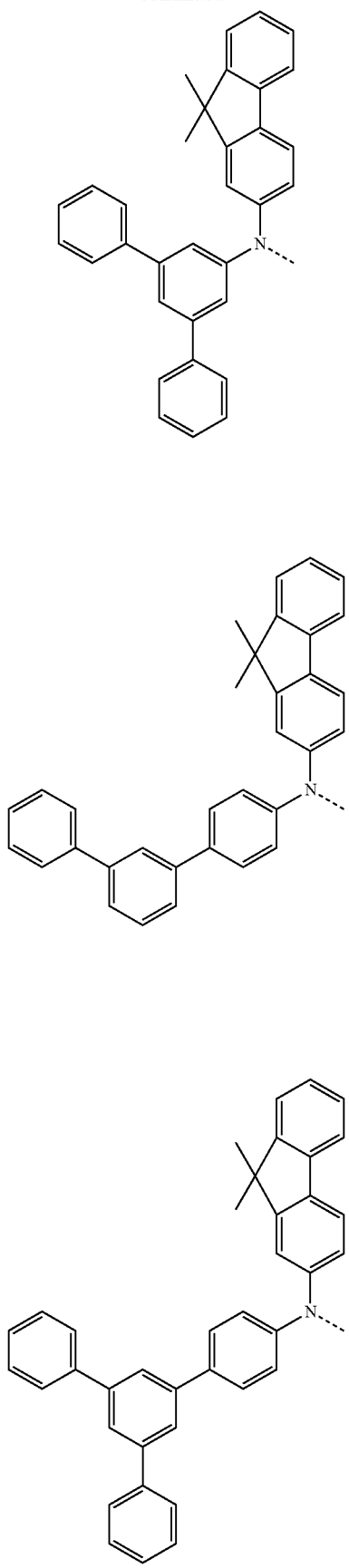
-continued
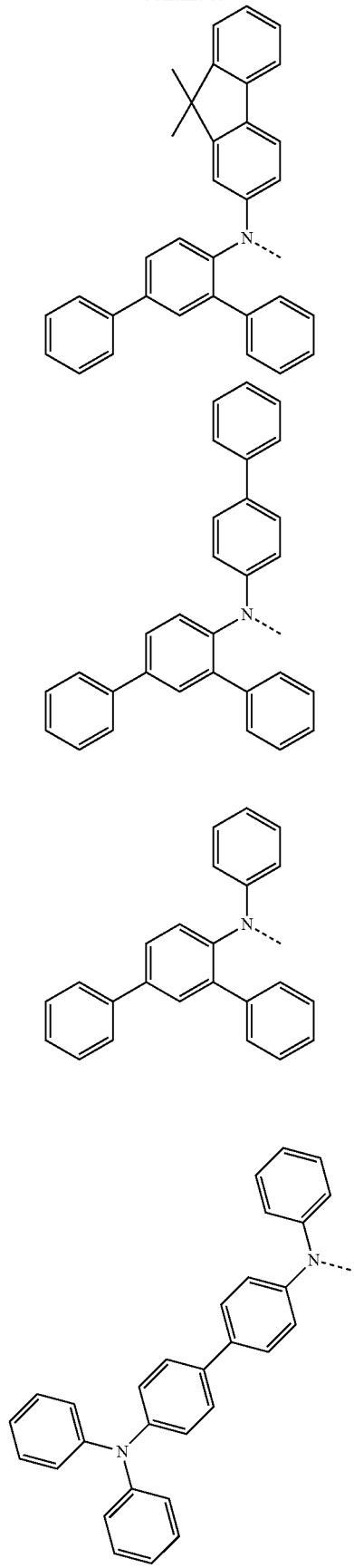

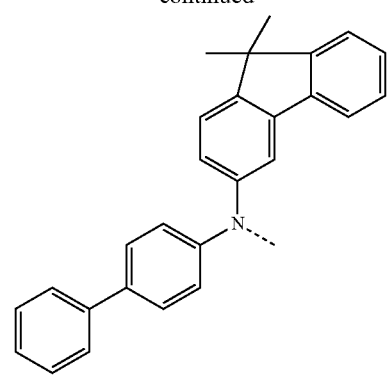
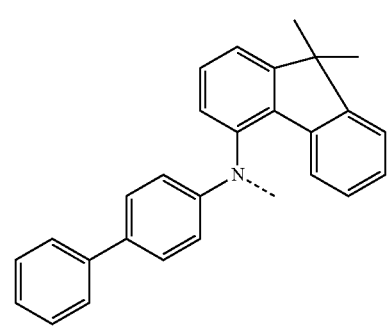
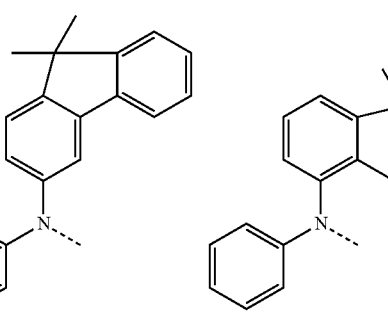
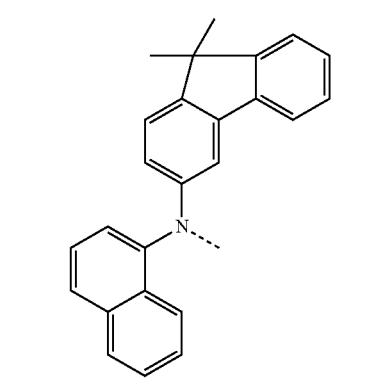
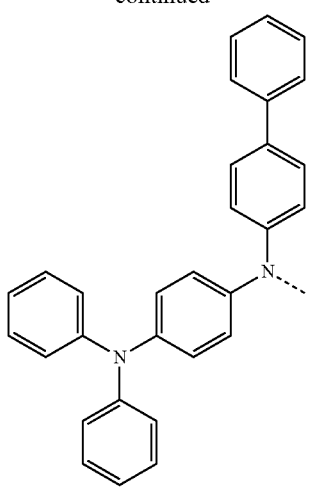
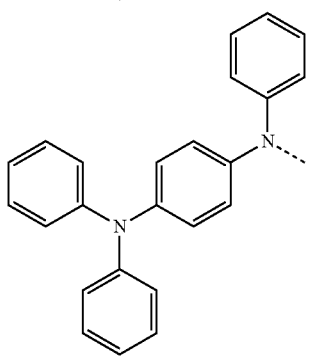
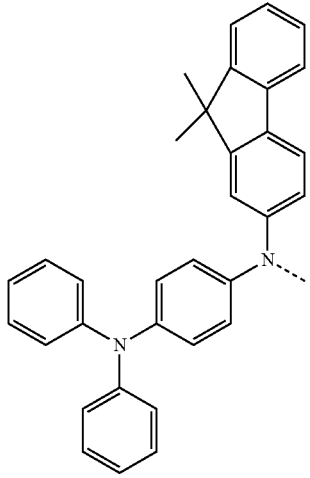
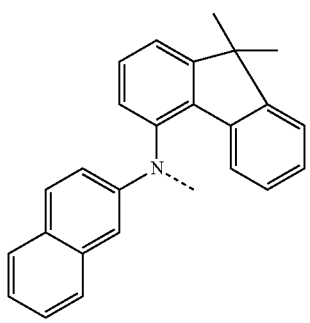

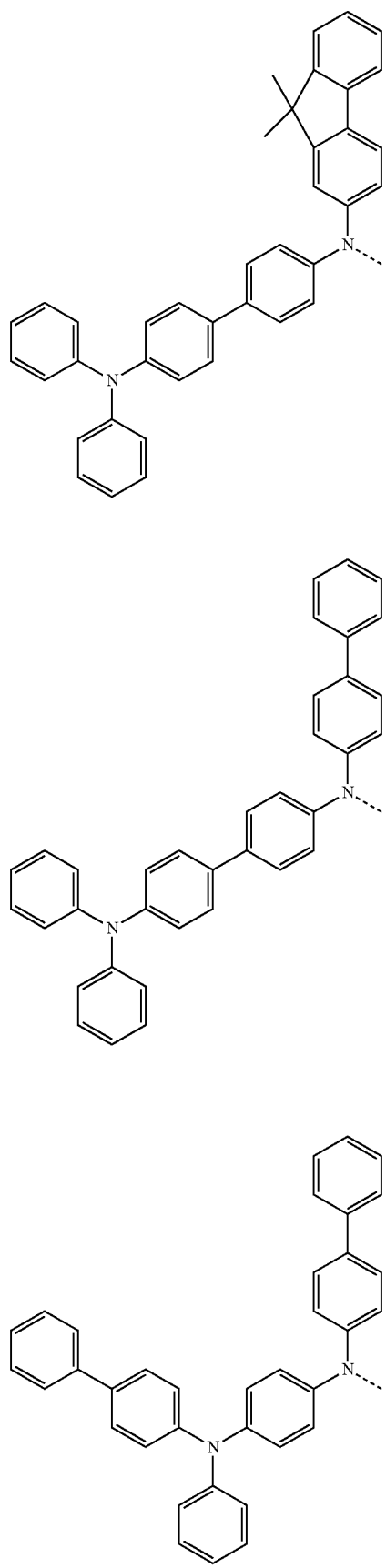
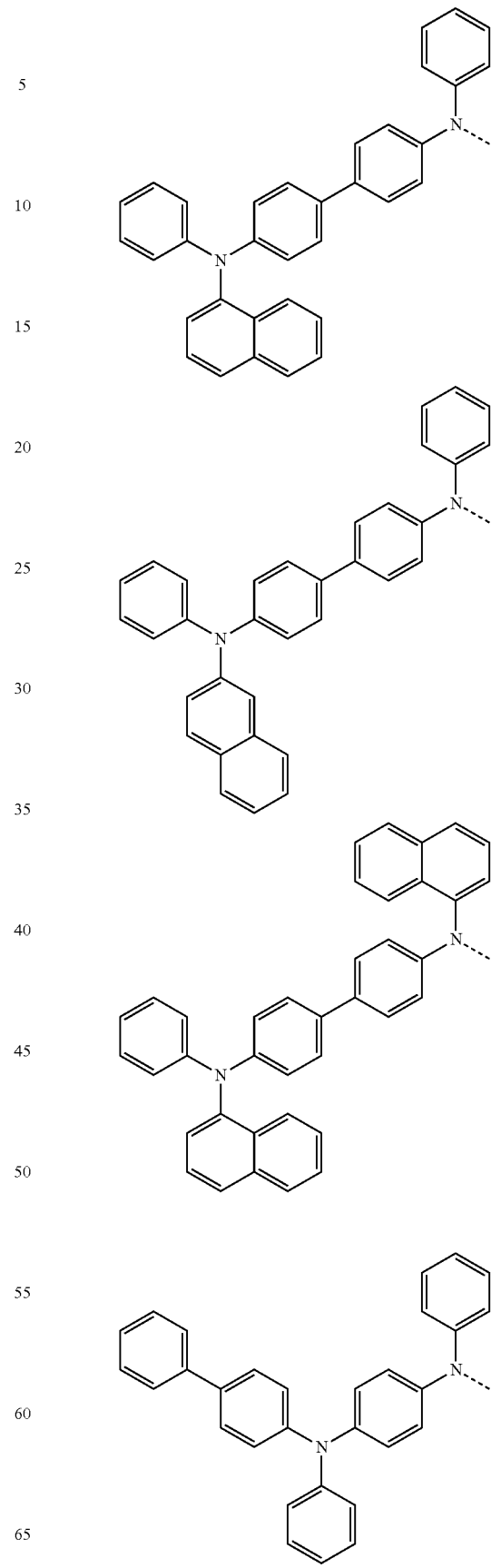

31
-continued
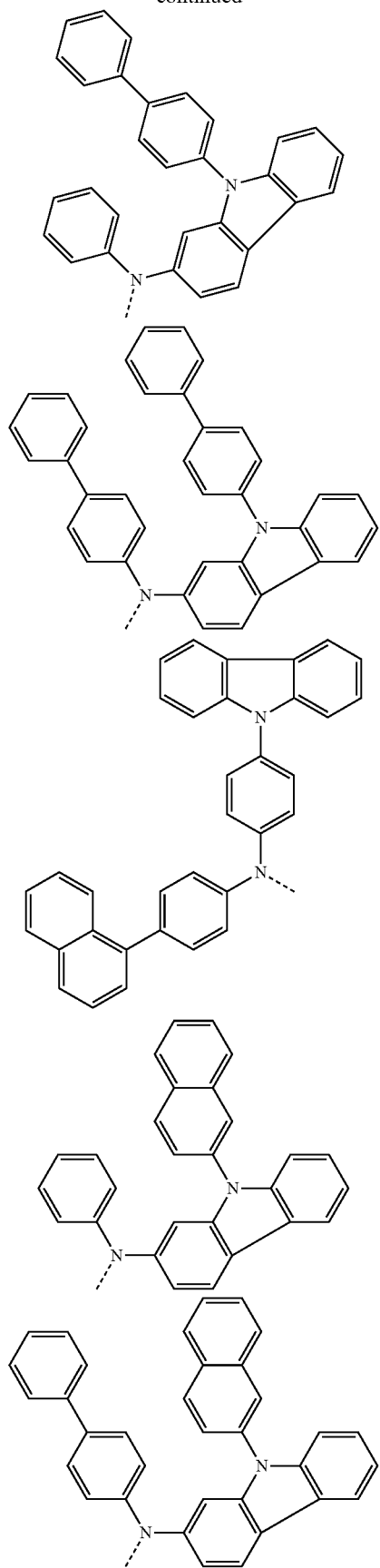
32
-continued
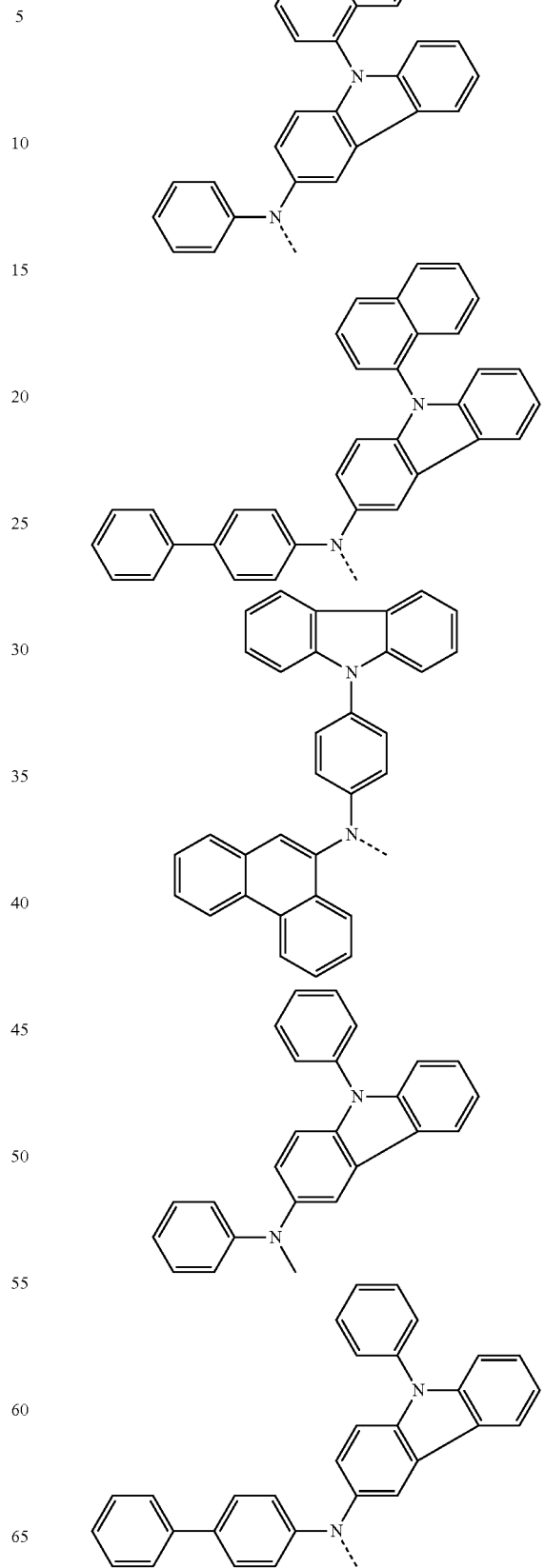

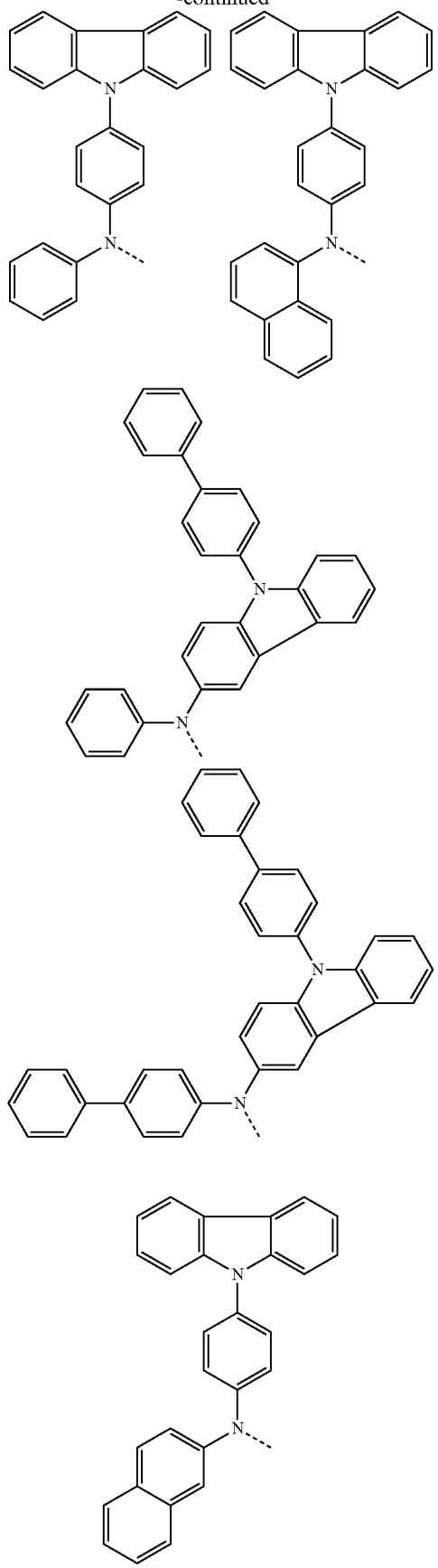
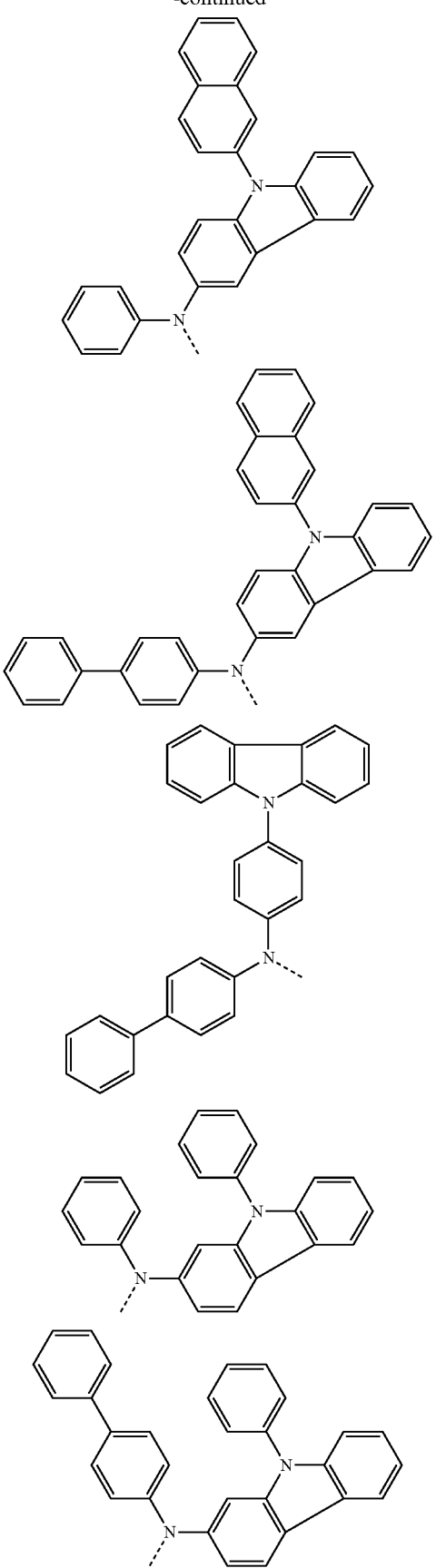

-continued
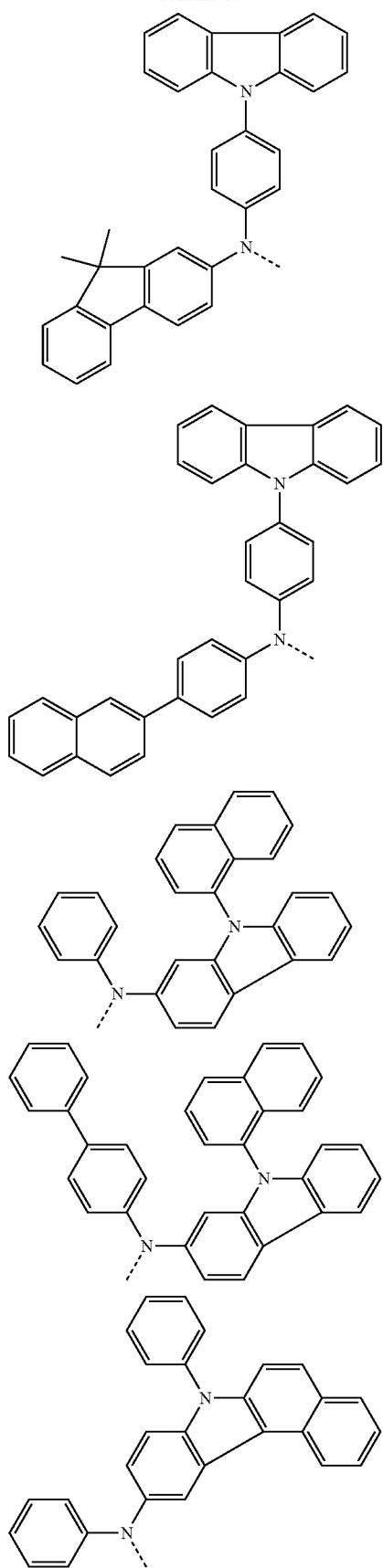
-continued
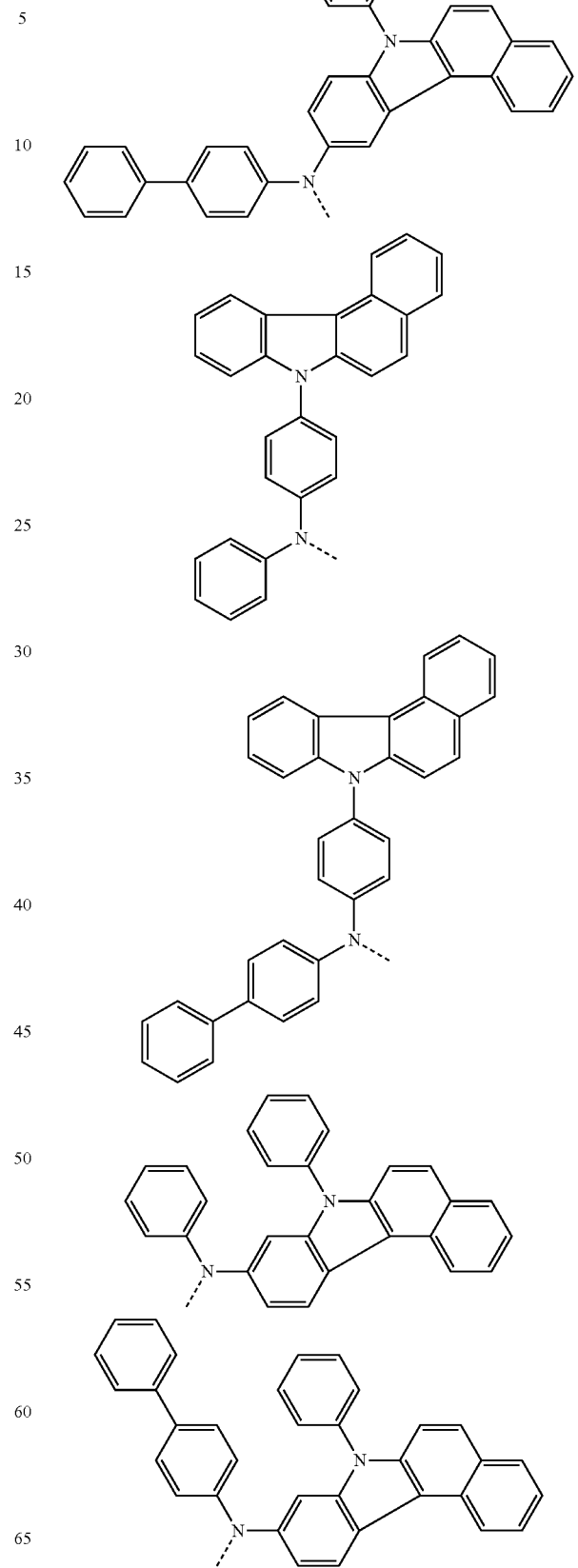

37
-continued
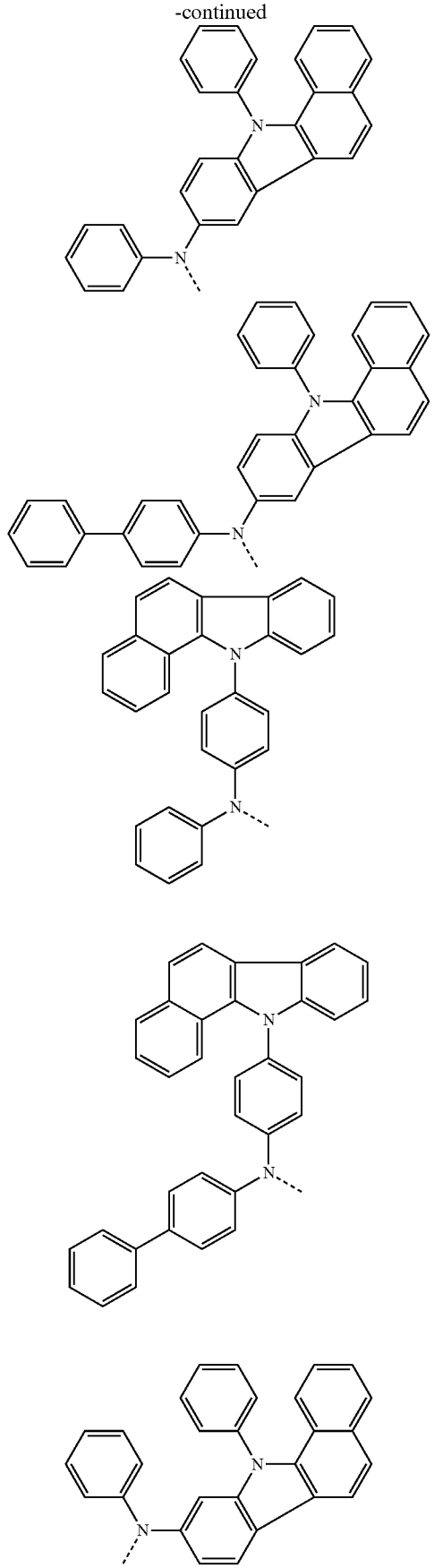
38
-continued
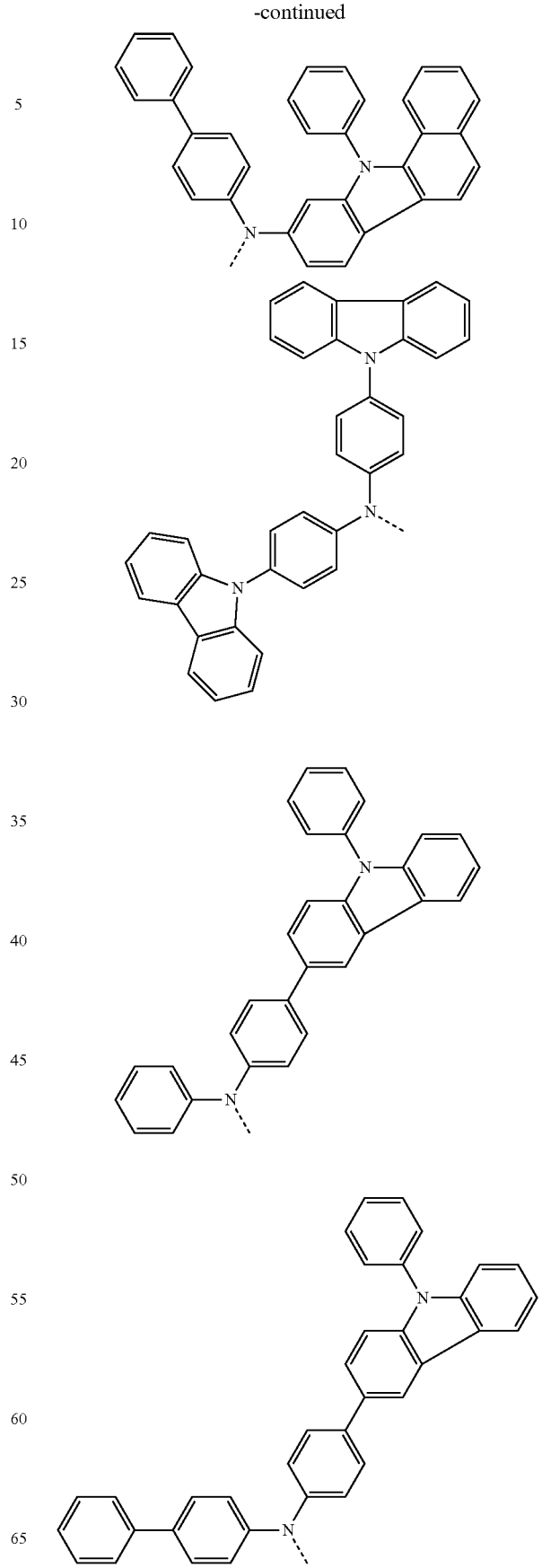

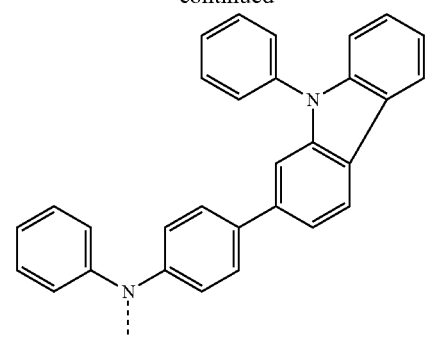
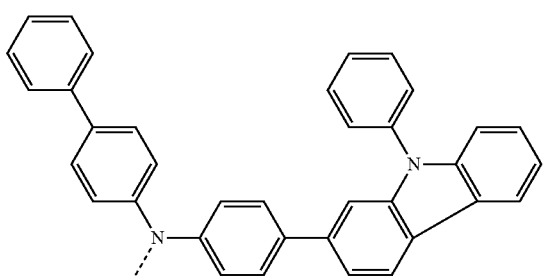
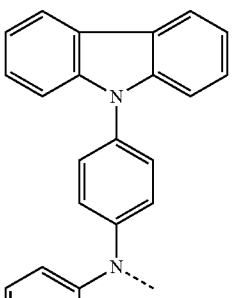
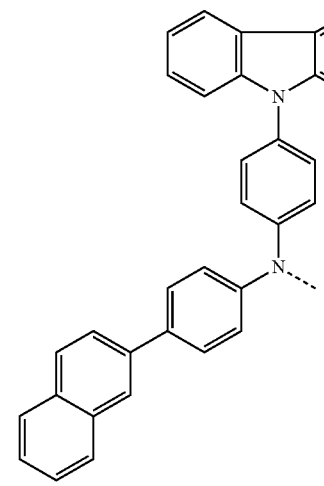
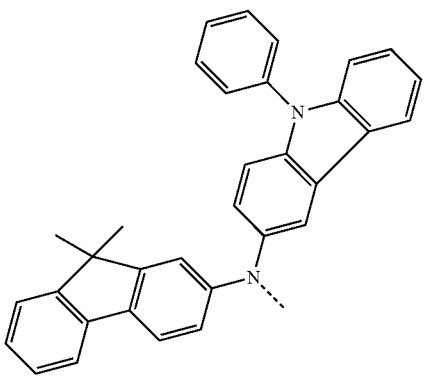
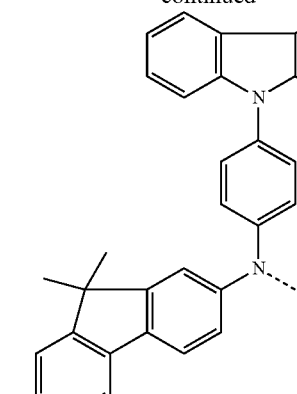
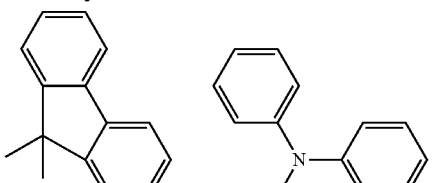
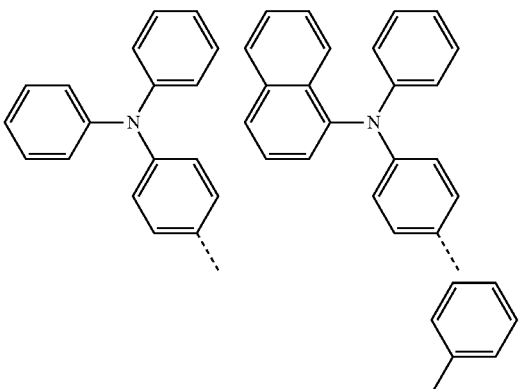
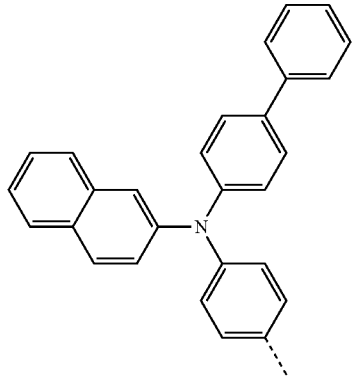

41
-continued
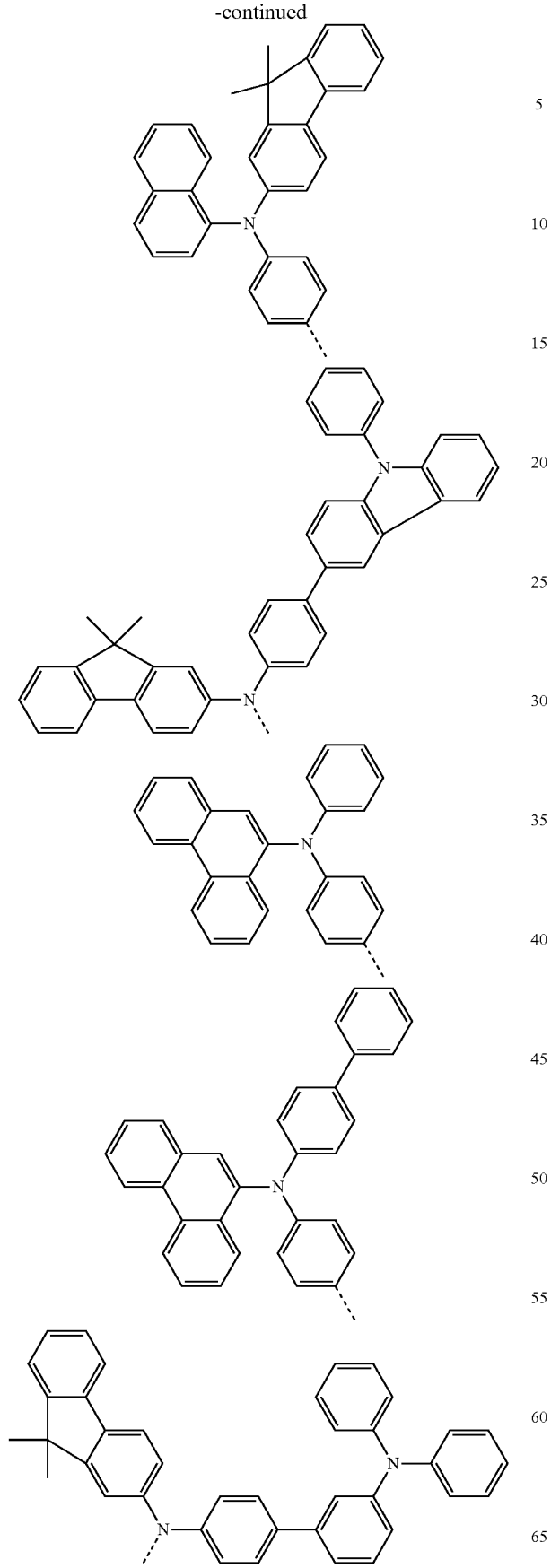
42
-continued
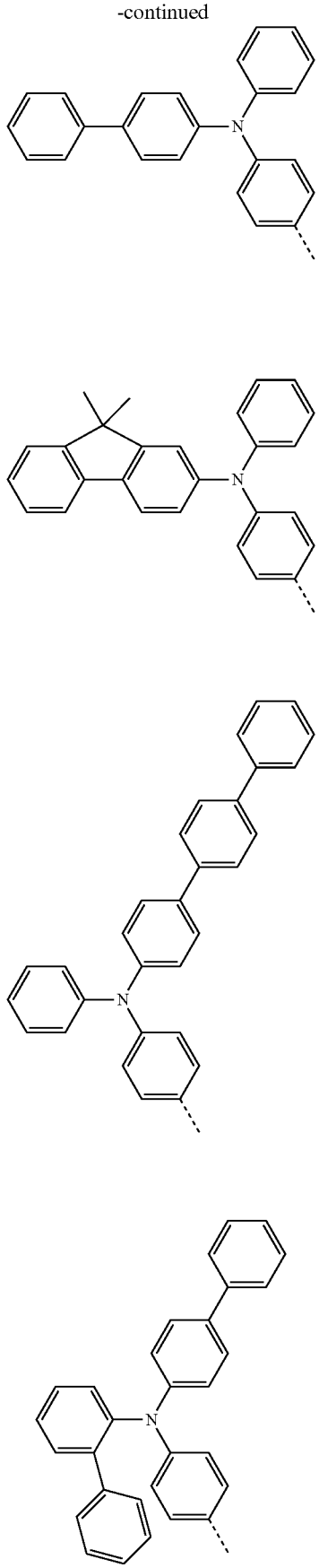

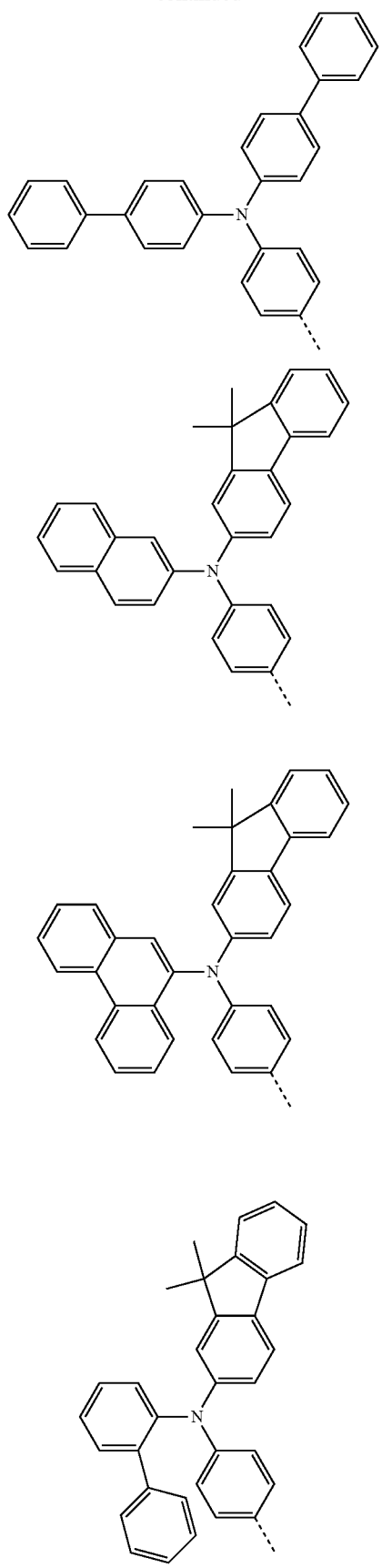
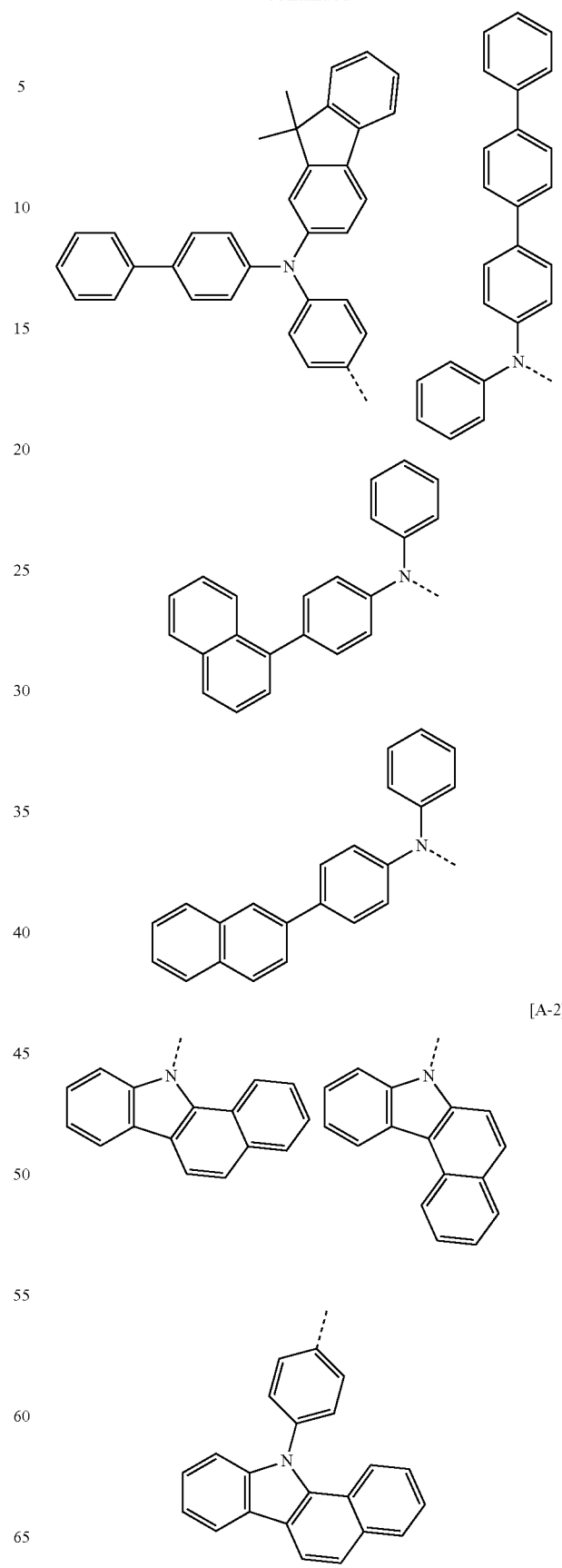
[A-2]

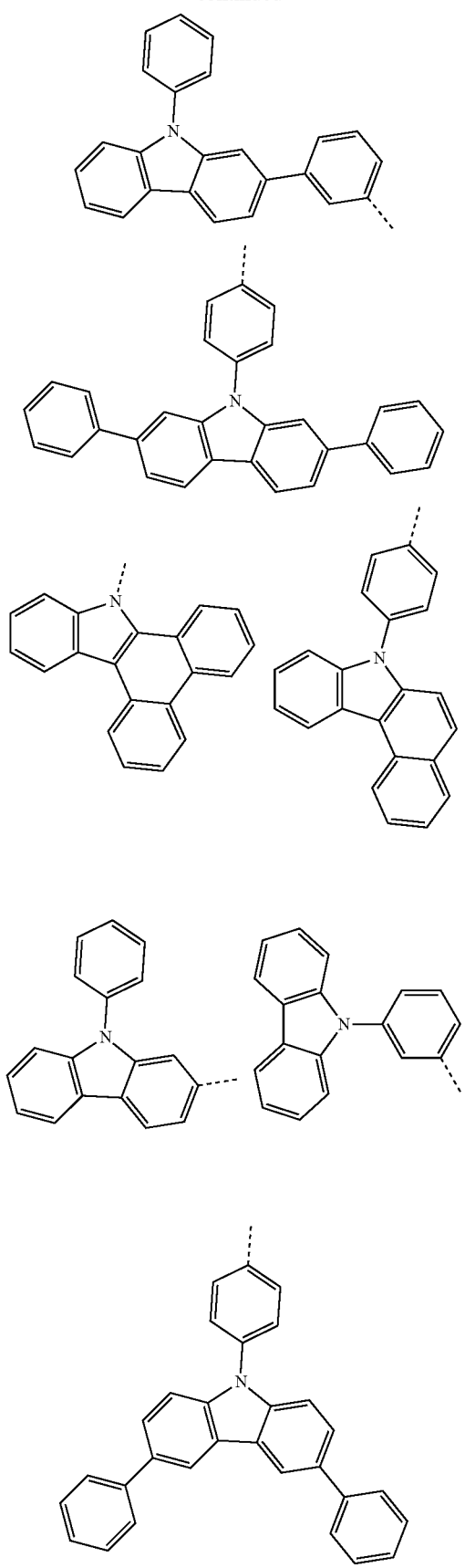
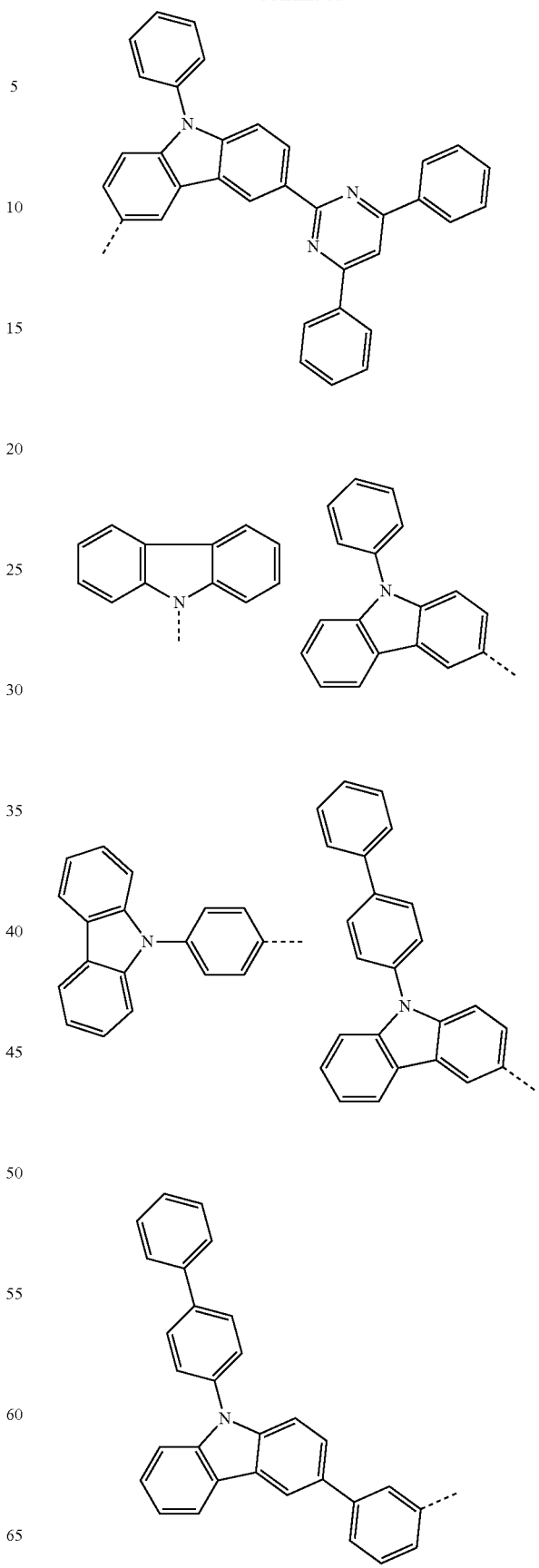

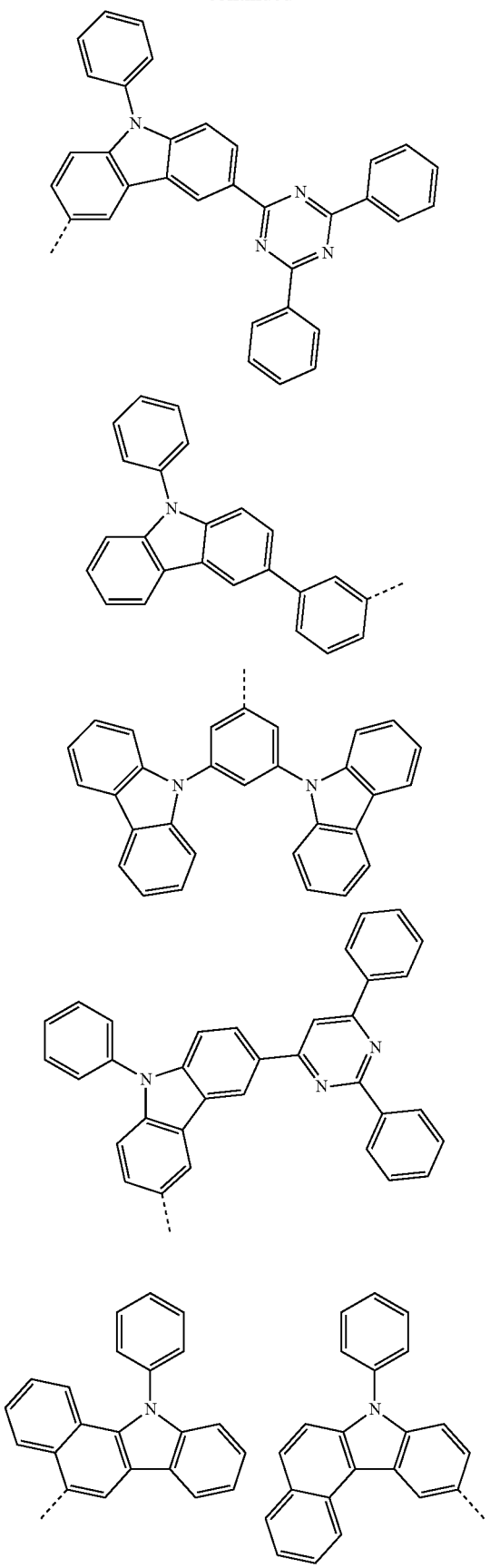
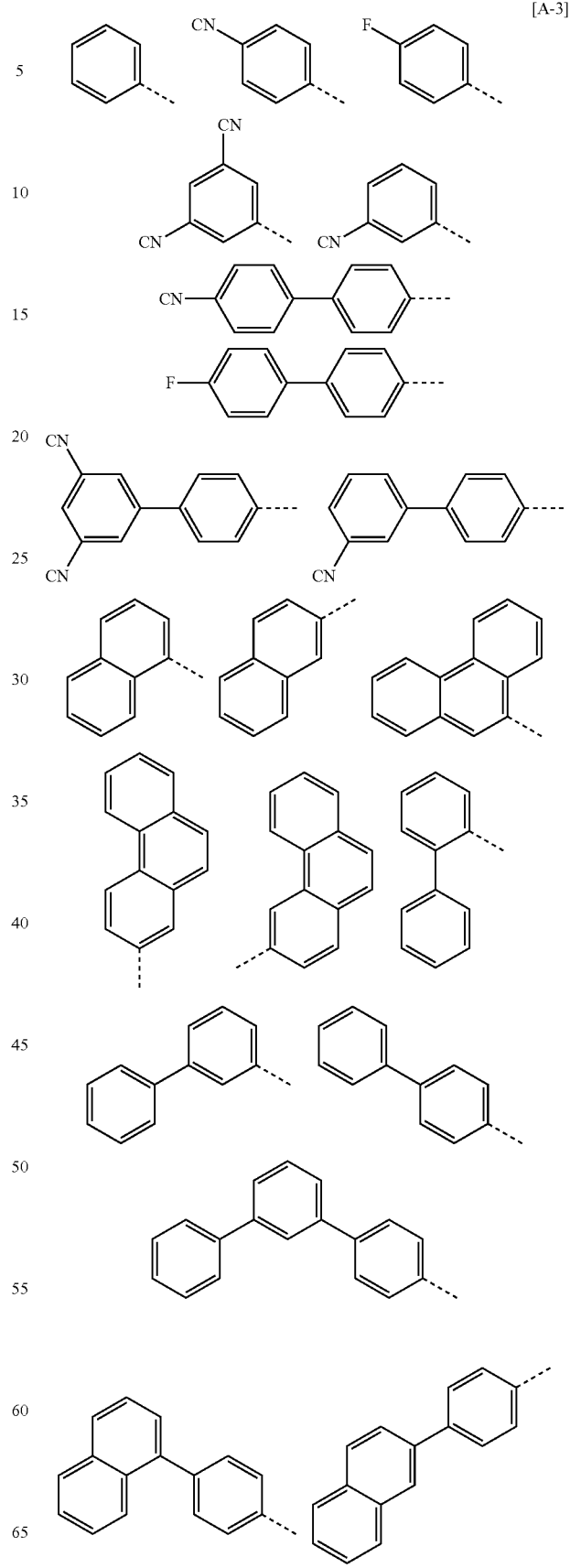

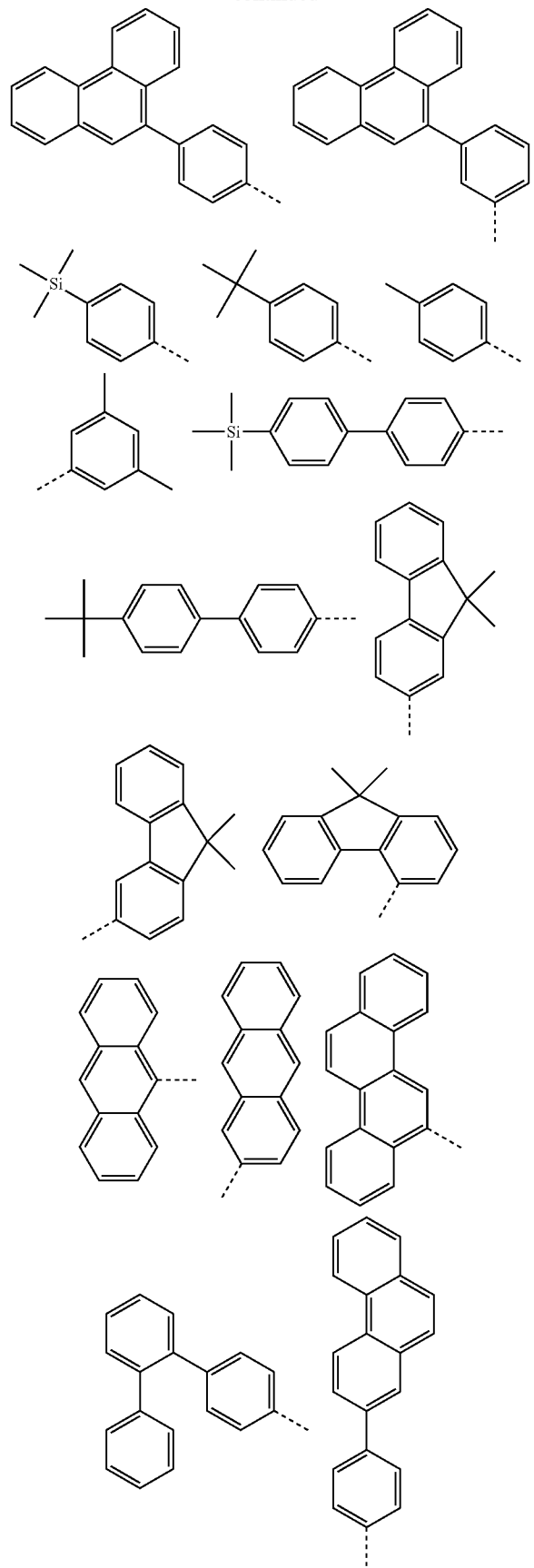
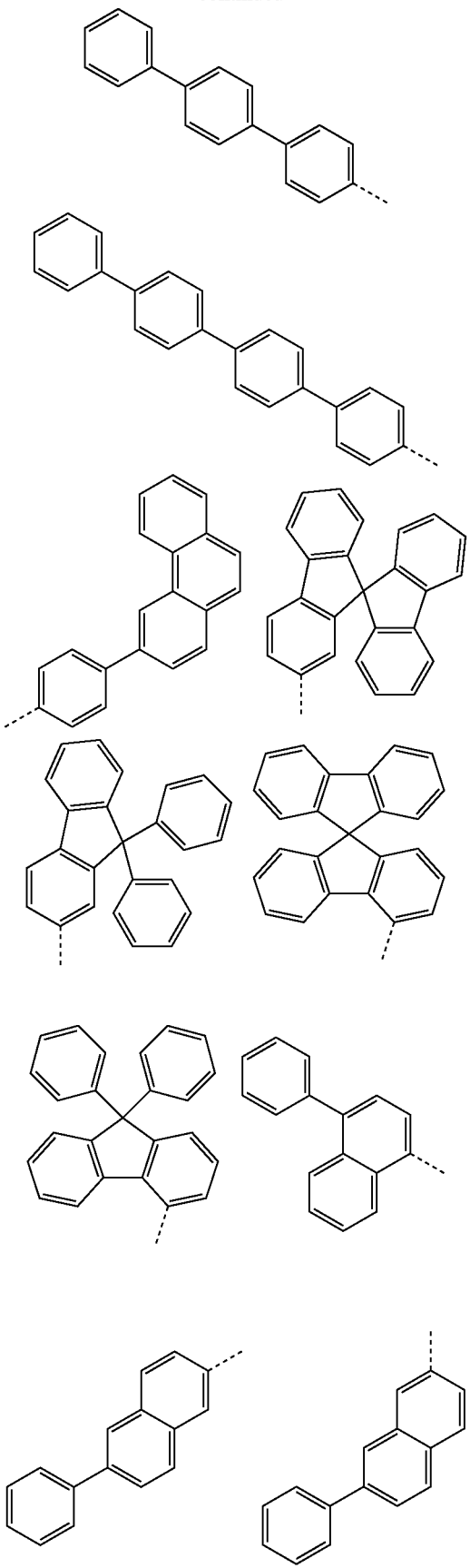

-continued
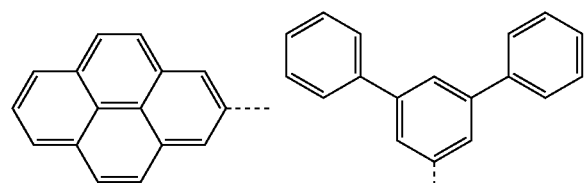
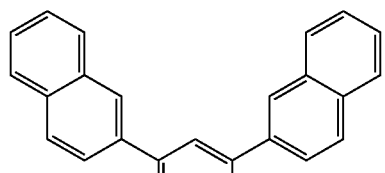
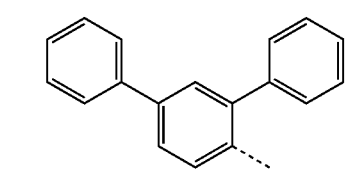
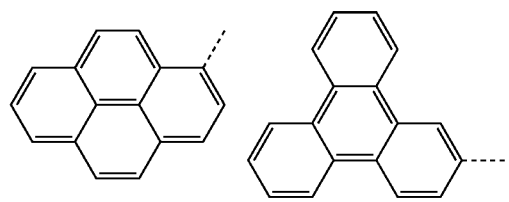
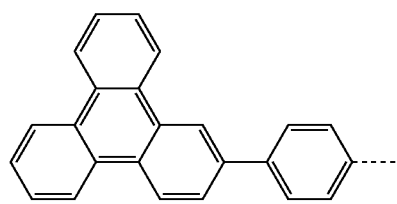
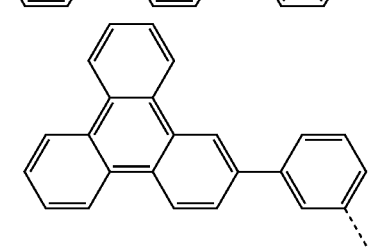
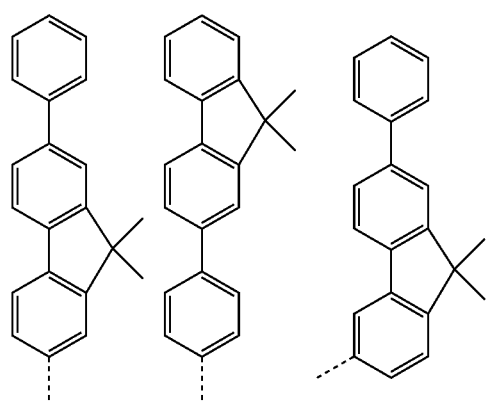
-continued
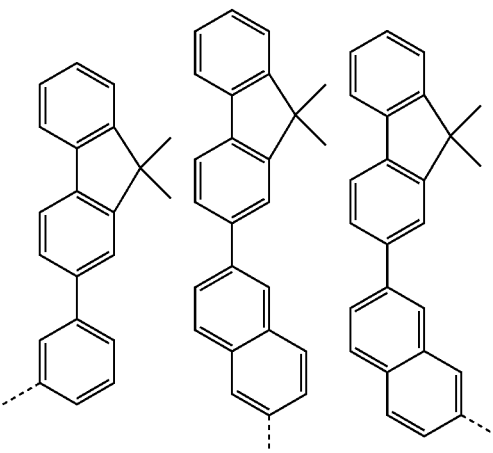
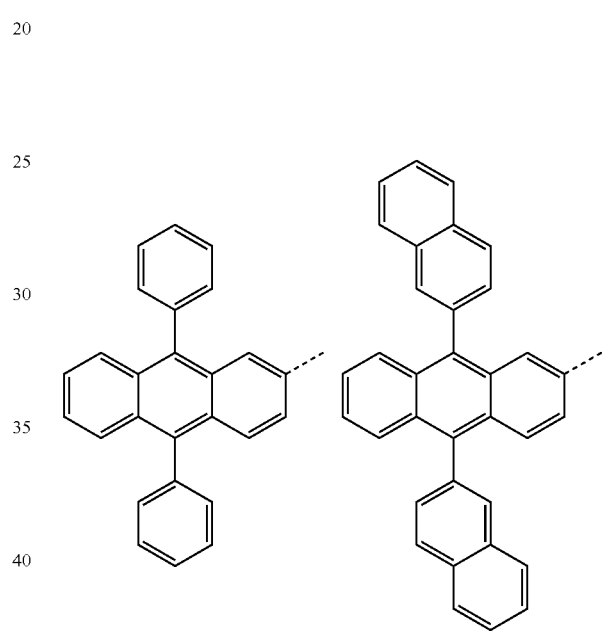
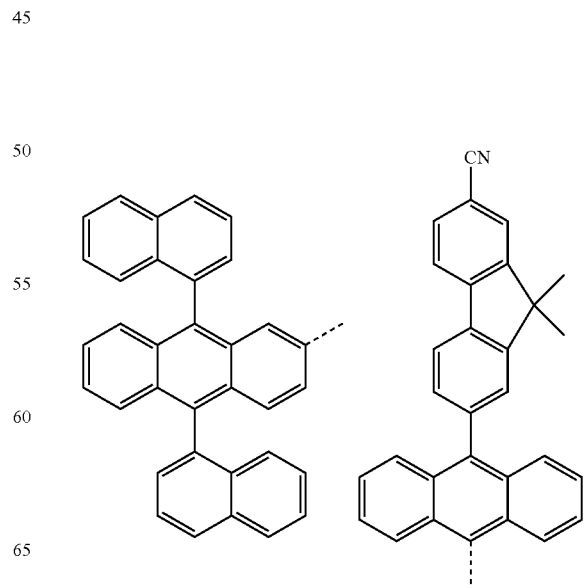

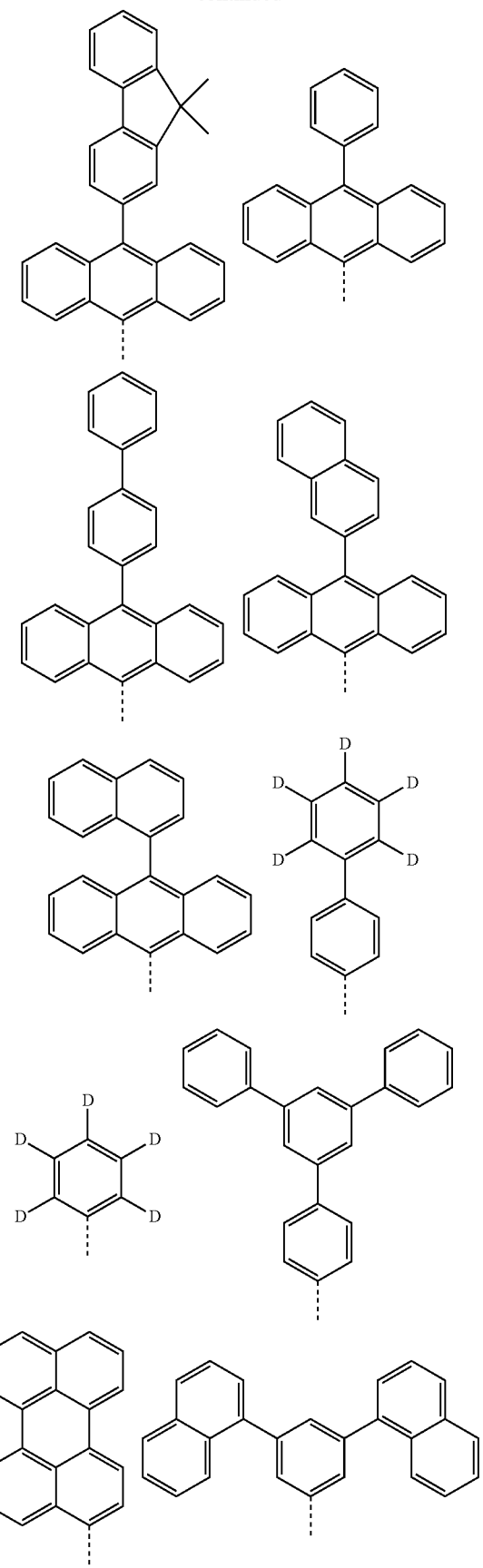
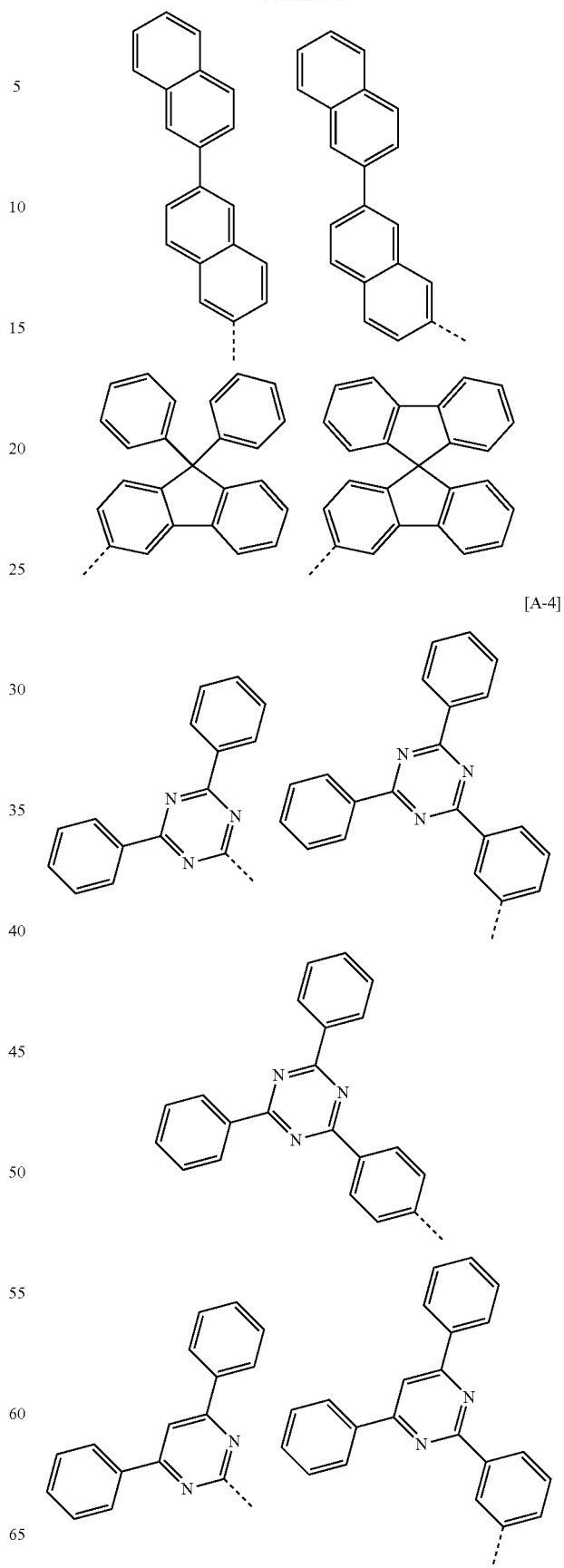
[A-4]

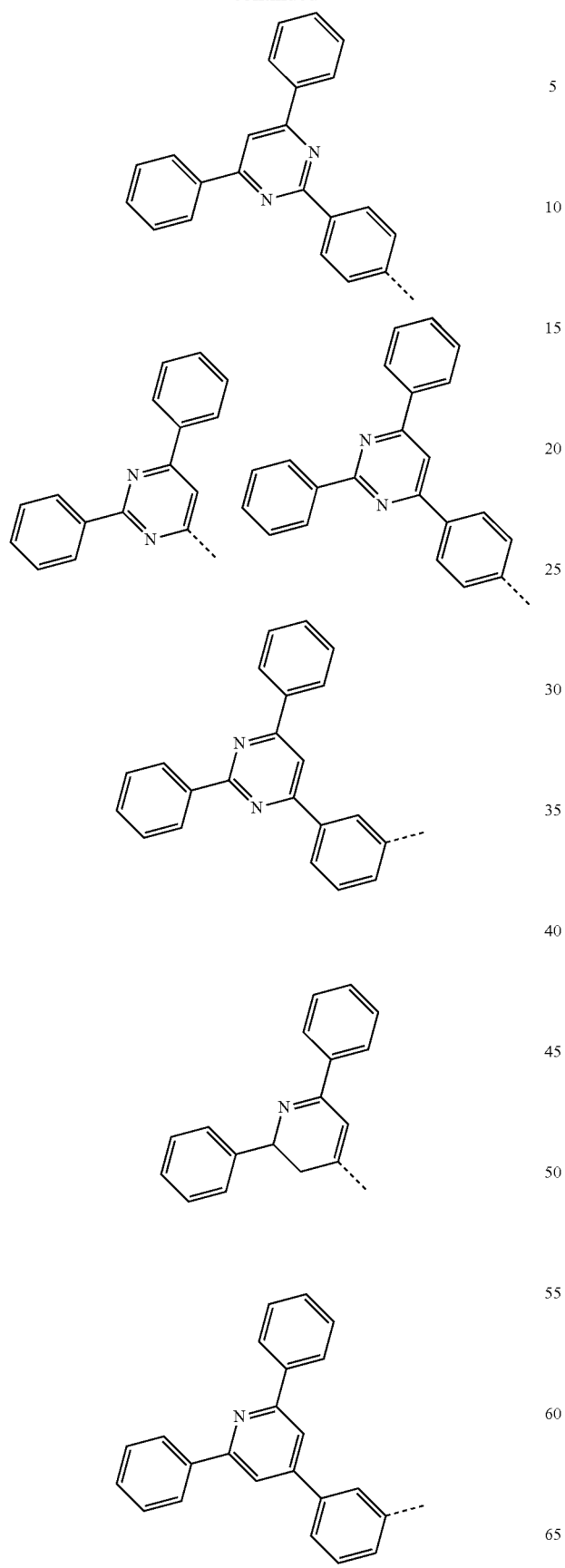
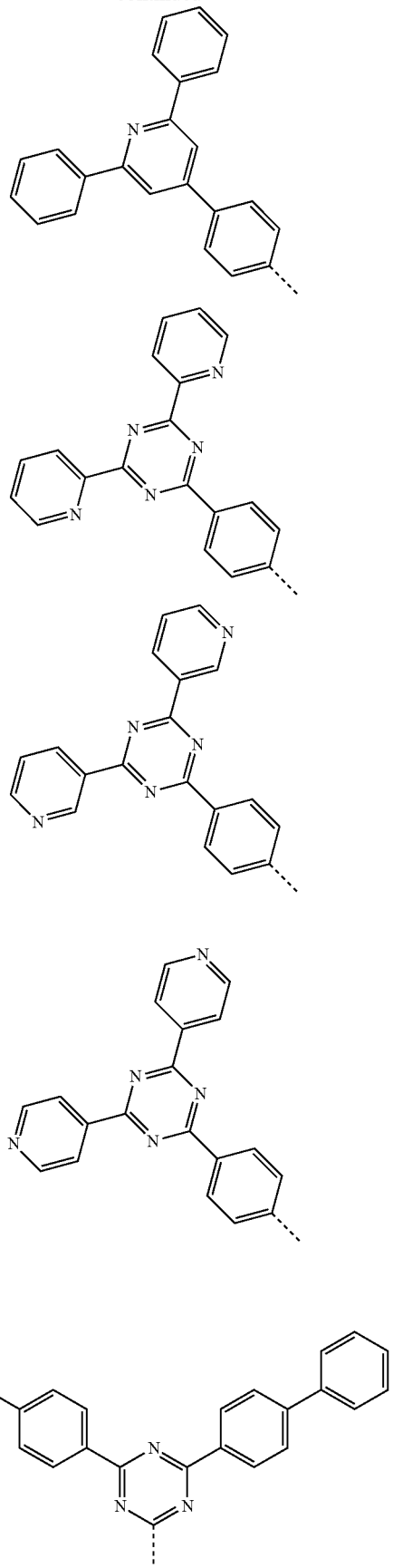

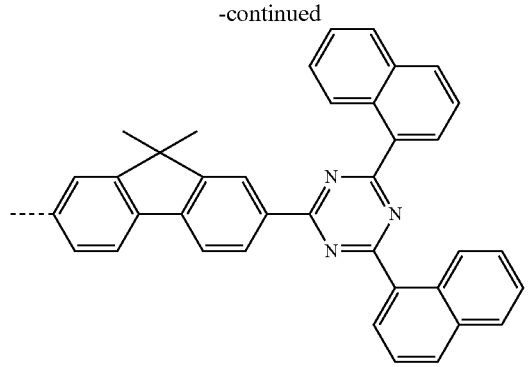
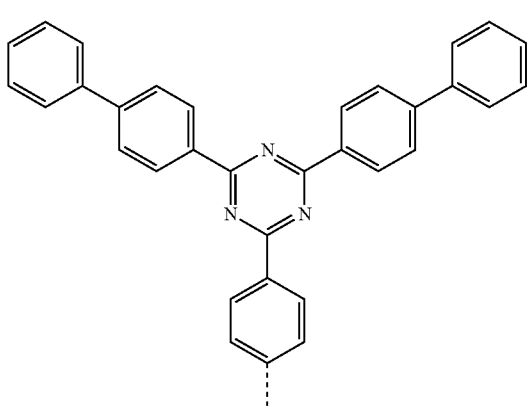
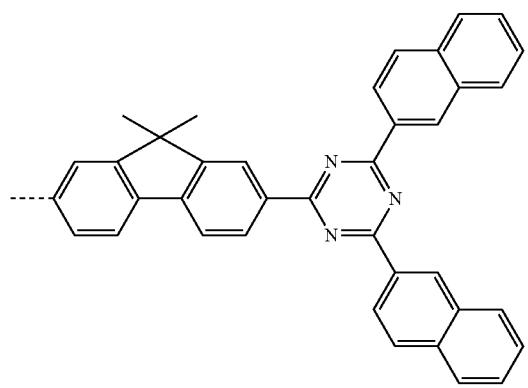
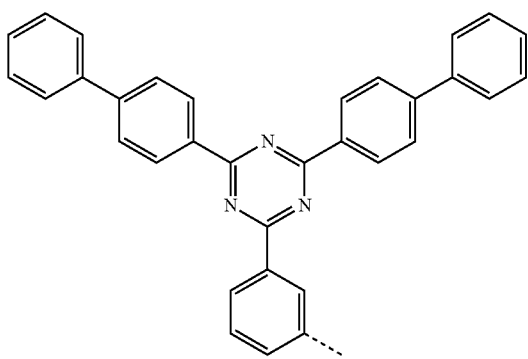

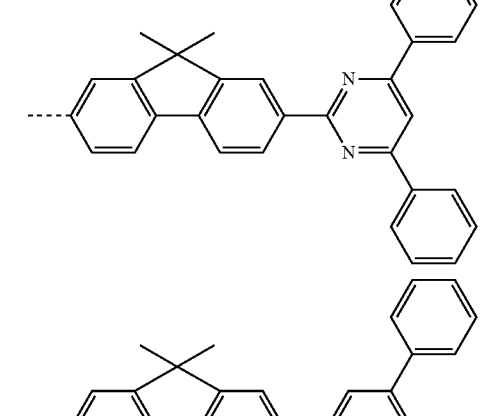
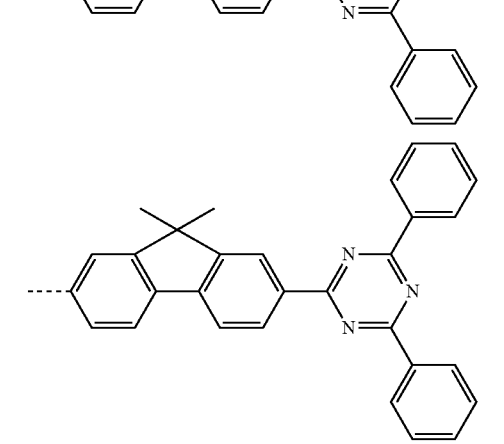
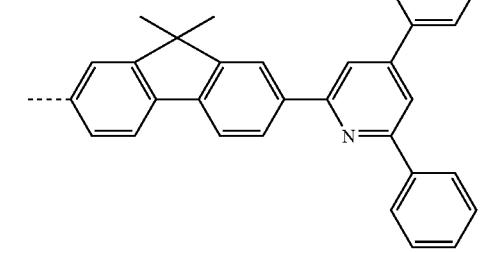

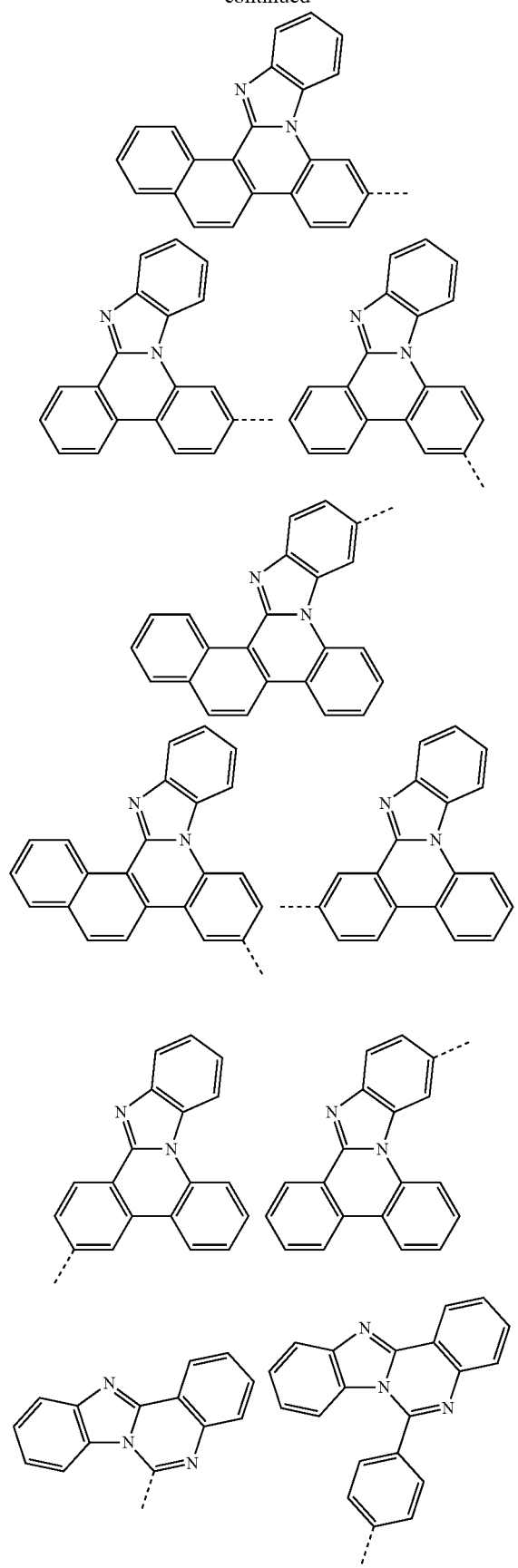
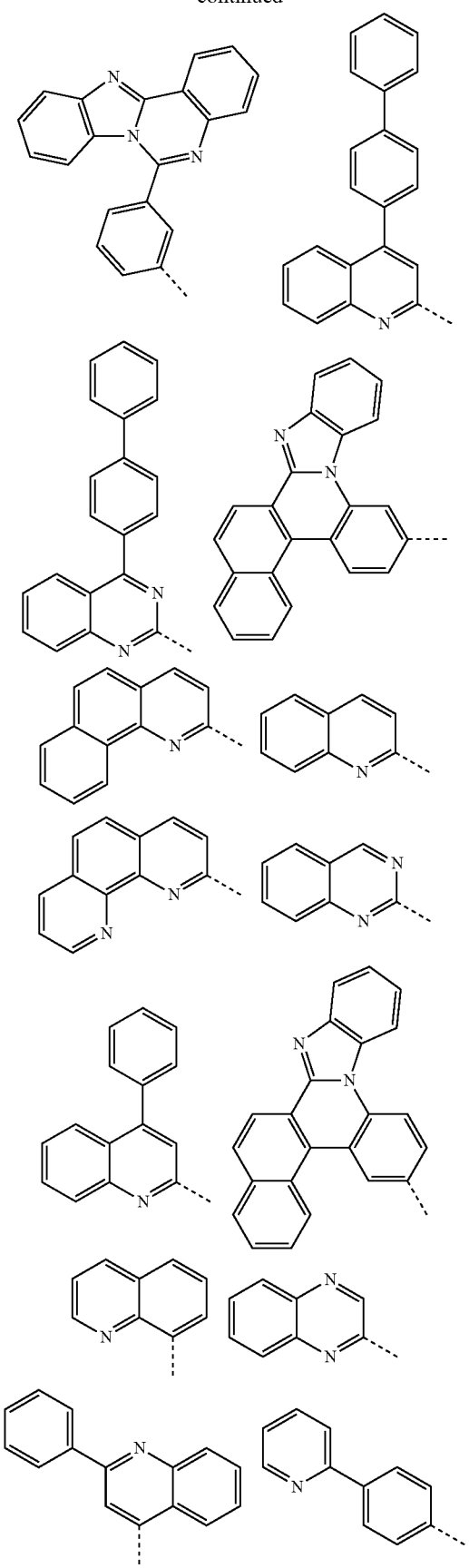

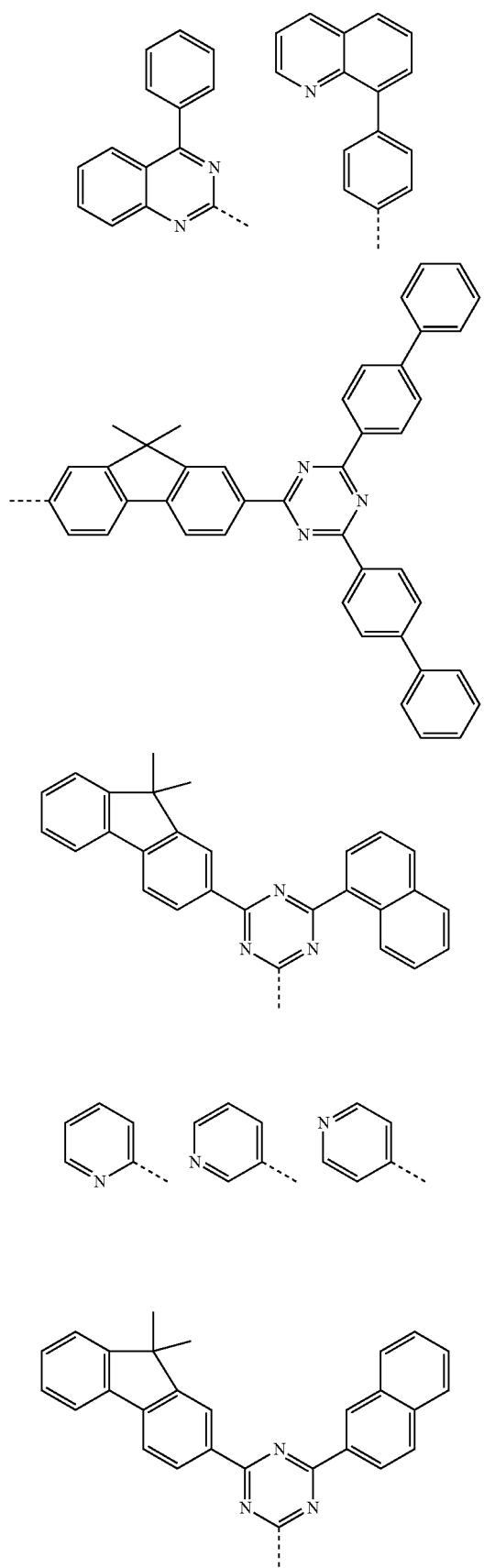
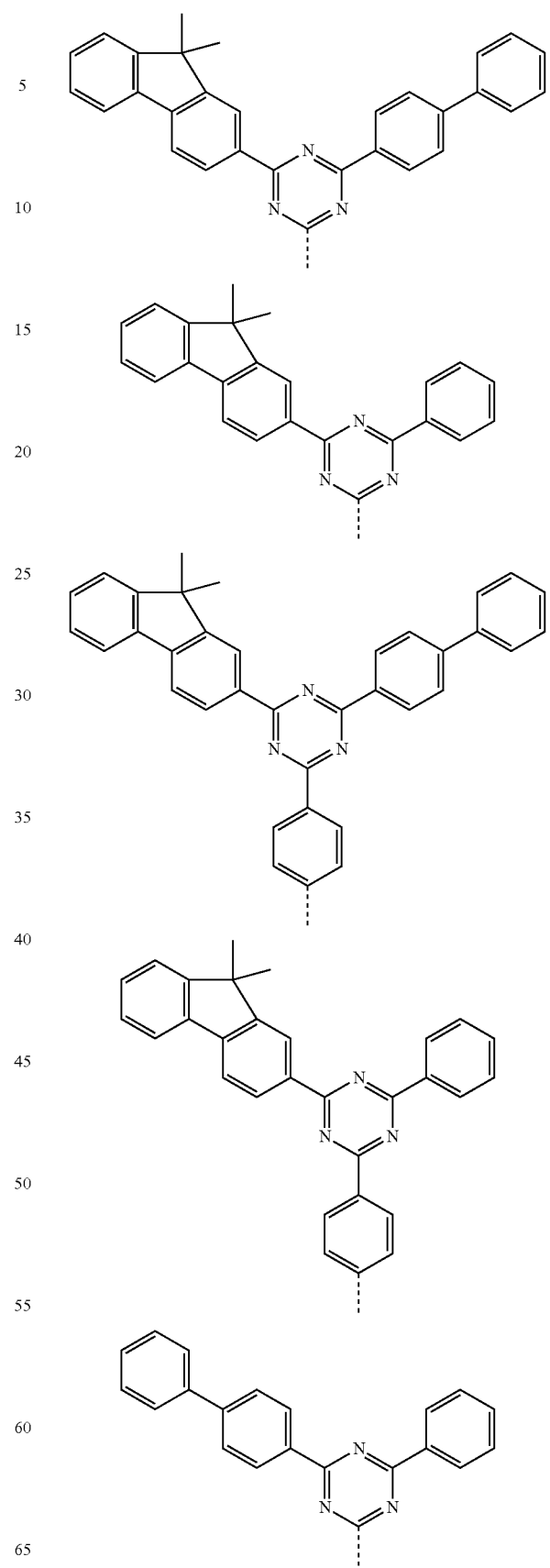

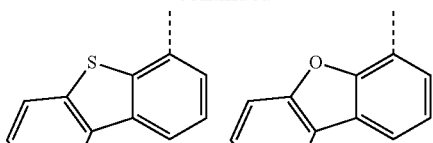
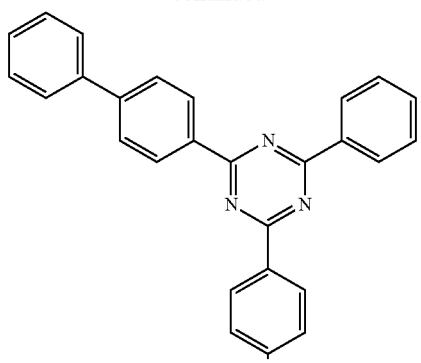
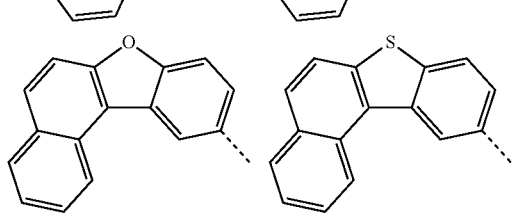
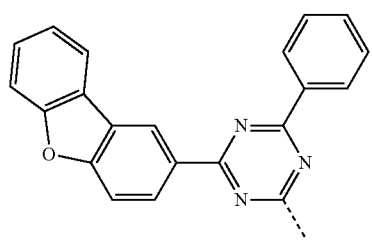
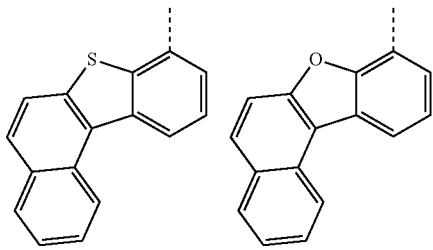
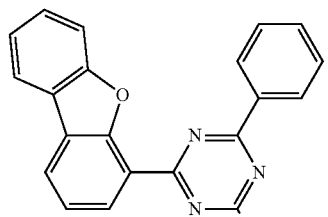
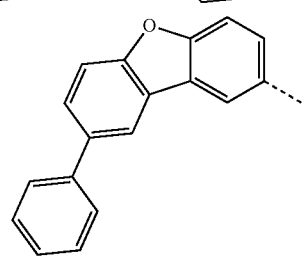
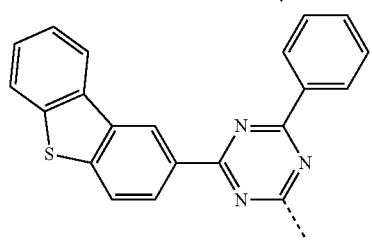
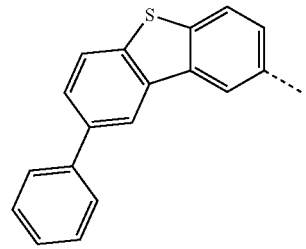
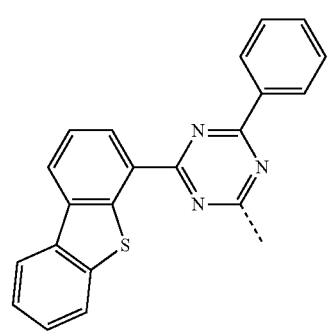
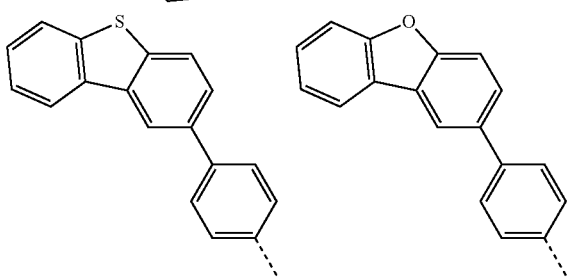
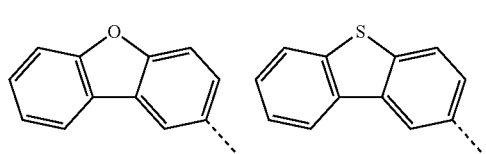
[A-5]
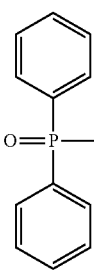
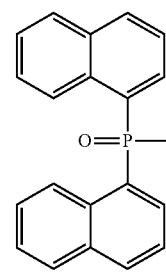

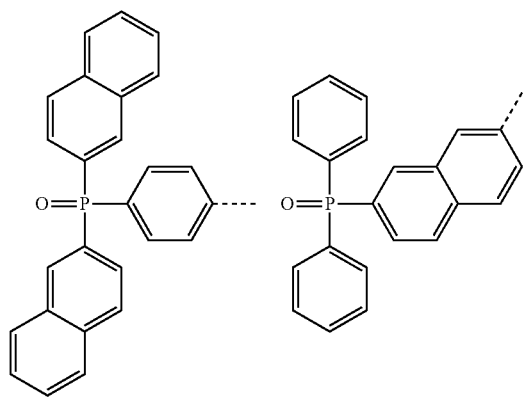
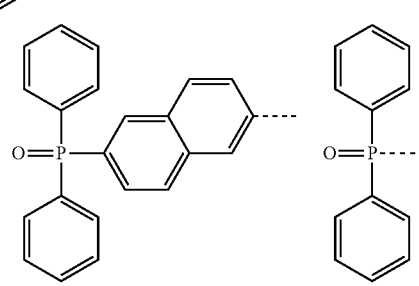
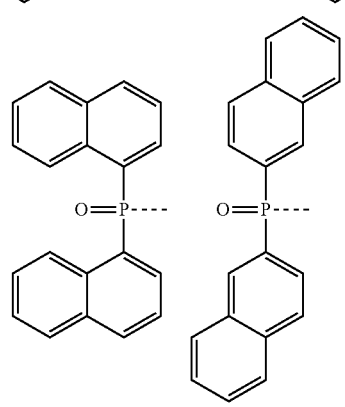
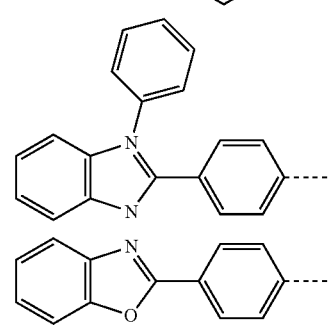
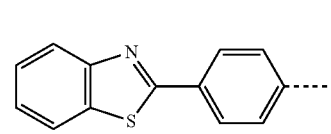
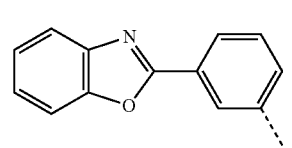
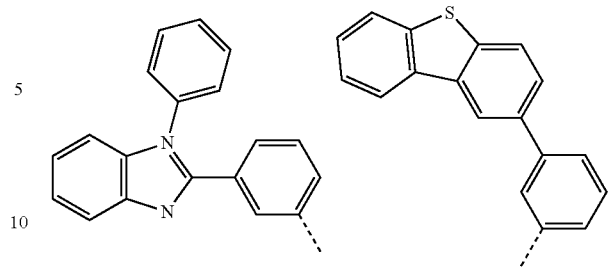
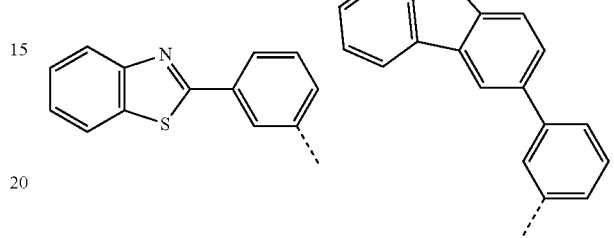
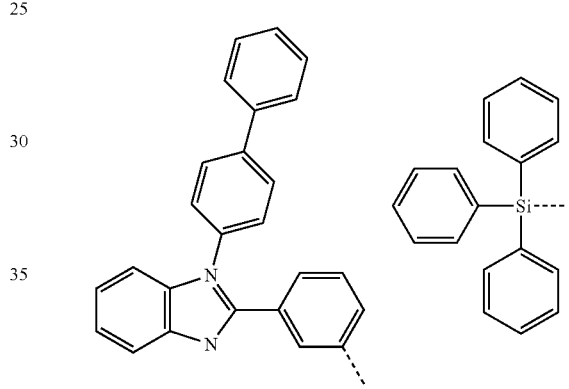
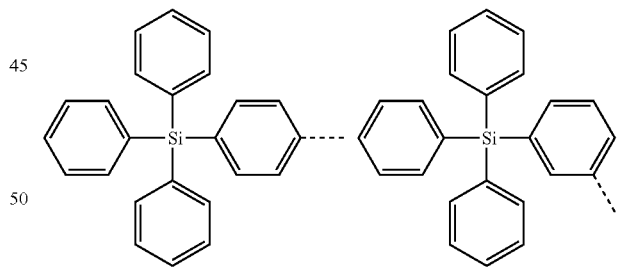
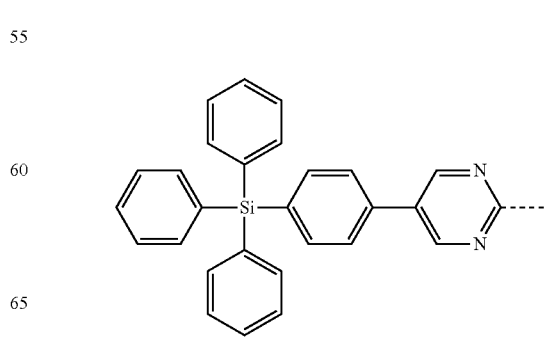

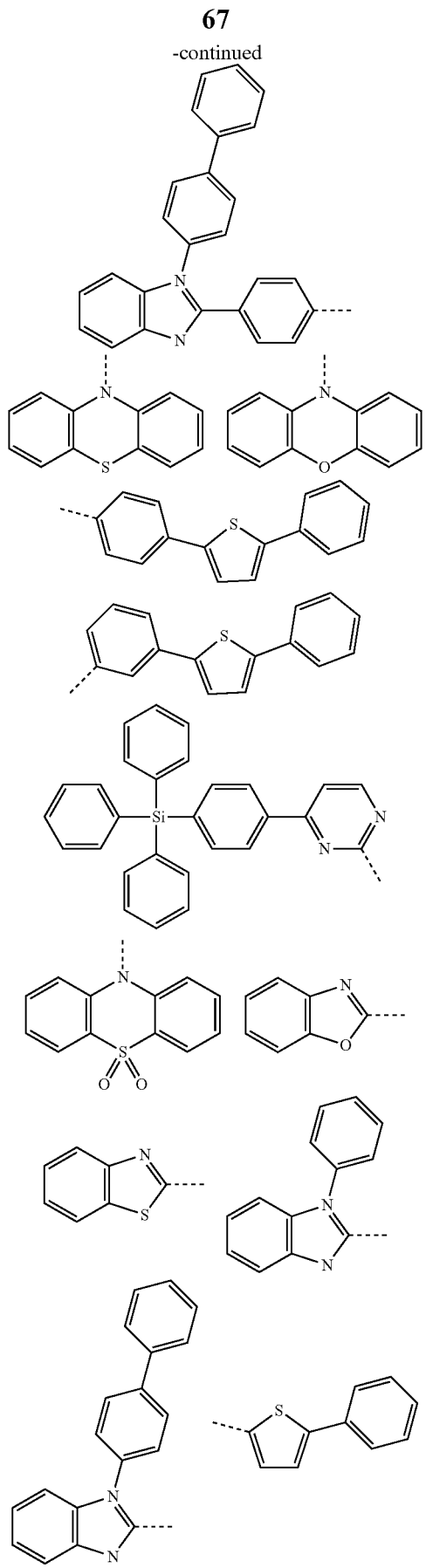

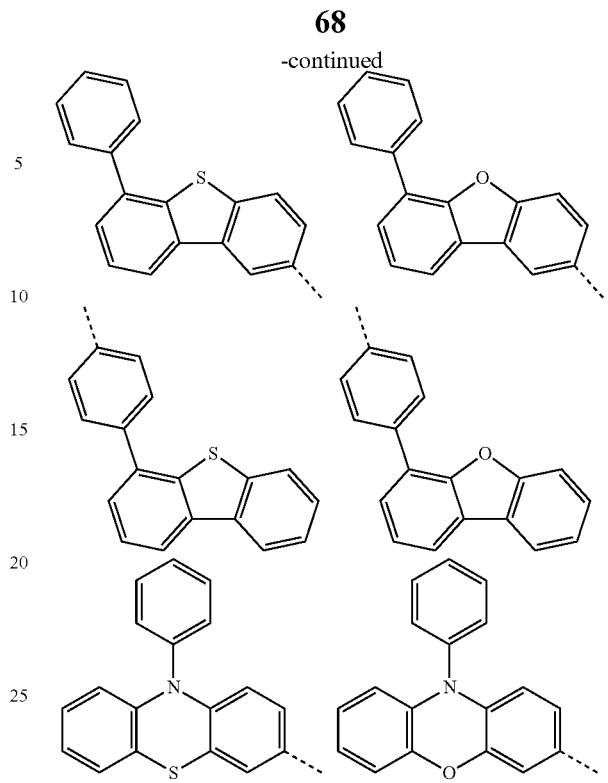

In the structural formulae, --- means a site bonding to Chemical Formula 1 through L1 or L2.

According to one embodiment of the present specification, in Chemical Formula 1, Ar1 is a substituted or unsubstituted amine group; a substituted or unsubstituted phosphine oxide group; a substituted or unsubstituted phenyl group; a substituted or unsubstituted biphenyl group; a substituted or unsubstituted terphenyl group; a substituted or unsubstituted quaterphenyl group; a substituted or unsubstituted multicyclic aryl group; or a substituted or unsubstituted monocyclic or multicyclic heteroaryl group.

According to one embodiment of the present specification, in Chemical Formula 1, Ar1 is an arylamine group unsubstituted or substituted with an alkyl group; a phosphine oxide group substituted with an aryl group; a phenyl group unsubstituted or substituted with a nitrile group; a biphenyl group; a multicyclic aryl group unsubstituted or substituted with an alkyl group; a monocyclic heteroaryl group unsubstituted or substituted with an aryl group; or a multicyclic heteroaryl group unsubstituted or substituted with an aryl group unsubstituted or substituted with an alkyl group.

According to one embodiment of the present specification, in Chemical Formula 1, Ar1 is a diphenylamine group; an N-phenylbiphenylamine group; a dibiphenylamine group; an N-phenylfluorenylamine group substituted with an alkyl group; a phosphine oxide group substituted with an aryl group; a phenyl group unsubstituted or substituted with a nitrile group; a biphenyl group; a naphthyl group; a triphenylenyl group; a fluorenyl group substituted with an alkyl group; a pyridyl group unsubstituted or substituted with an aryl group; a pyrimidyl group unsubstituted or substituted with an aryl group; a triazinyl group unsubstituted or substituted with an aryl group; a carbazolyl group unsubstituted or substituted with an aryl group unsubstituted or substituted with an alkyl group; a quinazolinyl group unsubstituted or substituted with an aryl group; a quinolinyl group unsubstituted or substituted with an aryl group; a benzimidazolyl group unsubstituted or substituted with an aryl group; a dibenzofuranyl group; a dibenzothiophene group; a benzoxazolyl group; or a benzothiazolyl group.

According to one embodiment of the present specification, in Chemical Formula 1, Ar1 is a diphenylamine group; an N-phenylbiphenylamine group; a dibiphenylamine group; an N-phenylfluorenylamine group substituted with a methyl group; a phosphine oxide group substituted with a phenyl group; a phenyl group unsubstituted or substituted with a nitrile group; a biphenyl group; a naphthyl group; a triphenylenyl group; a fluorenyl group substituted with a methyl group; a pyridyl group unsubstituted or substituted with a phenyl group; a pyrimidyl group unsubstituted or substituted with a phenyl group; a triazinyl group unsubstituted or substituted with a phenyl group or a biphenyl group; a carbazolyl group unsubstituted or substituted with a methyl group-substituted fluorenyl group, a phenyl group, a naphthyl group or a biphenyl group; a quinazolinyl group unsubstituted or substituted with a phenyl group, a naphthyl group or a biphenyl group; a quinolinyl group unsubstituted or substituted with a phenyl group, a naphthyl group or a biphenyl group; a benzimidazolyl group unsubstituted or substituted with a phenyl group; a dibenzofuranyl group; a dibenzothiophene group; a benzoxazolyl group; or a benzothiazolyl group.

According to one embodiment of the present specification, in Chemical Formula 1, Ar2 is a substituted or unsubstituted amine group; a substituted or unsubstituted phosphine oxide group; a substituted or unsubstituted monocyclic or multicyclic aryl group; or a substituted or unsubstituted monocyclic or multicyclic heteroaryl group.

According to one embodiment of the present specification, in Chemical Formula 1, Ar2 is an arylamine group unsubstituted or substituted with an alkyl group; a phosphine oxide group substituted with an aryl group; a monocyclic or multicyclic aryl group unsubstituted or substituted with a nitrile group or an alkyl group; a monocyclic heteroaryl group unsubstituted or substituted with an aryl group; or a multicyclic heteroaryl group unsubstituted or substituted with an aryl group unsubstituted or substituted with an alkyl group.

According to one embodiment of the present specification, in Chemical Formula 1, Ar2 is an arylamine group unsubstituted or substituted with an alkyl group; a phosphine oxide group substituted with an aryl group; a phenyl group unsubstituted or substituted with a nitrile group; a biphenyl group; a multicyclic aryl group unsubstituted or substituted with an alkyl group; a monocyclic heteroaryl group unsubstituted or substituted with an aryl group; or a multicyclic heteroaryl group unsubstituted or substituted with an aryl group unsubstituted or substituted with an alkyl group.

According to one embodiment of the present specification, in Chemical Formula 1, Ar2 is a diphenylamine group; an N-phenylbiphenylamine group; a dibiphenylamine group; an N-phenylfluorenylamine group substituted with an alkyl group; a phosphine oxide group substituted with an aryl group; a phenyl group unsubstituted or substituted with a nitrile group; a biphenyl group; a naphthyl group; a triphenylenyl group; a fluorenyl group substituted with an alkyl group; a pyridyl group unsubstituted or substituted with an aryl group; a pyrimidyl group unsubstituted or substituted with an aryl group; a triazinyl group unsubstituted or substituted with an aryl group; a carbazolyl group unsubstituted or substituted with an aryl group unsubstituted or substituted with an alkyl group; a quinazolinyl group unsubstituted or substituted with an aryl group; a quinolinyl group unsubstituted or substituted with an aryl group; a benzimidazolyl group unsubstituted or substituted with an aryl group; a dibenzofuranyl group; a dibenzothiophene group; a benzoxazolyl group; or a benzothiazolyl group.

According to one embodiment of the present specification, in Chemical Formula 1, Ar2 is a diphenylamine group; an N-phenylbiphenylamine group; a dibiphenylamine group; an N-phenylfluorenylamine group substituted with a methyl group; a phosphine oxide group substituted with a phenyl group; a phenyl group unsubstituted or substituted with a nitrile group; a biphenyl group; a naphthyl group; a triphenylenyl group; a fluorenyl group substituted with a methyl group; a pyridyl group unsubstituted or substituted with a phenyl group; a pyrimidyl group unsubstituted or substituted with a phenyl group; a triazinyl group unsubstituted or substituted with a phenyl group or a biphenyl group; a carbazolyl group unsubstituted or substituted with a methyl group-substituted fluorenyl group, a phenyl group, a naphthyl group or a biphenyl group; a quinazolinyl group unsubstituted or substituted with a phenyl group, a naphthyl group or a biphenyl group; a quinolinyl group unsubstituted or substituted with a phenyl group, a naphthyl group or a biphenyl group; a benzimidazolyl group unsubstituted or substituted with a phenyl group; a dibenzofuranyl group; a dibenzothiophene group; a benzoxazolyl group; or a benzothiazolyl group.

According to one embodiment of the present specification, Chemical Formula 1 is selected from among the following compounds.

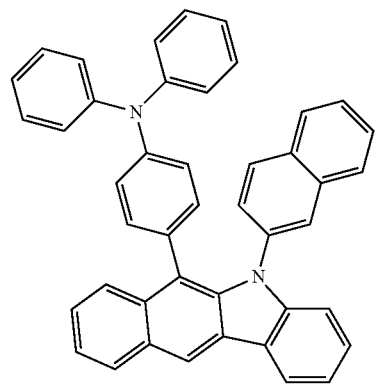

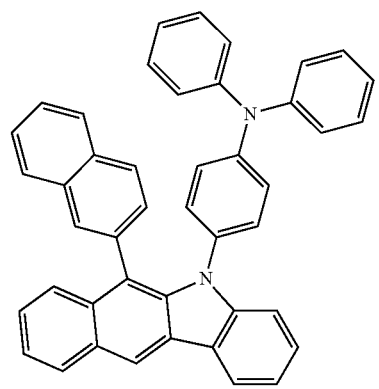

71
-continued
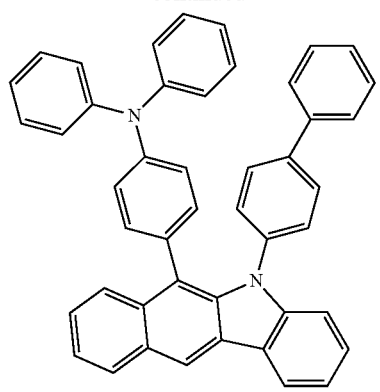
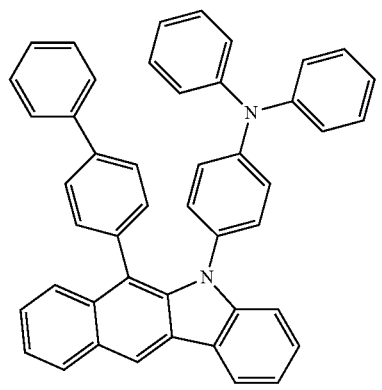
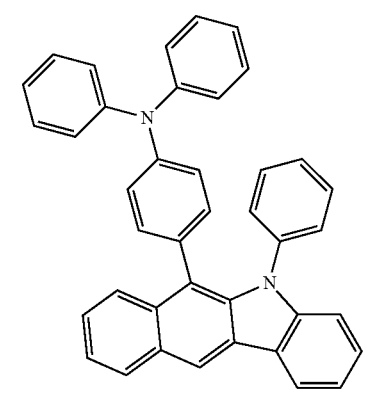
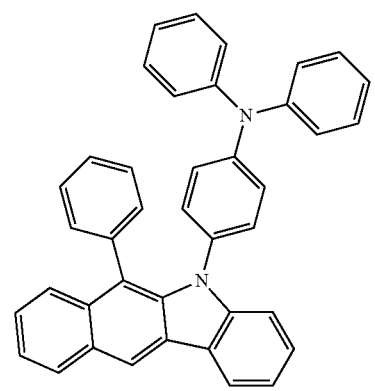
72
-continued
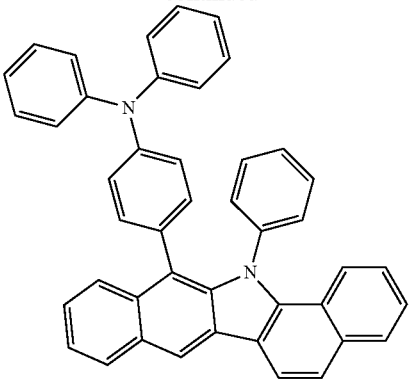
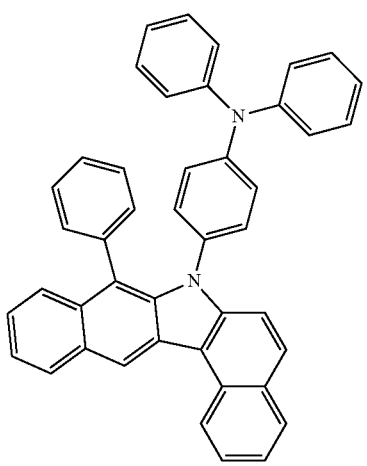
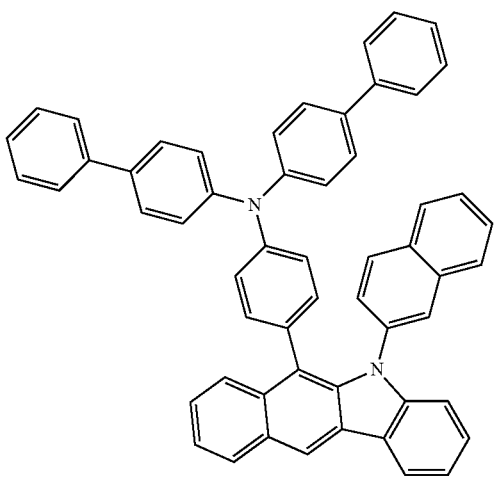

73
-continued
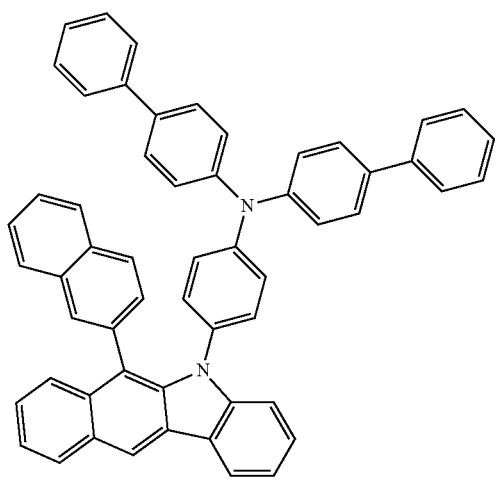
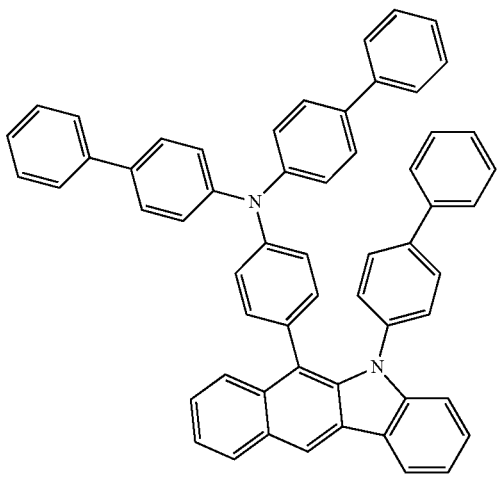
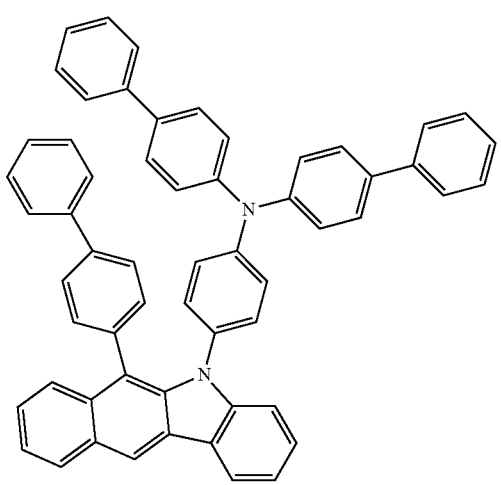
74
-continued
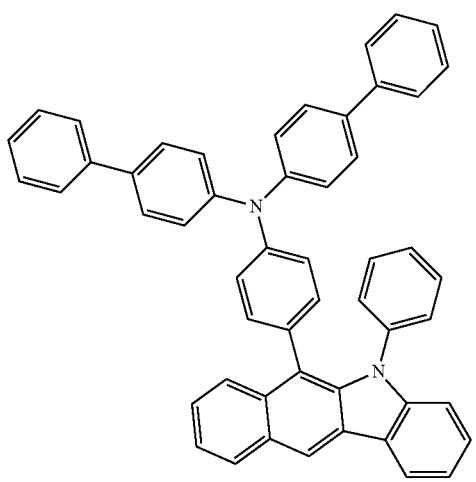
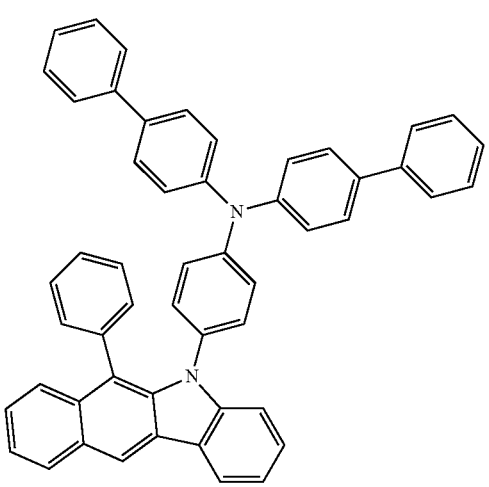
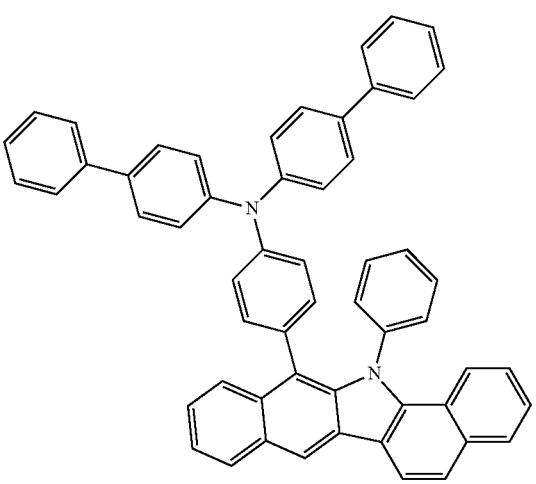

75
-continued
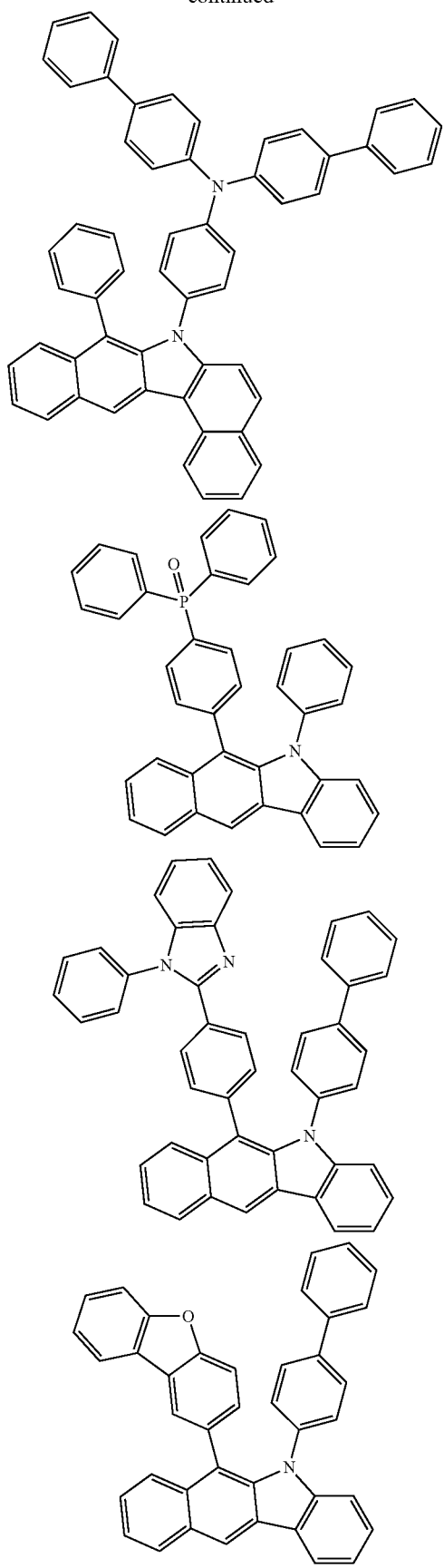
76
-continued
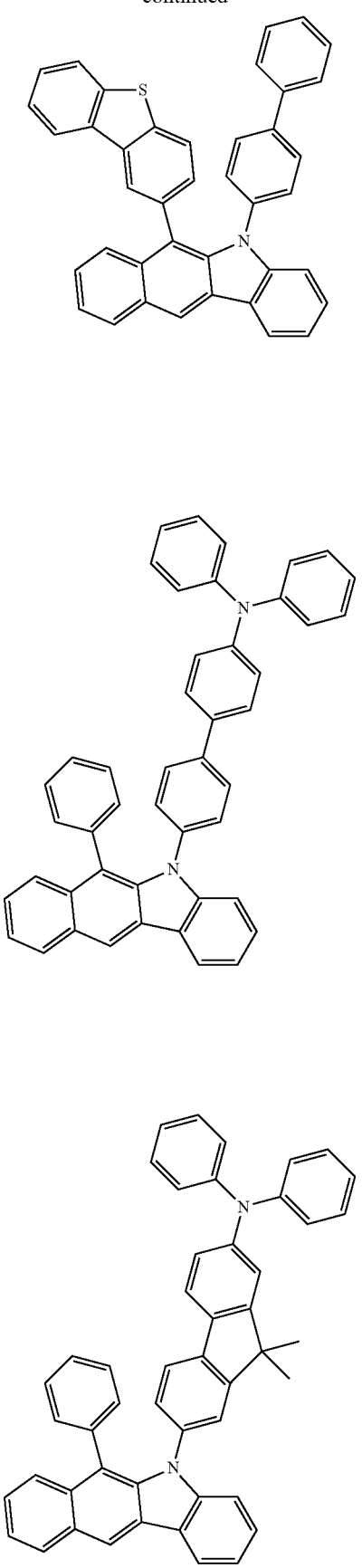

77
-continued
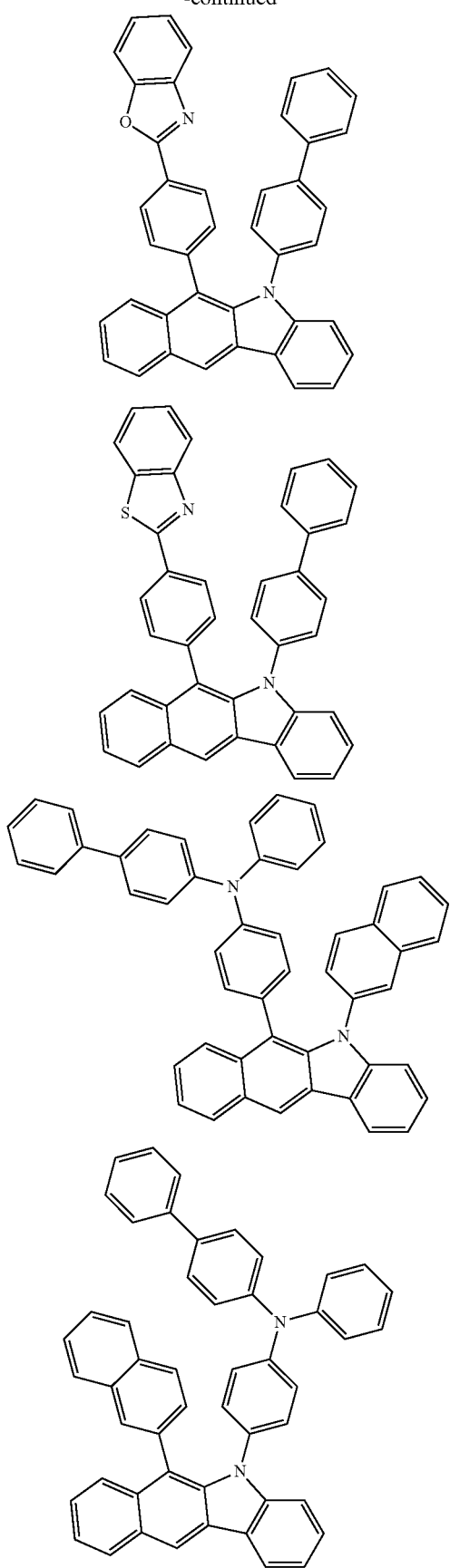
78
-continued
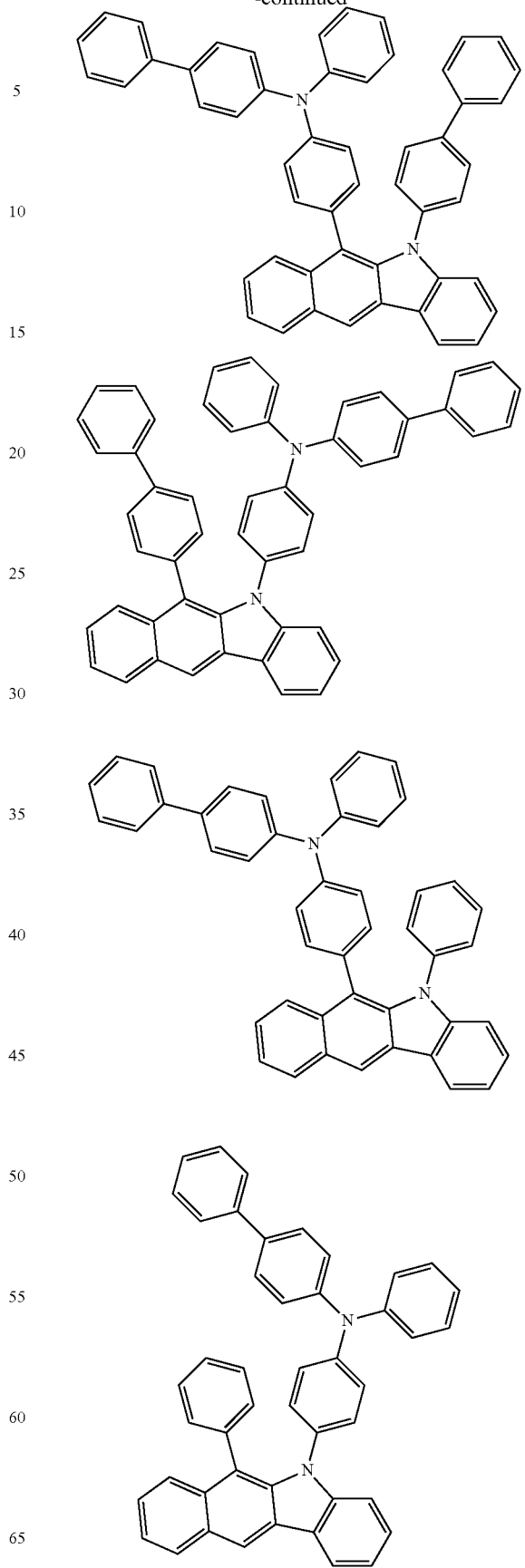

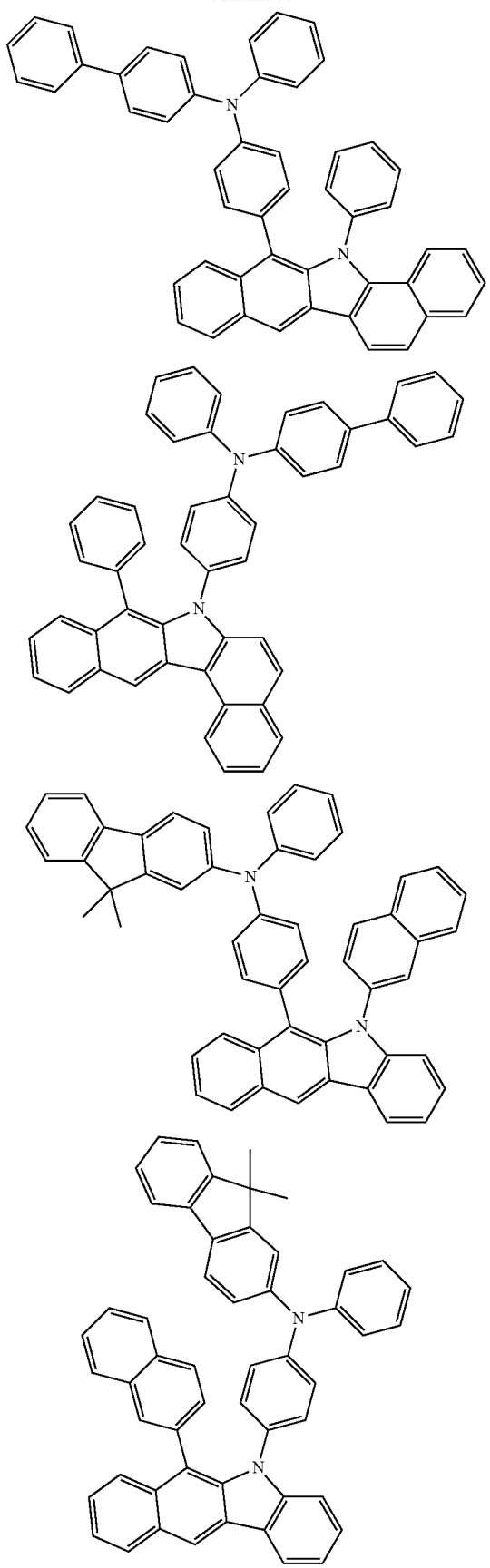
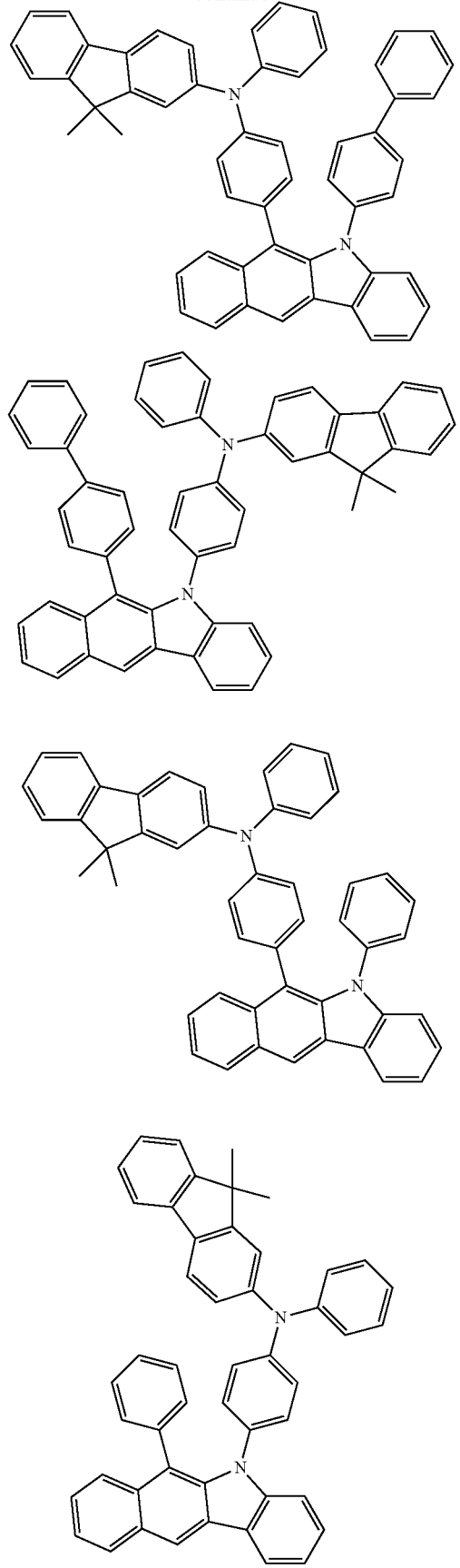

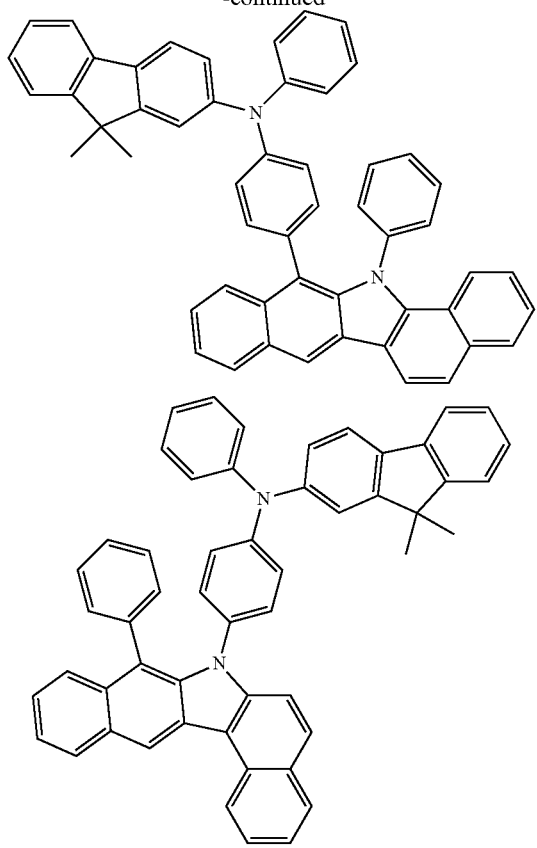
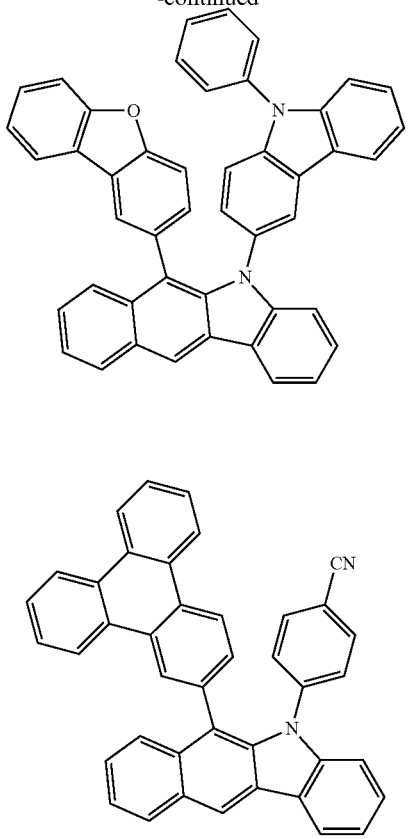
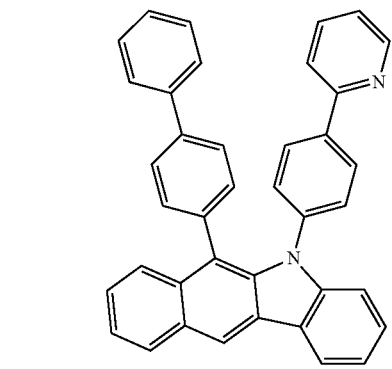
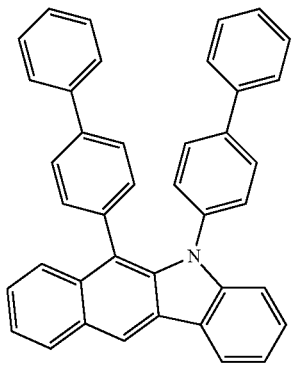
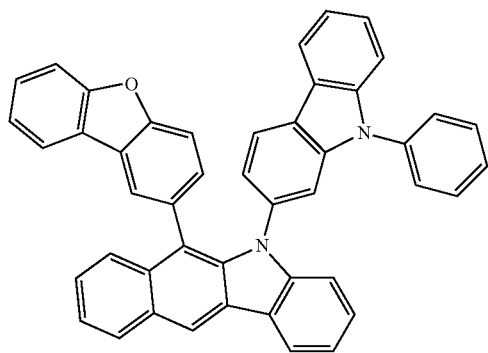
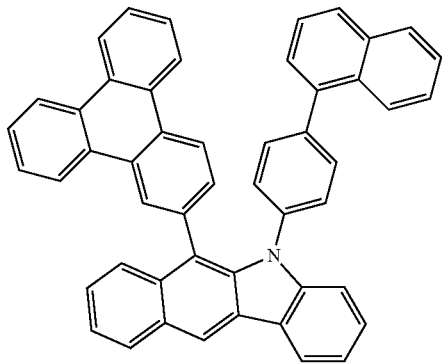

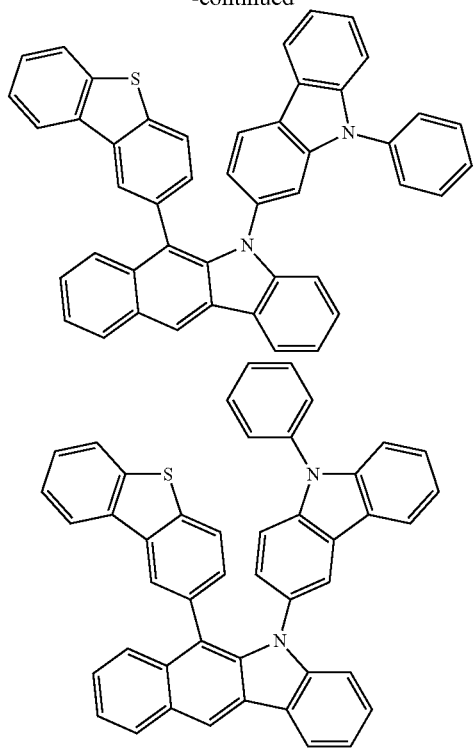
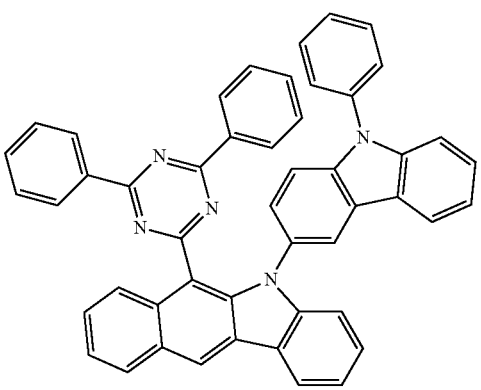
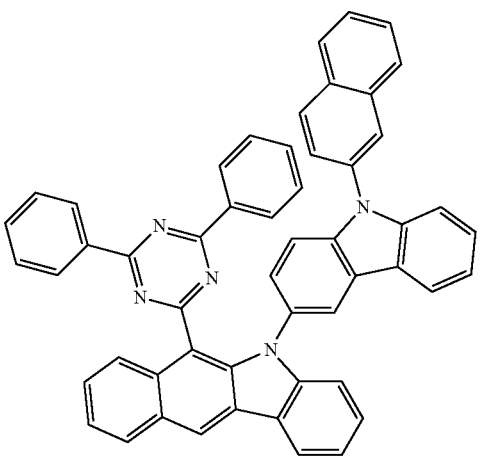
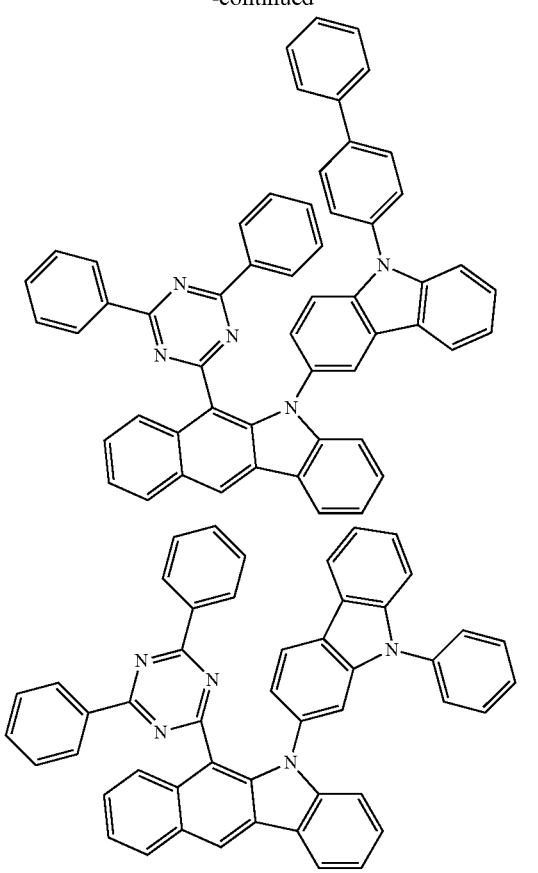
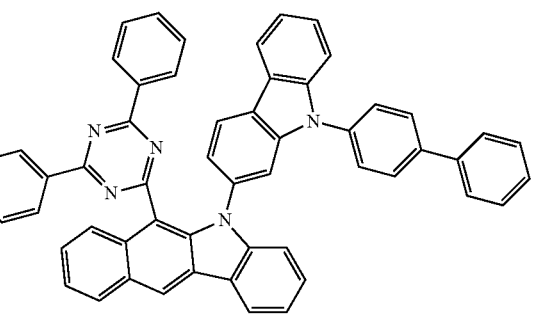
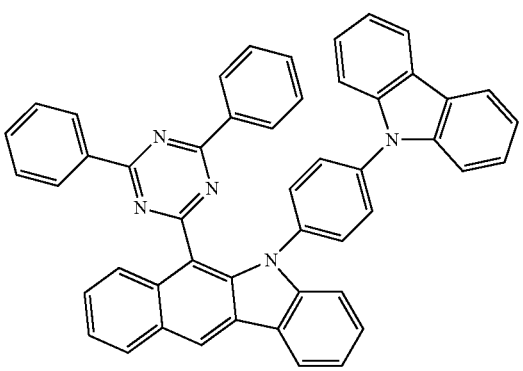

85
-continued
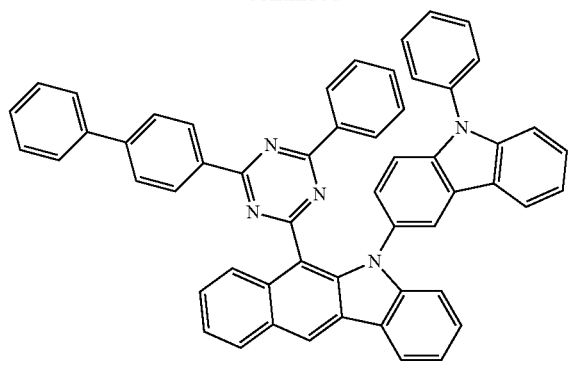
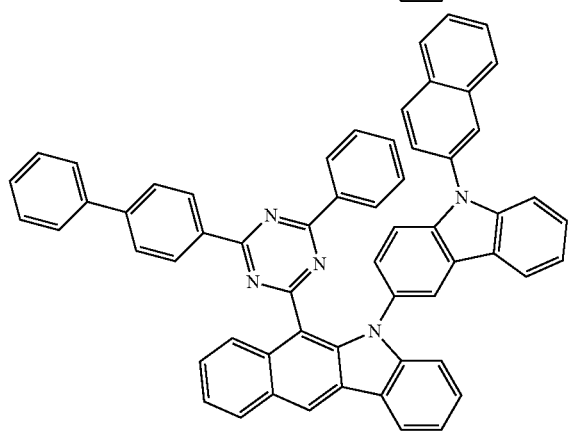
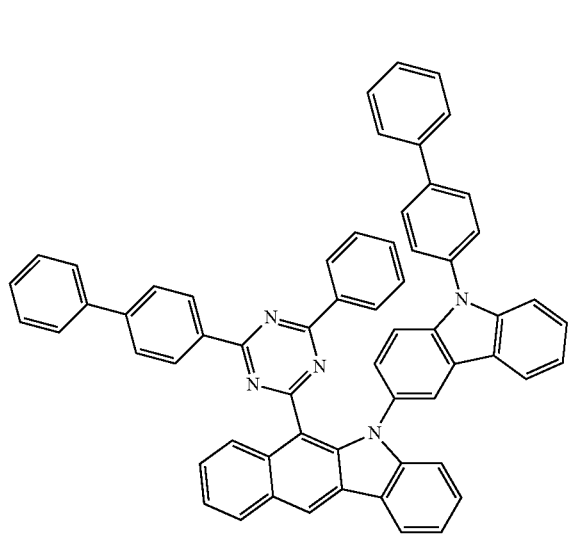
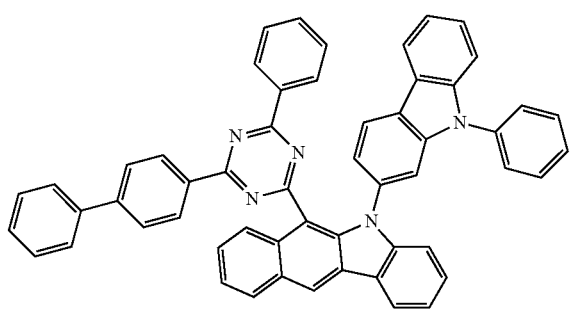
86
-continued
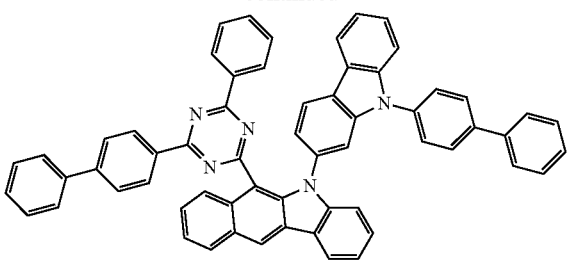
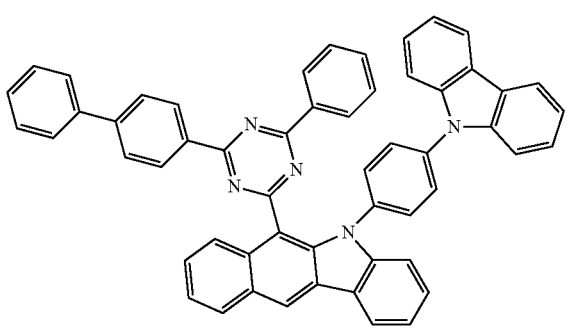
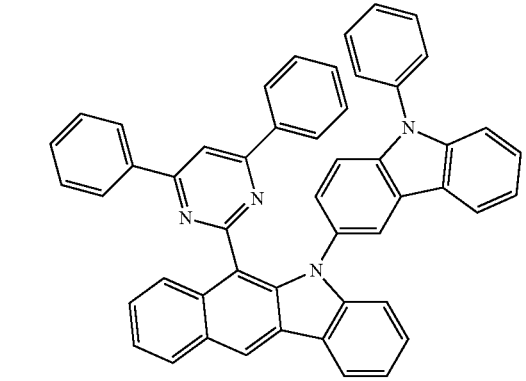
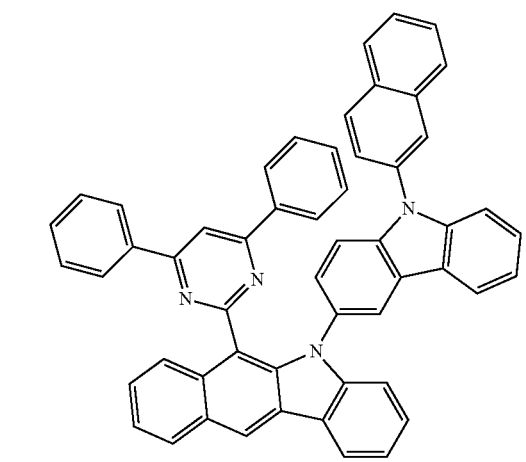

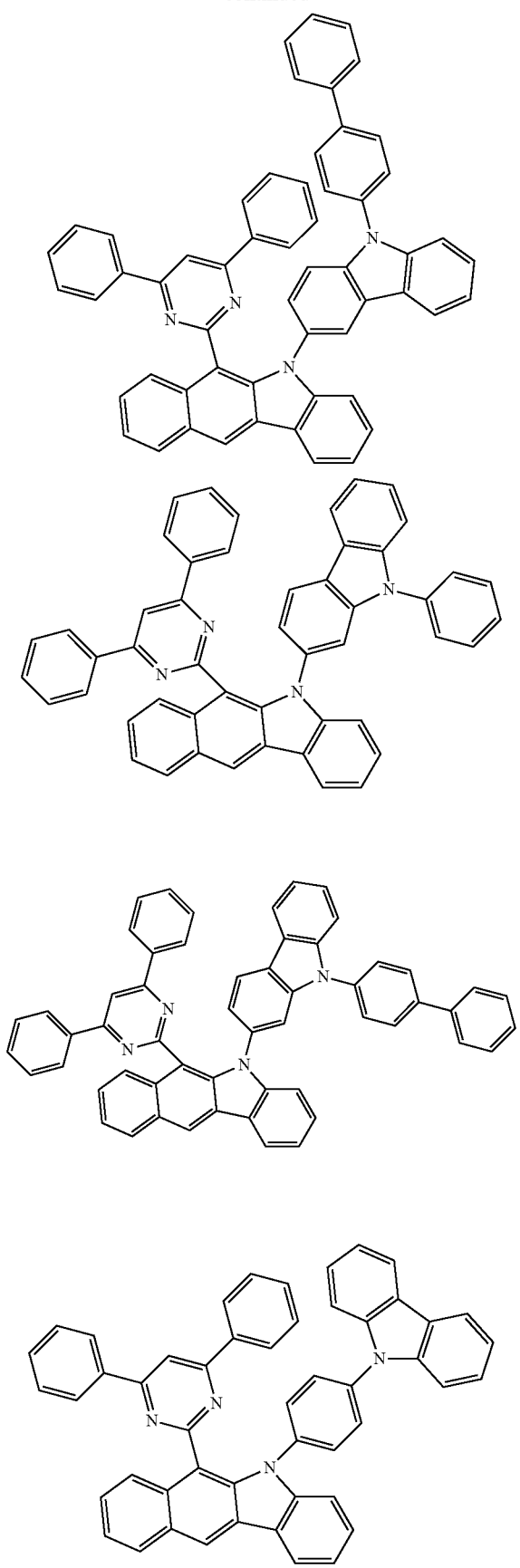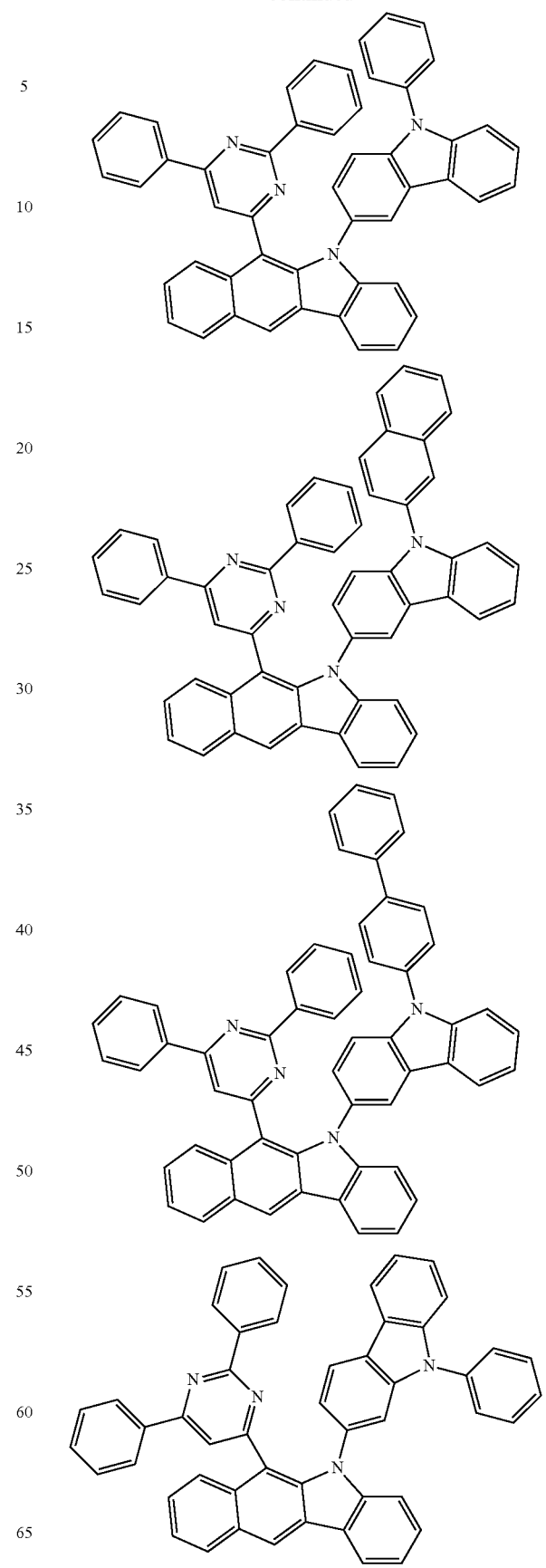

89
-continued
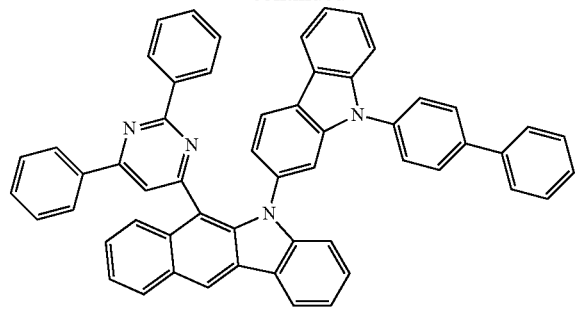
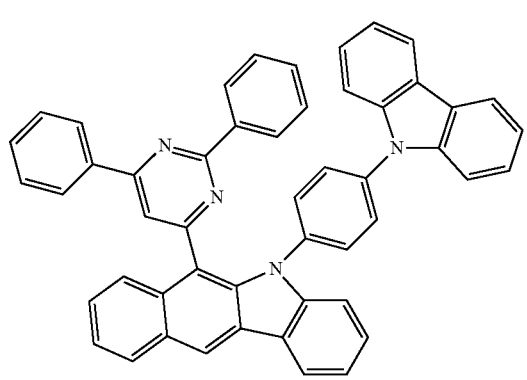
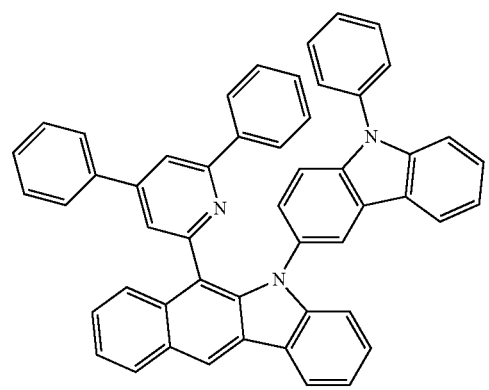
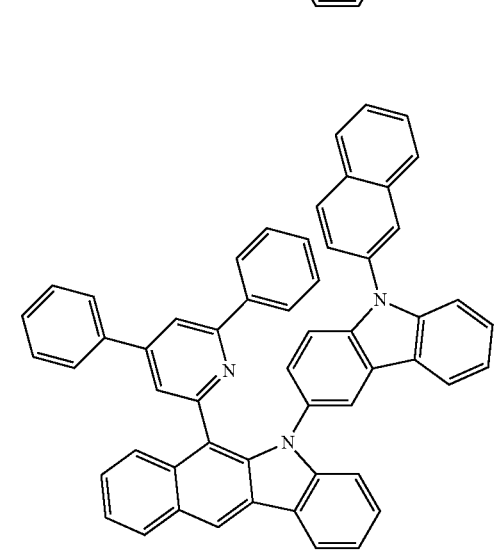
90
-continued
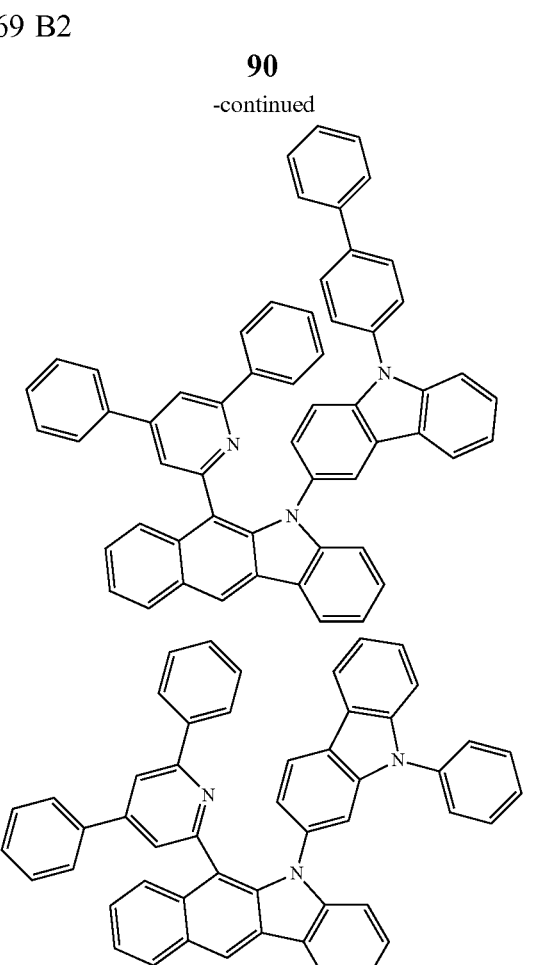
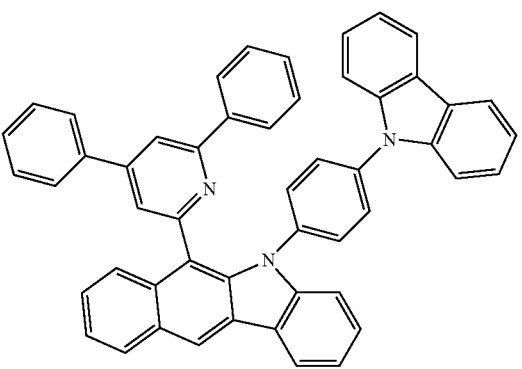

91
-continued
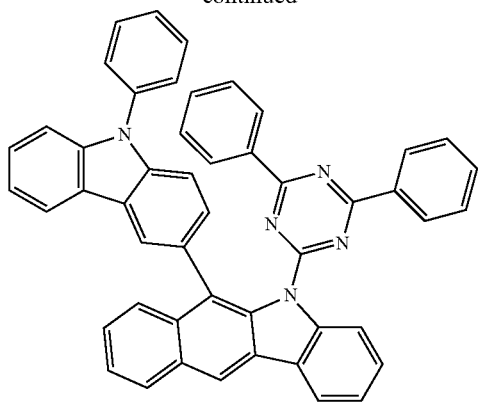
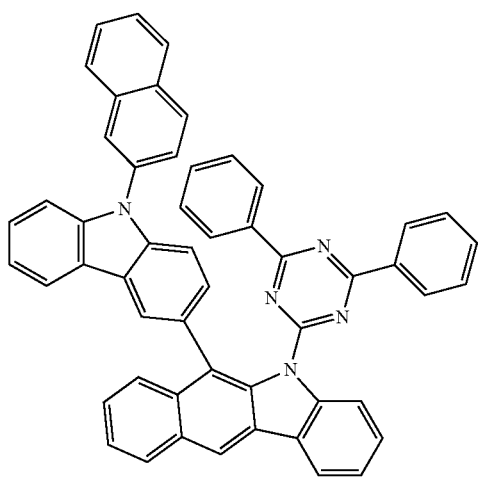
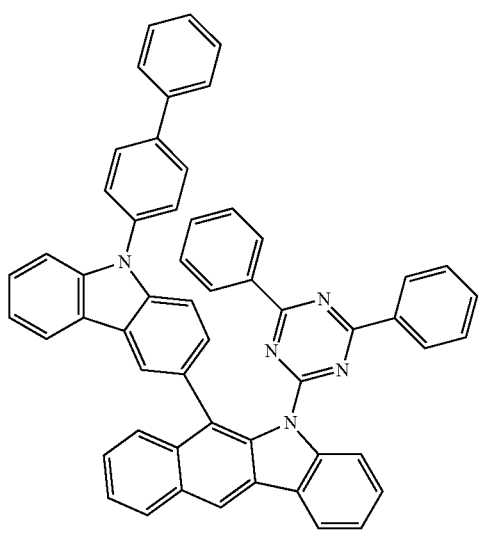
92
-continued
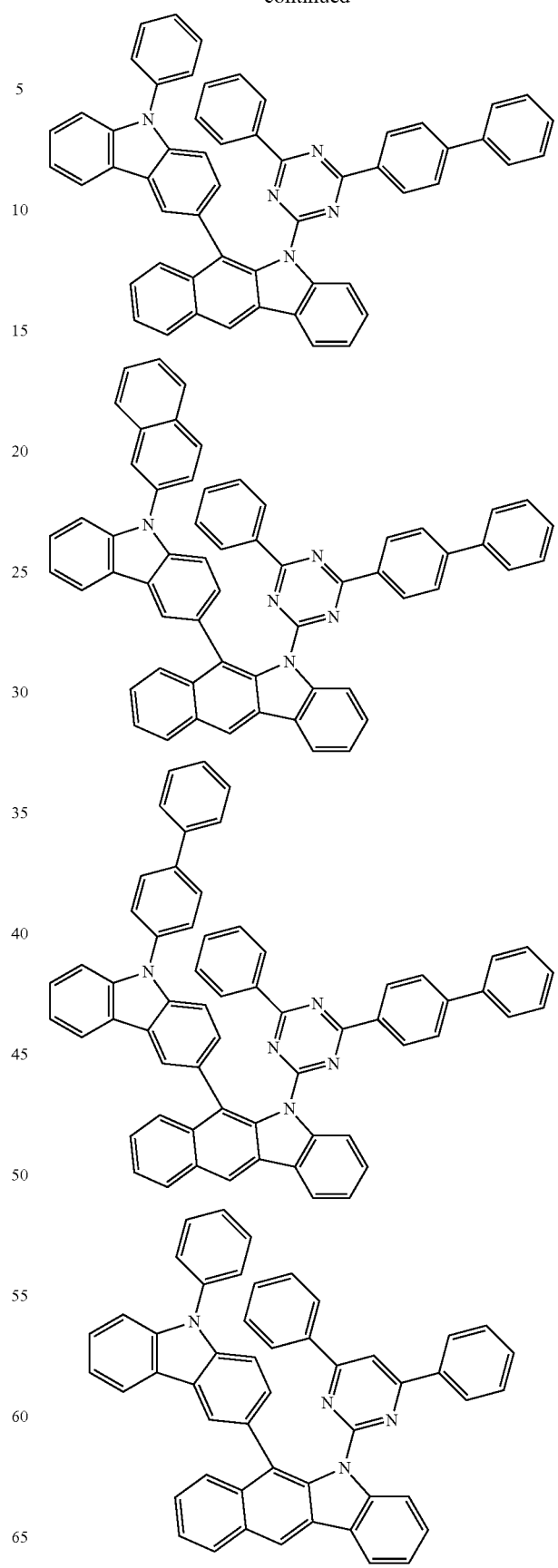

93
-continued
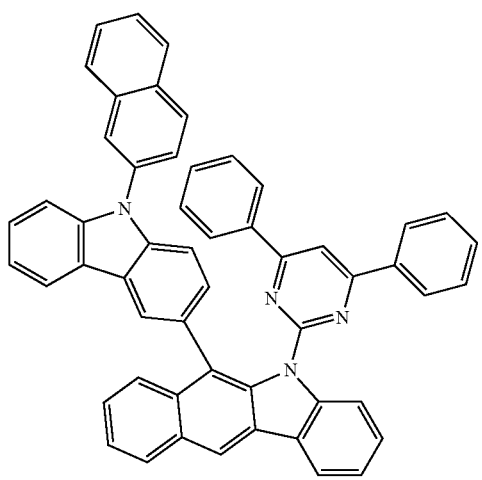
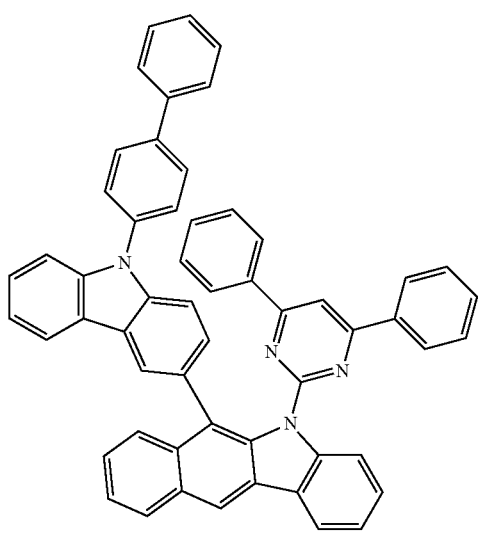
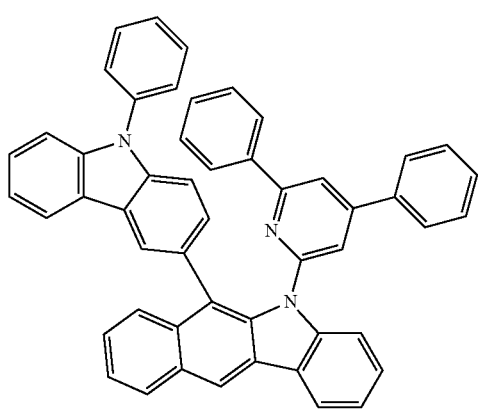
94
-continued
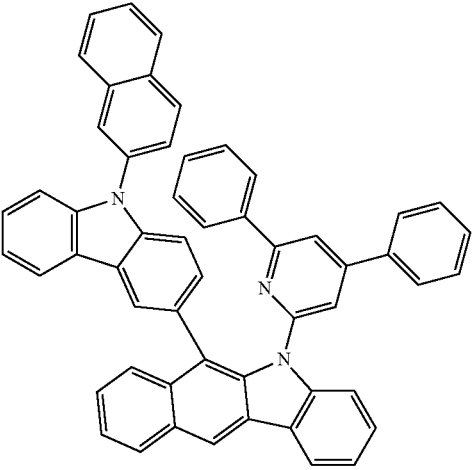
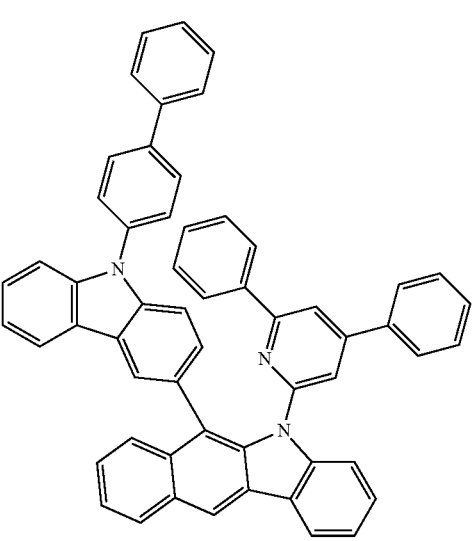
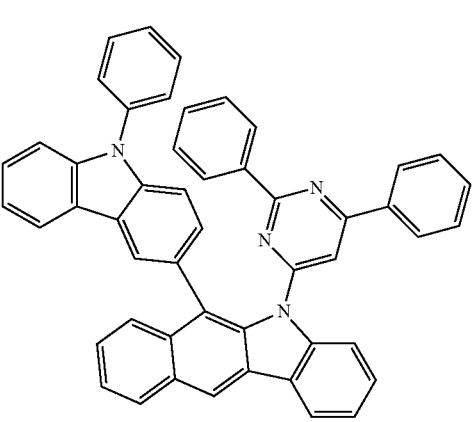

95
-continued
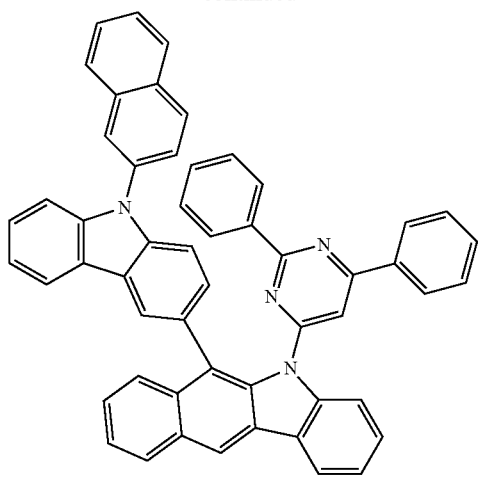
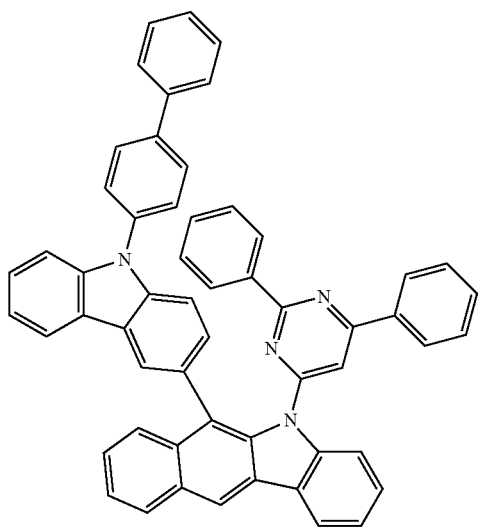
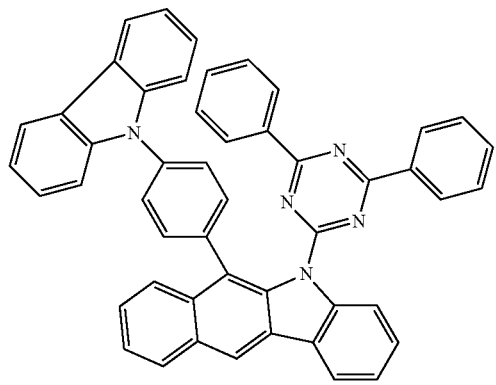
96
-continued
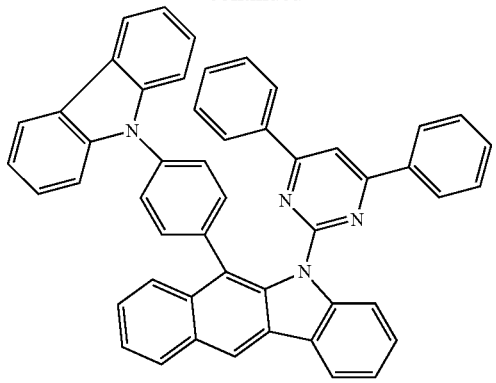
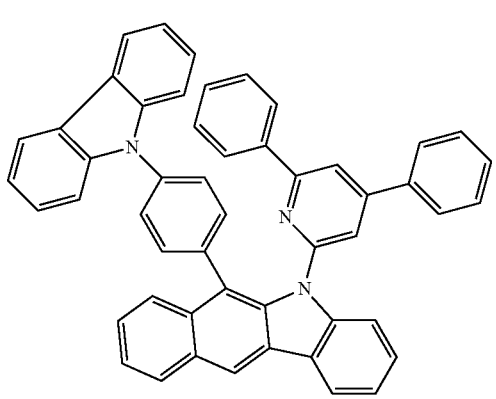
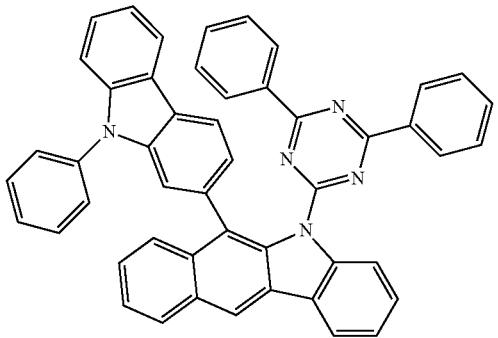
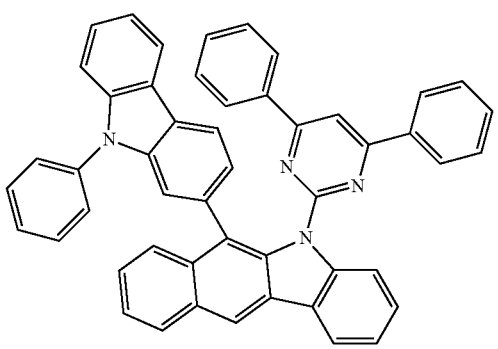

97
-continued
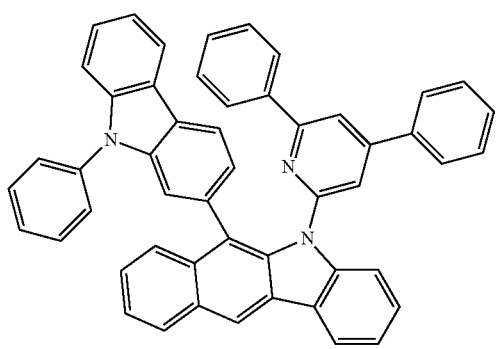
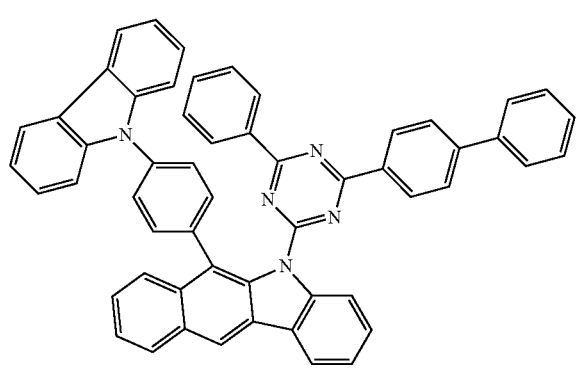
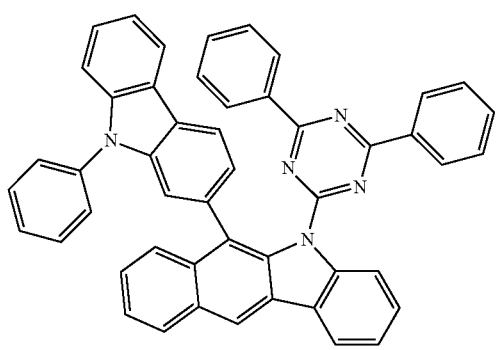
98
-continued
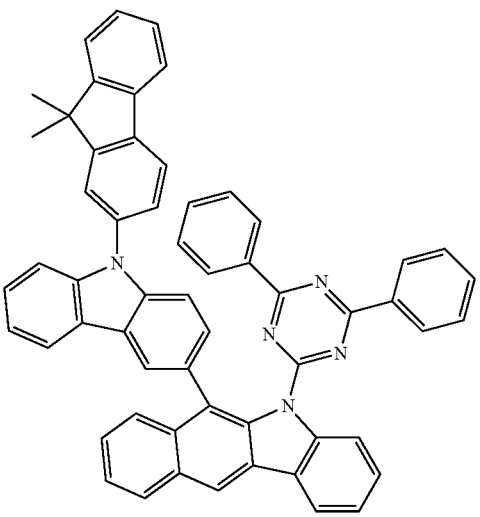
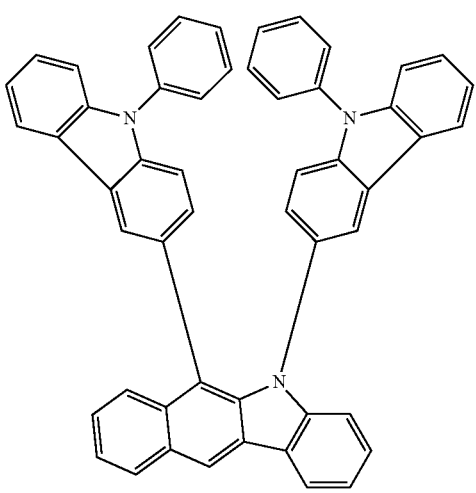
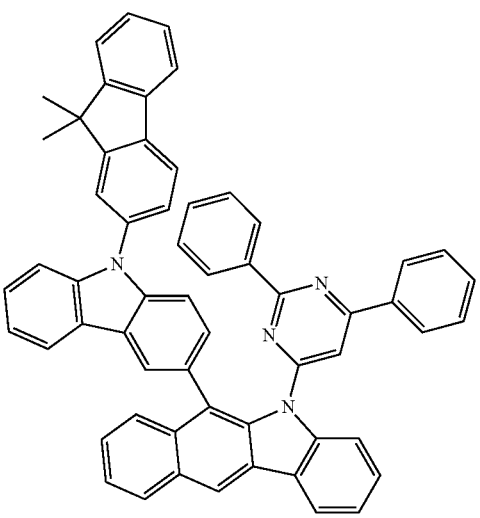
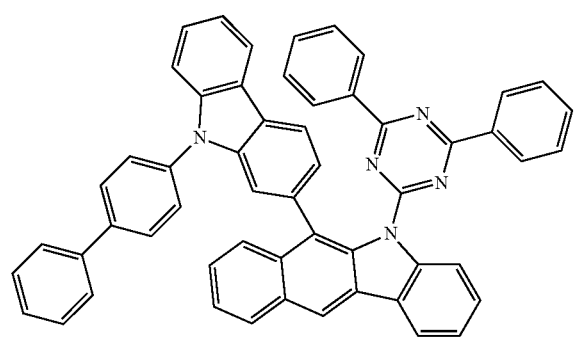

99
-continued
100
-continued
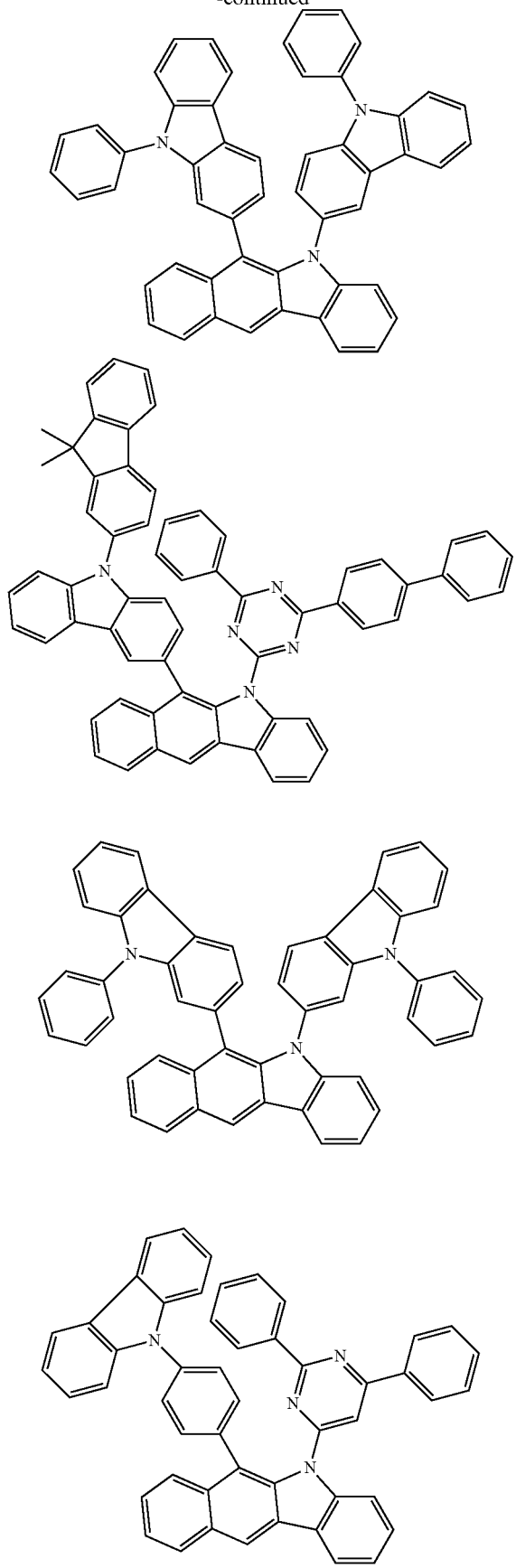
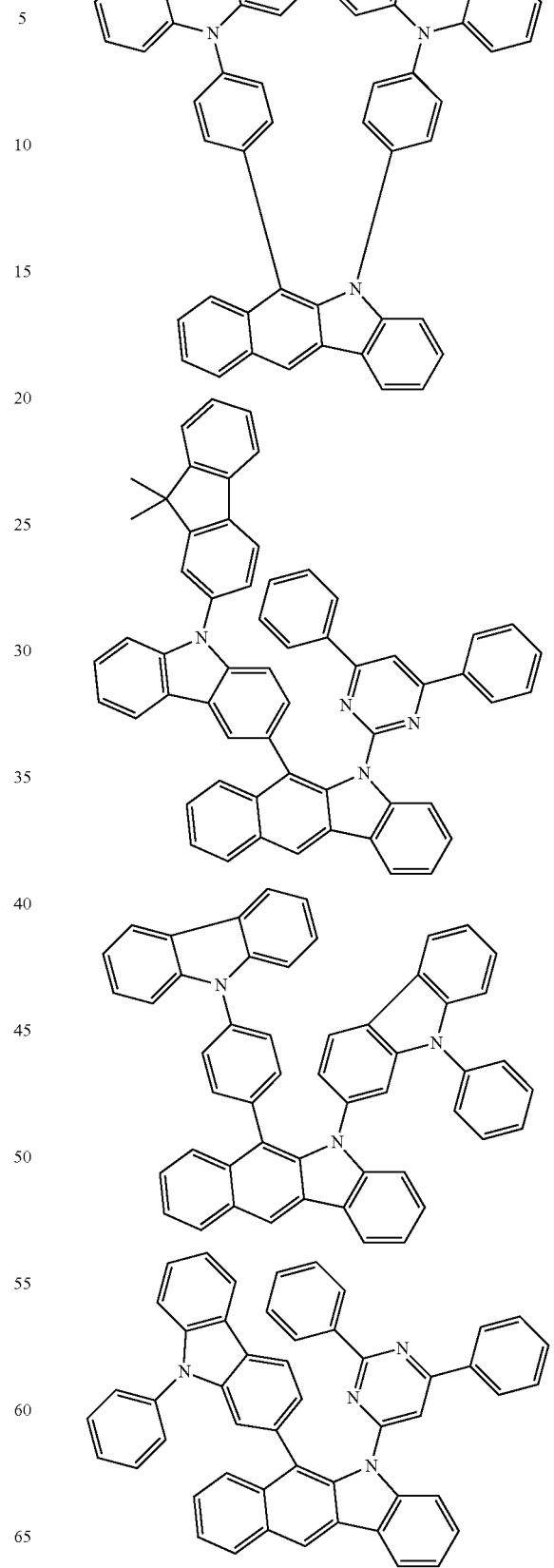

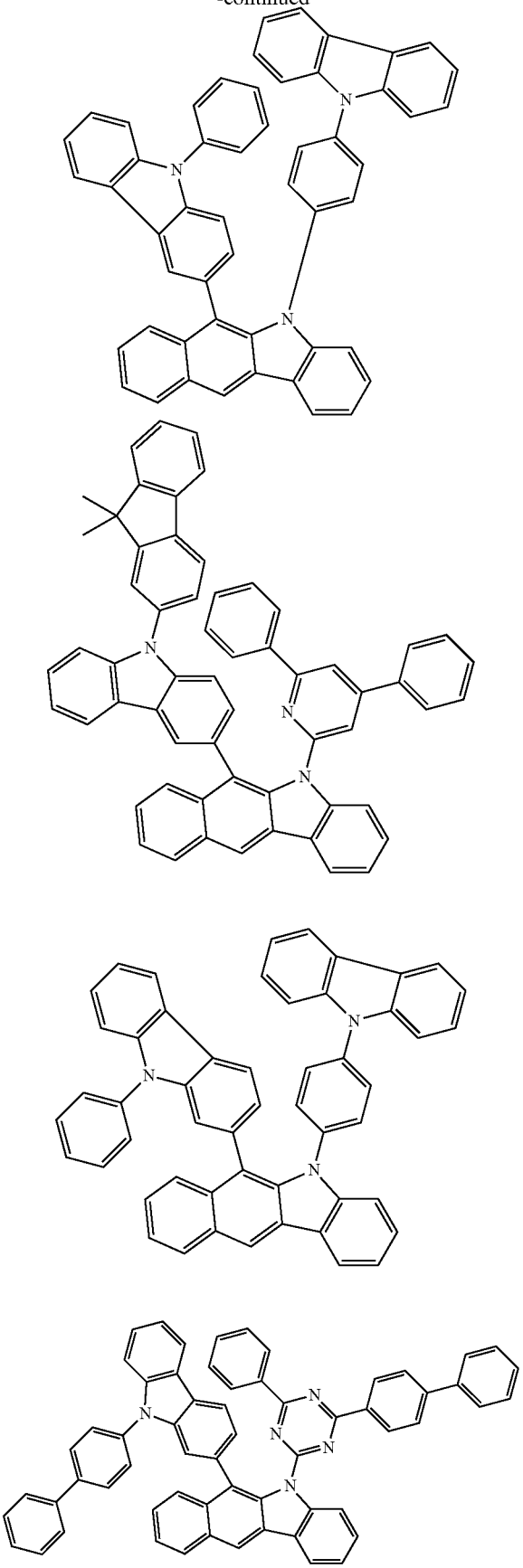

103
-continued
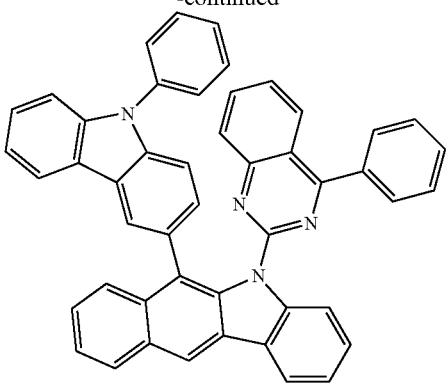
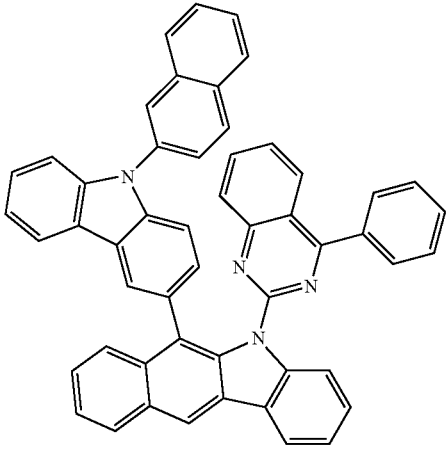
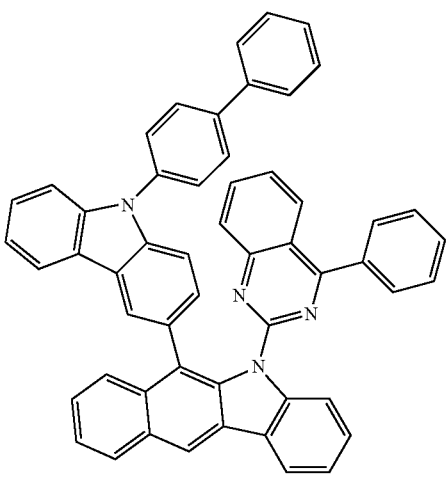
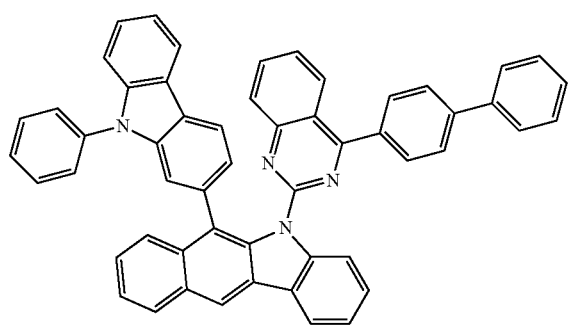
104
-continued
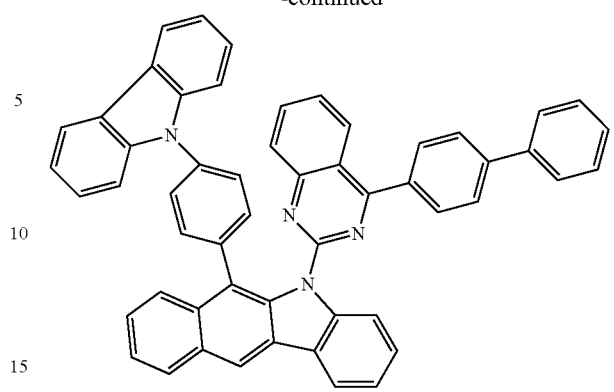
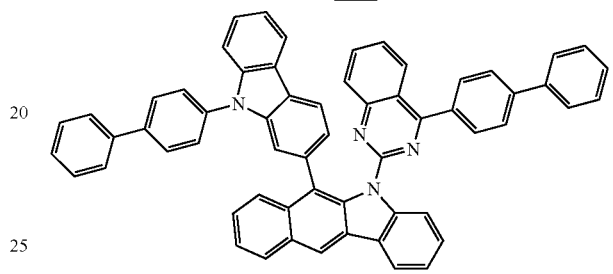
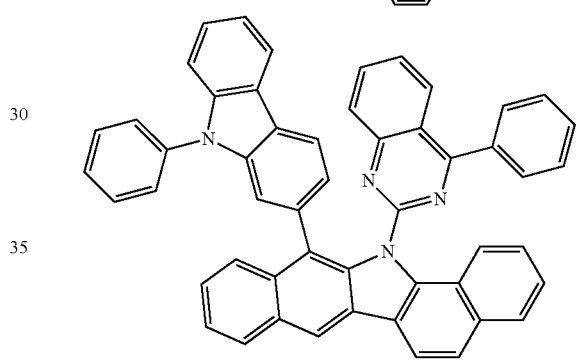
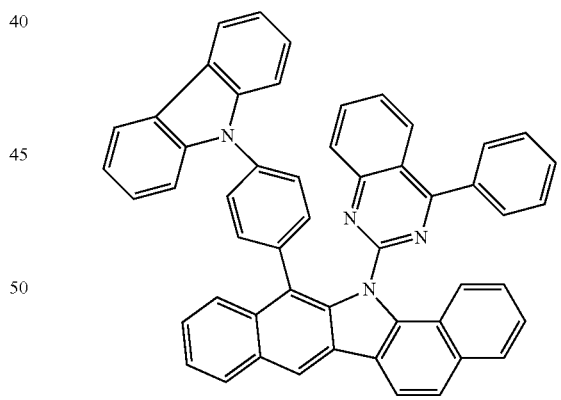
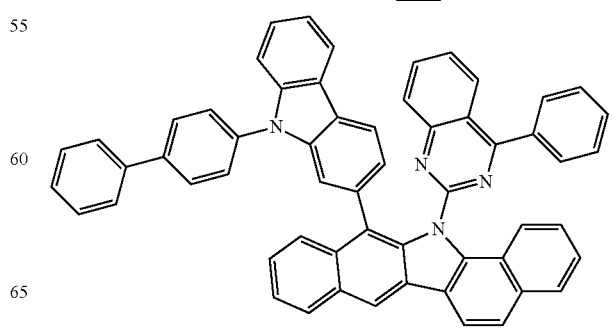

105
-continued
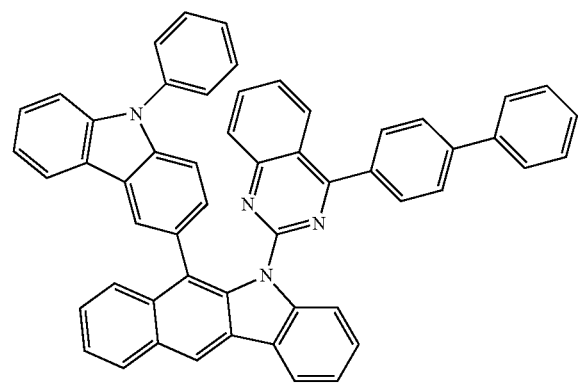
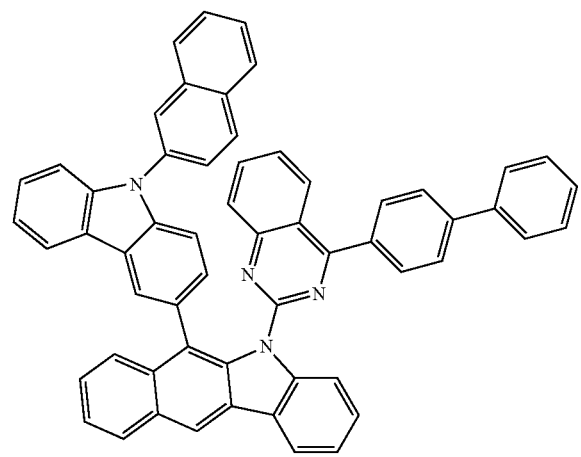
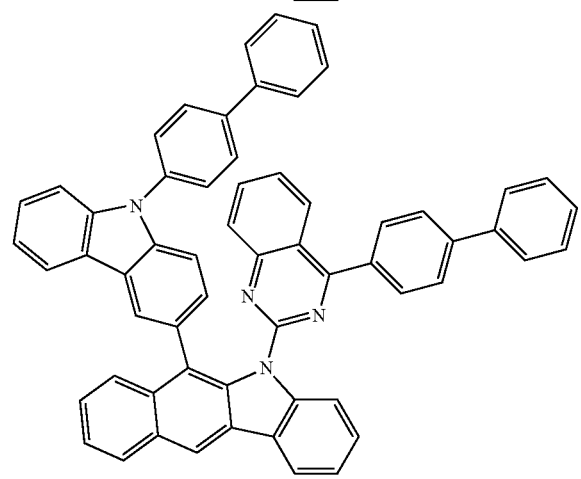
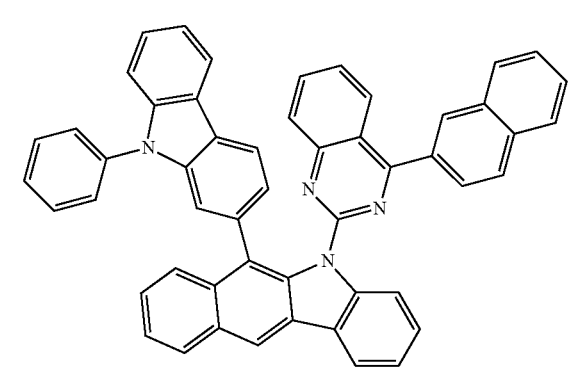
106
-continued
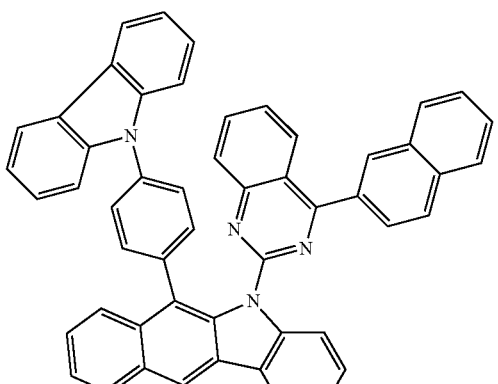
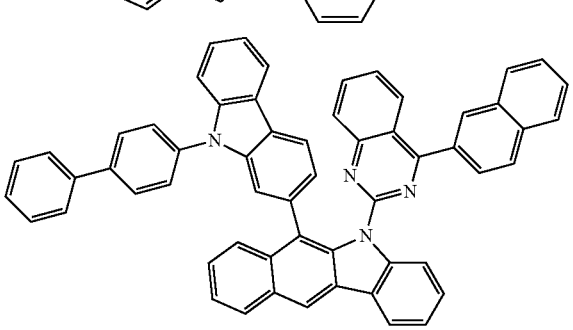
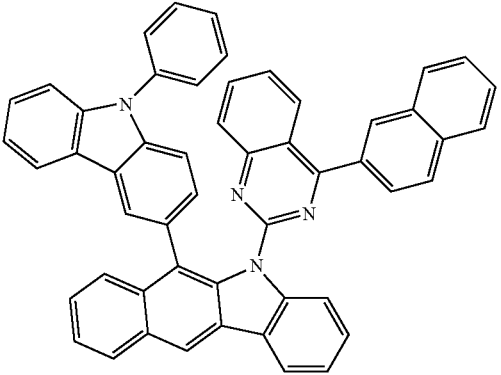
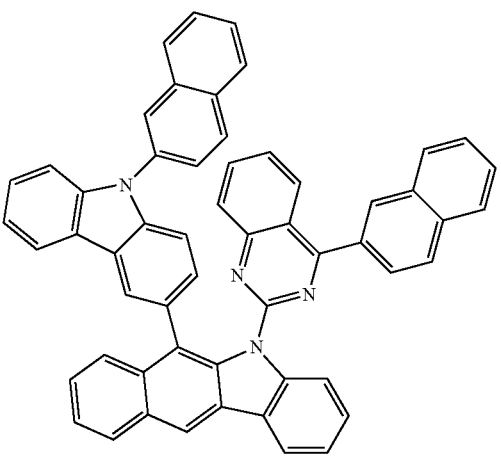

107
-continued
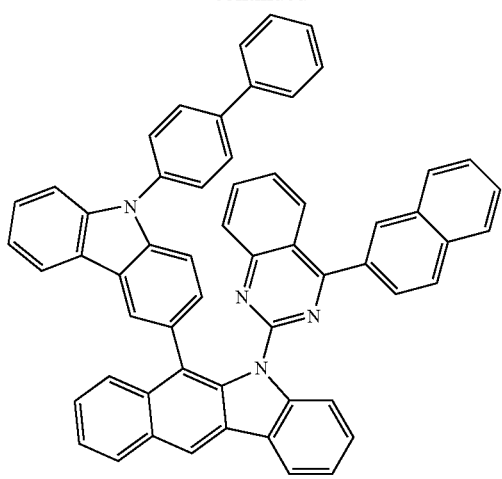
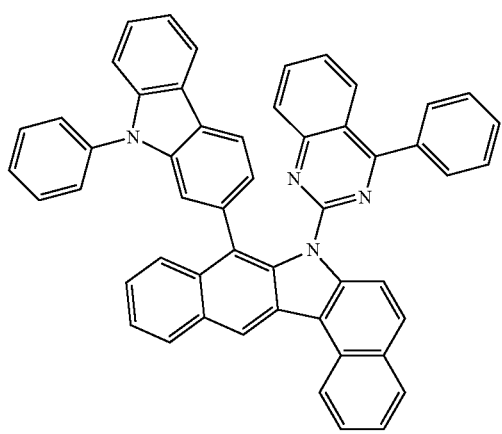
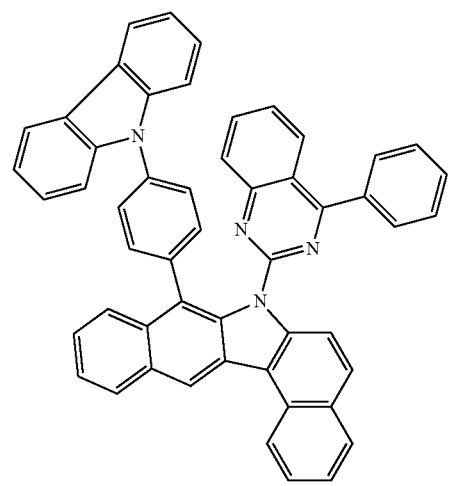
108
-continued
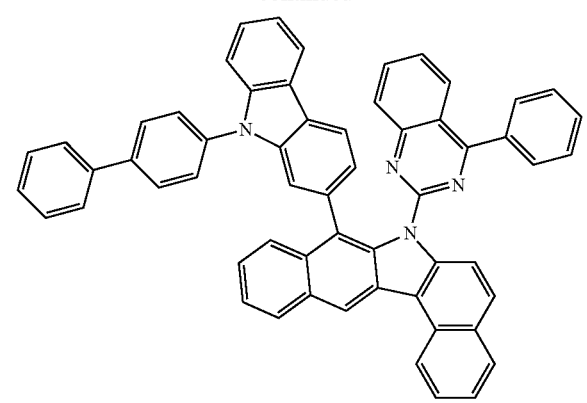
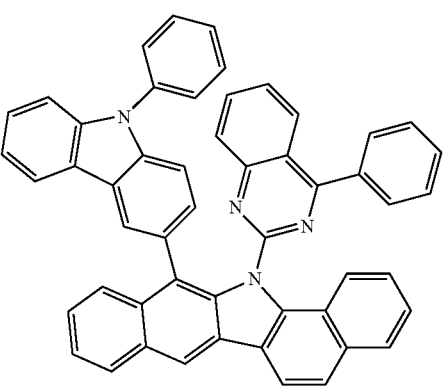
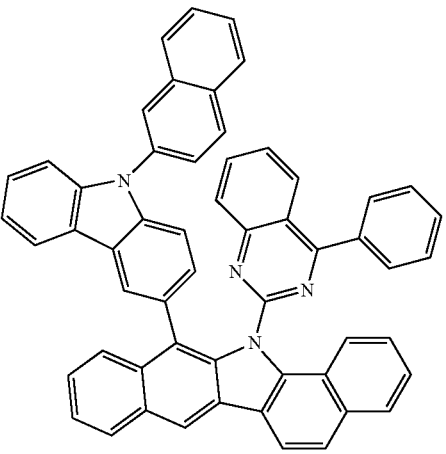
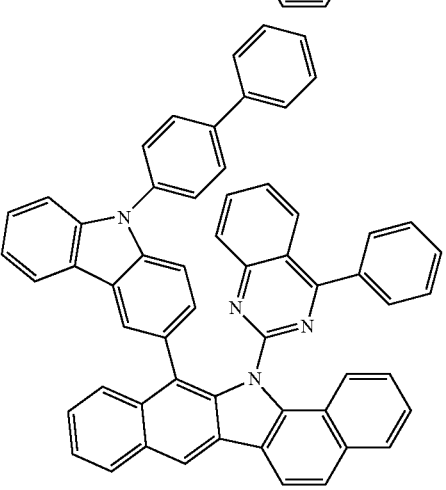

-continued
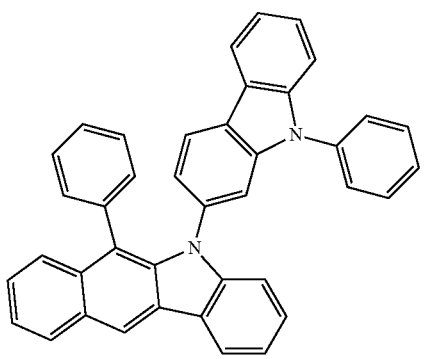
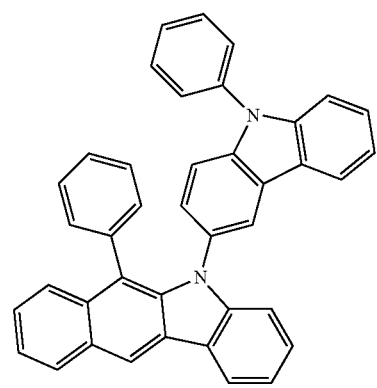
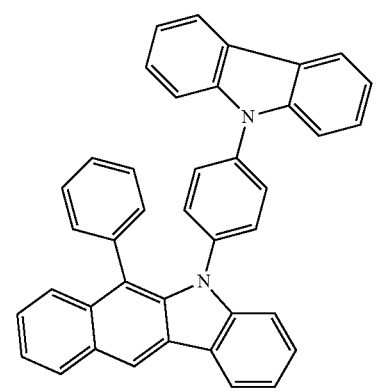
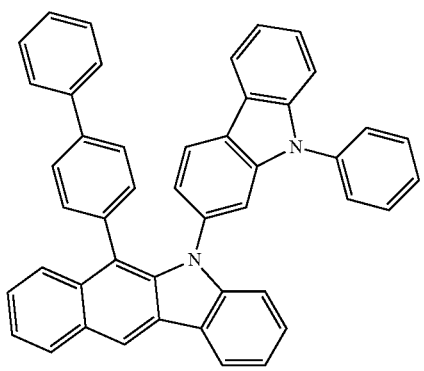
-continued
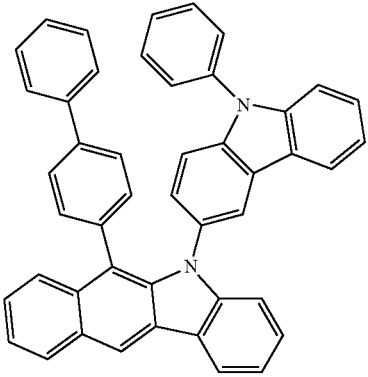
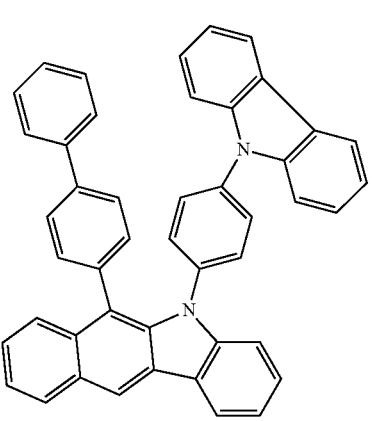
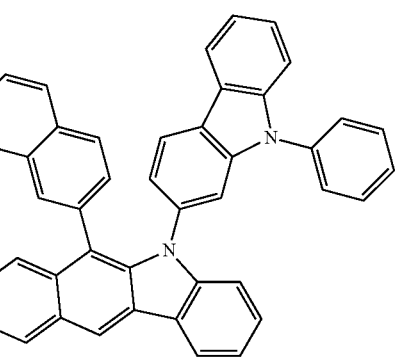
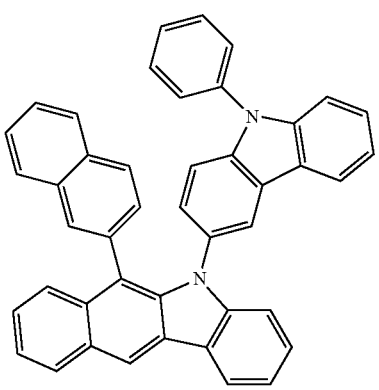

111
-continued
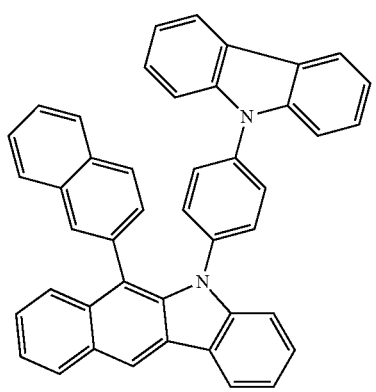
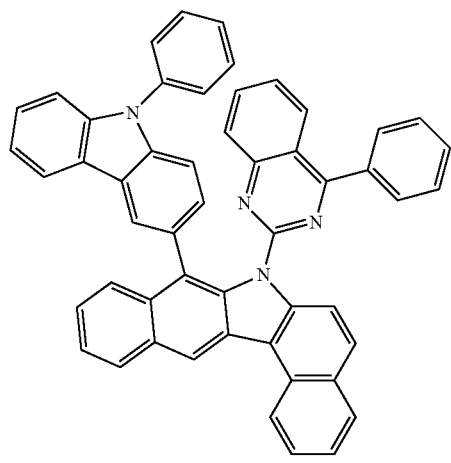
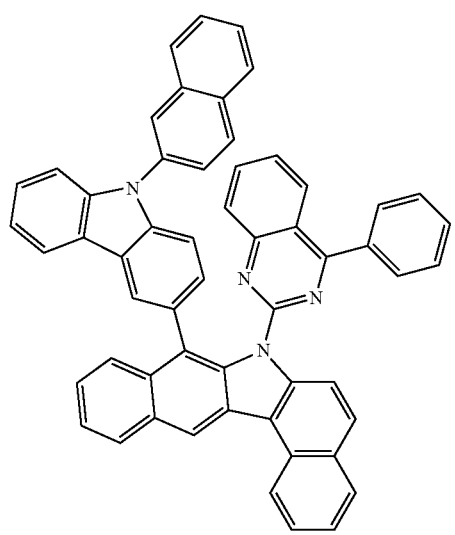
112
-continued
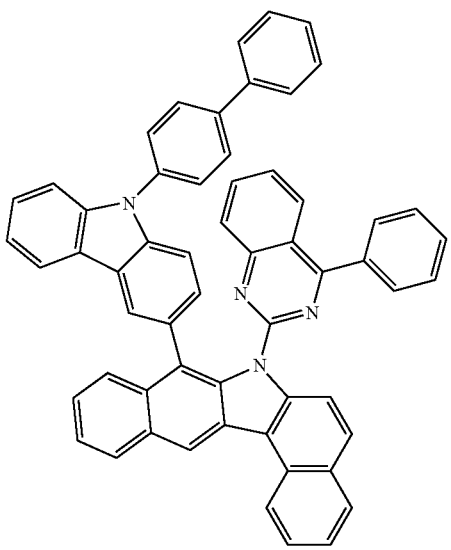
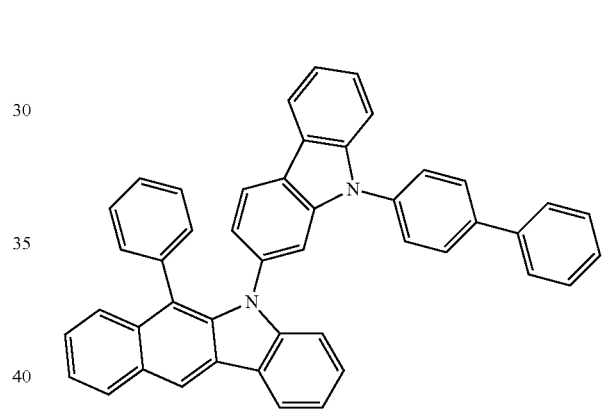
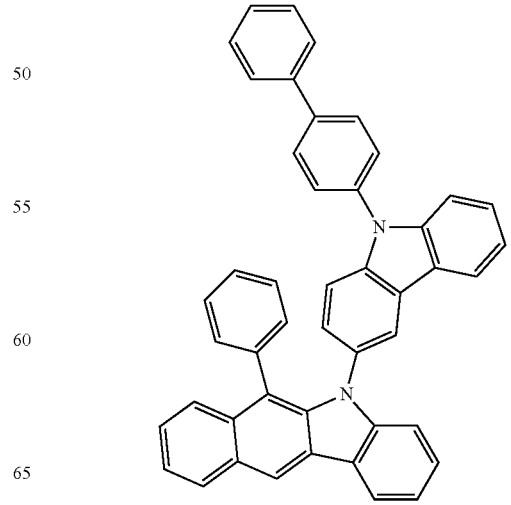

113
-continued
114
-continued
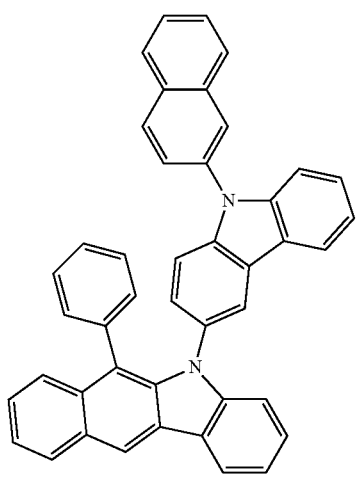
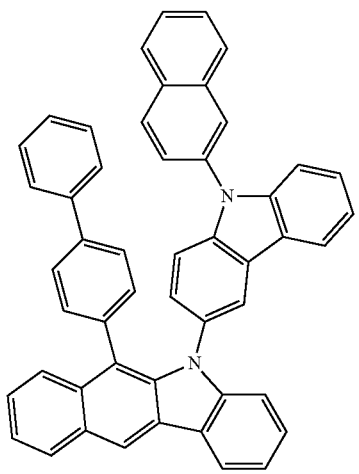
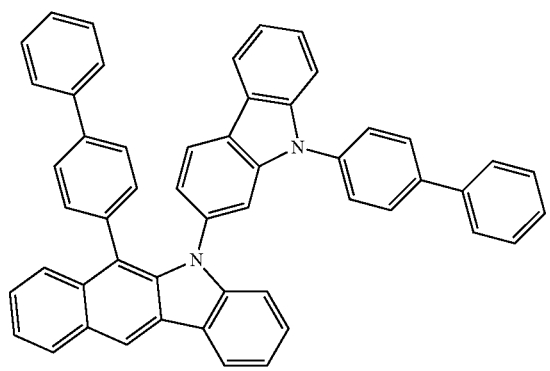
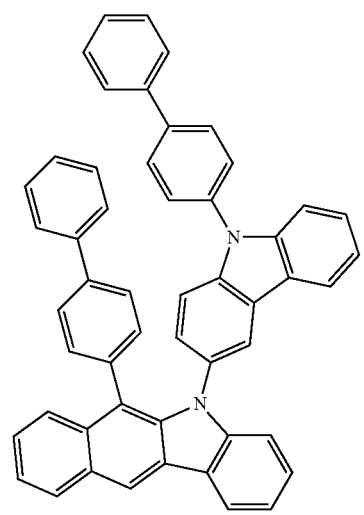
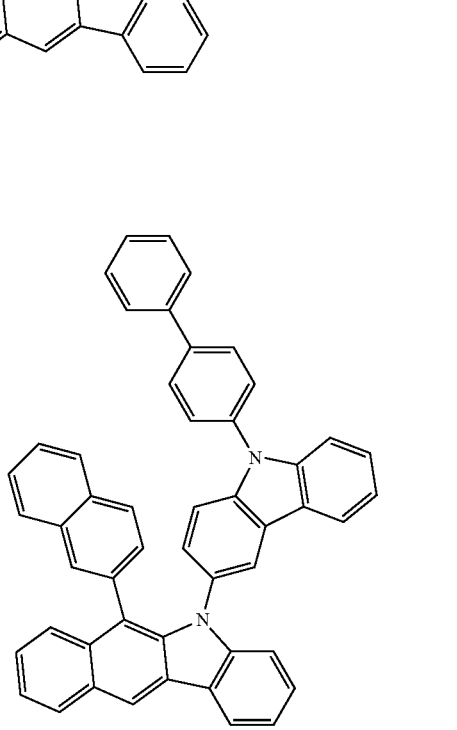

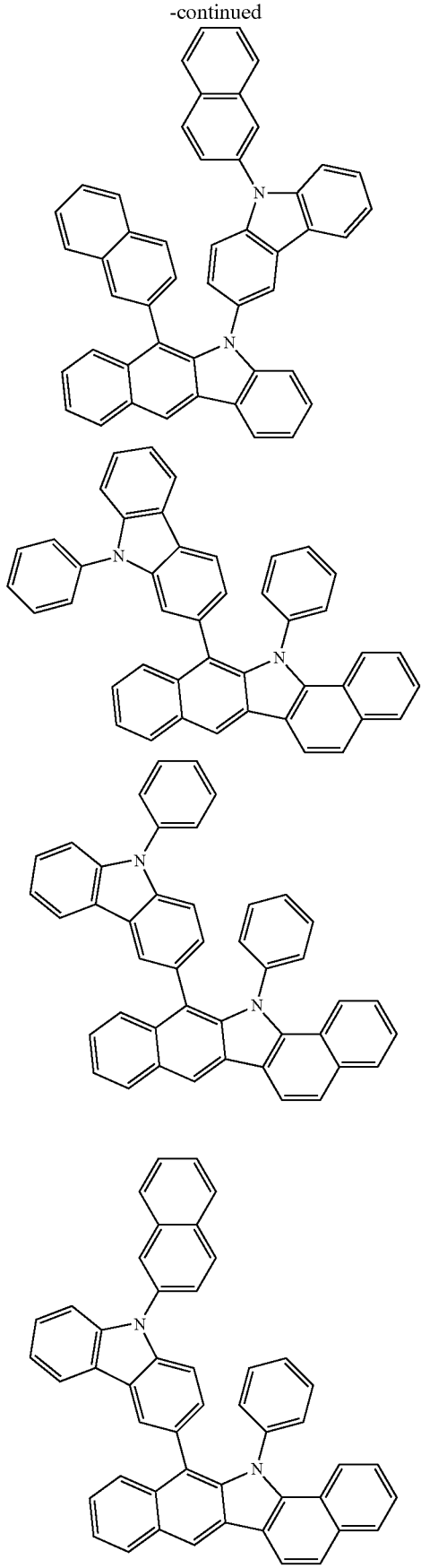

117
-continued
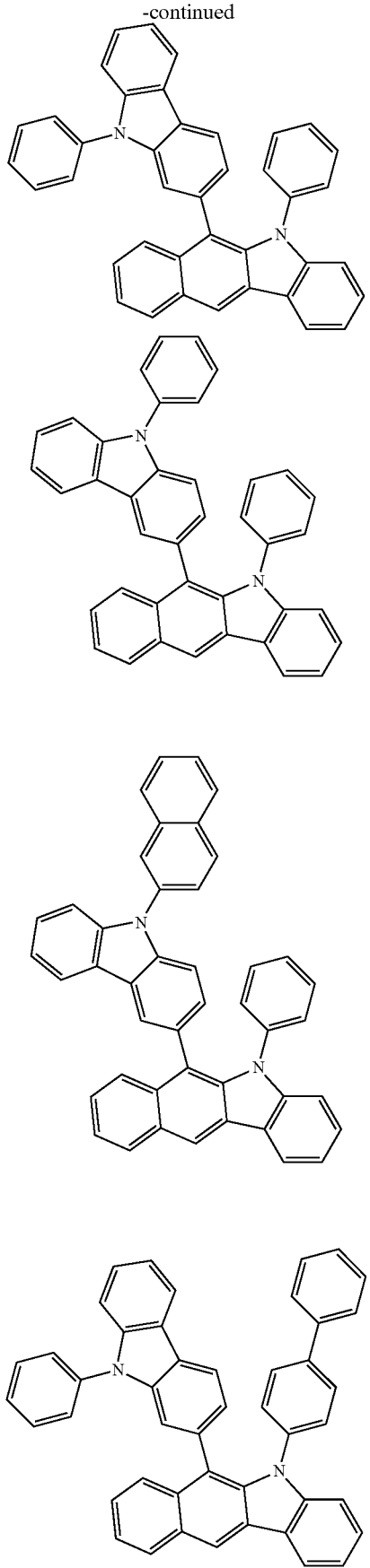
118
-continued
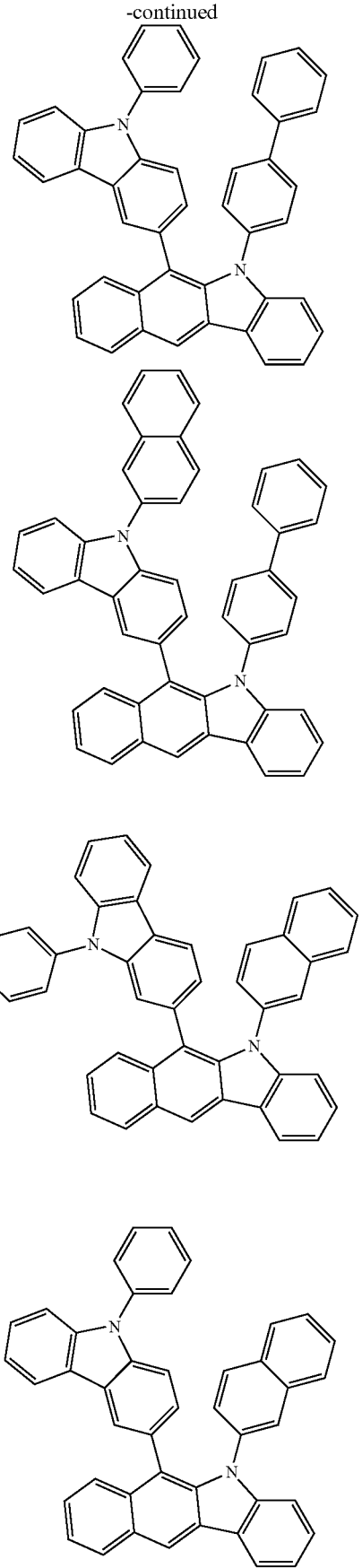

119
-continued
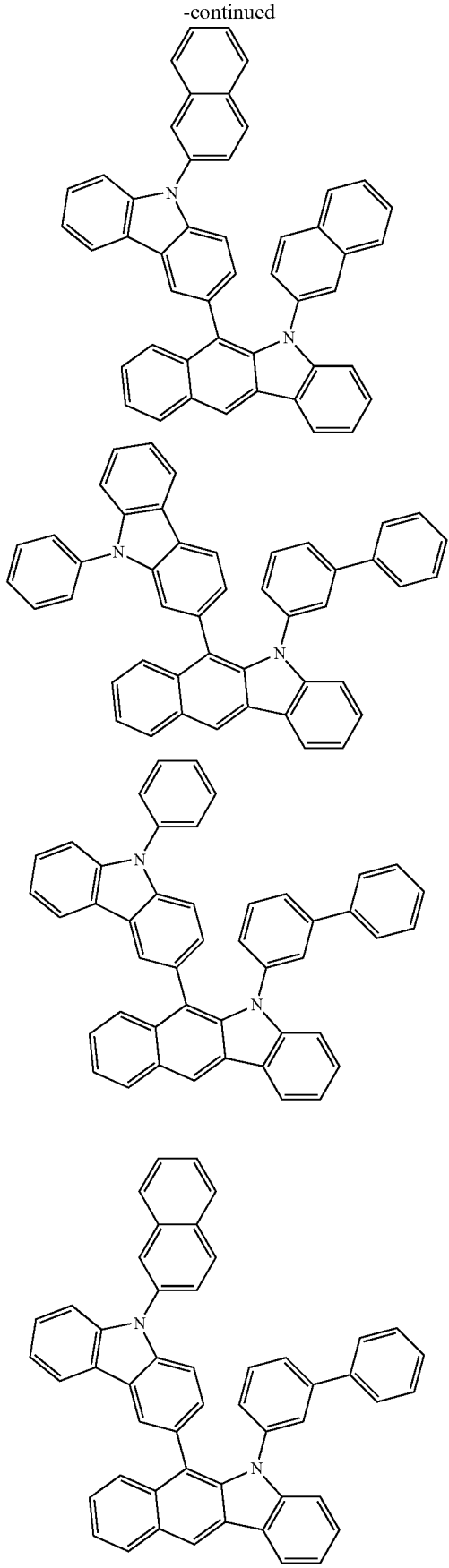
120
-continued
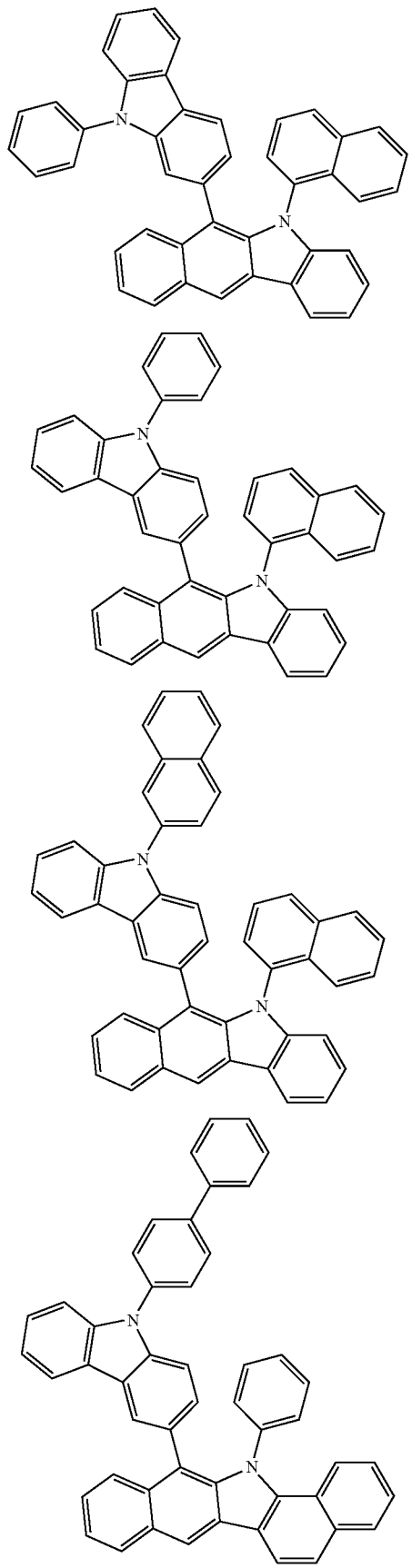

121
-continued
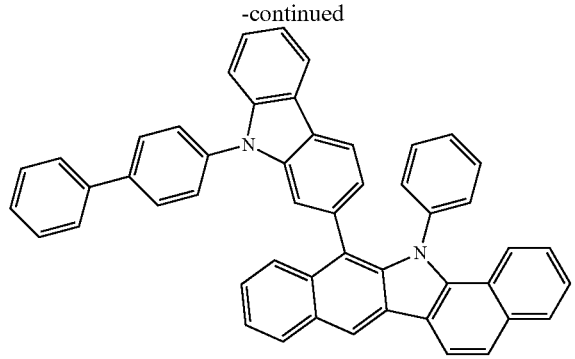
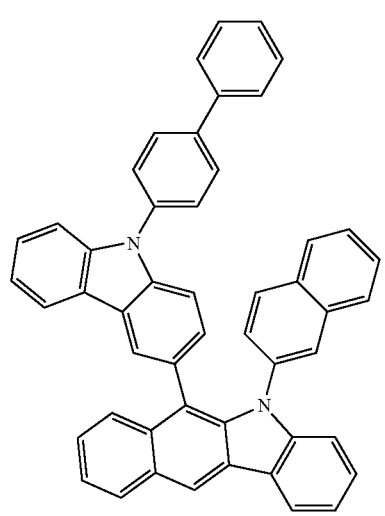
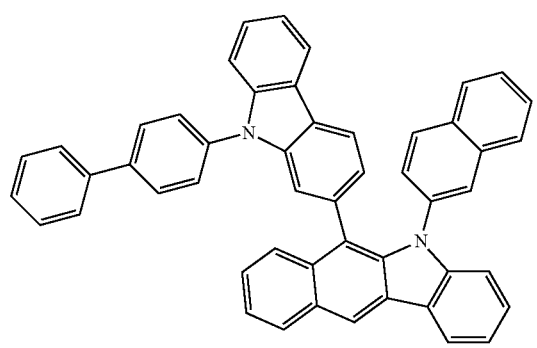
122
-continued
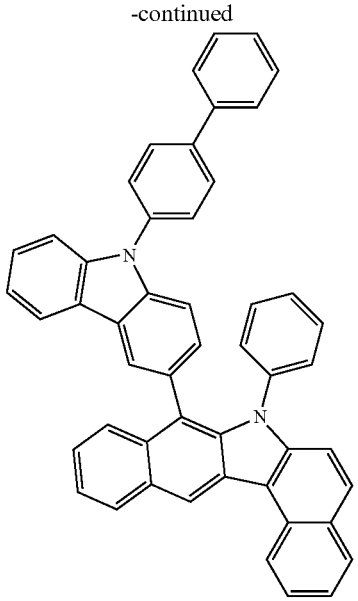
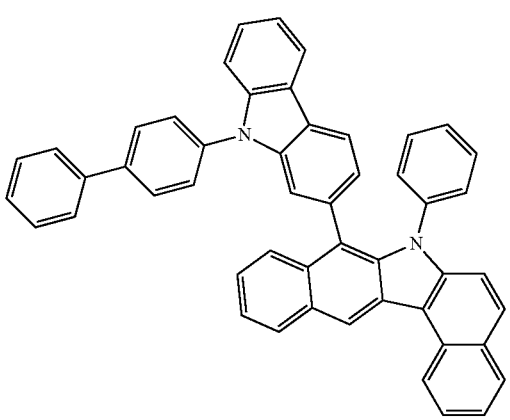
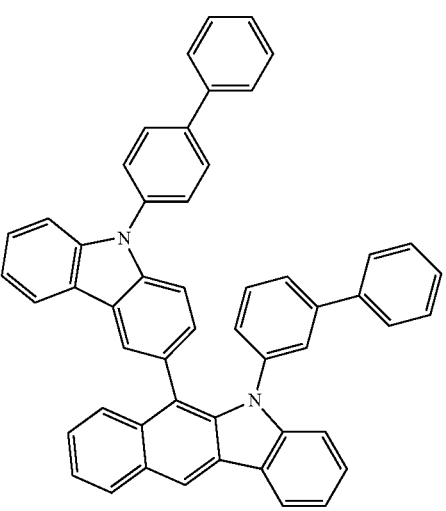

123
-continued
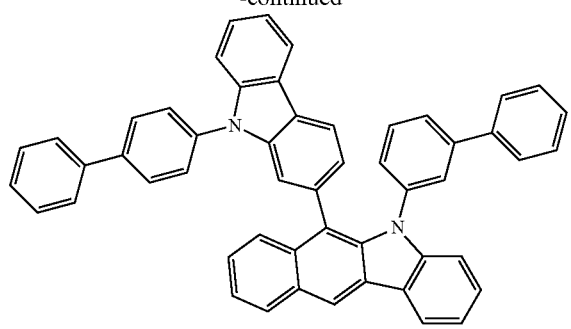
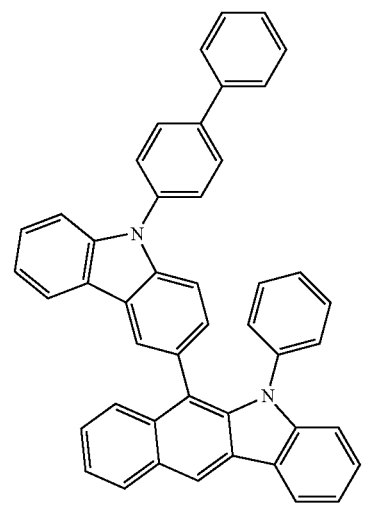
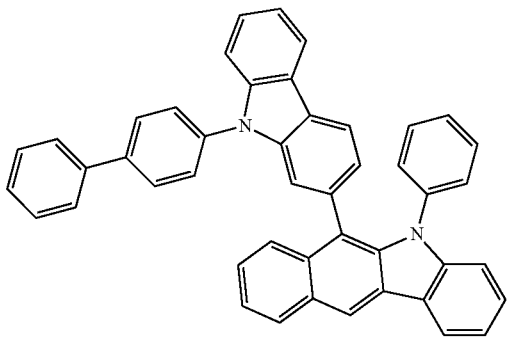
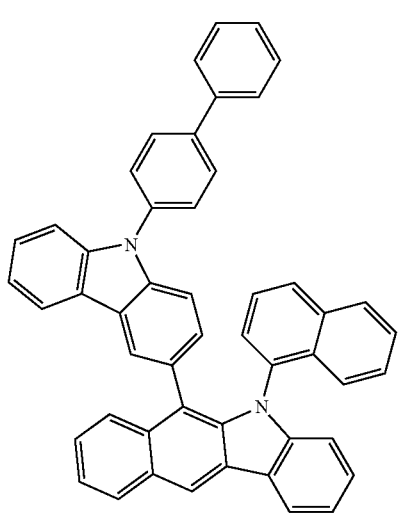
124
-continued
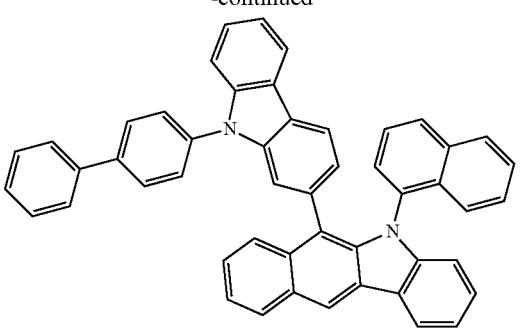
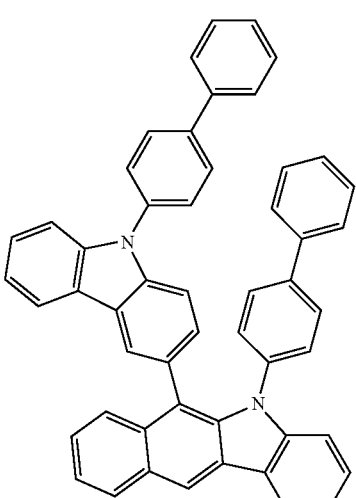
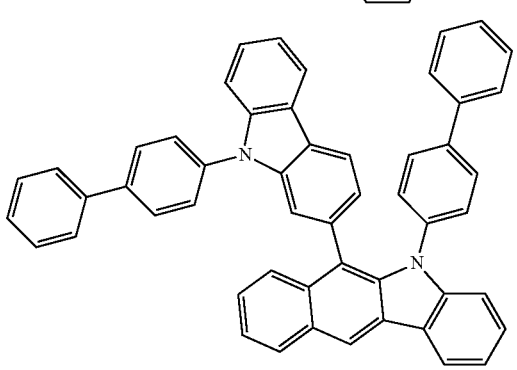
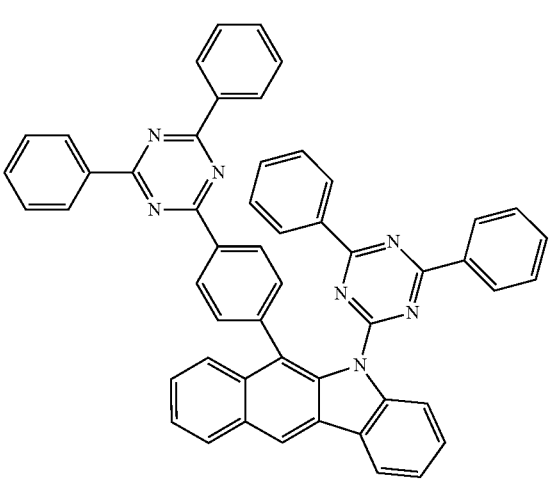

125
-continued
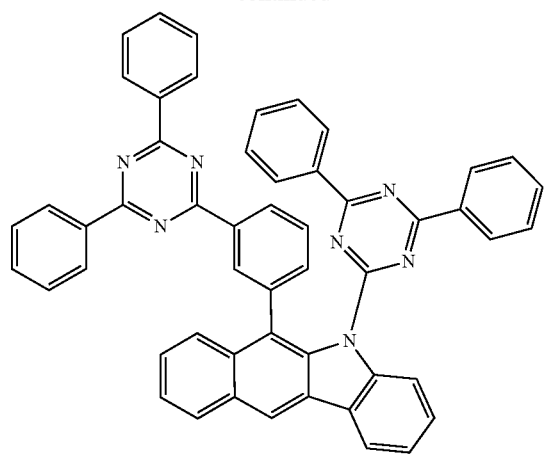
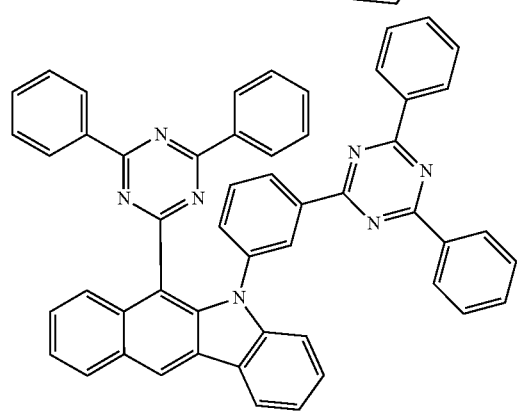
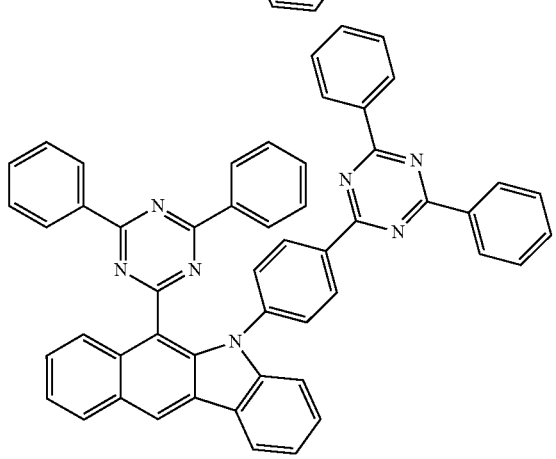
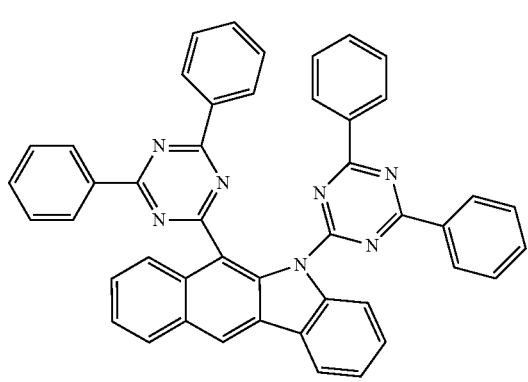
126
-continued
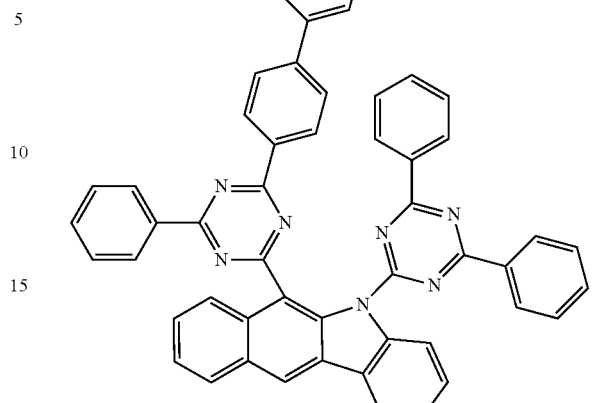
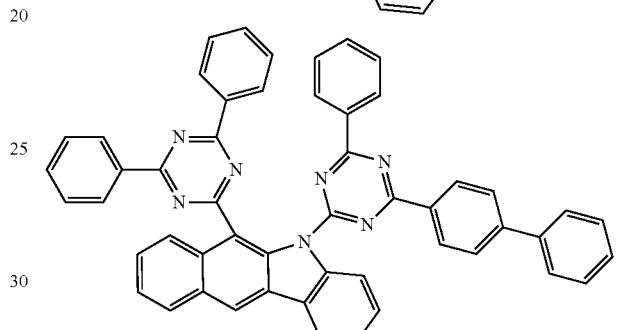
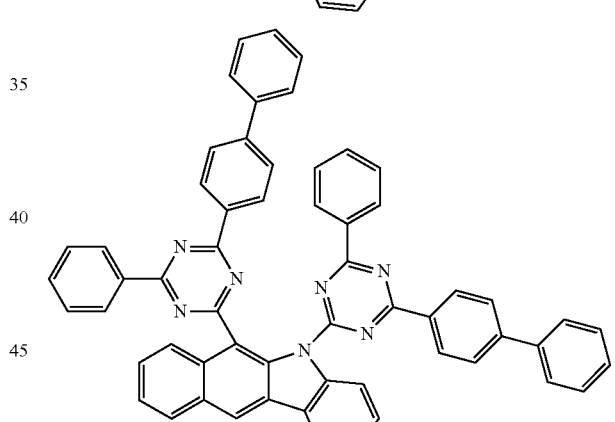
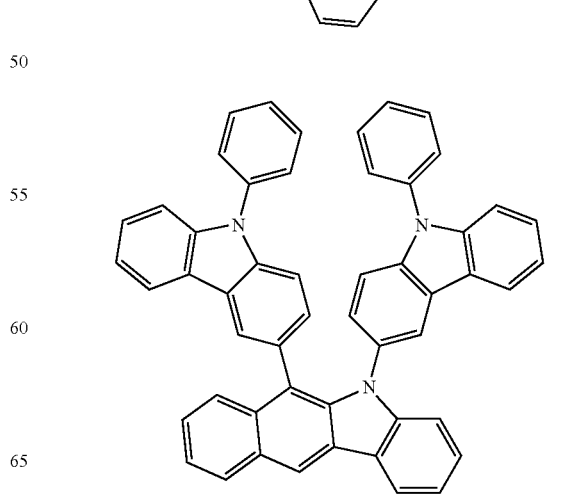

127
-continued
128
-continued
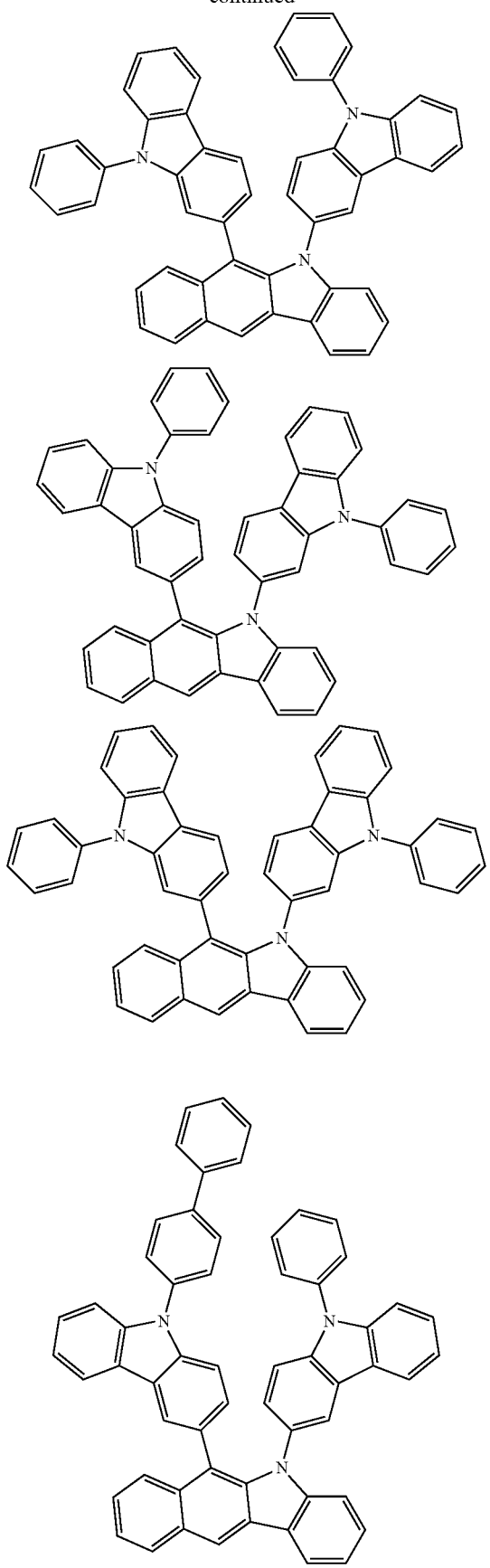
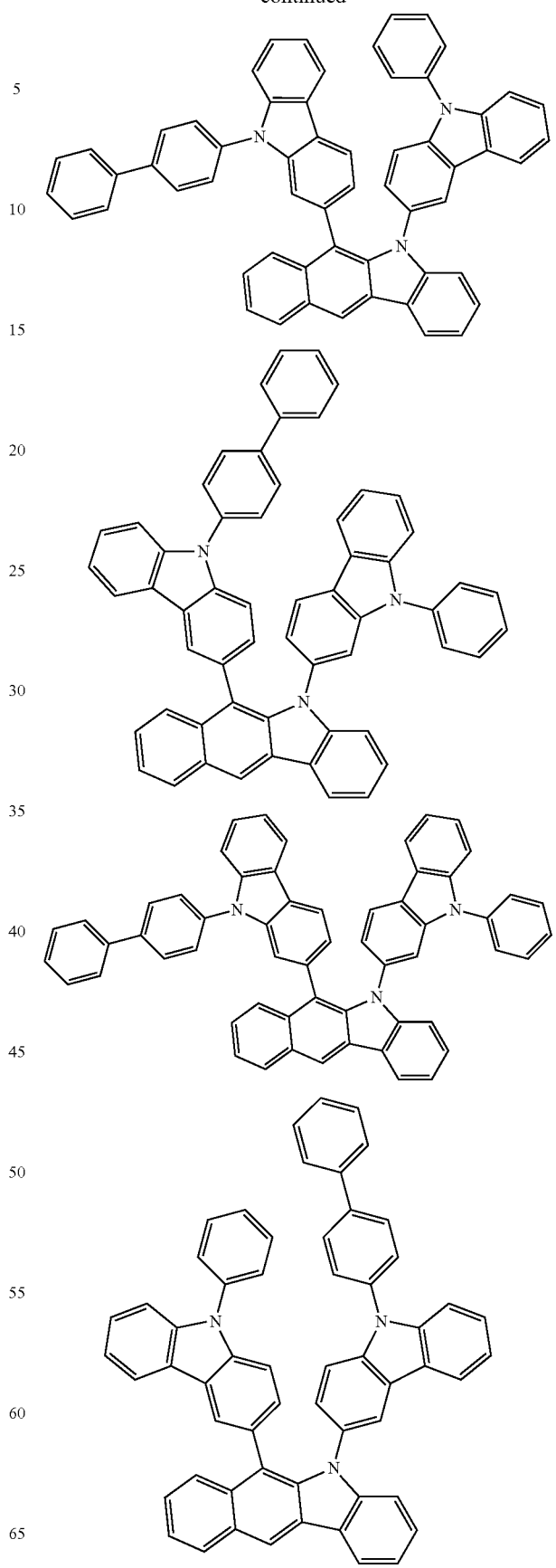

129
-continued
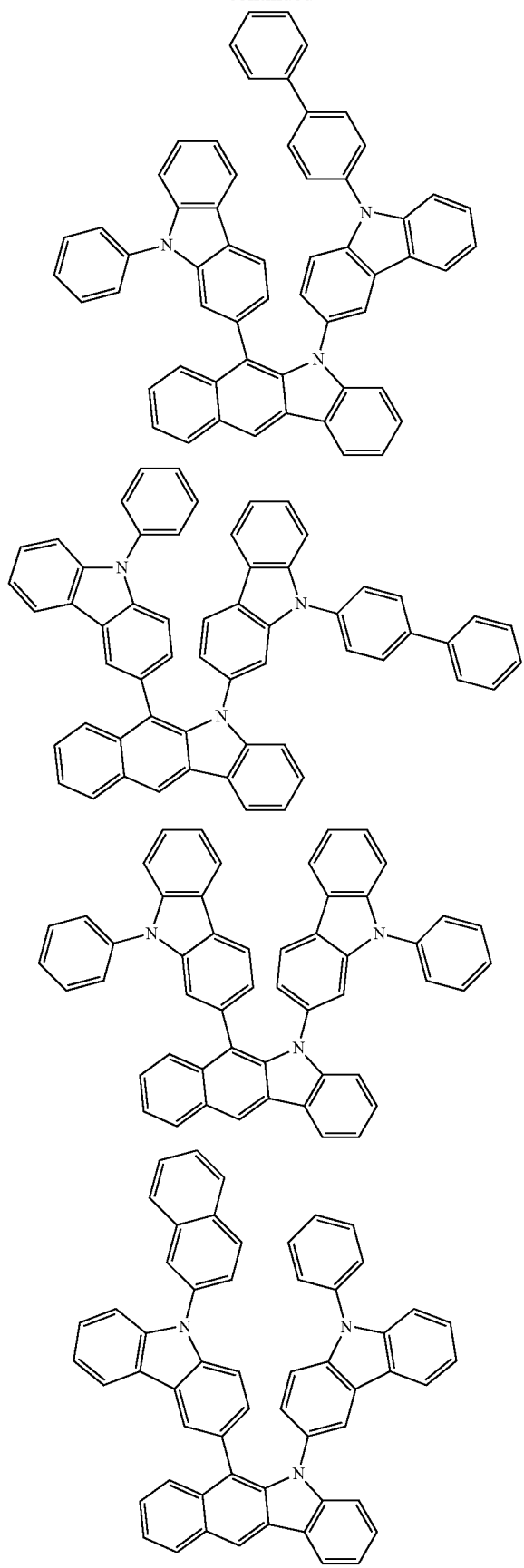
130
-continued
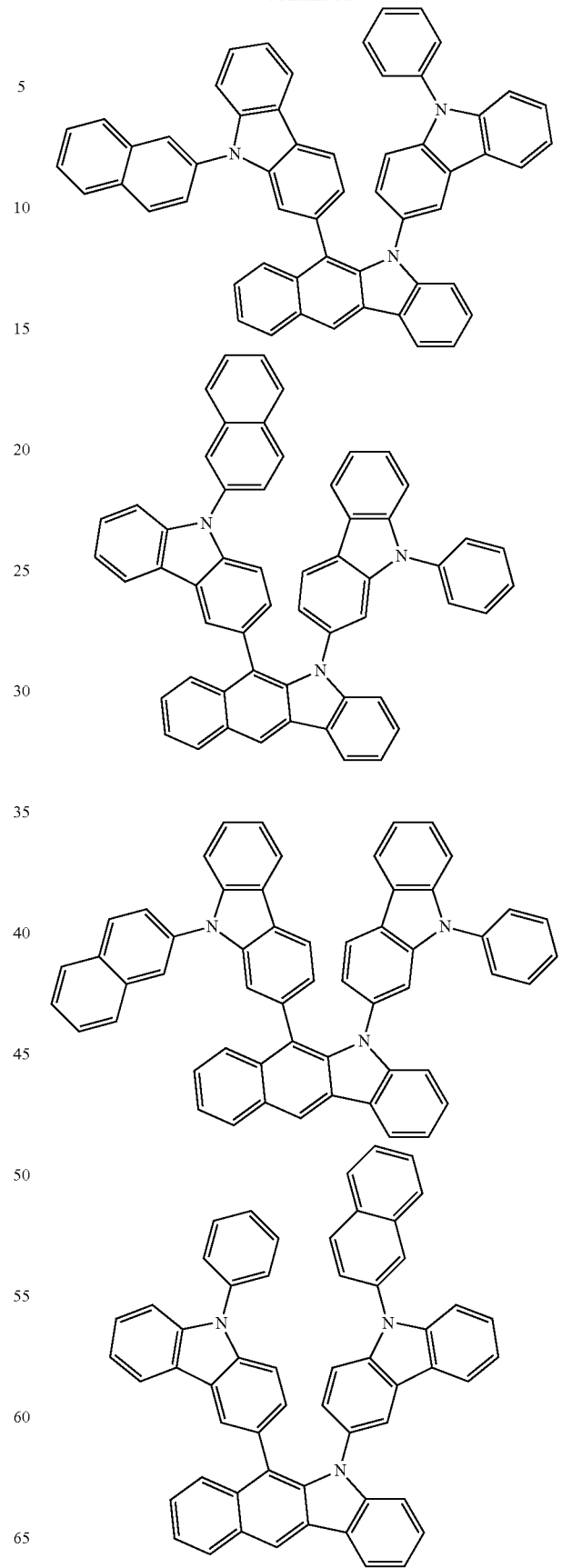

131
-continued
132
-continued
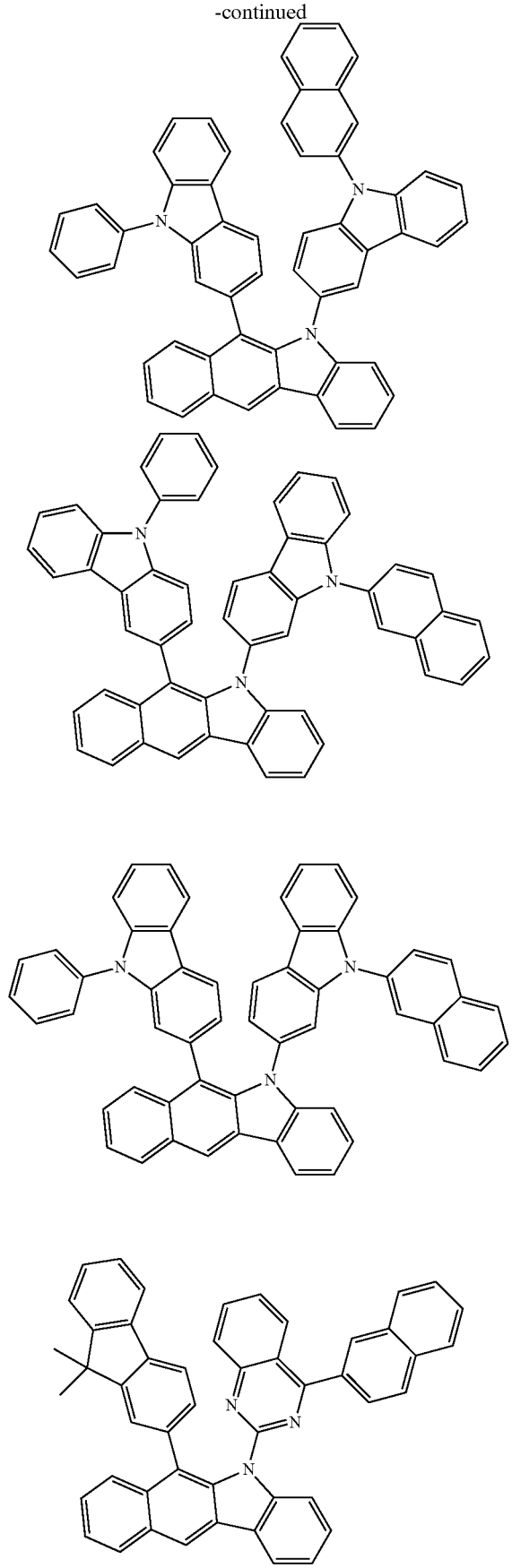
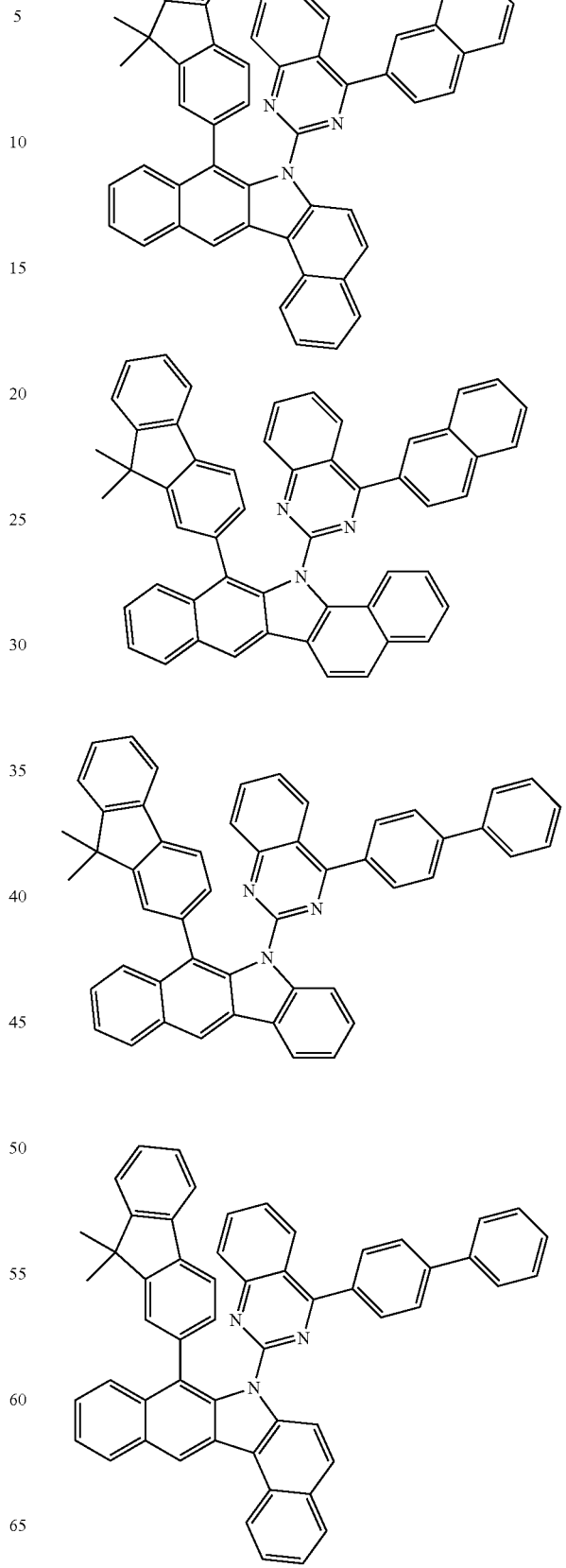

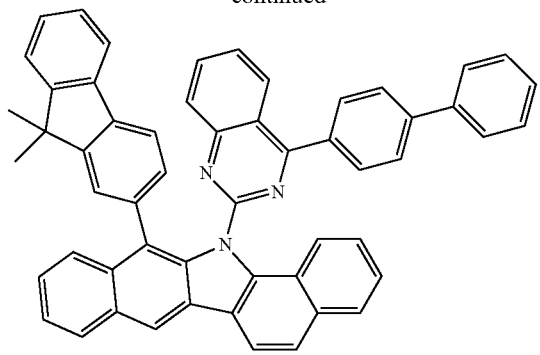
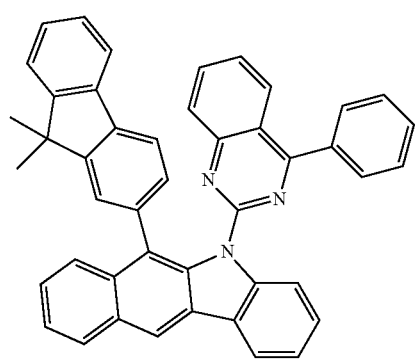
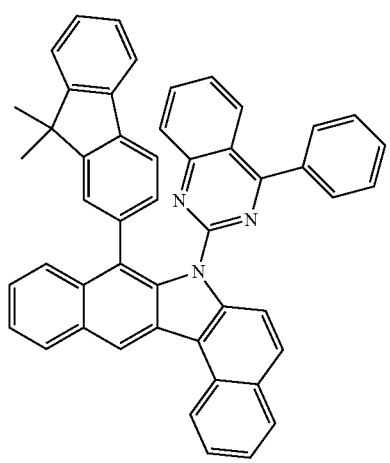
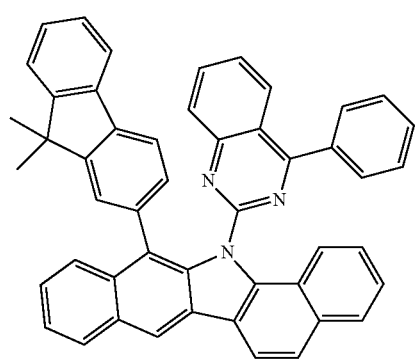
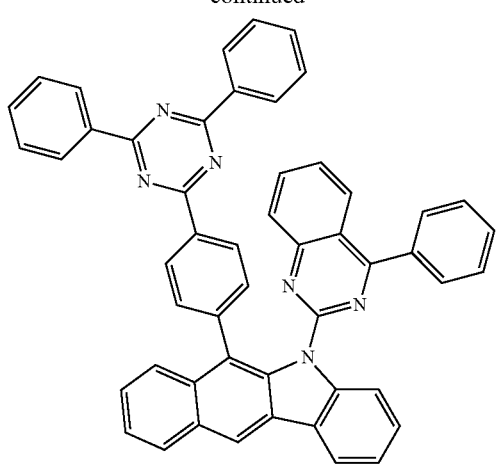
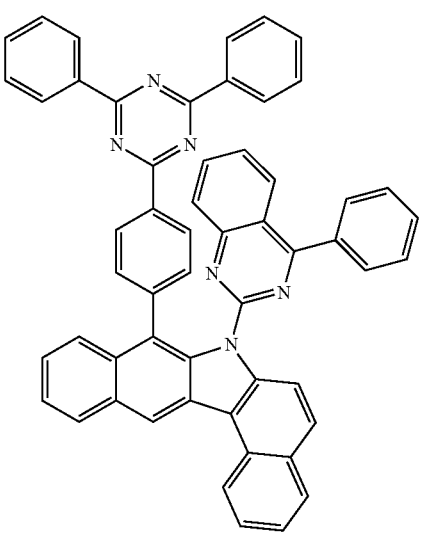
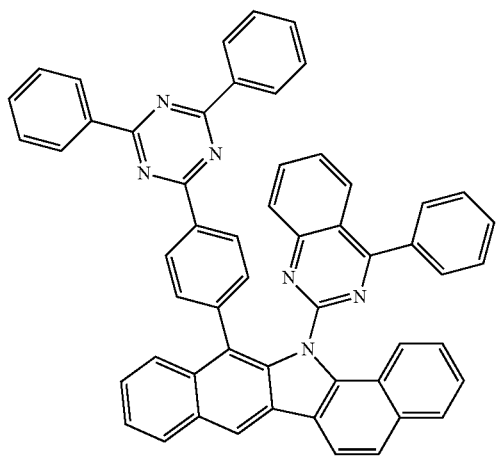 [SMILES: c1ccc(-c2nc(-c3ccccc3)nc(-c3ccc(-c4c5ccccc5cc5c6ccc7ccccc7c6n(-c6nc(-c7ccccc7)c7ccccc7n6)c45)cc3)n2)cc1]

135
-continued
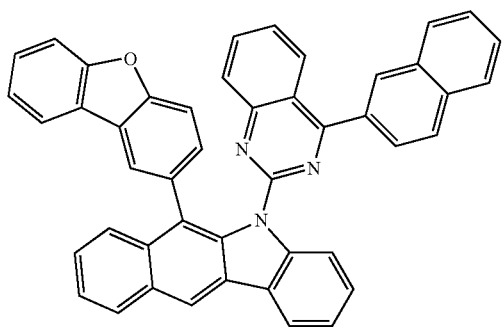
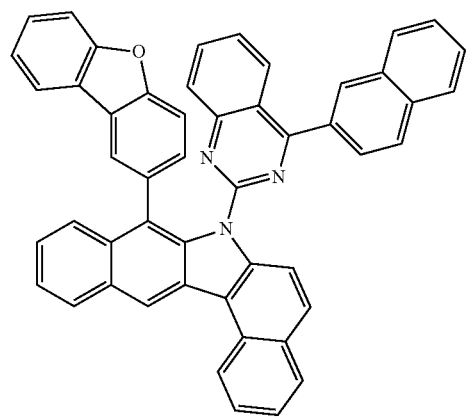
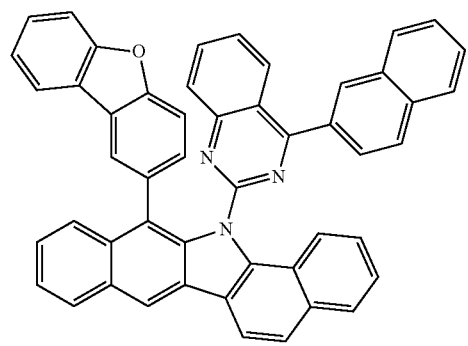
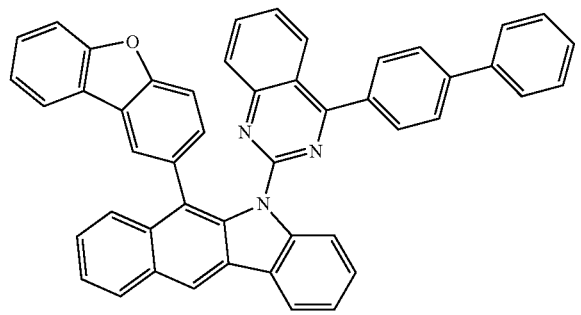
136
-continued
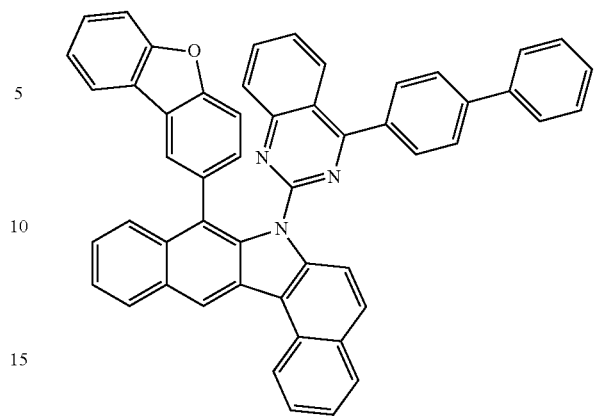
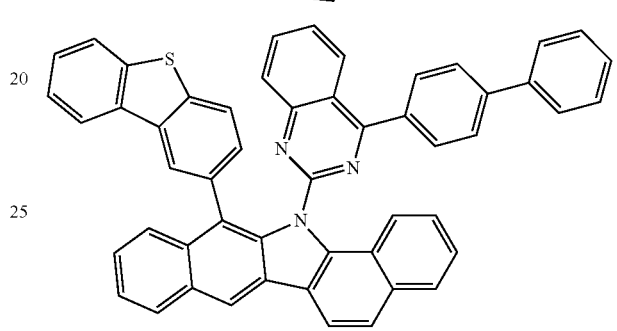
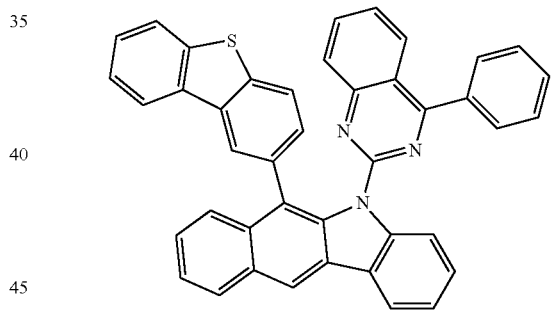
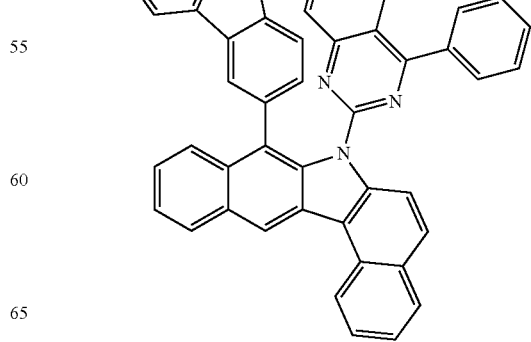

137
-continued
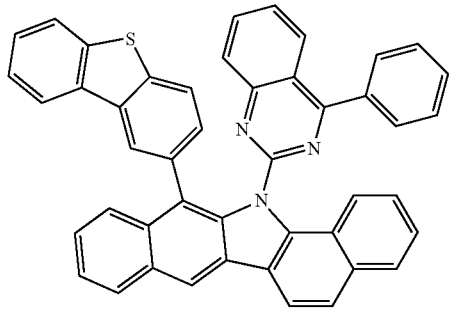
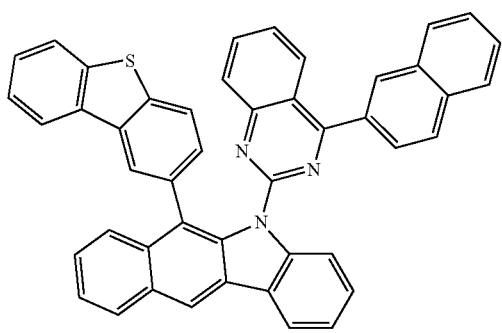
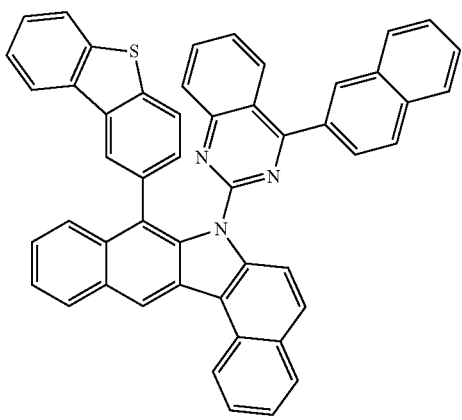
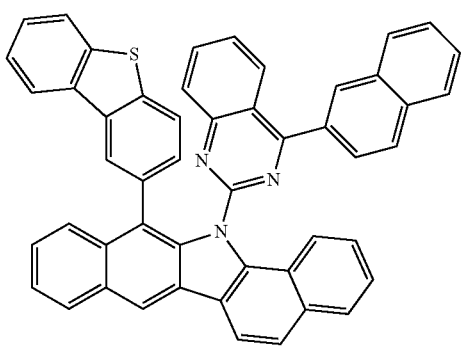
138
-continued
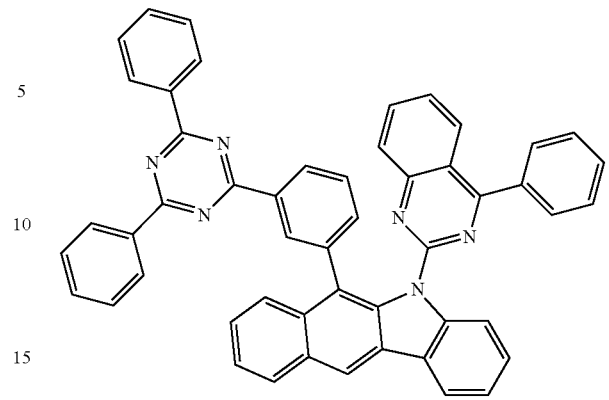
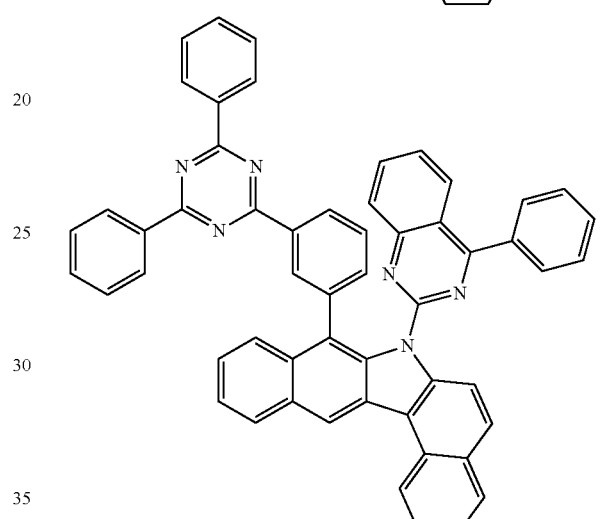
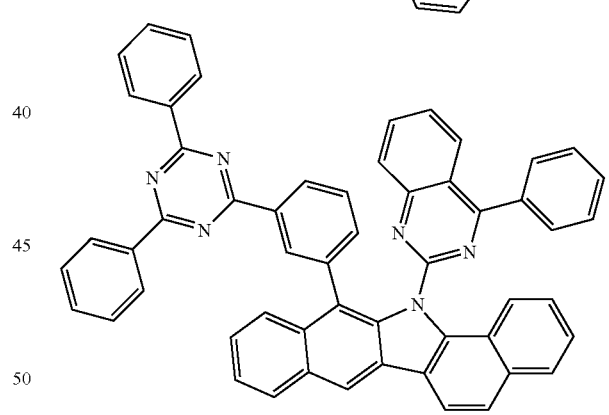
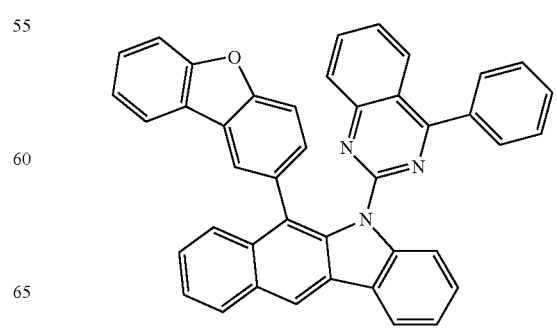

139
-continued
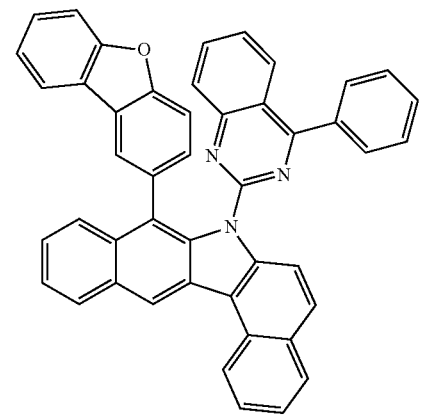
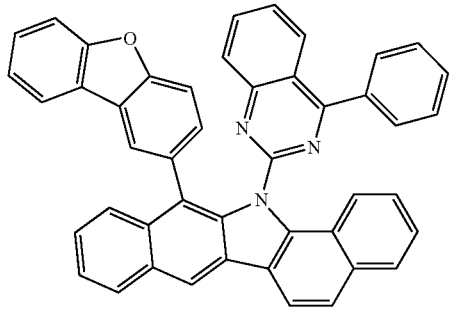
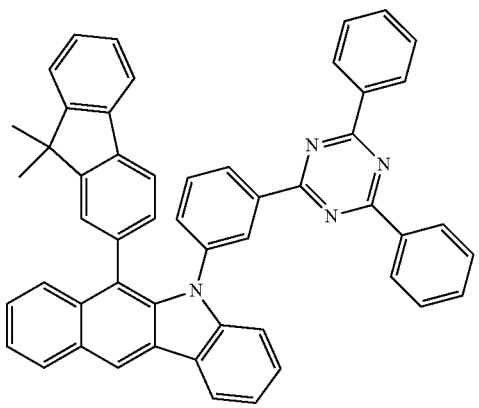
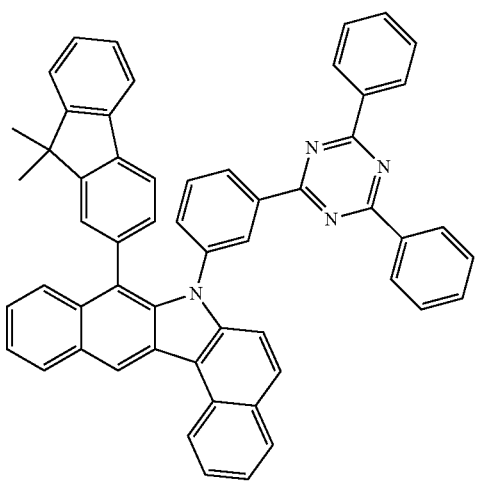
140
-continued
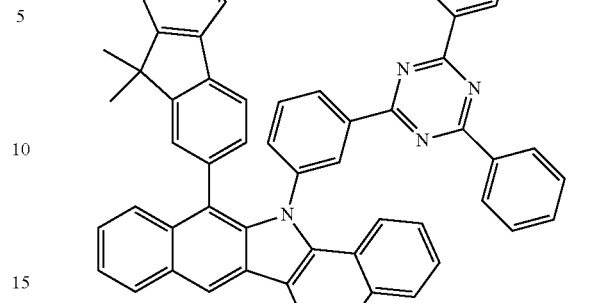
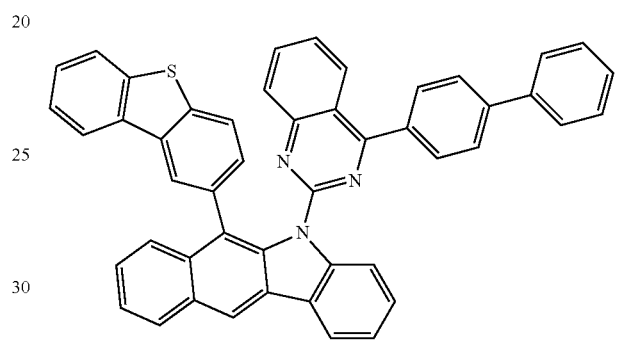
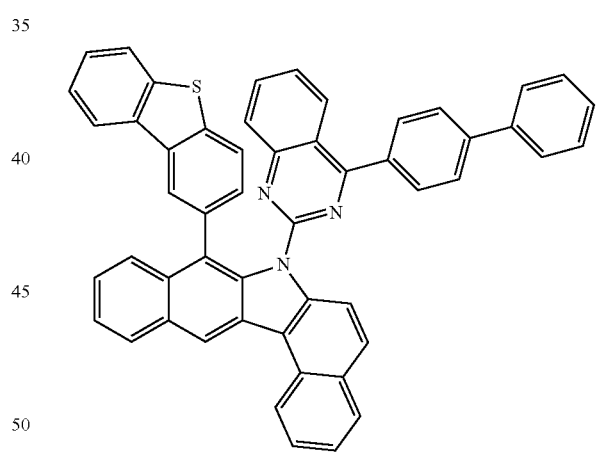
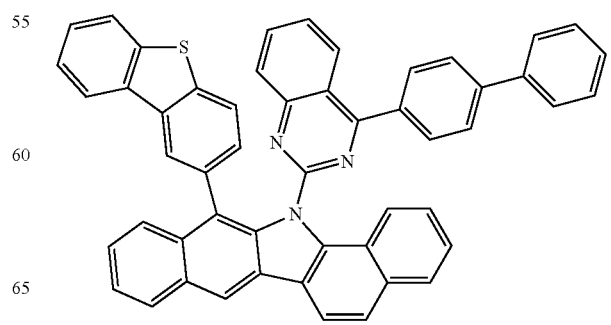

141
-continued
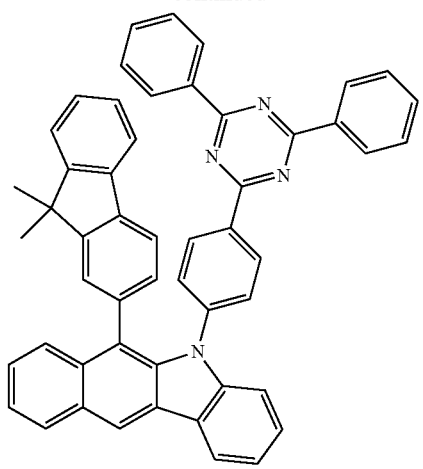
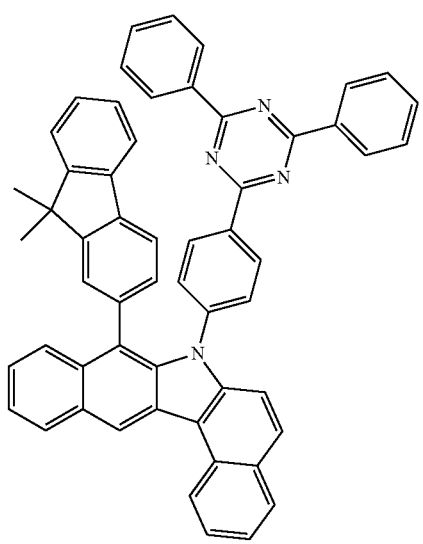
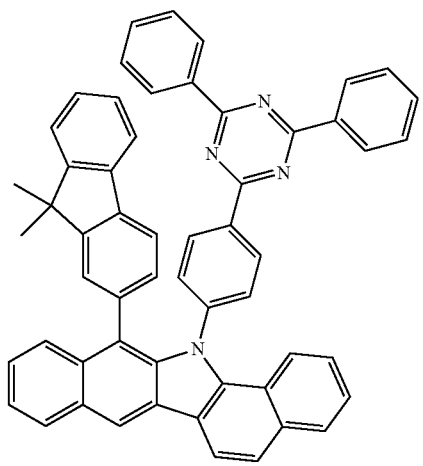
142
-continued
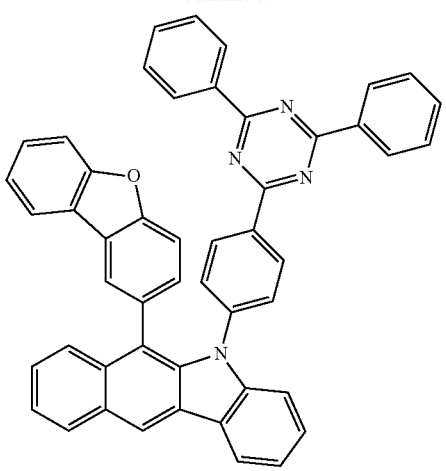
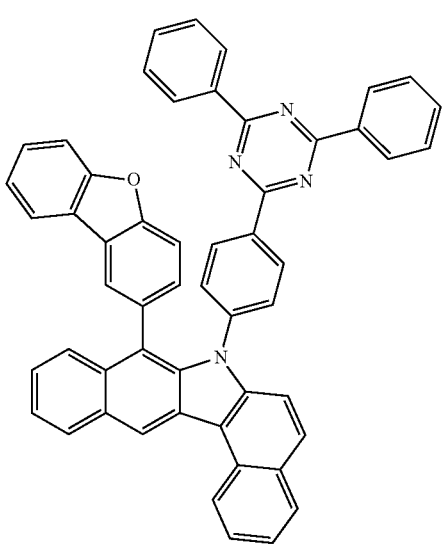
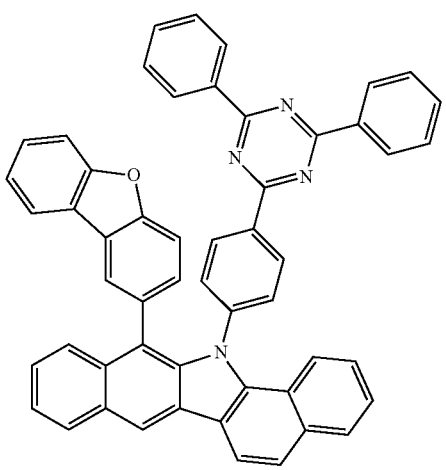

143
-continued
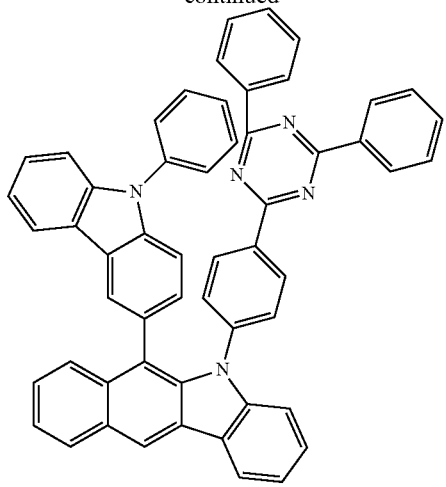
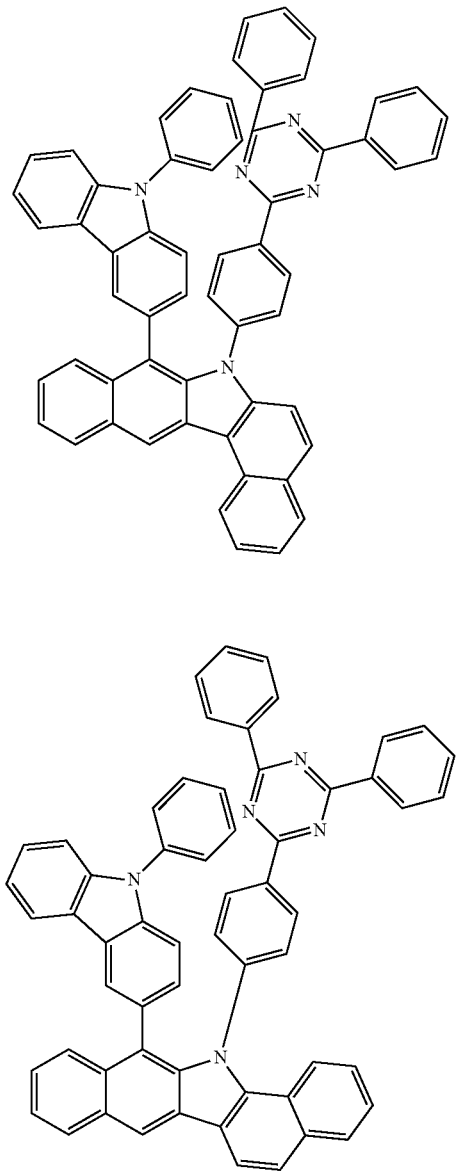
144
-continued
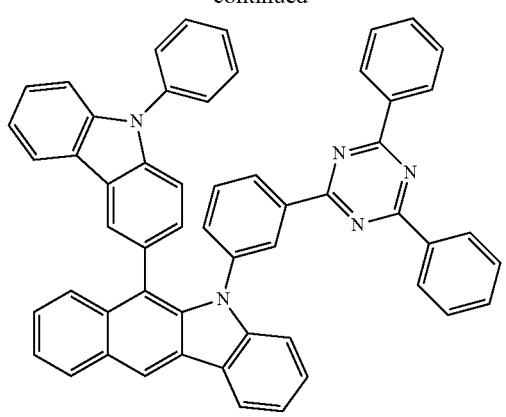
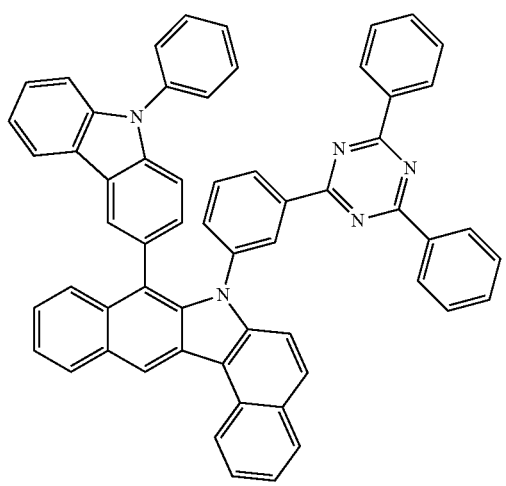
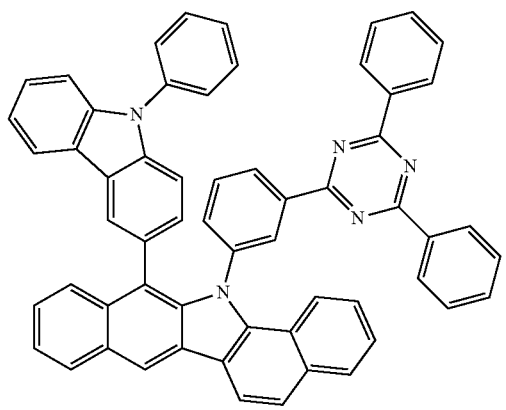
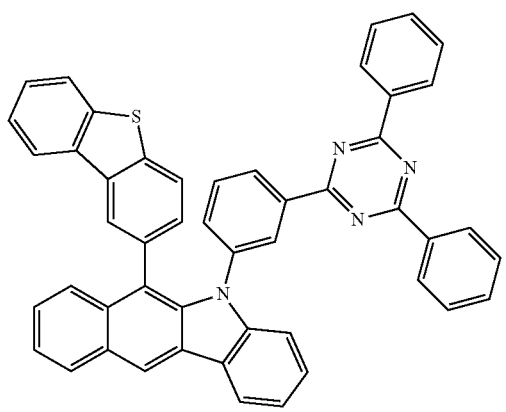

145
-continued
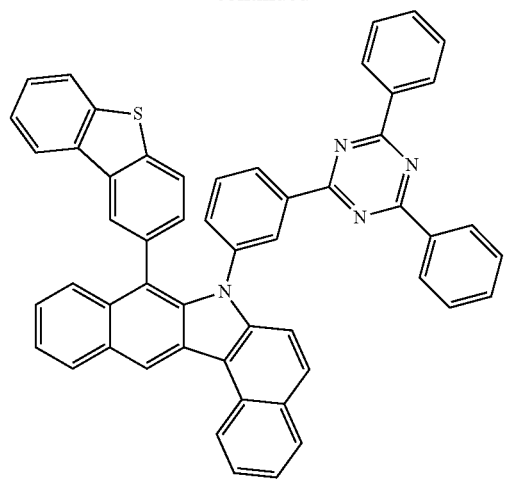
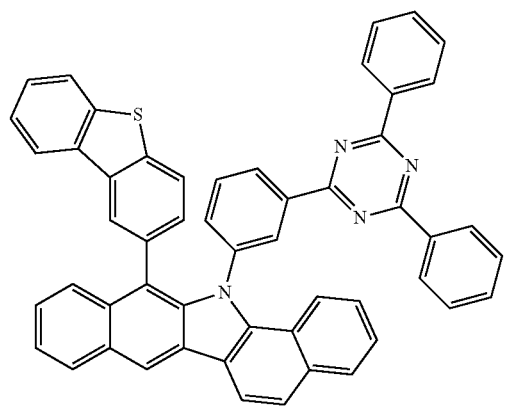
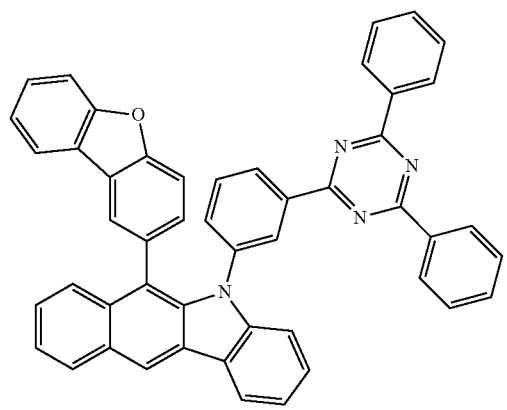
146
-continued
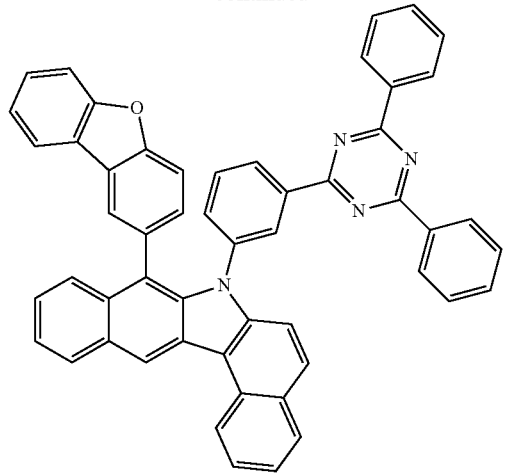
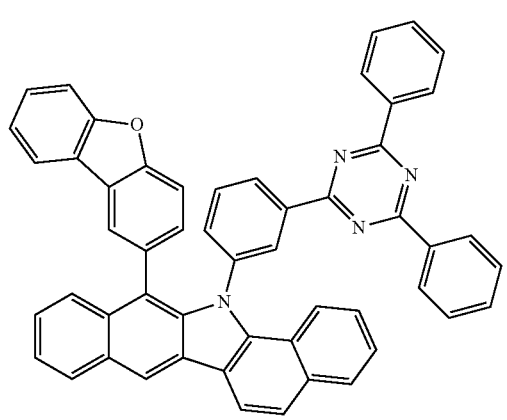
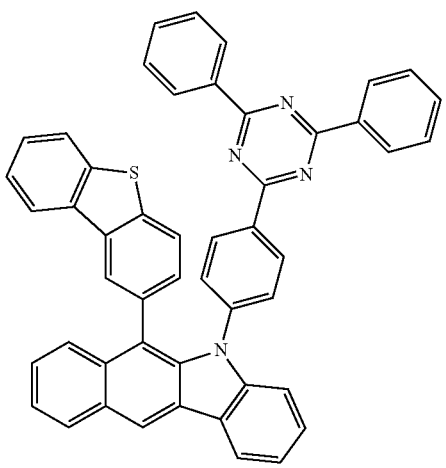

147
-continued
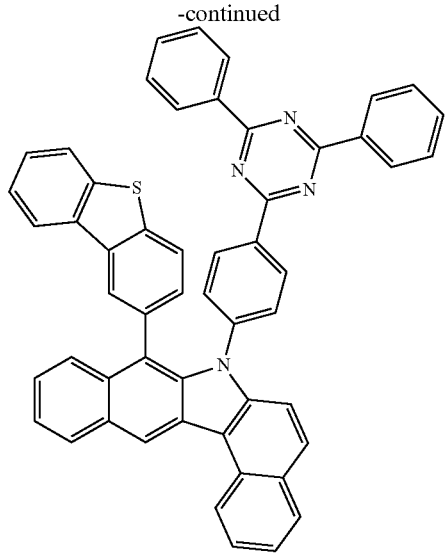
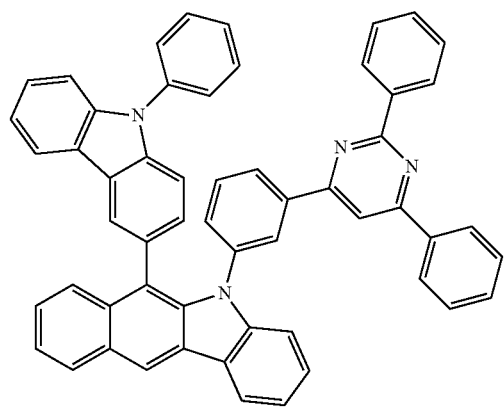
148
-continued
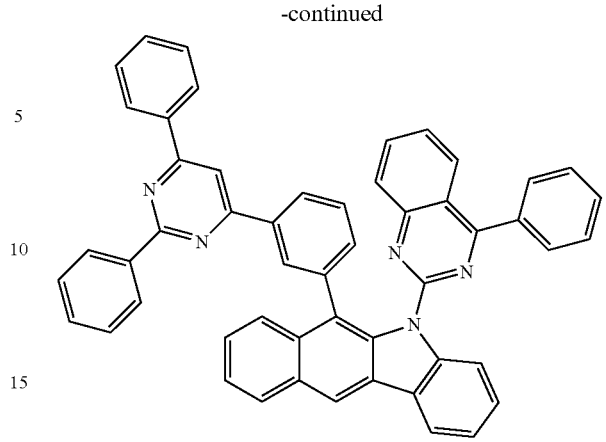
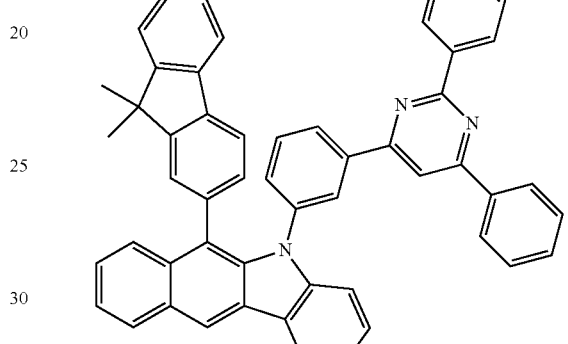
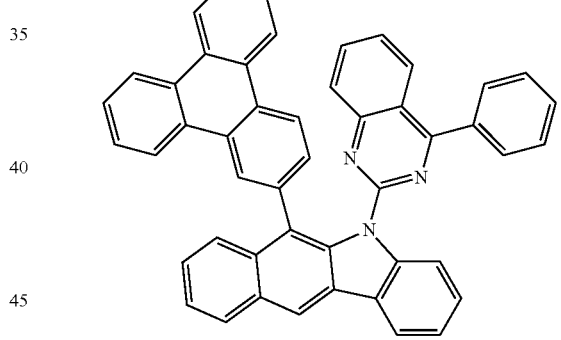
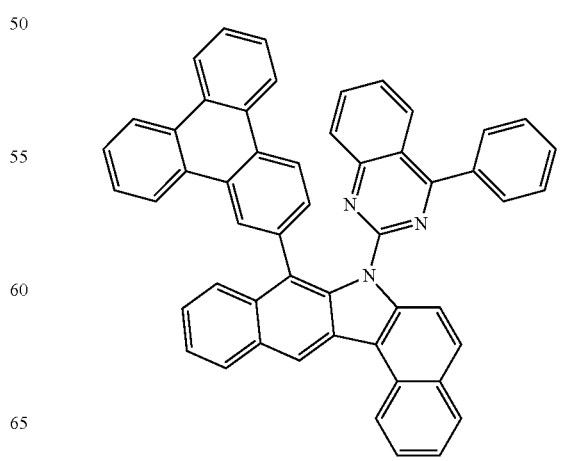

149
-continued
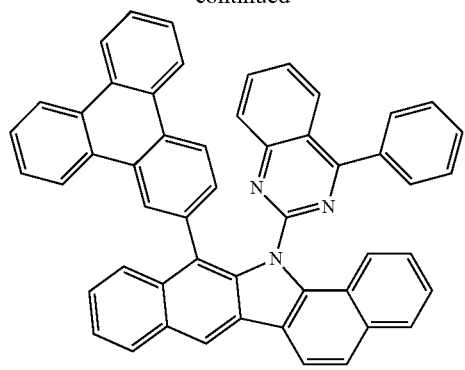
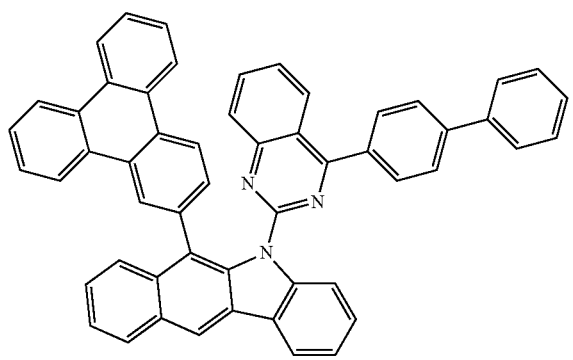
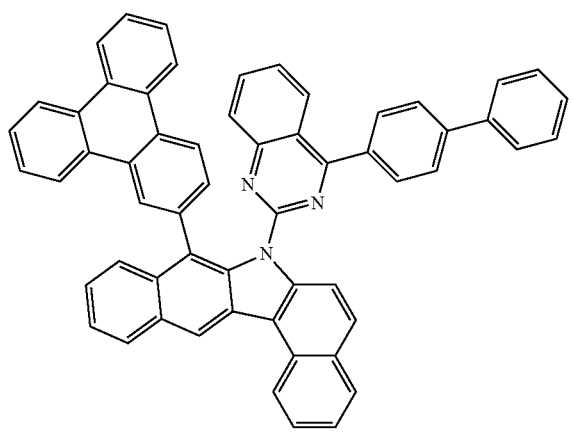
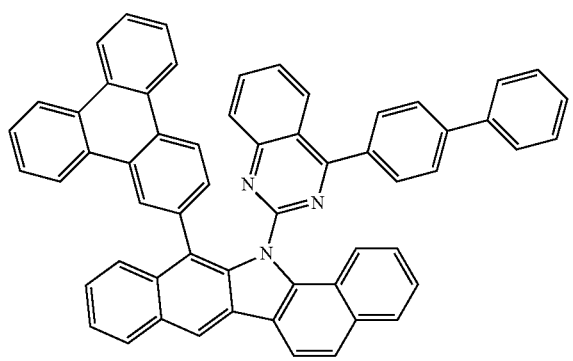
150
-continued
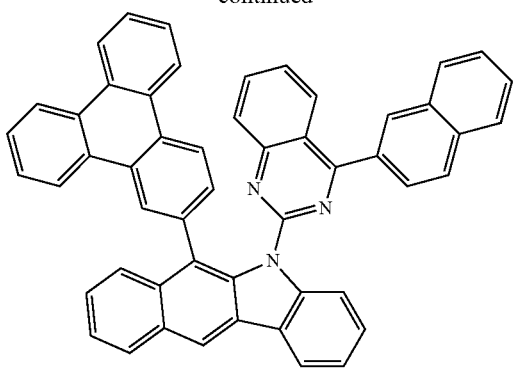
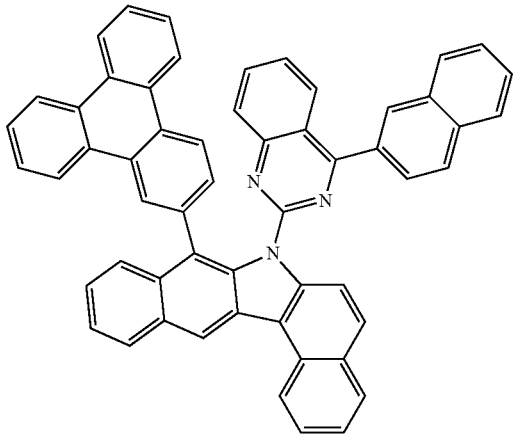
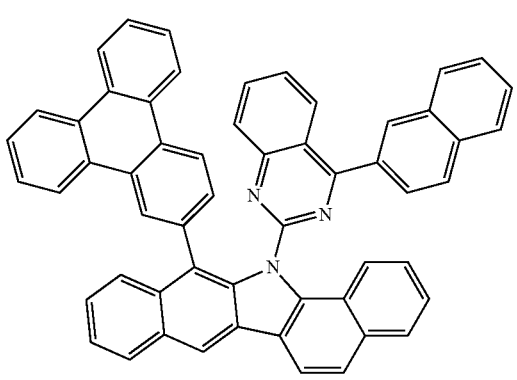 [SMILES: c1ccc2cc(-c3cc(-n4c5c(-c6ccc7c8ccccc8c8ccccc8c7c6)c6ccccc6cc5c5ccc6ccccc6c54)nc4ccccc34)ccc2c1]
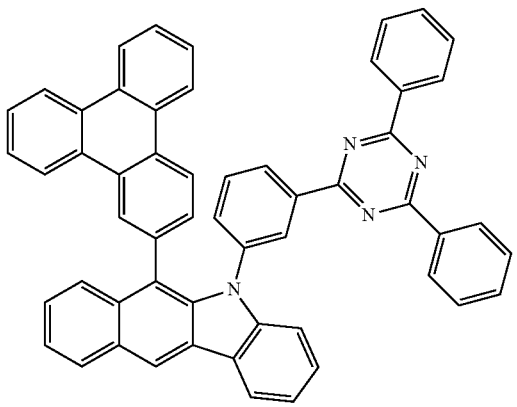

151
-continued
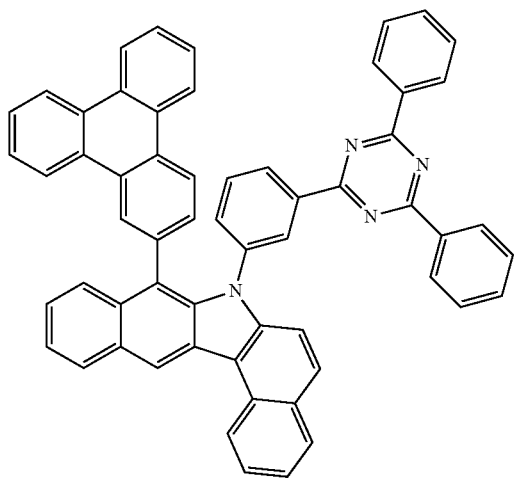
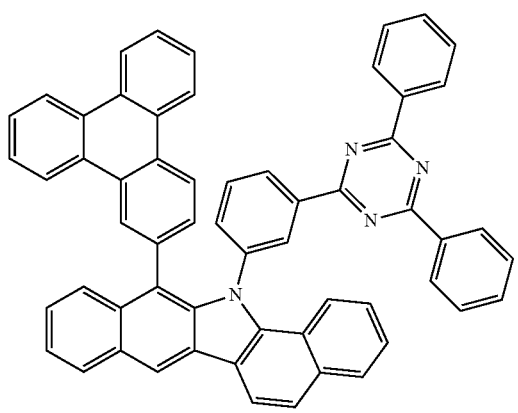
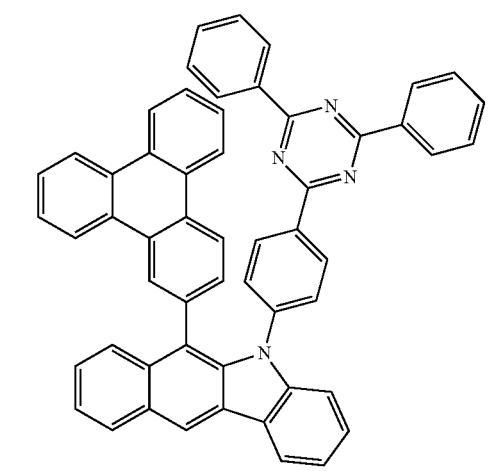
152
-continued
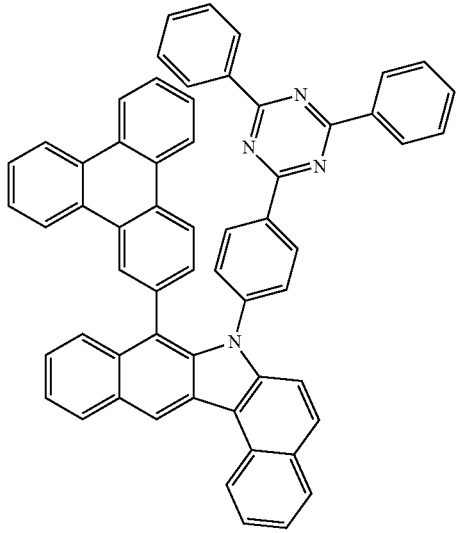
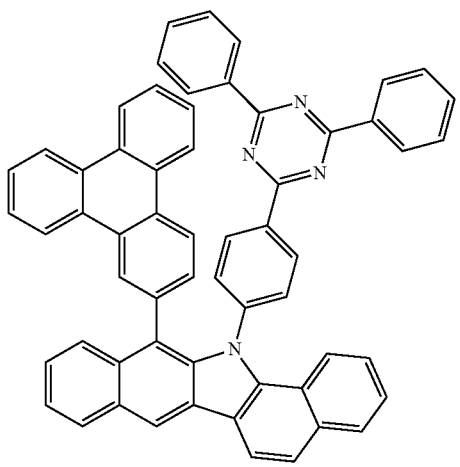
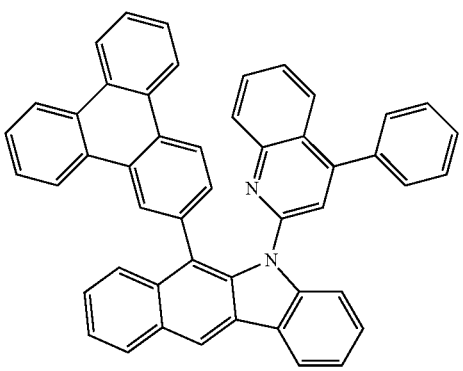

153
-continued
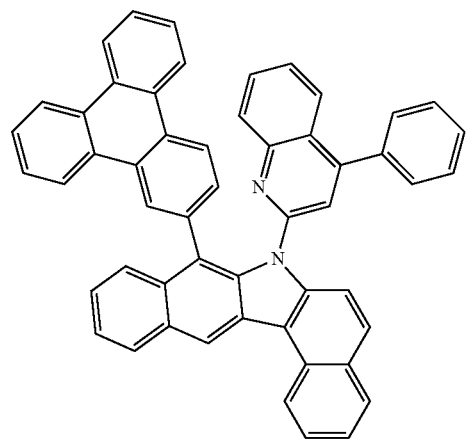
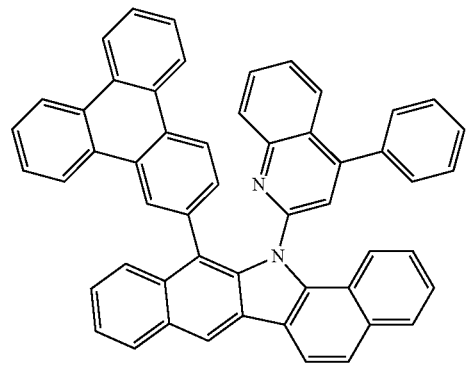
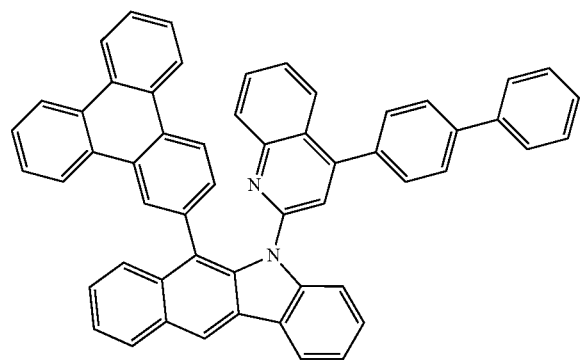
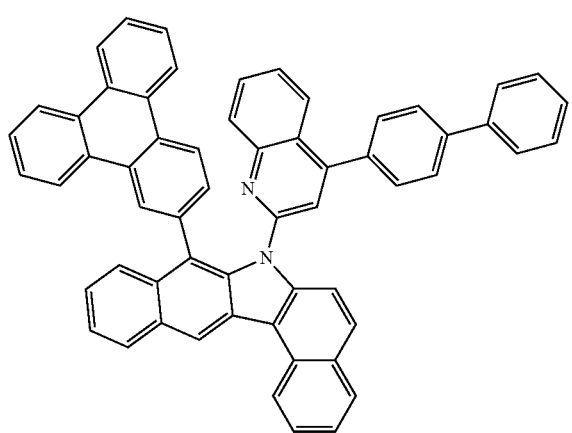
154
-continued
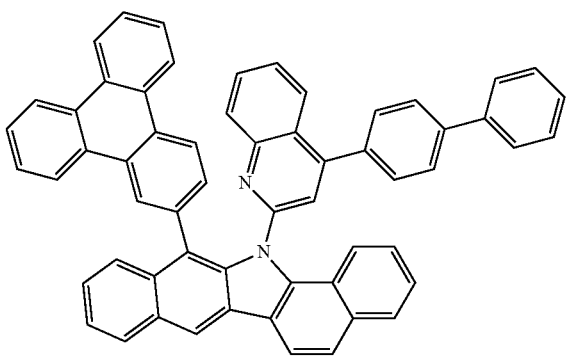
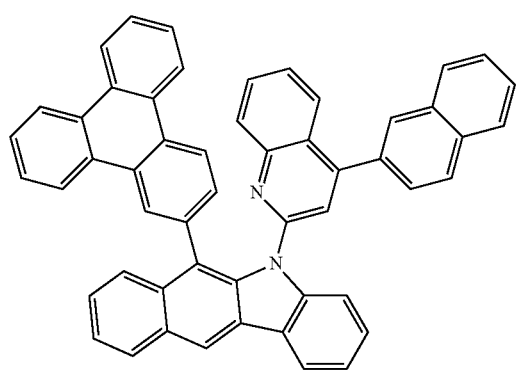
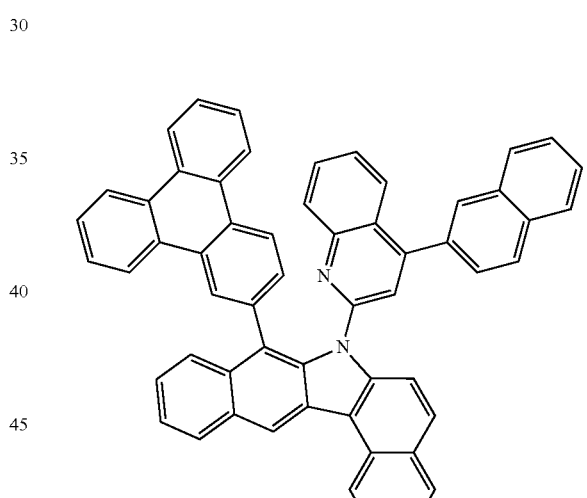
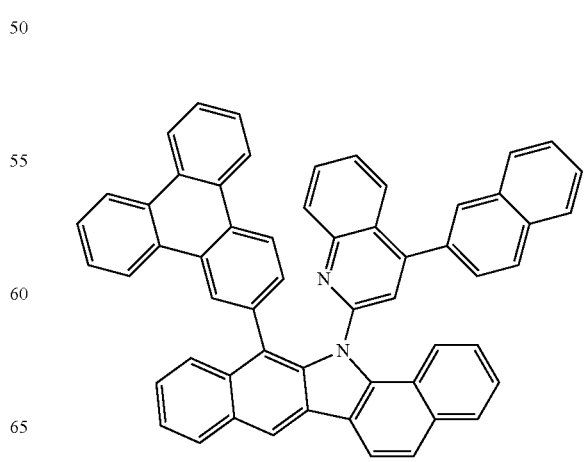

155
-continued

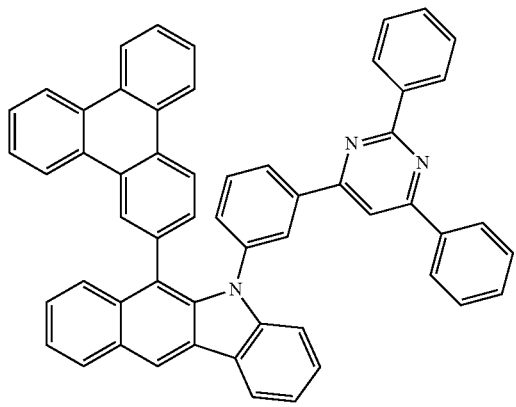

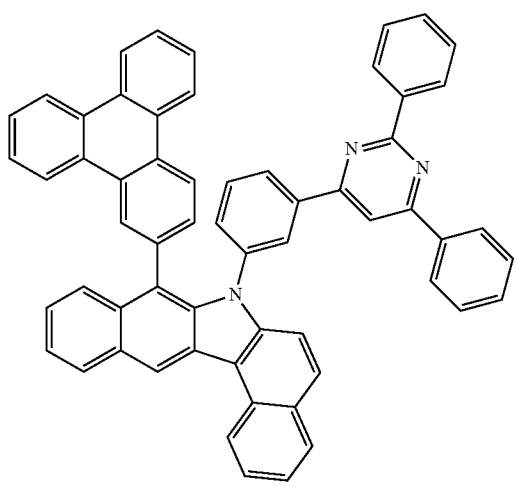

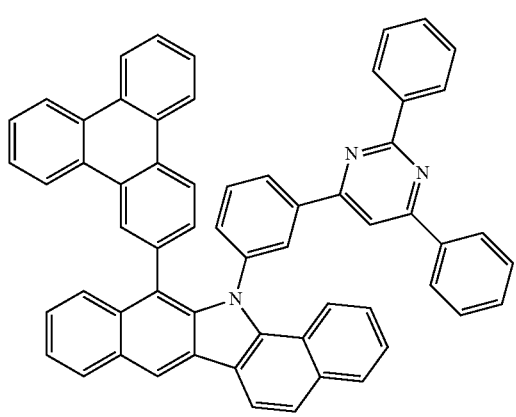

156
-continued

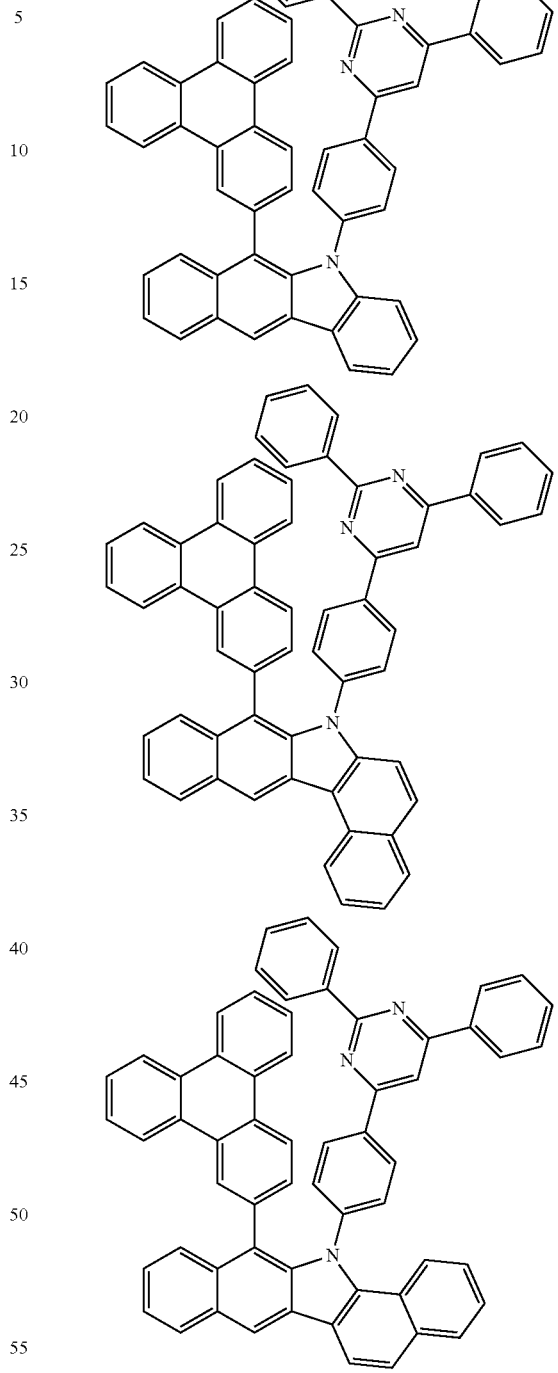

According to one embodiment of the present specification, the hetero-cyclic compound represented by Chemical Formula 1 may be represented by any one of Chemical Formulae 1-1 to 1-4, and among these, Chemical Formula 1-1 may be prepared using a method of the following General Formula 1, Chemical Formula 1-2 may be prepared using a method of the following General Formula 2, and Chemical Formula 1-4 may be prepared using a method of the following General Formula 3, however, the methods are not limited thereto.

[General Formula 1]
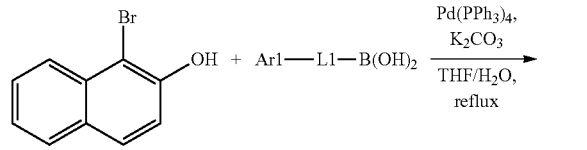
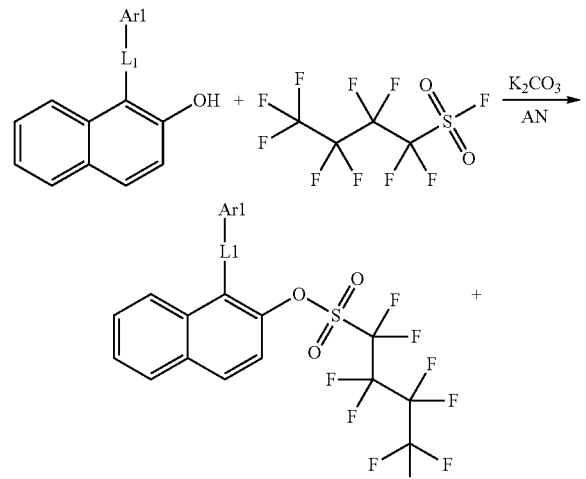
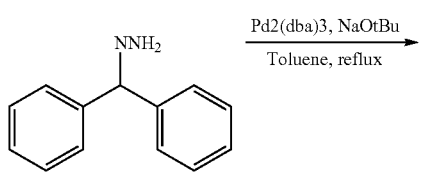
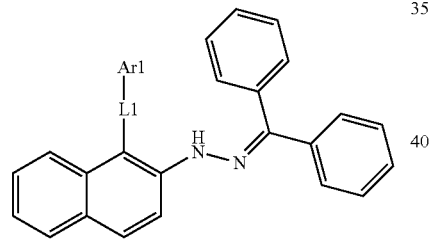
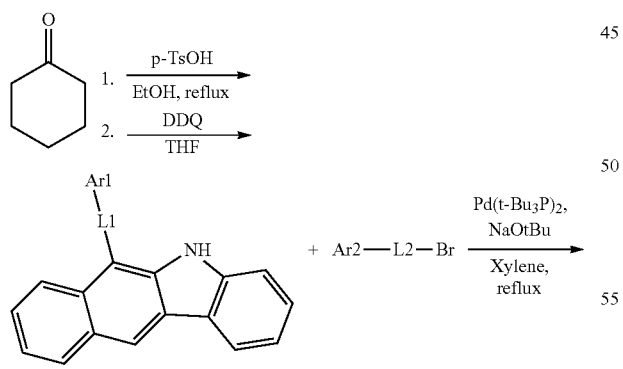
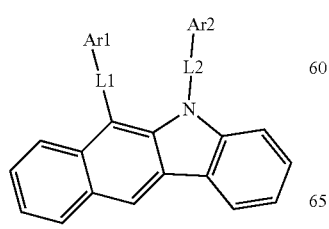
-continued
[General Formula 2]
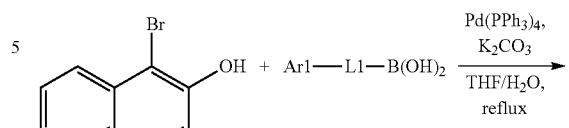
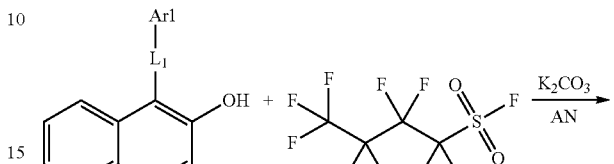
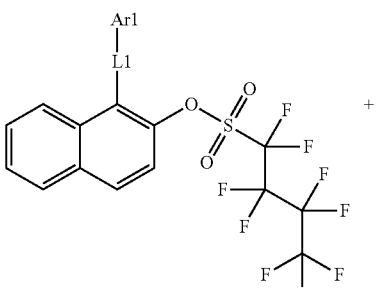
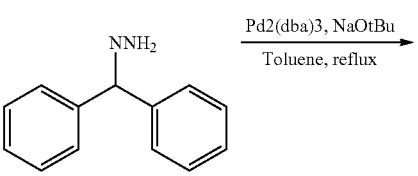
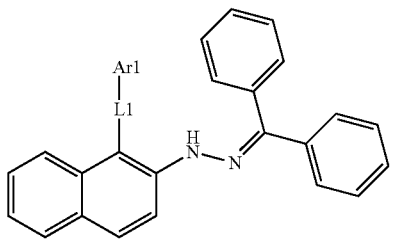
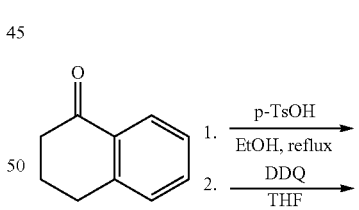
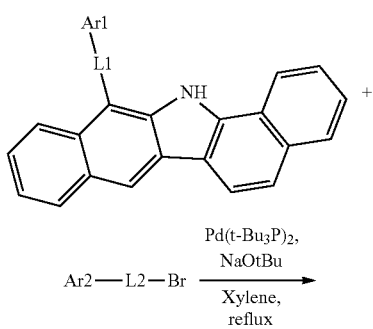

-continued

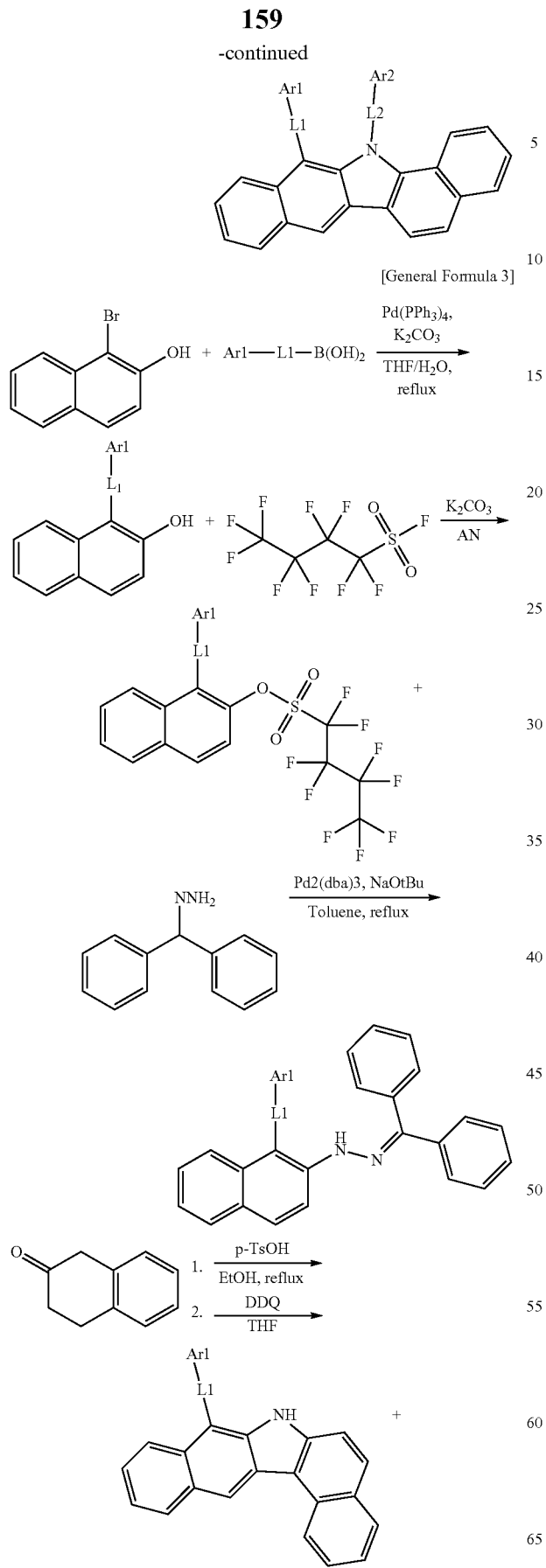

[General Formula 3]

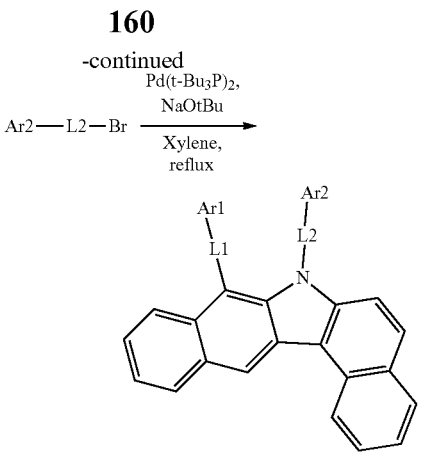

In General Formulae 1 to 3, definitions of L1, L2, Ar1 and Ar2 are the same as in Chemical Formula 1.

One embodiment of the present specification provides an organic light emitting device including a first electrode; a second electrode provided opposite to the first electrode; and one or more organic material layers provided between the first electrode and the second electrode, wherein one or more layers of the organic material layers include the hetero-cyclic compound described above.

According to one embodiment of the present specification, the organic material layer of the organic light emitting device of the present specification may be formed in a single layer structure, but may be formed in a multilayer structure in which two or more organic material layers are laminated. For example, the organic light emitting device of the present disclosure may have a structure including a hole injection layer, a hole transfer layer, an electron blocking layer, a light emitting layer, a hole blocking layer, an electron transfer layer, an electron injection layer and the like as the organic material layer. However, the structure of the organic light emitting device is not limited thereto, and may include less or more numbers of organic material layers.

For example, structures of an organic light emitting device of the present specification may be as shown in FIG. 1 and FIG. 2, but are not limited thereto.

FIG. 1 illustrates a structure of an organic light emitting device (10) in which a first electrode (30), a light emitting layer (40) and a second electrode (50) are consecutively laminated on a substrate (20). FIG. 1 is an exemplary structure of an organic light emitting device according to one embodiment of the present specification, and other organic material layers may be further included.

FIG. 2 illustrates a structure of an organic light emitting device in which a first electrode (30), a hole injection layer (60), a hole transfer layer (70), a light emitting layer (40), an electron transfer layer (80), an electron injection layer (90) and a second electrode (50) are consecutively laminated on a substrate (20). FIG. 2 is an exemplary structure of an organic light emitting device according to one embodiment of the present specification, and other organic material layers may be further included.

According to one embodiment of the present specification, the organic material layer includes a hole transfer layer, and the hole transfer layer includes the hetero-cyclic compound represented by Chemical Formula 1.

According to one embodiment of the present specification, the organic material layer includes an electron blocking layer, and the electron blocking layer includes the hetero-cyclic compound represented by Chemical Formula 1.

According to one embodiment of the present specification, the organic material layer includes a light emitting layer, and the light emitting layer includes the hetero-cyclic compound represented by Chemical Formula 1.

According to one embodiment of the present specification, the organic material layer includes a light emitting layer, and the light emitting layer includes the hetero-cyclic compound represented by Chemical Formula 1 as a host of the light emitting layer.

According to another embodiment of the present specification, the organic material layer includes a green light emitting layer, and the green light emitting layer includes the hetero-cyclic compound represented by Chemical Formula 1 as a host of the green light emitting layer.

According to another embodiment of the present specification, the organic material layer includes a red light emitting layer, and the red light emitting layer includes the hetero-cyclic compound represented by Chemical Formula 1 as a host of the red light emitting layer.

According to another embodiment of the present specification, the organic material layer includes a blue light emitting layer, and the blue light emitting layer includes the hetero-cyclic compound represented by Chemical Formula 1 as a host of the blue light emitting layer.

According to one embodiment of the present specification, the organic material layer includes a light emitting layer, and the light emitting layer includes the hetero-cyclic compound represented by Chemical Formula 1 as a dopant of the light emitting layer.

According to one embodiment of the present specification, the organic material layer includes a hole blocking layer, and the hole blocking layer includes the hetero-cyclic compound represented by Chemical Formula 1.

According to one embodiment of the present specification, the organic material layer includes an electron injection layer, and the electron injection layer includes the hetero-cyclic compound represented by Chemical Formula 1.

According to one embodiment of the present specification, the organic material layer includes an electron transfer layer, and the electron transfer layer includes the hetero-cyclic compound represented by Chemical Formula 1.

According to one embodiment of the present specification, the organic material layer may further include one or more layers selected from the group consisting of a hole injection layer, a hole transfer layer, a light emitting layer, an electron transfer layer and an electron injection layer.

According to one embodiment of the present specification, the organic material layer includes a light emitting layer, and the light emitting layer includes a compound represented by the following Chemical Formula 1-A.

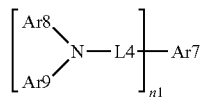

[Chemical Formula 1-A]

In Chemical Formula 1-A, n1 is an integer of 1 or greater,

Ar7 is a substituted or unsubstituted monovalent or higher benzofluorene group; a substituted or unsubstituted monovalent or higher fluoranthene group; a substituted or unsubstituted monovalent or higher pyrene group; or a substituted or unsubstituted monovalent or higher chrysene group, L4 is a direct bond; a substituted or unsubstituted arylene group; or a substituted or unsubstituted heteroarylene group, Ar8 and Ar9 are the same as or different from each other, and each independently a substituted or unsubstituted aryl group; a substituted or unsubstituted silyl group; a substituted or unsubstituted germanium group; a substituted or unsubstituted alkyl group; a substituted or unsubstituted arylalkyl group; or a substituted or unsubstituted heteroaryl group, or may bond to each other to form a substituted or unsubstituted ring, and when n1 is 2 or greater, structures in the 2 or more parentheses are the same or different from each other.

According to one embodiment of the present specification, the organic material layer includes a light emitting layer, and the light emitting layer includes the compound represented by Chemical Formula 1-A as a dopant of the light emitting layer.

According to one embodiment of the present specification, L4 is a direct bond.

According to one embodiment of the present specification, n1 is 2.

In one embodiment of the present specification, Ar7 is a divalent pyrene group unsubstituted or substituted with deuterium, a methyl group, an ethyl group or a tert-butyl group.

According to one embodiment of the present specification, Ar8 and Ar9 are the same as or different from each other, and each independently a substituted or unsubstituted aryl group having 6 to 30 carbon atoms.

According to one embodiment of the present specification, Ar8 and Ar9 are the same as or different from each other, and each independently an aryl group unsubstituted or substituted with a germanium group substituted with an alkyl group.

According to one embodiment of the present specification, Ar8 and Ar9 are the same as or different from each other, and each independently an aryl group unsubstituted or substituted with a trimethylgermanium group.

According to one embodiment of the present specification, Ar8 and Ar9 are the same as or different from each other, and each independently a substituted or unsubstituted phenyl group.

According to one embodiment of the present specification, Ar8 and Ar9 are a phenyl group unsubstituted or substituted with a trimethylgermanium group.

According to one embodiment of the present specification, Chemical Formula 1-A is represented by the following compound.

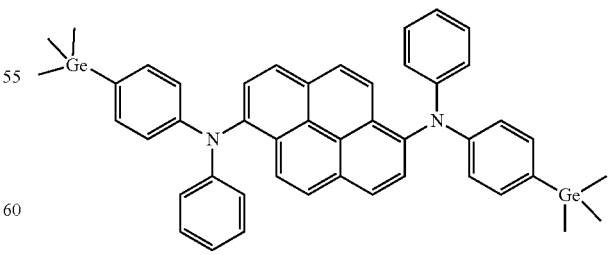

According to one embodiment of the present specification, the organic material layer includes a light emitting layer, and the light emitting layer includes a compound represented by the following Chemical Formula 2-A.

[Chemical Formula 2-A]

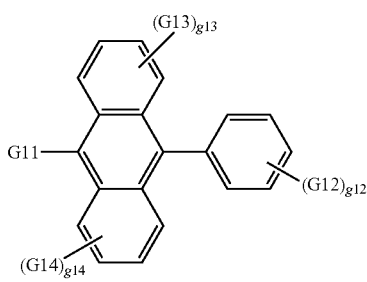

In Chemical Formula 2-A,

G11 is a phenyl group, a 1-naphthyl group, a 2-naphthyl group, a 1-anthryl group, a 2-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 3-methyl-2-naphthyl group, a 4-methyl-1-naphthyl group, or the following chemical formula

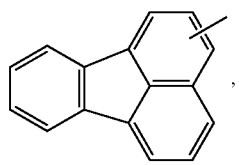

G12 is a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, an o-tolyl group, a m-tolyl group, a p-tolyl group, a p-t-butylphenyl group, a p-(2-phenylpropyl) phenyl group, a 3-methyl-2-naphthyl group, a 4-methyl-1-naphthyl group, a 4-methyl-1-anthryl group, a 4'-methylbiphenylyl group, a 4"-t-butyl-p-terphenyl-4-yl group or a 3-fluoranthenyl group, G13 and G14 are the same as or different from each other, and each independently hydrogen; a substituted or unsubstituted alkyl group; a substituted or unsubstituted alkoxy group; a substituted or unsubstituted aryl group; or a substituted or unsubstituted heteroaryl group, g12 is an integer of 1 to 5, g13 and g14 are each an integer of 1 to 4, and when g12 to g14 are each 2 or greater, structures in the 2 or more parentheses are the same as or different from each other.

According to one embodiment of the present specification, the organic material layer includes a light emitting layer, and the light emitting layer includes the compound represented by Chemical Formula 2-A as a host of the light emitting layer.

According to one embodiment of the present specification, G11 is a 1-naphthyl group.

According to one embodiment of the present specification, G12 is a 2-naphthyl group.

According to one embodiment of the present specification, G13 and G14 are hydrogen.

According to one embodiment of the present specification, Chemical Formula 2-A is represented by the following compound.

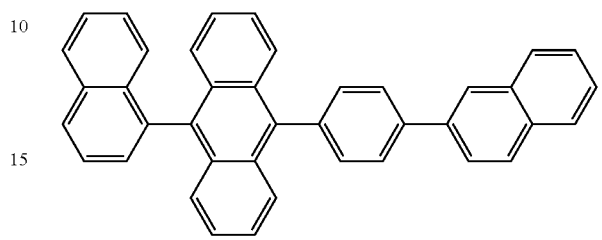

The organic light emitting device of the present specification may be manufactured using materials and methods known in the art, except that one or more layers of the organic material layers include the hetero-cyclic compound of the present specification, that is, the hetero-cyclic compound represented by Chemical Formula 1.

When the organic light emitting device includes a plurality of organic material layers, the organic material layers may be formed with materials the same as or different from each other.

For example, the organic light emitting device of the present specification may be manufactured by consecutively laminating a first electrode, an organic material layer and a second electrode on a substrate. Herein, the organic light emitting device may be manufactured by forming a first electrode on a substrate by depositing a metal, a metal oxide having conductivity, or an alloy thereof using a physical vapor deposition (PVD) method such as sputtering or e-beam evaporation, and forming an organic material layer including a hole injection layer, a hole transfer layer, a light emitting layer and an electron transfer layer thereon, and then depositing a material capable of being used as a second electrode thereon. In addition to such a method, the organic light emitting device may also be manufactured by consecutively depositing a second electrode material, an organic material layer and a first electrode material on a substrate. In addition, the hetero-cyclic compound represented by Chemical Formula 1 may be formed into an organic material layer using a solution coating method as well as a vacuum deposition method when manufacturing the organic light emitting device. Herein, the solution coating method means spin coating, dip coating, doctor blading, inkjet printing, screen printing, a spray method, roll coating and the like, but is not limited thereto.

According to one embodiment of the present specification, the first electrode is an anode, and the second electrode is a cathode.

According to another embodiment of the present specification, the first electrode is a cathode, and the second electrode is an anode.

As the anode material, materials having large work function are normally preferable so that hole injection to an organic material layer is smooth. Specific examples of the anode material capable of being used in the present disclosure include metals such as vanadium, chromium, copper, zinc and gold, or alloys thereof; metal oxides such as zinc oxide, indium oxide, indium tin oxide (ITO) and indium zinc oxide (IZO); combinations of metals and oxides such as ZnO:Al or SnO$_2$:Sb; conductive polymers such as poly(3-methylthiophene), poly[3,4-(ethylene-1,2-dioxy)thiophene] (PEDOT), polypyrrole and polyaniline, but are not limited thereto.

As the cathode material, materials having small work function are normally preferable so that electron injection to an organic material layer is smooth. Specific examples of the cathode material include metals such as magnesium, calcium, sodium, potassium, titanium, indium, yttrium, lithium, gadolinium, aluminum, silver, tin and lead, or alloys thereof; multilayer structure materials such as LiF/Al, LiO$_2$/Al or Mg/Ag, and the like, but are not limited thereto.

The hole injection layer is a layer that injects holes from an electrode, and the hole injection material is preferably a compound that has an ability to transfer holes, therefore, has a hole injection effect in an anode, has an excellent hole injection effect for a light emitting layer or a light emitting material, prevents excitons generated in the light emitting layer from moving to an electron injection layer or an electron injection material, and in addition, has an excellent thin film forming ability. The highest occupied molecular orbital (HOMO) of the hole injection material is preferably in between the work function of an anode material and the HOMO of surrounding organic material layers. Specific examples of the hole injection material include metal porphyrins, oligothiophene, arylamine-based organic materials, hexanitrile hexaazatriphenylene-based organic materials, quinacridone-based organic materials, perylene-based organic materials, anthraquinone, and polyaniline- and polythiophene-based conductive polymers, and the like, but are not limited thereto.

The hole transfer layer is a layer that receives holes from a hole injection layer and transfers the holes to a light emitting layer, and as the hole transfer material, materials capable of receiving holes from an anode or a hole injection layer, moving the holes to a light emitting layer, and having high mobility for the holes are suitable. Specific examples thereof include arylamine-based organic materials, conductive polymers, block copolymers having conjugated parts and non-conjugated parts together, and the like, but are not limited thereto.

The light emitting material of the light emitting layer is a material capable of emitting light in a visible light region by receiving holes and electrons from a hole transfer layer and an electron transfer layer, respectively, and binding the holes and the electrons, and is preferably a material having favorable quantum efficiency for fluorescence or phosphorescence. Specific examples thereof include 8-hydroxyquinoline aluminum complexes (Alq$_3$); carbazole series compounds; dimerized styryl compounds; BAlq; 10-hydroxybenzo quinoline-metal compounds; benzoxazole, benzthiazole and benzimidazole series compounds; poly(p-phenylenevinylene) (PPV) series polymers; spiro compounds; polyfluorene, rubrene, and the like, but are not limited thereto.

The light emitting layer may include a host material and a dopant material. The host material includes fused aromatic ring derivatives, heteroring-containing compounds or the like. Specifically, the fused aromatic ring derivative includes anthracene derivatives, pyrene derivatives, naphthalene derivatives, pentacene derivatives, phenanthrene compounds, fluoranthene compounds and the like, and the heteroring-containing compound includes carbazole derivatives, dibenzofuran derivatives, ladder-type furan compounds, pyrimidine derivatives and the like, but the material is not limited thereto.

The dopant material includes aromatic amine derivatives, styrylamine compounds, boron complexes, fluoranthene compounds, metal complexes and the like. Specifically, the aromatic amine derivative is a fused aromatic ring derivative having a substituted or unsubstituted arylamine group and includes arylamine group-including pyrene, anthracene, chrysene, peryflanthene and the like, and the styrylamine compound is a compound in which substituted or unsubstituted arylamine is substituted with at least one arylvinyl group, and one, two or more substituents selected from the group consisting of an aryl group, a silyl group, an alkyl group, a cycloalkyl group and an arylamine group are substituted or unsubstituted. Specifically, styrylamine, styryldiamine, styryltriamine, styryltetramine or the like is included, but the styrylamine compound is not limited thereto. In addition, the metal complex includes iridium complexes, platinum complexes or the like, but is not limited thereto.

The electron transfer layer is a layer that receives electrons from an electron injection layer and transfers the electrons to a light emitting layer, and as the electron transfer material, materials capable of favorably receiving electrons from a cathode, moving the electrons to a light emitting layer, and having high mobility for the electrons are suitable. Specific examples thereof include Al complexes of 8-hydroxyquinoline; complexes including Alq$_3$; organic radical compounds; hydroxyflavon-metal complexes, and the like, but are not limited thereto. The electron transfer layer may be used together with any desired cathode material as used in the art. Particularly, examples of the suitable cathode material include common materials that have small work function, and in which an aluminum layer or a silver layer follows. Specifically, the cathode material includes cesium, barium, calcium, ytterbium and samarium, and in each case, an aluminum layer or a silver layer follows.

The electron injection layer is a layer that injects electrons from an electrode, and the electron injection material is preferably a compound that has an ability to transfer electrons, has an electron injection effect from a cathode, has an excellent electron injection effect for a light emitting layer or a light emitting material, prevents excitons generated in the light emitting layer from moving to a hole injection layer, and in addition, has an excellent thin film forming ability. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone or the like, and derivatives thereof, metal complex compounds, nitrogen-containing 5-membered ring derivatives, and the like, but are not limited thereto.

The metal complex compound includes 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato) gallium, bis(10-hydroxybenzo[h]quinolinato)berylium, bis(10-hydroxybenzo[h]quinolinato)zinc, bis(2-methyl-8-quinolinato)chlorogallium, bis(2-methyl-8-quinolinato)(0-cresolato)gallium, bis(2-methyl-8-quinolinato) (1-naphtholato)aluminum, bis(2-methyl-8-quinolinato) (2-naphtholato)gallium and the like, but is not limited thereto.

The organic light emitting device according to the present specification may be a top-emission type, a bottom-emission type or a dual-emission type depending on the materials used.

According to one embodiment of the present specification, the hetero-cyclic compound represented by Chemical Formula 1 may be included in organic solar cells or organic transistors in addition to organic light emitting devices.

Hereinafter, the present specification will be described in detail with reference to examples. However, the examples according to the present specification may be modified to various other forms, and the scope of the present specification is not to be construed as being limited to the examples described below. Examples of the present specification are provided in order to more completely describe the present specification to those having average knowledge in the art.

Synthesis Example

Synthesis of Compounds A to C

[Reaction Formula 1]

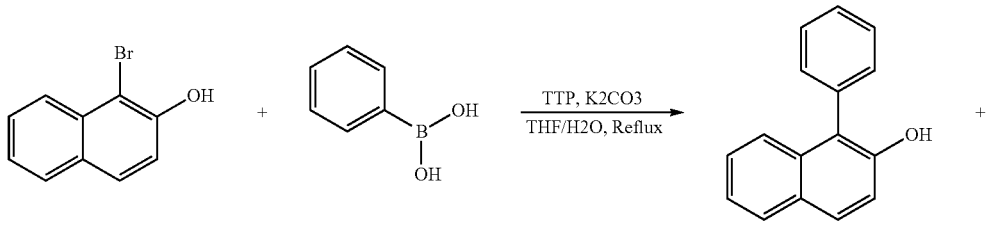

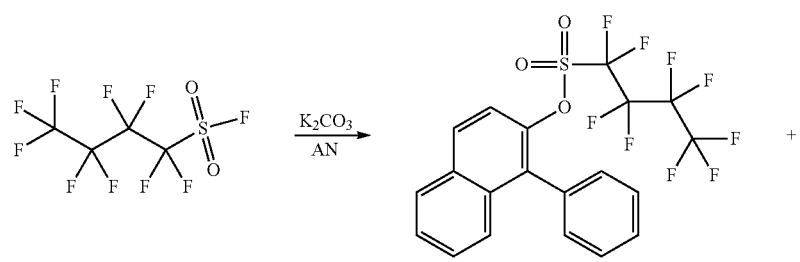

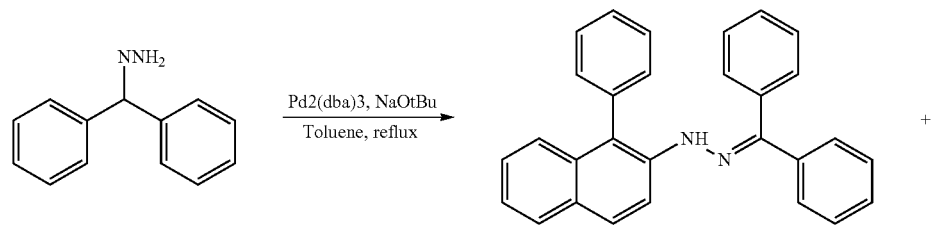

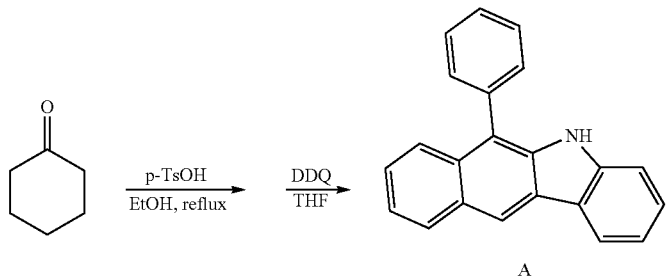

A

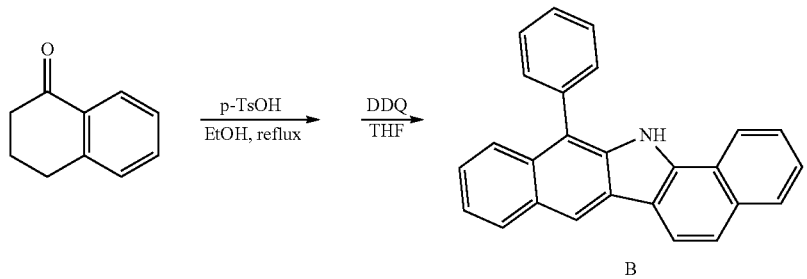

B

-continued

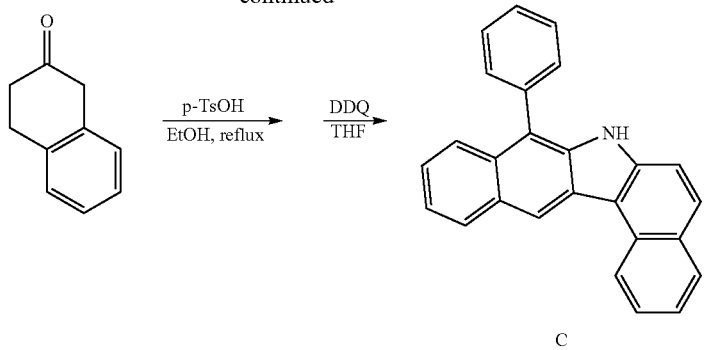

C

Using Reaction Formula 1, Compounds A to C, which are intermediates, may be synthesized.

Preparation Example 1

Synthesis of Compound 1

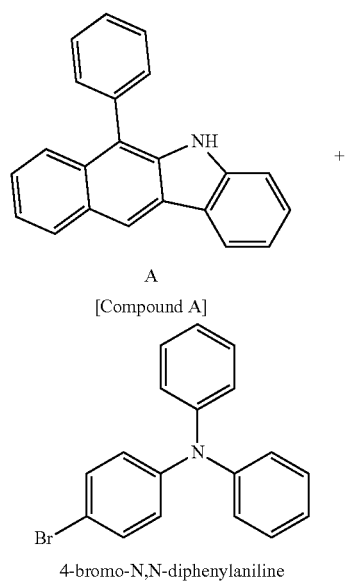

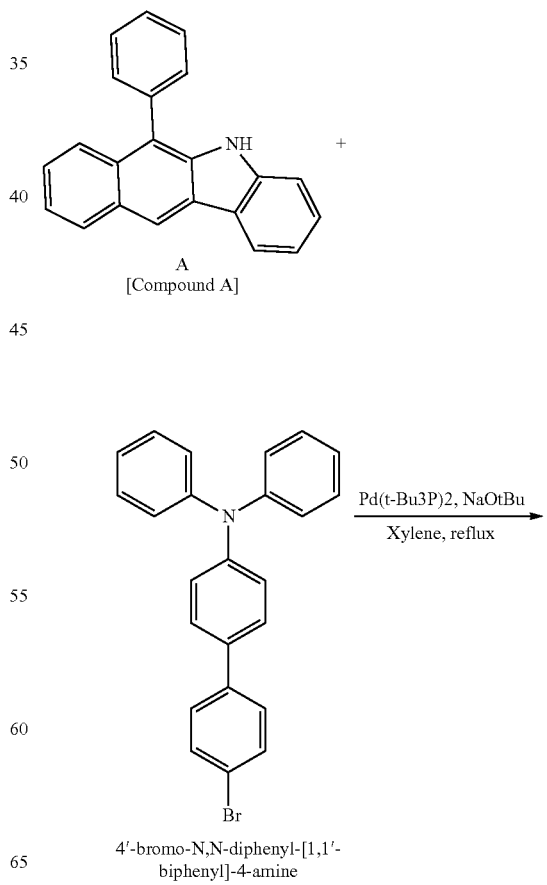

After completely dissolving Compound A (8.0 g, 27.30 mmol) and 4-bromo-N,N-diphenylaniline (8.41 g, 25.94 mmol) in 180 ml of xylene in a 500 ml round bottom flask under nitrogen atmosphere, sodium tert-butoxide (3.41 g, 35.49 mol) and then bis(tri-tert-butylphosphine) palladium (0) (0.07 g, 0.14 mmol) were added thereto, and the result was heated and stirred for 2 hours. After lowering the temperature to room temperature, the result was filtered to remove the base, xylene was vacuum concentrated, and then the result was columned using tetrahydrofuran:hexane=1:25 to prepare Compound 1 (9.84 g, yield: 67%).

MS[M+H]$^+$=537

Preparation Example 2

Synthesis of Compound 2

-continued

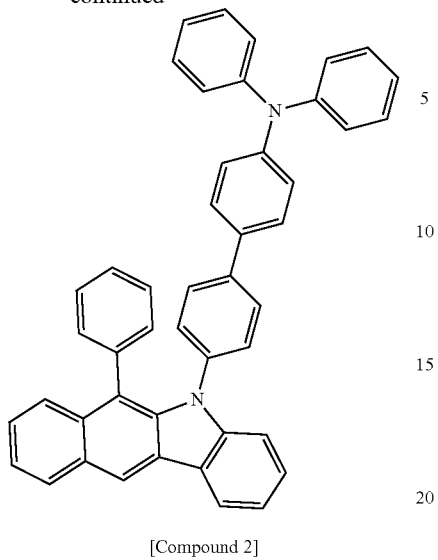

[Compound 2]

After completely dissolving Compound A (8.0 g, 27.30 mmol) and 4'-bromo-N,N-diphenyl-[1,1'-biphenyl]-4-amine (10.38 g, 25.94 mmol) in 200 ml of xylene in a 500 ml round bottom flask under nitrogen atmosphere, sodium tert-butoxide (3.41 g, 35.49 mol) and then bis(tri-tert-butylphosphine) palladium(0) (0.07 g, 0.14 mmol) were added thereto, and the result was heated and stirred for 6 hours. After lowering the temperature to room temperature, the result was filtered to remove the base, xylene was vacuum concentrated, and then the result was columned using tetrahydrofuran:hexane=1:15 to prepare Compound 2 (12.47 g, yield: 75%).

MS[M+H]⁺=613

Preparation Example 3

Synthesis of Compound 3

-continued

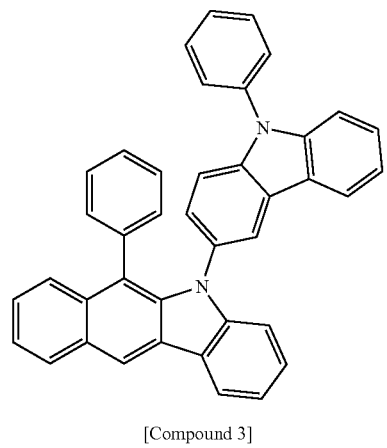

[Compound 3]

After completely dissolving Compound A (8.0 g, 27.30 mmol) and 3-bromo-9-phenyl-9H-carbazole (8.40 g, 25.94 mmol) in 160 ml of xylene in a 500 ml round bottom flask under nitrogen atmosphere, sodium tert-butoxide (3.41 g, 35.49 mol) and then bis(tri-tert-butylphosphine) palladium (0) (0.07 g, 0.14 mmol) were added thereto, and the result was heated and stirred for 3 hours. After lowering the temperature to room temperature, the result was filtered to remove the base, xylene was vacuum concentrated, and then the result was columned using tetrahydrofuran:hexane=1:25 to prepare Compound 3 (10.12 g, yield: 69%).

MS[M+H]⁺=535

Preparation Example 4

Synthesis of Compound 4

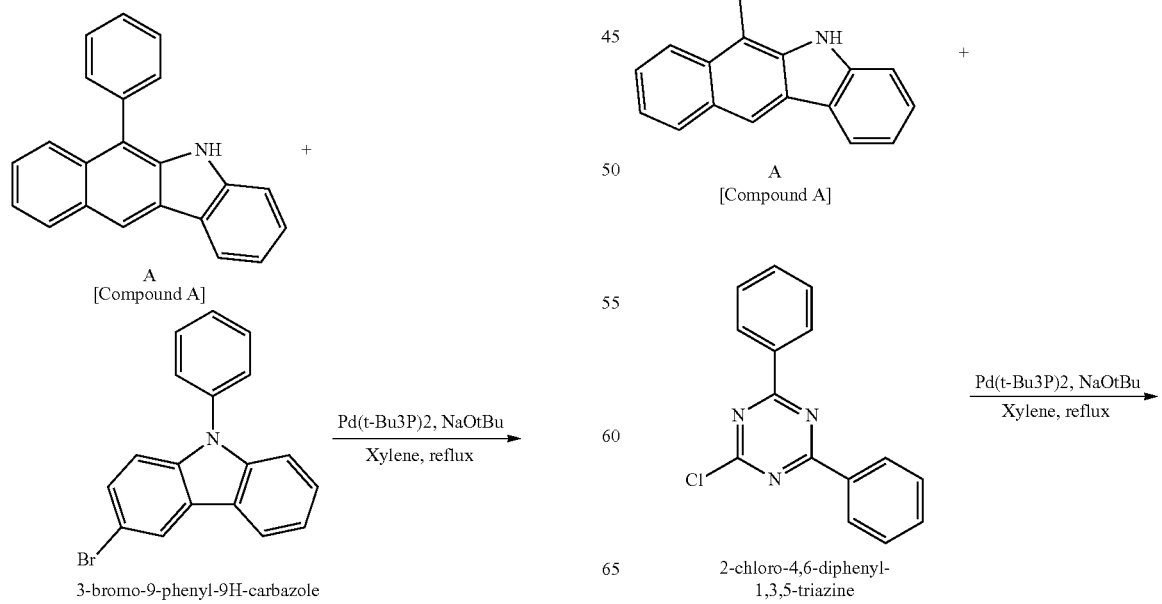

-continued

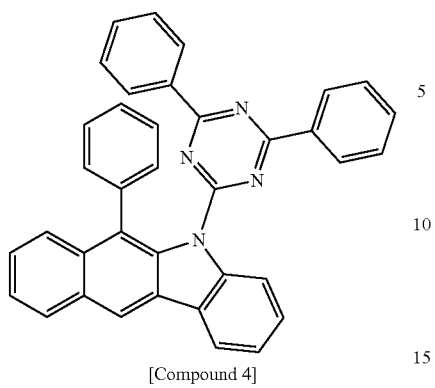

[Compound 4]

After completely dissolving Compound A (8.0 g, 27.30 mmol) and 2-chloro-4,6-diphenyl-1,3,5-triazine (6.93 g, 25.94 mmol) in 280 ml of xylene in a 500 ml round bottom flask under nitrogen atmosphere, sodium tert-butoxide (3.41 g, 35.49 mol) and then bis(tri-tert-butylphosphine) palladium(0) (0.07 g, 0.14 mmol) were added thereto, and the result was heated and stirred for 5 hours. After lowering the temperature to room temperature, the result was filtered to remove the base, xylene was vacuum concentrated, and then the result was recrystallized with 250 ml of ethyl acetate to prepare Compound 4 (11.45 g, yield: 80%).

MS[M+H]$^+$=525

Preparation Example 5

Synthesis of Compound 5

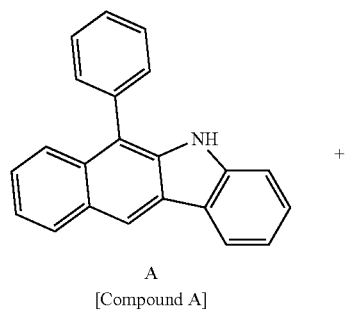

A
[Compound A]

+

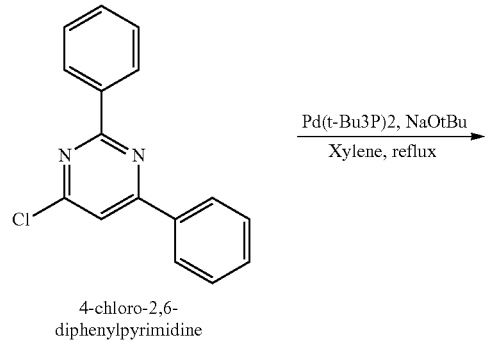

4-chloro-2,6-diphenylpyrimidine

-continued

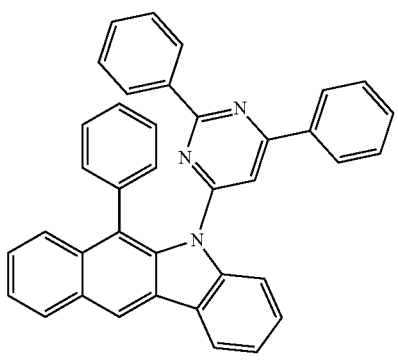

[Compound 5]

After completely dissolving Compound A (8.0 g, 27.30 mmol) and 4-chloro-2,6-diphenylpyrimidine (6.92 g, 25.94 mmol) in 230 ml of xylene in a 500 ml round bottom flask under nitrogen atmosphere, sodium tert-butoxide (3.41 g, 35.49 mol) and then bis(tri-tert-butylphosphine) palladium (0) (0.07 g, 0.14 mmol) were added thereto, and the result was heated and stirred for 7 hours. After lowering the temperature to room temperature, the result was filtered to remove the base, xylene was vacuum concentrated, and then the result was recrystallized with 210 ml of ethyl acetate to prepare Compound 5 (10.84 g, yield: 76%).

MS[M+H]$^+$=524

Preparation Example 6

Synthesis of Compound 6

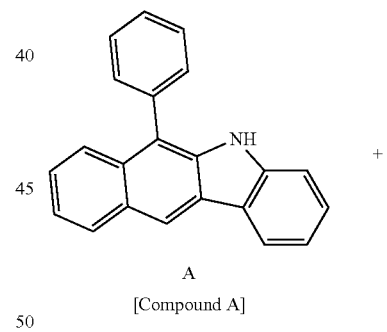

A
[Compound A]

+

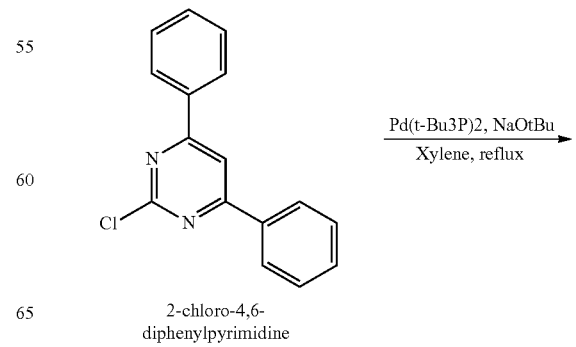

2-chloro-4,6-diphenylpyrimidine

-continued

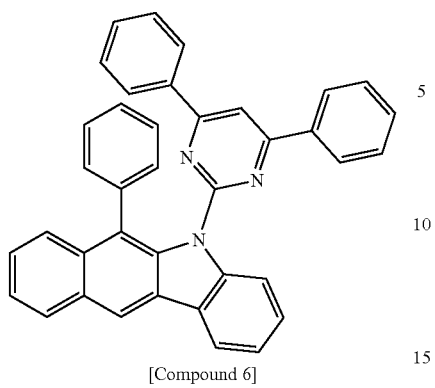

[Compound 6]

After completely dissolving Compound A (8.0 g, 27.30 mmol) and 2-chloro-4,6-diphenylpyrimidine (6.92 g, 25.94 mmol) in 240 ml of xylene in a 500 ml round bottom flask under nitrogen atmosphere, sodium tert-butoxide (3.41 g, 35.49 mol) and then bis(tri-tert-butylphosphine) palladium (0) (0.07 g, 0.14 mmol) were added thereto, and the result was heated and stirred for 6 hours. After lowering the temperature to room temperature, the result was filtered to remove the base, xylene was vacuum concentrated, and then the result was recrystallized with 250 ml of ethyl acetate to prepare Compound 6 (9.51 g, yield: 66%).

MS[M+H]$^+$=524

Preparation Example 7

Synthesis of Compound 7

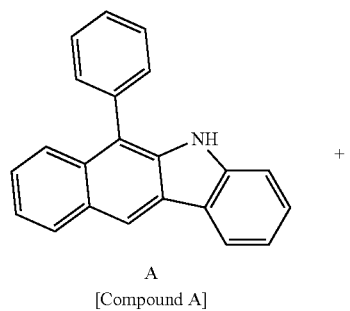

A
[Compound A]

+

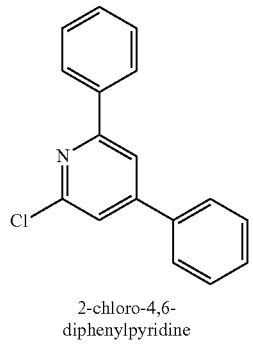

2-chloro-4,6-diphenylpyridine $\xrightarrow{\text{Pd(t-Bu3P)2, NaOtBu}}_{\text{Xylene, reflux}}$ -continued

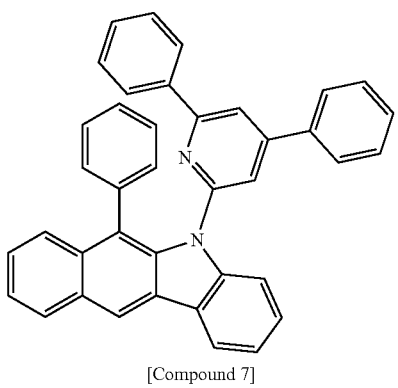

[Compound 7]

After completely dissolving Compound A (8.0 g, 27.30 mmol) and 2-chloro-4,6-diphenylpyridine (6.90 g, 25.94 mmol) in 200 ml of xylene in a 500 ml round bottom flask under nitrogen atmosphere, sodium tert-butoxide (3.41 g, 35.49 mol) and then bis(tri-tert-butylphosphine) palladium (0) (0.07 g, 0.14 mmol) were added thereto, and the result was heated and stirred for 3 hours. After lowering the temperature to room temperature, the result was filtered to remove the base, xylene was vacuum concentrated, and then the result was recrystallized with 250 ml of ethyl acetate to prepare Compound 7 (12.11 g, yield: 84%).

MS [M+H]$^+$=523

Preparation Example 8

Synthesis of Compound 8

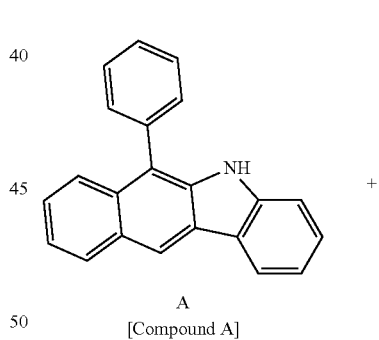

A
[Compound A]

+

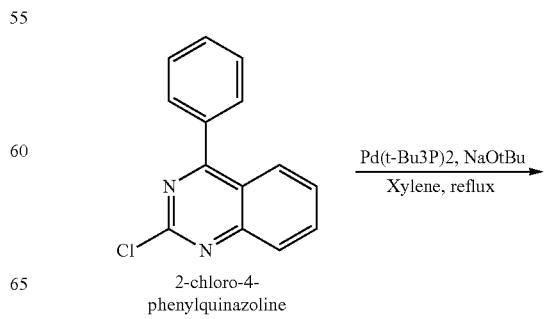

2-chloro-4-phenylquinazoline $\xrightarrow{\text{Pd(t-Bu3P)2, NaOtBu}}_{\text{Xylene, reflux}}$

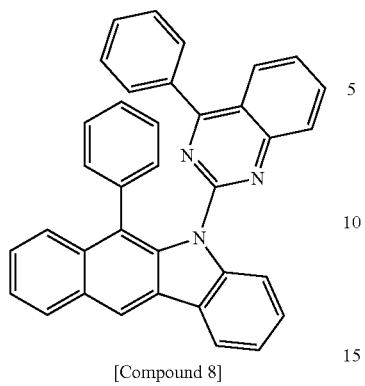

[Compound 8]

After completely dissolving Compound A (8.0 g, 27.30 mmol) and 2-chloro-4-phenylquinazoline (6.92 g, 28.75 mmol) in 160 ml of xylene in a 500 ml round bottom flask under nitrogen atmosphere, sodium tert-butoxide (3.41 g, 35.49 mol) and then bis(tri-tert-butylphosphine) palladium (0) (0.07 g, 0.14 mmol) were added thereto, and the result was heated and stirred for 1 hour. After lowering the temperature to room temperature, the result was filtered to remove the base, xylene was vacuum concentrated, and then the result was recrystallized with 150 ml of ethyl acetate to prepare Compound 8 (13.26 g, yield: 93%).

MS[M+H]$^+$=498

Preparation Example 9

Synthesis of Compound 9

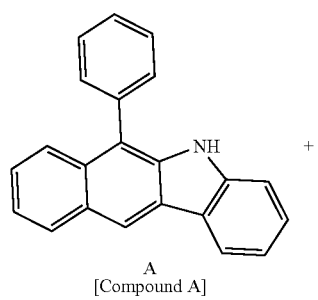

A
[Compound A]

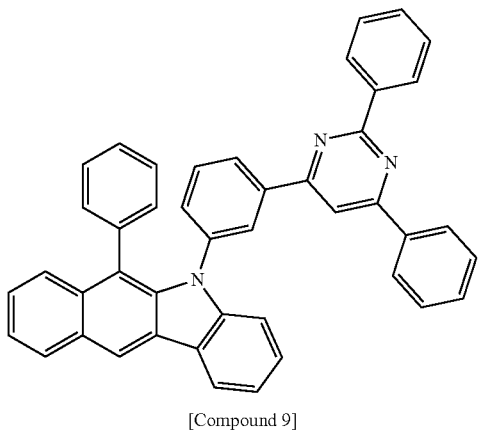

[Compound 9]

After completely dissolving Compound A (8.0 g, 27.30 mmol) and 4-(3-bromophenyl)-2,6-diphenylpyrimidine (1.12 g, 28.73 mmol) in 340 ml of xylene in a 500 ml round bottom flask under nitrogen atmosphere, sodium tert-butoxide (3.41 g, 35.49 mmol) and then bis(tri-tert-butylphosphine) palladium(0) (0.07 g, 0.14 mmol) were added thereto, and the result was heated and stirred for 5 hours. After lowering the temperature to room temperature, the result was filtered to remove the base, xylene was vacuum concentrated, and then the result was recrystallized with 150 ml of tetrahydrofuran to prepare Compound 9 (15.47 g, yield: 90%).

MS[M+H]$^+$=600

Preparation Example 10

1) Synthesis of Compound 10-1

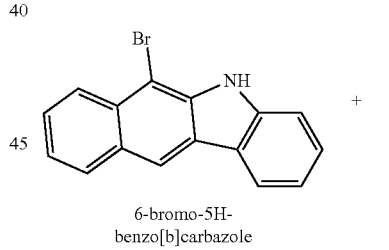

6-bromo-5H-benzo[b]carbazole

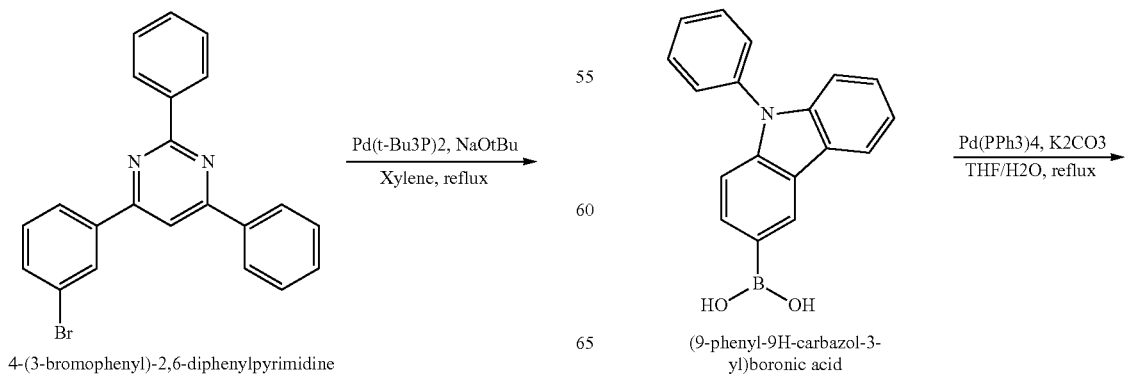

4-(3-bromophenyl)-2,6-diphenylpyrimidine (9-phenyl-9H-carbazol-3-yl)boronic acid -continued

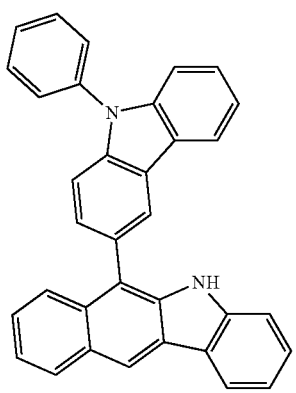

[Compound 10-1]

After completely dissolving compounds of 6-bromo-5H-benzo[b]carbazole (10.0 g, 33.90 mmol) and (9-phenyl-9H-carbazol-3-yl)boronic acid (11.19 g, 38.98 mmol) in 240 ml of tetrahydrofuran in a 500 ml round bottom flask under nitrogen atmosphere, a 2 M aqueous potassium carbonate solution (120 ml) and then tetrakis-(triphenylphosphine) palladium (1.17 g, 1.02 mmol) were added thereto, and the result was heated and stirred for 3 hours. After lowering the temperature to room temperature, the water layer was removed, and the result was dried with anhydrous magnesium sulfate, vacuum concentrated, and then recrystallized with 300 ml of ethanol to prepare Compound 10-1 (14.47 g, yield: 81%).

MS[M+H]$^+$=459

2) Synthesis of Compound 10

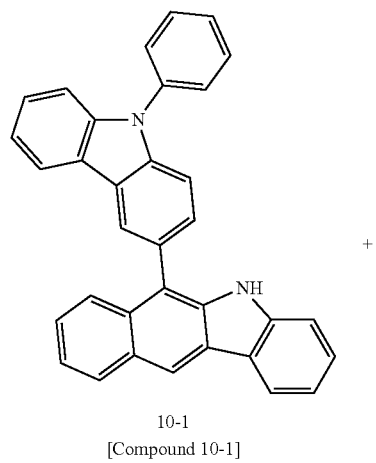

10-1
[Compound 10-1]

+

-continued

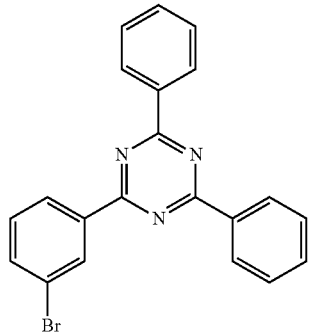

2-(3-bromophenyl)-4,6-diphenyl-1,3,5-triazine $\xrightarrow{\text{Pd(t-Bu3P)2, NaOtBu}}{\text{Xylene, reflux}}$

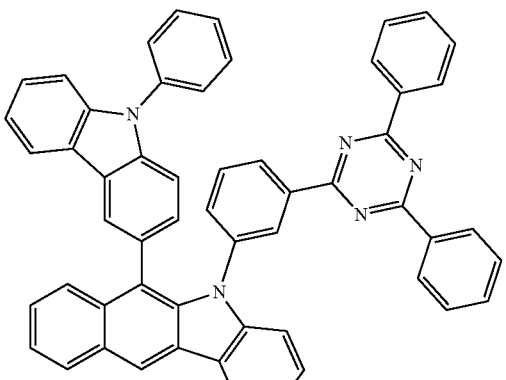

[Compound 10]

After completely dissolving Compound 10-1 (7.25 g, 15.83 mmol) and 2-(3-bromophenyl)-4,6-diphenyl-1,3,5-triazine (5.83 g, 15.04 mmol) in 240 ml of xylene in a 500 ml round bottom flask under nitrogen atmosphere, sodium tert-butoxide (1.98 g, 20.58 mmol) and then bis(tri-tert-butylphosphine) palladium(0) (0.08 g, 0.16 mmol) were added thereto, and the result was heated and stirred for 8 hours. After lowering the temperature to room temperature, the result was filtered to remove the base, xylene was vacuum concentrated, and then the result was recrystallized with 320 ml of tetrahydrofuran to prepare Compound 10 (9.88 g, yield: 82%).

MS[M+H]$^+$=766

Preparation Example 11

Synthesis of Compound 11

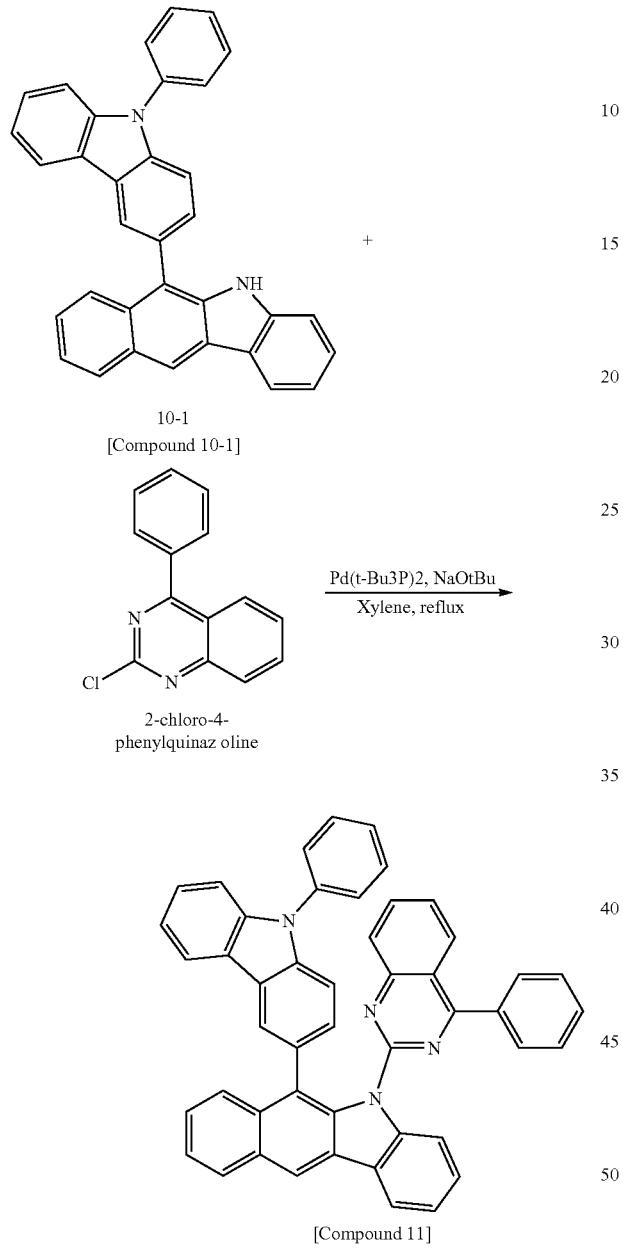

After completely dissolving Compound 10-1 (6.42 g, 14.02 mmol) and 2-chloro-4-phenylquinazoline (3.20 g, 13.32 mmol) in 241 ml of xylene in a 500 ml round bottom flask under nitrogen atmosphere, sodium tert-butoxide (1.75 g, 18.22 mmol) and then bis(tri-tert-butylphosphine) palladium(0) (0.07 g, 0.14 mmol) were added thereto, and the result was heated and stirred for 3 hours. After lowering the temperature to room temperature, the result was filtered to remove the base, xylene was vacuum concentrated, and then the result was recrystallized with 230 ml of tetrahydrofuran to prepare Compound 11 (7.11 g, yield: 77%).

MS[M+H]$^+$=663

Preparation Example 12

Synthesis of Compound 12

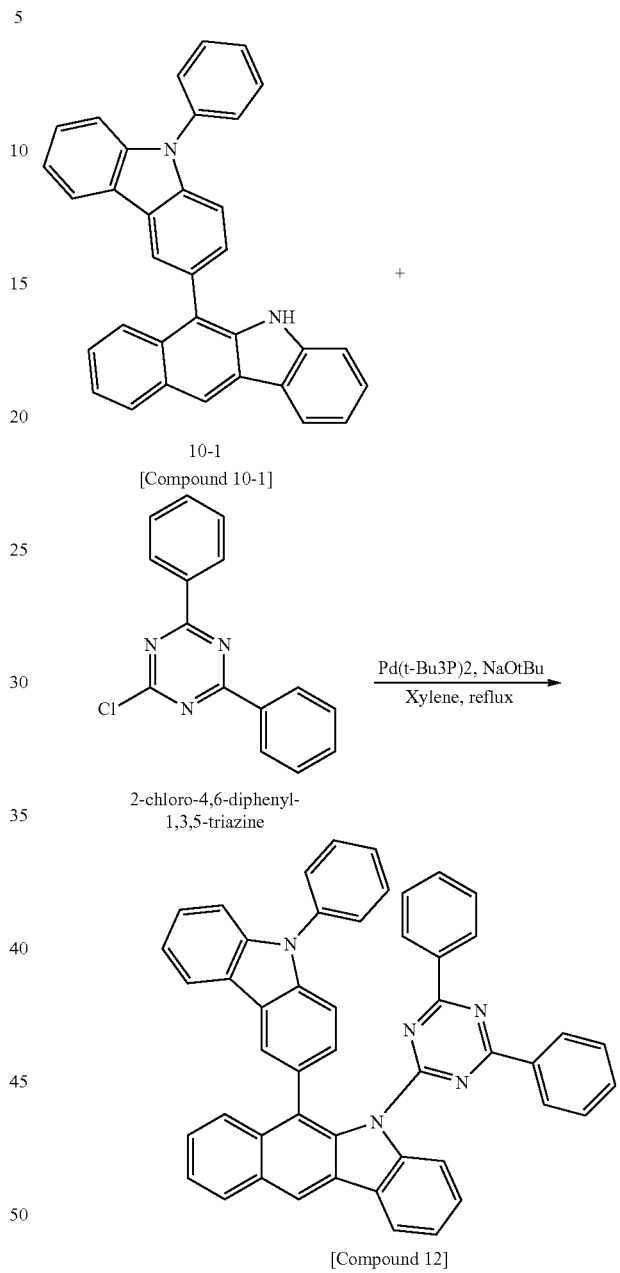

After completely dissolving Compound 10-1 (6.11 g, 15.83 mmol) and 2-chloro-4,6-diphenyl-1,3,5-triazine (3.38 g, 12.67 mmol) in 210 ml of xylene in a 500 ml round bottom flask under nitrogen atmosphere, sodium tert-butoxide (1.67 g, 17.34 mmol) and then bis(tri-tert-butylphosphine) palladium(0) (0.07 g, 0.13 mmol) were added thereto, and the result was heated and stirred for 4 hours. After lowering the temperature to room temperature, the result was filtered to remove the base, xylene was vacuum concentrated, and then the result was recrystallized with 200 ml of tetrahydrofuran to prepare Compound 12 (6.18 g, yield: 67%).

MS[M+H]$^+$=690

Preparation Example 13

Synthesis of Compound 13

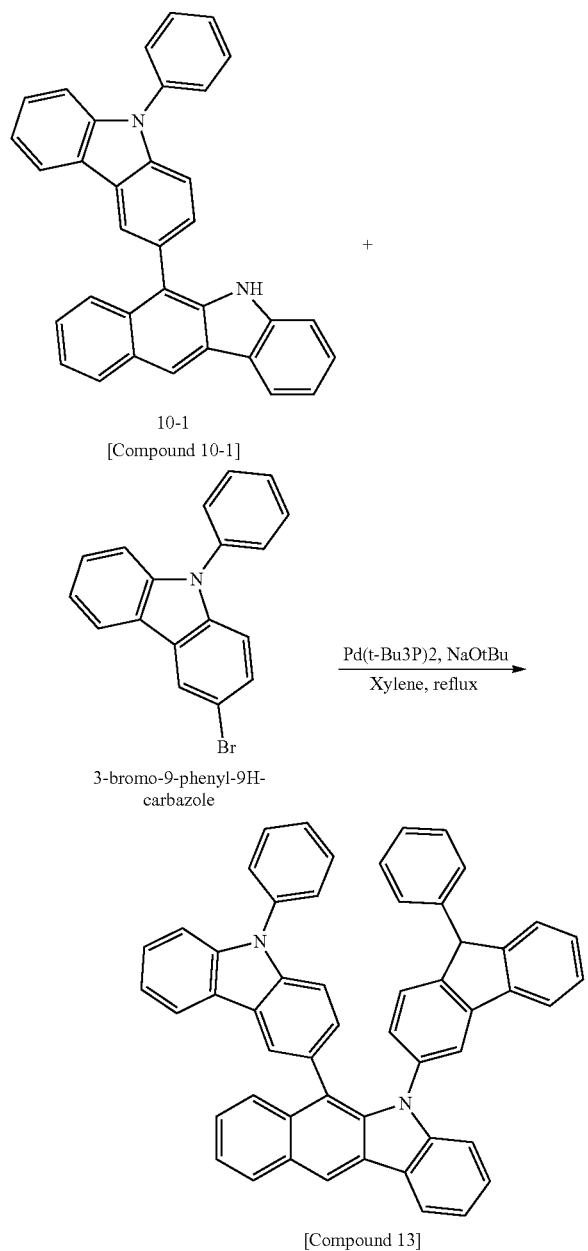

10-1
[Compound 10-1]

3-bromo-9-phenyl-9H-carbazole

Pd(t-Bu3P)2, NaOtBu
Xylene, reflux

[Compound 13]

After completely dissolving Compound 10-1 (8.45 g, 18.45 mmol) and 3-bromo-9-phenyl-9H-carbazole (5.64 g, 17.53 mmol) in 240 ml of xylene in a 500 ml round bottom flask under nitrogen atmosphere, sodium tert-butoxide (2.30 g, 23.98 mmol) and then bis(tri-tert-butylphosphine) palladium(0) (0.07 g, 0.13 mmol) were added thereto, and the result was heated and stirred for 2 hours. After lowering the temperature to room temperature, the result was filtered to remove the base, xylene was vacuum concentrated, and then the result was recrystallized with 120 ml of tetrahydrofuran to prepare Compound 13 (10.05 g, yield: 78%).

MS[M+H]$^+$=700

Preparation Example 14

Synthesis of Compound 14

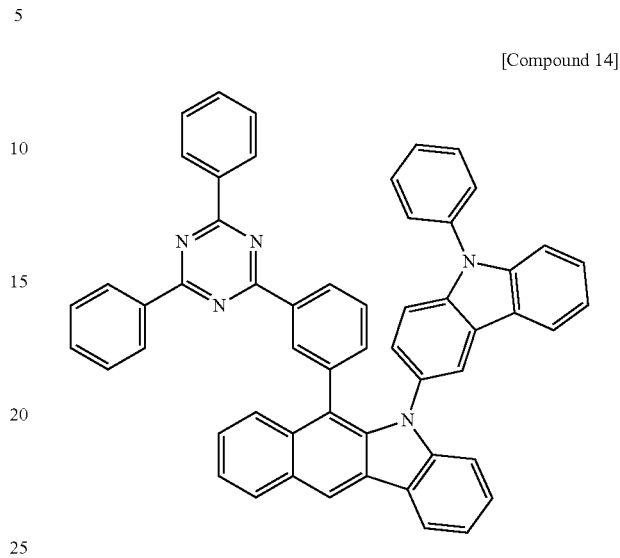

[Compound 14]

Compound 14 was prepared in the same manner as in Preparation Example 10 preparing Compound 10 except that, as the starting materials, a 2,4-diphenyl-6-(3-(4,4,5,5-tetramethyl-1,3,2-dioxaborolan-2-yl)phenyl)-1,3,5-triazine compound was used instead of the (9-phenyl-9H-carbazol-3-yl)boronic acid compound, and a 3-bromo-9-phenyl-9H-carbazole compound was used instead of the 2-(3-bromophenyl)-4,6-diphenyl-1,3,5-triazine compound.

MS[M+H]$^+$=766

Preparation Example 15

Synthesis of Compound 15

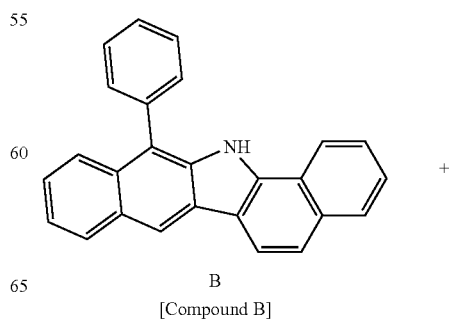

B
[Compound B]

-continued

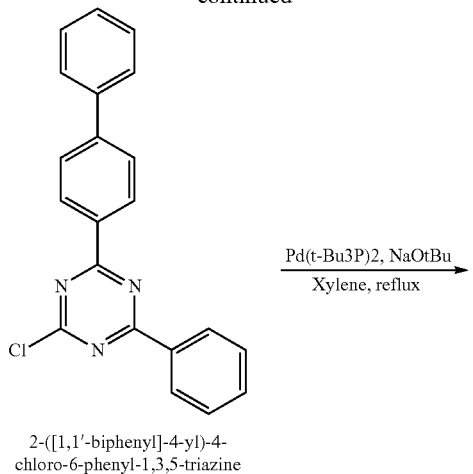

2-([1,1'-biphenyl]-4-yl)-4-chloro-6-phenyl-1,3,5-triazine

Pd(t-Bu3P)2, NaOtBu
———————————→
Xylene, reflux

[Compound 15]

Preparation Example 16

Synthesis of Compound 16

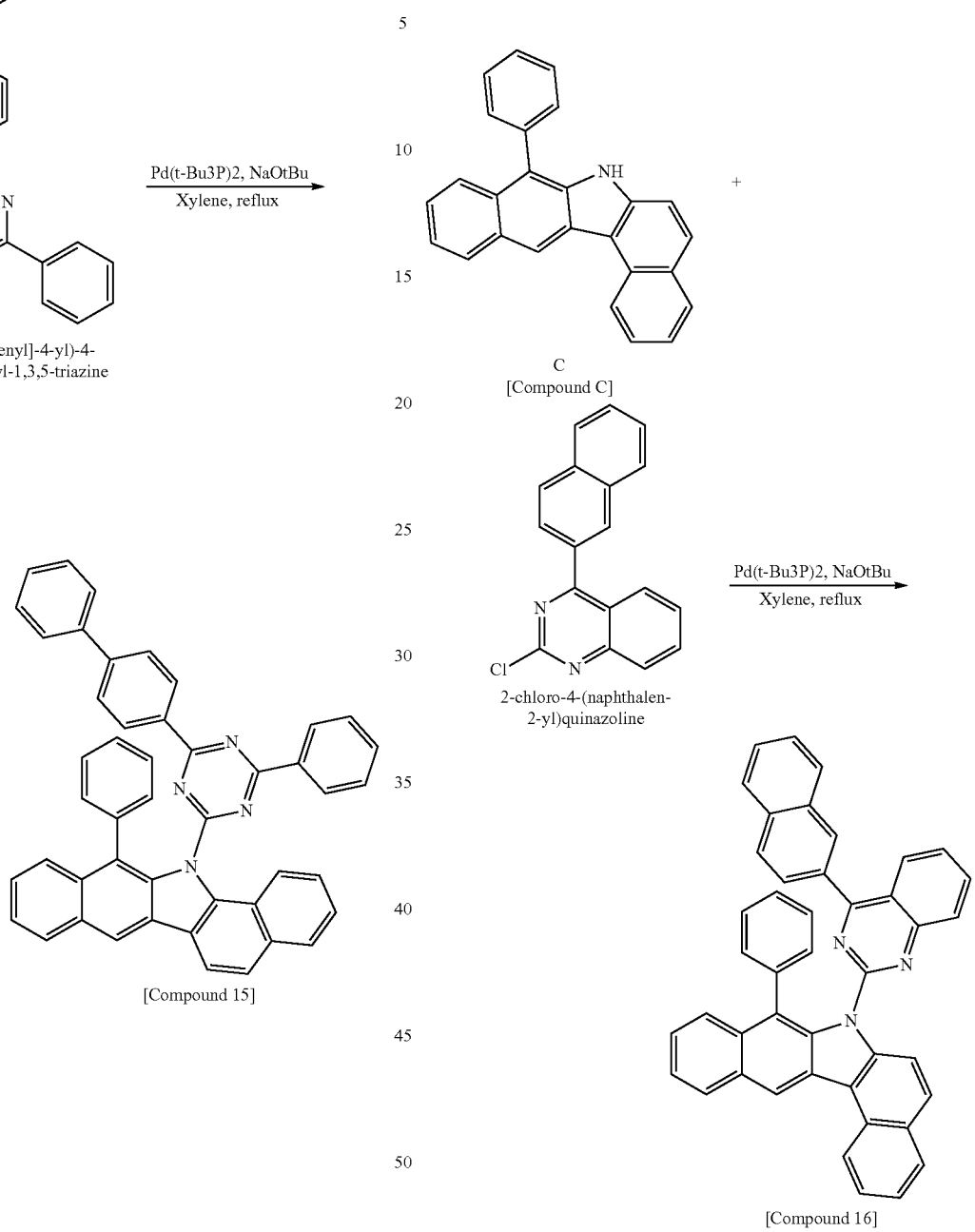

[Compound C]

2-chloro-4-(naphthalen-2-yl)quinazoline

Pd(t-Bu3P)2, NaOtBu
———————————→
Xylene, reflux

[Compound 16]

After completely dissolving Compound B (10.0 g, 29.16 mmol) and 2-([1,1'-biphenyl]-4-yl)-4-chloro-6-phenyl-1,3,5-triazine (10.53 g, 30.70 mmol) in 230 ml of xylene in a 500 ml round bottom flask under nitrogen atmosphere, sodium tert-butoxide (3.84 g, 39.91 mol) and then bis(tri-tert-butylphosphine) palladium(0) (0.16 g, 0.31 mmol) were added thereto, and the result was heated and stirred for 4 hours. After lowering the temperature to room temperature, the result was filtered to remove the base, xylene was vacuum concentrated, and then the result was recrystallized with 220 ml of ethyl acetate to prepare Compound 15 (16.65 g, yield: 83%).

MS[M+H]$^+$=651

After completely dissolving Compound C (10.0 g, 29.16 mmol) and 2-chloro-4-(naphthalen-2-yl)quinazoline (7.76 g, 26.76 mmol) in 220 ml of xylene in a 500 ml round bottom flask under nitrogen atmosphere, sodium tert-butoxide (3.84 g, 39.91 mol) and then bis(tri-tert-butylphosphine) palladium(0) (0.16 g, 0.31 mmol) were added thereto, and the result was heated and stirred for 3 hours. After lowering the temperature to room temperature, the result was filtered to remove the base, xylene was vacuum concentrated, and then the result was recrystallized with 290 ml of ethyl acetate to prepare Compound 16 (13.24 g, yield: 79%).

MS[M+H]$^+$=598

Preparation Example 17

Synthesis of Compound 17

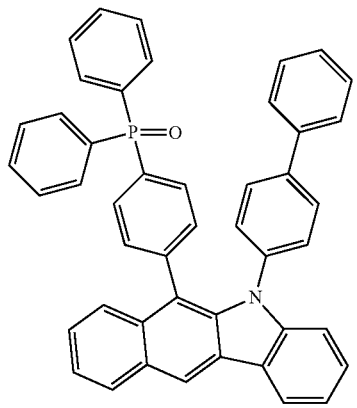

[Compound 17]

Compound 17 was prepared in the same manner as in Preparation Example 10 preparing Compound 10 except that a (4-(diphenylphosphoryl)phenyl)boronic acid compound was used instead of the (9-phenyl-9H-carbazol-3-yl)boronic acid compound, and a 4-iodobiphenyl compound was used instead of the 2-(3-bromophenyl)-4,6-diphenyl-1,3,5-triazine compound.

MS[M+H]$^+$=646

Preparation Example 18

Synthesis of Compound 18

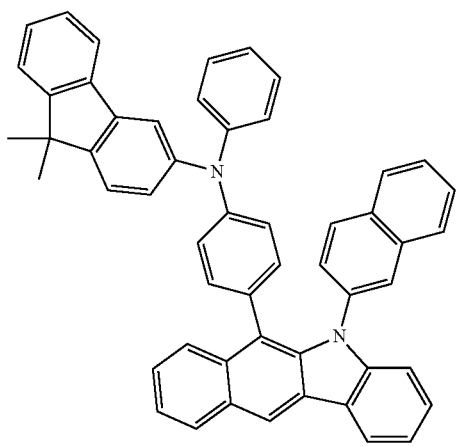

[Compound 18]

Compound 18 was prepared in the same manner as in Preparation Example 10 preparing Compound 10 except that a (4-((9,9-dimethyl-9H-fluoren-3-yl)(phenyl)amino)phenyl) boronic acid compound was used instead of the (9-phenyl-9H-carbazol-3-yl)boronic acid compound, and a 2-bromonapthalene compound was used instead of the 2-(3-bromophenyl)-4,6-diphenyl-1,3,5-triazine compound.

MS[M+H]$^+$=703

Preparation Example 19

Synthesis of Compound 19

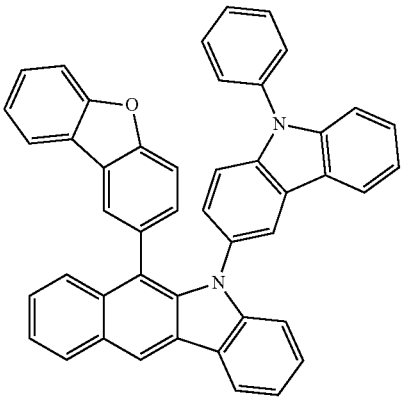

[Compound 19]

Compound 19 was prepared in the same manner as in Preparation Example 10 preparing Compound 10 except that a dibenzo[b,d]furan-2-ylboronic acid compound was used instead of the (9-phenyl-9H-carbazol-3-yl)boronic acid compound, and a 3-bromo-9-phenyl-9H-carbazole compound was used instead of the 2-(3-bromophenyl)-4,6-diphenyl-1,3,5-triazine compound.

MS[M+H]$^+$=625

Preparation Example 20

Synthesis of Compound 20

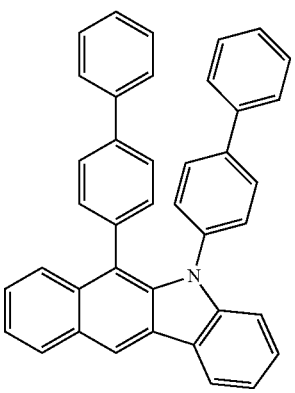

[Compound 20]

Compound 20 was prepared in the same manner as in Preparation Example 10 preparing Compound 10 except that a 4-biphenylboronic acid compound was used instead of the (9-phenyl-9H-carbazol-3-yl)boronic acid compound, and a 4-bromobiphenyl compound was used instead of the 2-(3-bromophenyl)-4,6-diphenyl-1,3,5-triazine compound.

MS[M+H]$^+$=522

189

Preparation Example 21

Synthesis of Compound 21

[Compound 21]

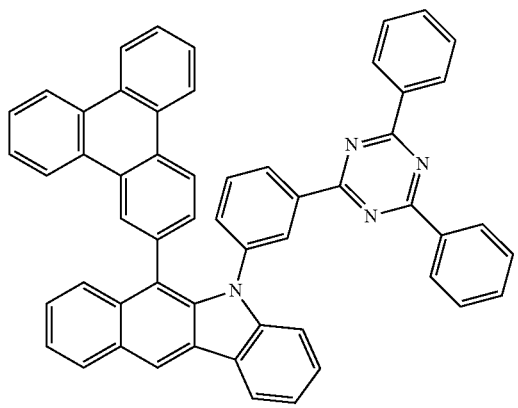

Compound 21 was prepared in the same manner as in Preparation Example 10 preparing Compound 10 except that a triphenylen-2-ylboronic acid compound was used instead of the (9-phenyl-9H-carbazol-3-yl)boronic acid compound, and a 2-(3-bromophenyl)-4,6-diphenyl-1,3,5-triazine compound was used instead of the 2-(3-bromophenyl)-4,6-diphenyl-1,3,5-triazine compound.

MS[M+H]$^+$=751

Preparation Example 22

Synthesis of Compound 22

[Compound 22]

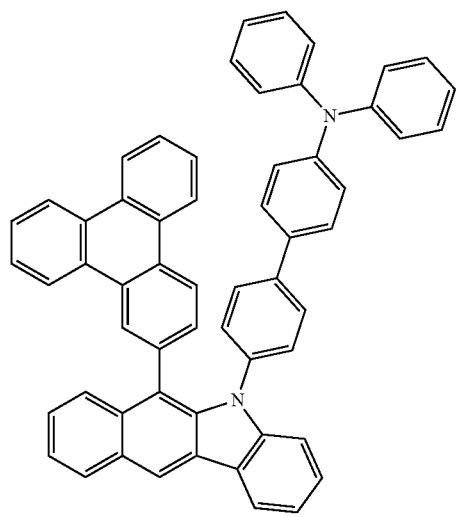

Compound 22 was prepared in the same manner as in Preparation Example 21 preparing Compound 21 except that 4'-bromo-N,N-diphenyl-[1,1'-biphenyl]-4-amine was used instead of 2-(3-bromophenyl)-4,6-diphenyl-1,3,5-triazine.

MS[M+H]$^+$=763

190

Preparation Example 23

Synthesis of Compound 23

[Compound 23]

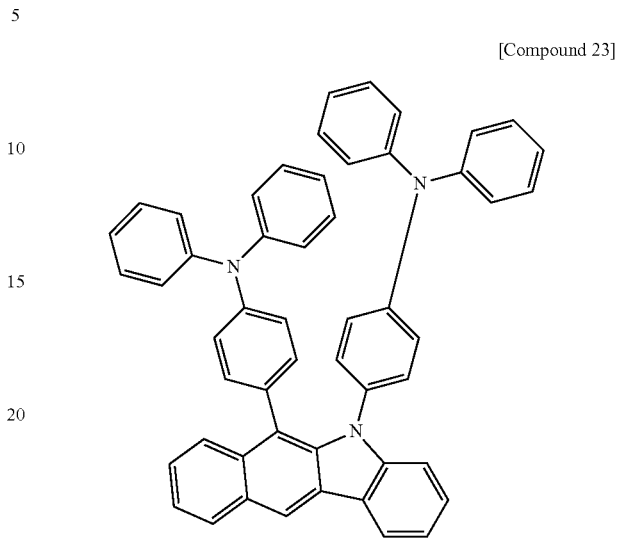

Compound 23 was prepared in the same manner as in Preparation Example 10 preparing Compound 10 except that a (4-(diphenylamino)phenyl)boronic acid compound was used instead of the (9-phenyl-9H-carbazol-3-yl)boronic acid compound, and a 4-bromo-N,N-diphenylaniline compound was used instead of the 2-(3-bromophenyl)-4,6-diphenyl-1,3,5-triazine compound.

MS[M+H]$^+$=704

Example 1-1

A glass substrate on which indium tin oxide (ITO) was coated as a thin film to a thickness of 1,000 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

On the transparent ITO electrode prepared as above, a hole injection layer was formed by thermal vacuum depositing hexanitrile hexaazatriphenylene (HAT) of the following chemical formula to a thickness of 500 Å.

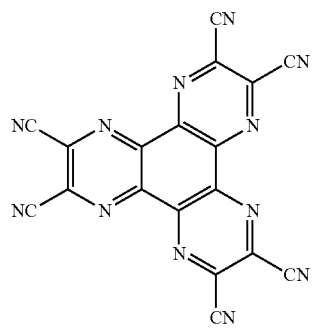

[HAT]

A hole transfer layer was formed on the hole injection layer by vacuum depositing the following compound 4-4'-bis[N-(1-naphthyl)-N-phenylamino]biphenyl (NPB) (300 Å), a material transferring holes.

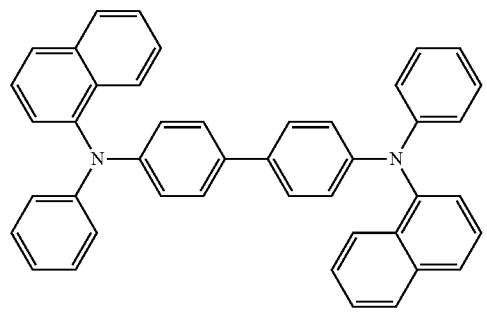

[NPB]

Subsequently, an electron blocking layer was formed on the hole transfer layer to a film thickness of 100 Å by vacuum depositing the following Compound 1.

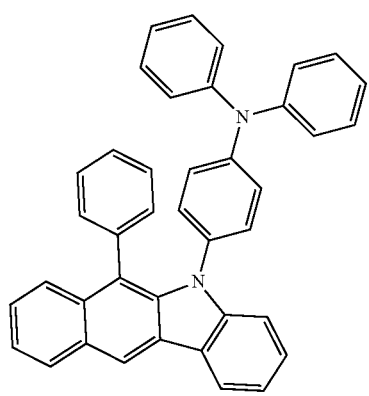

[Compound 1]

Next, a light emitting layer was formed on the electron blocking layer to a film thickness of 300 Å by vacuum depositing BH and BD shown below in a weight ratio of 25:1.

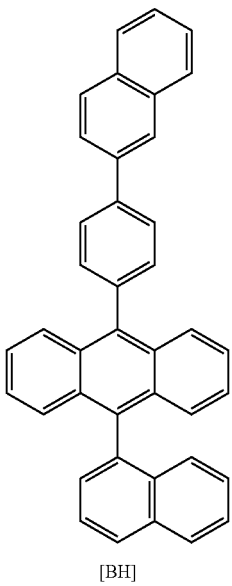

[BH]

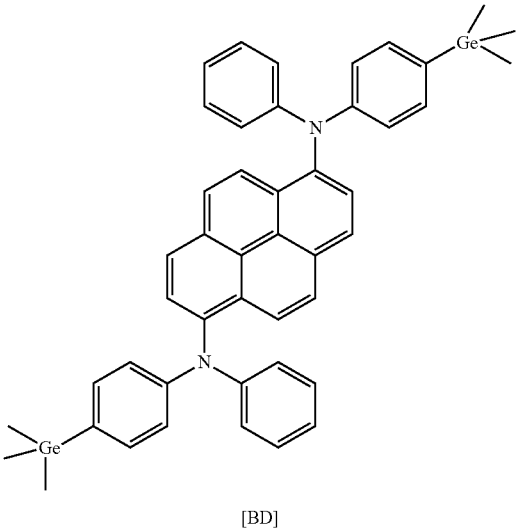

[BD]

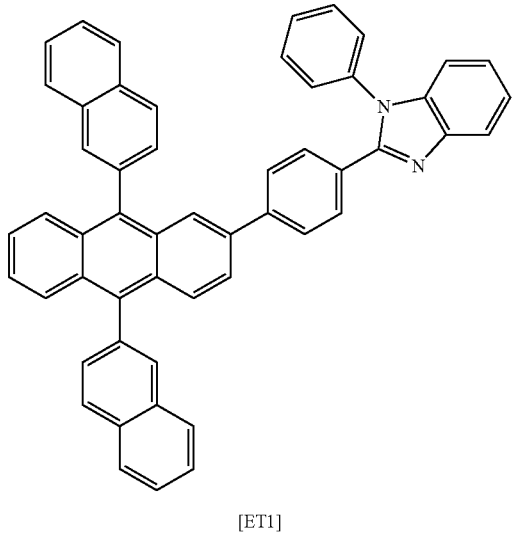

[ET1]

-continued

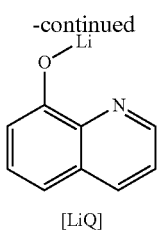

[LiQ]

An electron injection and transfer layer was formed on the light emitting layer to a thickness of 300 Å by vacuum depositing the compound ET1 and the lithium quinolate (LiQ) compound in a weight ratio of 1:1. A cathode was formed on the electron injection and transfer layer by depositing lithium fluoride (LiF) to a thickness of 12 Å and aluminum to a thickness of 2,000 Å in consecutive order.

An organic light emitting device was manufactured by maintaining, in the above-mentioned processes, the deposition rates of the organic materials at 0.4 Å/sec to 0.7 Å/sec, the deposition rates of the lithium fluoride and the aluminum of the cathode at 0.3 Å/sec and 2 Å/sec, respectively, and the degree of vacuum during the deposition at $2\times10^{-7}$ torr to $5\times10^{-6}$ torr.

Example 1-2

An organic light emitting device was manufactured in the same manner as in Example 1-1 except that Compound 2 was used instead of Compound 1.

Example 1-3

An organic light emitting device was manufactured in the same manner as in Example 1-1 except that Compound 3 was used instead of Compound 1.

Example 1-4

An organic light emitting device was manufactured in the same manner as in Example 1-1 except that Compound 13 was used instead of Compound 1.

Example 1-5

An organic light emitting device was manufactured in the same manner as in Example 1-1 except that Compound 18 was used instead of Compound 1.

Example 1-6

An organic light emitting device was manufactured in the same manner as in Example 1-1 except that Compound 19 was used instead of Compound 1.

Example 1-7

An organic light emitting device was manufactured in the same manner as in Example 1-1 except that Compound 20 was used instead of Compound 1.

Example 1-8

An organic light emitting device was manufactured in the same manner as in Example 1-1 except that Compound 22 was used instead of Compound 1.

Example 1-9

An organic light emitting device was manufactured in the same manner as in Example 1-1 except that Compound 23 was used instead of Compound 1.

Comparative Example 1-1

An organic light emitting device was manufactured in the same manner as in Example 1-1 except that EB 1 was used instead of Compound 1.

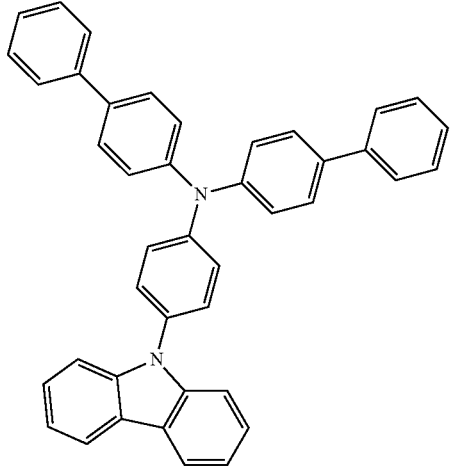

[EB 1]

Comparative Example 1-2

An organic light emitting device was manufactured in the same manner as in Example 1-1 except that EB 2 was used instead of Compound 1.

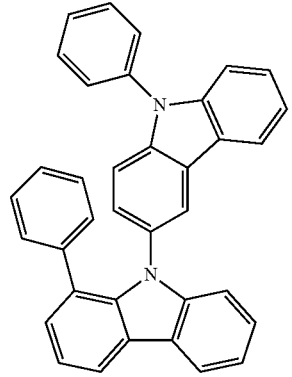

[EB 2]

Comparative Example 1-3

An organic light emitting device was manufactured in the same manner as in Example 1-1 except that EB 3 was used instead of Compound 1.

[EB 3]

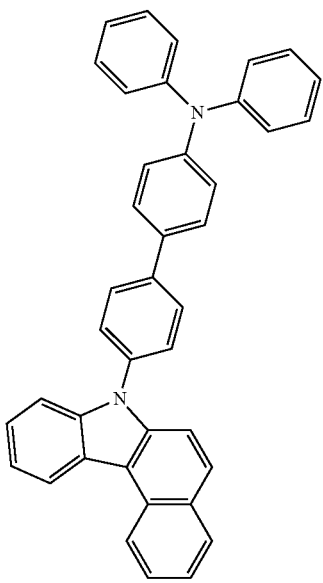

When a current was applied to the organic light emitting devices manufactured in Examples 1-1 to 1-9 and Comparative Examples 1-1 to 1-3, results of Table 1 were obtained.

TABLE 1

| | Compound (Electron Blocking Layer) | Voltage (V@10 mA/cm$^2$) | Efficiency (cd/A@10 mA/cm$^2$) | Color Coordinate (x, y) |
|---|---|---|---|---|
| Example 1-1 | Compound 1 | 3.70 | 5.31 | (0.137, 0.126) |
| Example 1-2 | Compound 2 | 3.61 | 5.42 | (0.137, 0.126) |
| Example 1-3 | Compound 3 | 3.46 | 5.80 | (0.137, 0.127) |
| Example 1-4 | Compound 13 | 3.47 | 5.62 | (0.137, 0.126) |
| Example 1-5 | Compound 18 | 3.48 | 5.83 | (0.136, 0.126) |
| Example 1-6 | Compound 19 | 3.49 | 5.71 | (0.136, 0.127) |
| Example 1-7 | Compound 20 | 3.44 | 5.76 | (0.136, 0.125) |
| Example 1-8 | Compound 22 | 3.43 | 5.79 | (0.137, 0.125) |
| Example 1-9 | Compound 23 | 3.52 | 5.67 | (0.137, 0.125) |
| Comparative Example 1-1 | EB 1 | 4.11 | 4.88 | (0.138, 0.128) |
| Comparative Example 1-2 | EB 2 | 4.36 | 4.64 | (0.139, 0.128) |
| Comparative Example 1-3 | EB 3 | 4.55 | 4.35 | (0.139, 0.129) |

As shown in Table 1, the compounds used in Examples 1-1 to 1-9 were used as an electron blocking layer in the organic light emitting device, and it was seen that the devices of Examples 1-1 to 1-9 exhibited properties of lower voltage and higher efficiency compared to Comparative Examples 1-1 to 1-3 formed by linking substituents to materials having cores similar to the compounds of the present disclosure.

It was identified that derivatives of the hetero-cyclic compound represented by Chemical Formula 1 according to the present specification had an excellent electron blocking ability and thereby exhibited properties of low voltage and high efficiency, and as a result, were capable of being used in an organic light emitting device.

Example 2-1

The compounds synthesized in the synthesis examples were high-purity sublimation purified using commonly known methods, and then a green organic light emitting device was manufactured using a method as below.

A glass substrate on which indium tin oxide (ITO) was coated as a thin film to a thickness of 1,000 Å was placed in detergent-dissolved distilled water and ultrasonic cleaned. Herein, a product of Fischer Co. was used as the detergent, and as the distilled water, distilled water filtered twice with a filter manufactured by Millipore Co. was used. After the ITO was cleaned for 30 minutes, ultrasonic cleaning was repeated twice using distilled water for 10 minutes. After the cleaning with distilled water was finished, the substrate was ultrasonic cleaned with solvents of isopropyl alcohol, acetone and methanol, then dried, and then transferred to a plasma cleaner. In addition, the substrate was cleaned for 5 minutes using oxygen plasma, and then transferred to a vacuum depositor.

An organic light emitting device was manufactured by forming a light emitting element in the order of m-MTDATA (60 nm)/TCTA (80 nm)/Compound 4+10% Ir(ppy)$_3$ (300 nm)/BCP (10 nm)/Alq$_3$ (30 nm)/LiF (1 nm)/Al (200 nm) on the transparent ITO electrode prepared as above using Compound 4 as a host.

Structures of the m-MTDATA, the TCTA, the Ir(ppy)$_3$ and the BCP are as follows.

[m-MTDATA]

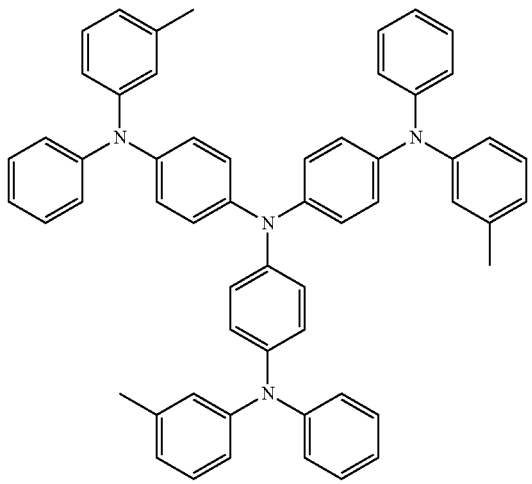

[TCTA]

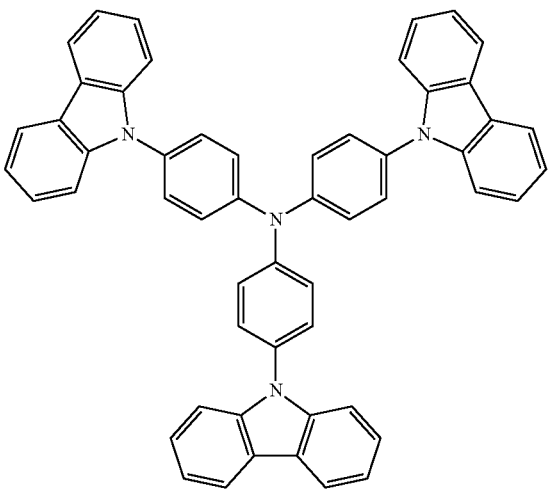

-continued

[Ir(ppy)₃]

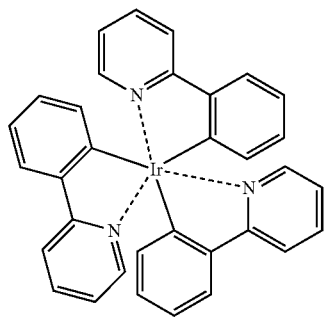

[BCP]

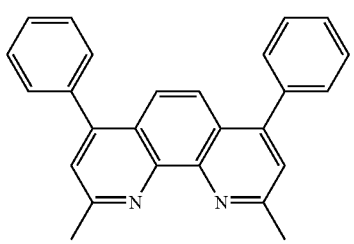

[Compound 4]

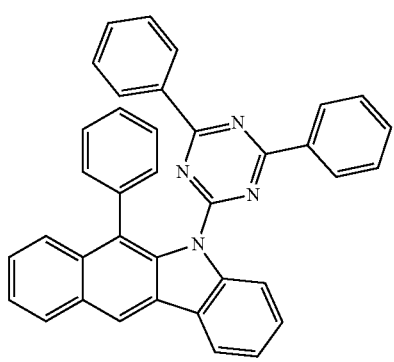

Example 2-2

An organic light emitting device was manufactured in the same manner as in Example 2-1 except that Compound 5 was used instead of Compound 4.

Example 2-3

An organic light emitting device was manufactured in the same manner as in Example 2-1 except that Compound 6 was used instead of Compound 4.

Example 2-4

An organic light emitting device was manufactured in the same manner as in Example 2-1 except that Compound 7 was used instead of Compound 4.

Example 2-5

An organic light emitting device was manufactured in the same manner as in Example 2-1 except that Compound 9 was used instead of Compound 4.

Example 2-6

An organic light emitting device was manufactured in the same manner as in Example 2-1 except that Compound 10 was used instead of Compound 4.

Example 2-7

An organic light emitting device was manufactured in the same manner as in Example 2-1 except that Compound 12 was used instead of Compound 4.

Example 2-8

An organic light emitting device was manufactured in the same manner as in Example 2-1 except that Compound 14 was used instead of Compound 4.

Example 2-9

An organic light emitting device was manufactured in the same manner as in Example 2-1 except that Compound 15 was used instead of Compound 4.

Example 2-10

An organic light emitting device was manufactured in the same manner as in Example 2-1 except that Compound 21 was used instead of Compound 4.

Comparative Example 2-1

An organic light emitting device was manufactured in the same manner as in Example 2-1 except that GH 1 was used instead of Compound 4.

[GH 1]

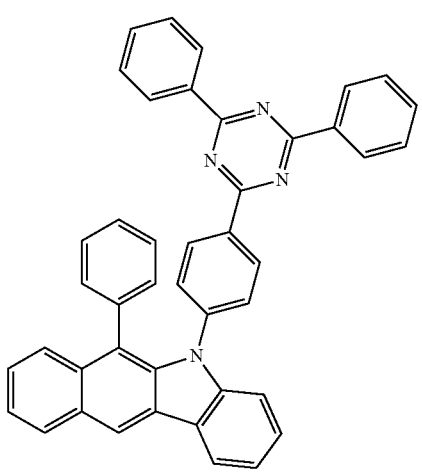

Comparative Example 2-2

An organic light emitting device was manufactured in the same manner as in Example 2-1 except that GH 2 was used instead of Compound 4.

[GH 2]

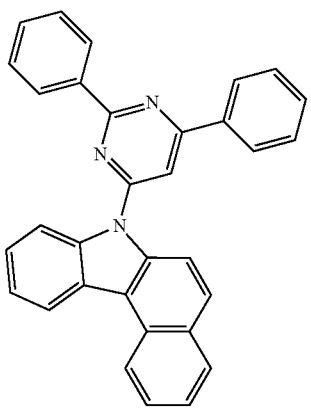

Comparative Example 2-3

An organic light emitting device was manufactured in the same manner as in Example 2-1 except that GH 3 was used instead of Compound 4.

[GH 3]

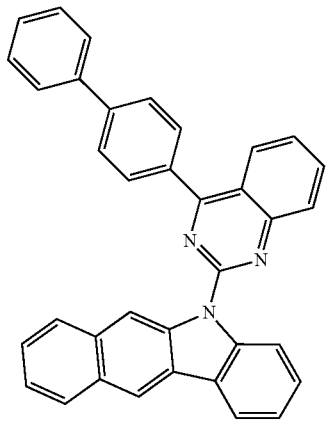

When a current was applied to the organic light emitting devices manufactured in Examples 2-1 to 2-10 and Comparative Examples 2-1 to 2-3, results of Table 2 were obtained.

TABLE 2

| | Compound (Host) | Voltage (V@10 mA/cm$^2$) | Efficiency (cd/A@10 mA/cm$^2$) | Light Emission Peak (nm) |
|---|---|---|---|---|
| Example 2-1 | Compound 4 | 5.38 | 45.64 | 517 |
| Example 2-2 | Compound 5 | 5.34 | 45.68 | 516 |
| Example 2-3 | Compound 6 | 5.23 | 46.83 | 518 |
| Example 2-4 | Compound 7 | 5.28 | 46.93 | 517 |
| Example 2-5 | Compound 9 | 5.36 | 45.24 | 515 |
| Example 2-6 | Compound 10 | 5.20 | 46.79 | 516 |
| Example 2-7 | Compound 12 | 5.31 | 45.15 | 516 |
| Example 2-8 | Compound 14 | 5.23 | 46.31 | 517 |
| Example 2-9 | Compound 15 | 5.38 | 45.63 | 518 |
| Example 2-10 | Compound 21 | 5.29 | 46.62 | 517 |
| Comparative Example 2-1 | GH 1 | 6.81 | 36.45 | 517 |
| Comparative Example 2-2 | GH 2 | 6.51 | 38.08 | 518 |

TABLE 2-continued

| | Compound (Host) | Voltage (V@10 mA/cm$^2$) | Efficiency (cd/A@10 mA/cm$^2$) | Light Emission Peak (nm) |
|---|---|---|---|---|
| Comparative Example 2-3 | GH 3 | 6.65 | 37.11 | 517 |

From the test results, it was identified that the green organic light emitting devices of Examples 2-1 to 2-10 using the hetero-cyclic compound represented by Chemical Formula 1 according to the present disclosure as a host material of a green light emitting layer exhibited superior performance in terms of current efficiency and driving voltage compared to the green organic light emitting devices of Comparative Examples 2-1 to 2-3 formed by linking substituents to materials having cores similar to the compounds of the present specification.

Example 3-1

The compounds synthesized in the preparation examples were high-purity sublimation purified using commonly known methods, and then a red organic light emitting device was manufactured using a method as below.

An ITO glass was patterned so that a light emitting area became a 2 mm×2 mm size, and then cleaned. After installing the substrate in a vacuum chamber, the base pressure was set at 1×10$^{-6}$ torr, and as organic materials on the ITO, DNTPD (700 Å) and α-NPB (300 Å) were formed, Compound 8 was used as a host (90 wt %), the following (piq)$_2$Ir(acac) (10 wt %) was vacuum deposited (300 Å) as a dopant, and Alq$_3$ (350 Å) LiF (5 Å) and Al (1,000 Å) were formed in a film form in this order, and measurements were carried out at 0.4 mA.

Structures of the DNTPD, the α-NPB, the (piq)$_2$Ir(acac) and the Alq$_3$ are as follows.

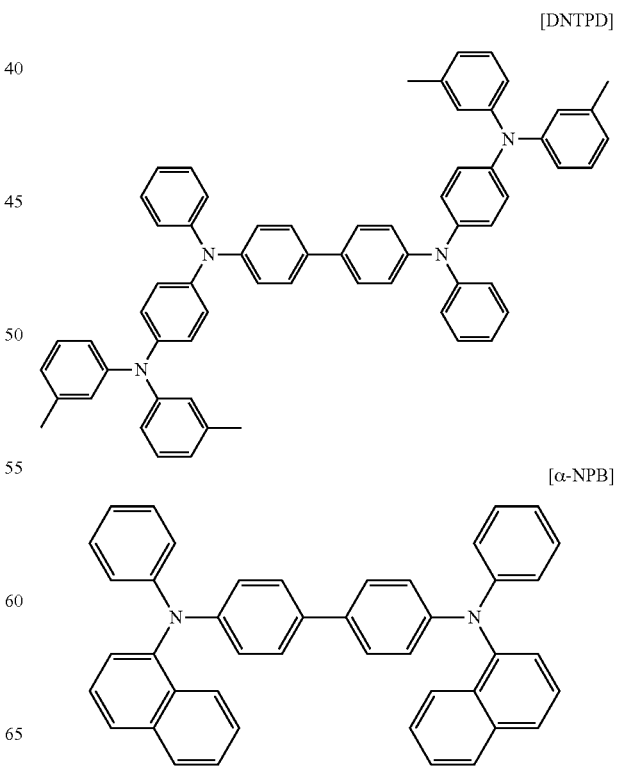

[DNTPD]

[α-NPB]

-continued

[(piq)₂Ir(acac)]

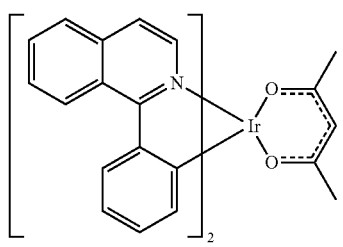

[Alq₃]

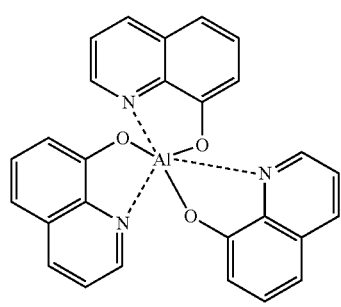

[Compound 8]

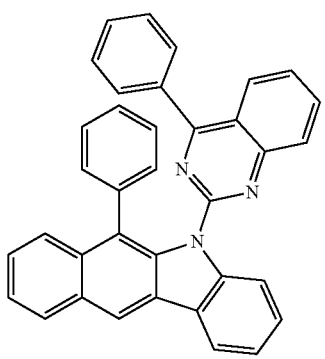

Example 3-2

An organic light emitting device was manufactured in the same manner as in Example 3-1 except that Compound 11 was used instead of Compound 8.

Example 3-3

An organic light emitting device was manufactured in the same manner as in Example 3-1 except that Compound 16 was used instead of Compound 8.

Comparative Example 3-1

An organic light emitting device was manufactured in the same manner as in Example 3-1 except that the following Compound RH 1 (CBP) was used instead of Compound 8.

[RH 1]

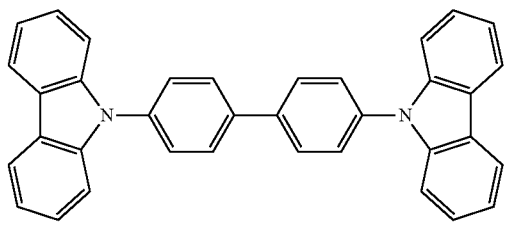

Comparative Example 3-2

An organic light emitting device was manufactured in the same manner as in Example 3-1 except that the following Compound RH 2 was used instead of Compound 8.

[RH 2]

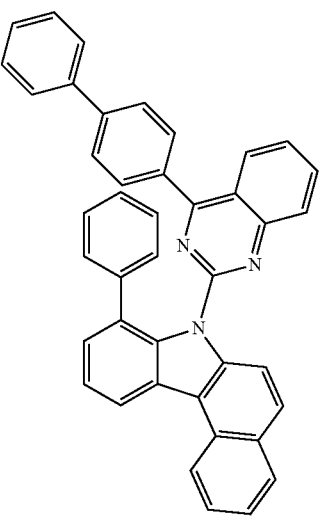

Comparative Example 3-3

An organic light emitting device was manufactured in the same manner as in Example 3-1 except that the following Compound RH 3 was used instead of Compound 8.

[RH 3]

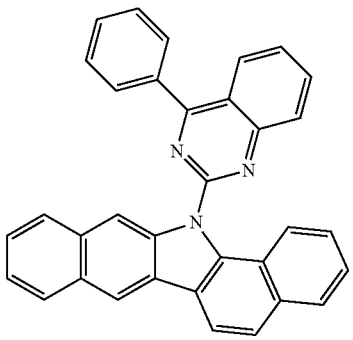

For the organic light emitting devices manufactured according to Examples 3-1 to 3-3 and Comparative Examples 3-1 to 3-3, a voltage, current density, luminance, a color coordinate and a lifespan were measured, and the results are shown in the following Table 3. T95 means time taken for the luminance decreasing to 95% of its initial luminance (5000 nit).

TABLE 3

| Category | Host | Voltage (V) | Luminance (cd/m2) | Color Coordinate (x, y) | T95 (hr) |
|---|---|---|---|---|---|
| Example 3-1 | Compound 8 | 4.4 | 1850 | (0.670, 0.329) | 435 |
| Example 3-2 | Compound 11 | 4.5 | 1750 | (0.674, 0.325) | 445 |
| Example 3-3 | Compound 16 | 4.6 | 1600 | (0.672, 0.327) | 460 |
| Comparative Example 3-1 | RH 1 | 5.9 | 1300 | (0.670, 0.325) | 285 |
| Comparative Example 3-2 | RH 2 | 6.1 | 1250 | (0.671, 0.327) | 295 |
| Comparative Example 3-3 | RH 3 | 6.5 | 1150 | (0.674, 0.329) | 315 |

From the test results, it was identified that the red organic light emitting devices of Examples 3-1 to 3-3 using the compounds according to the present specification as a host material of a light emitting layer exhibited superior performance in terms of current efficiency, driving voltage and lifespan compared to the organic light emitting devices of Comparative Examples 3-1 to 3-3 formed by linking substituents to materials having cores similar to the compounds of the present specification.

Hereinbefore, preferred embodiments of the present disclosure (electron blocking layer, green light emitting layer, red light emitting layer) have been described, however, the present disclosure is not limited thereto, and various modifications may be made within the scope of the claims and the detailed descriptions, and the modifications are also included in the scope of the present disclosure.

REFERENCE NUMERAL 10, 11: Organic Light Emitting Device
20: Substrate
30: First Electrode
40: Light Emitting Layer
50: Second Electrode
60: Hole Injection Layer
70: Hole Transfer Layer
80: Electron Transfer Layer
90: Electron Injection Layer

The invention claimed is:

1. A hetero-cyclic compound represented by the following Chemical Formula 1:

[Chemical Formula 1]

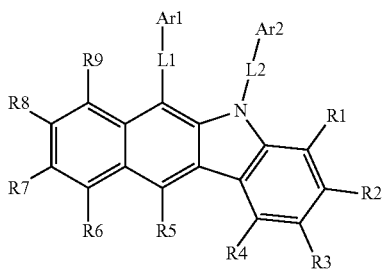

wherein, in Chemical Formula 1,

L1 and L2 are the same as or different from each other, and each independently a direct bond; a substituted or unsubstituted monocyclic or multicyclic arylene group; or a substituted or unsubstituted monocyclic or multicyclic heteroarylene group;

Ar1 is a substituted or unsubstituted amine group; a substituted or unsubstituted silyl group; a substituted or unsubstituted phosphine oxide group; a substituted or unsubstituted phenyl group; a substituted or unsubstituted biphenyl group; a substituted or unsubstituted terphenyl group; a substituted or unsubstituted quaterphenyl group; a substituted or unsubstituted multicyclic aryl group; or a substituted or unsubstituted monocyclic or multicyclic heteroaryl group;

Ar2 is a substituted or unsubstituted amine group; a substituted or unsubstituted silyl group; a substituted or unsubstituted phosphine oxide group; a substituted or unsubstituted monocyclic or multicyclic aryl group; or a substituted or unsubstituted monocyclic or multicyclic heteroaryl group;

provided that when L1 is a direct bond, Ar1 is an unsubstituted phenyl group, and L2 is a direct bond or a substituted or unsubstituted monocyclic arylene group, then Ar2 is a substituted or unsubstituted amine group; a substituted or unsubstituted phosphine oxide group; a monocyclic or multicyclic aryl group unsubstituted or substituted with a nitrile group or an aryl group; or a multicyclic heteroaryl group unsubstituted or substituted with an aryl group unsubstituted or substituted with an alkyl group; and R1 to R9 are hydrogen, or adjacent groups bond to each other to form a substituted or unsubstituted ring.

2. The hetero-cyclic compound of claim 1, wherein R1 to R4 are hydrogen, or adjacent groups bond to each other to form a substituted or unsubstituted ring.

3. The hetero-cyclic compound of claim 1, wherein L1 and L2 are the same as or different from each other, and each independently a direct bond; or a monocyclic or multicyclic arylene group unsubstituted or substituted with an alkyl group.

4. The hetero-cyclic compound of claim 1, wherein Ar1 is an arylamine group unsubstituted or substituted with an alkyl group; a phosphine oxide group substituted with an aryl group; a phenyl group unsubstituted or substituted with a nitrile group; a biphenyl group; a multicyclic aryl group unsubstituted or substituted with an alkyl group; a monocyclic heteroaryl group unsubstituted or substituted with an aryl group; or a multicyclic heteroaryl group unsubstituted or substituted with an aryl group unsubstituted or substituted with an alkyl group.

5. The hetero-cyclic compound of claim 1, wherein Ar2 is an arylamine group unsubstituted or substituted with an alkyl group; a phosphine oxide group substituted with an aryl group; a monocyclic or multicyclic aryl group unsubstituted or substituted with a nitrile group or an aryl group; a monocyclic heteroaryl group unsubstituted or substituted with an aryl group; or a multicyclic heteroaryl group unsubstituted or substituted with an aryl group unsubstituted or substituted with an alkyl group.

6. The hetero-cyclic compound of claim 1, wherein Chemical Formula 1 is selected from among the following compounds:

205
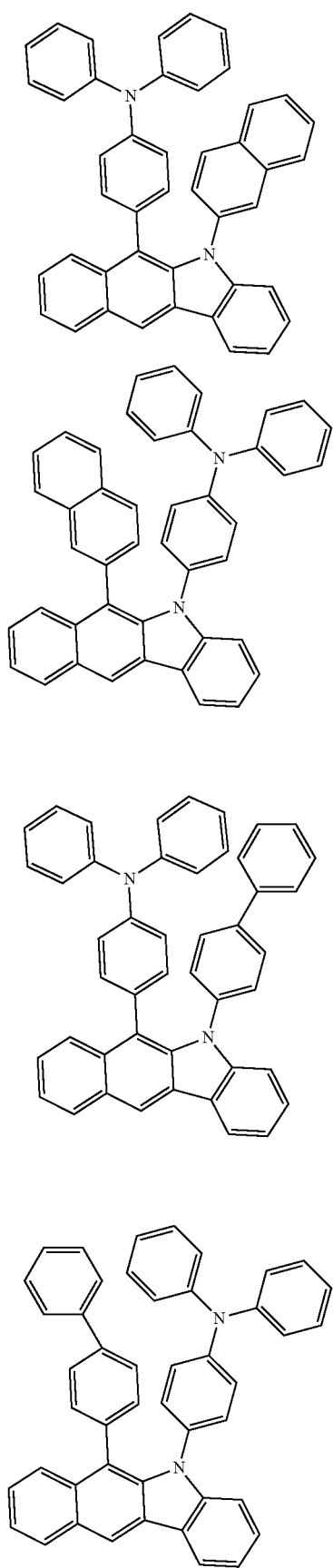
206
-continued
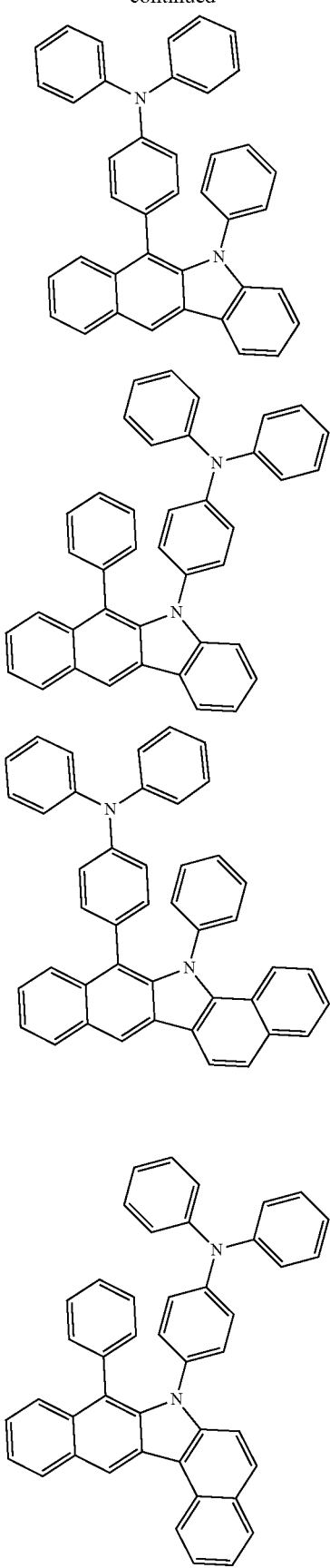

207
-continued
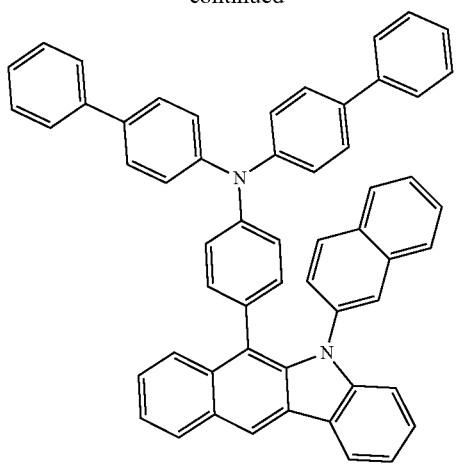
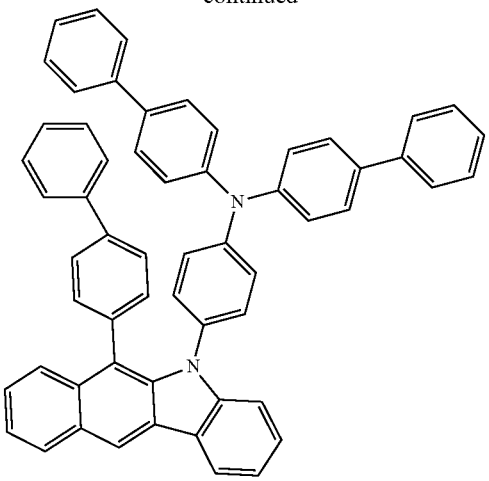
208
-continued
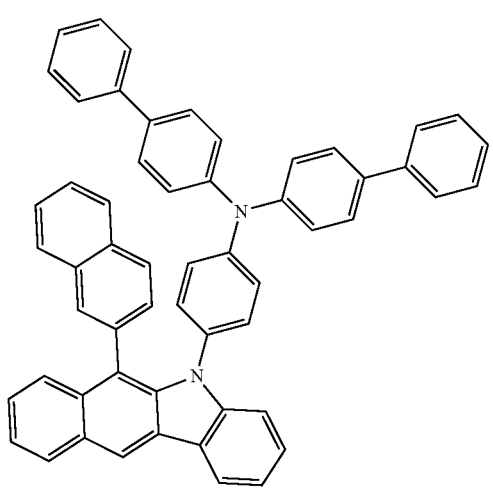
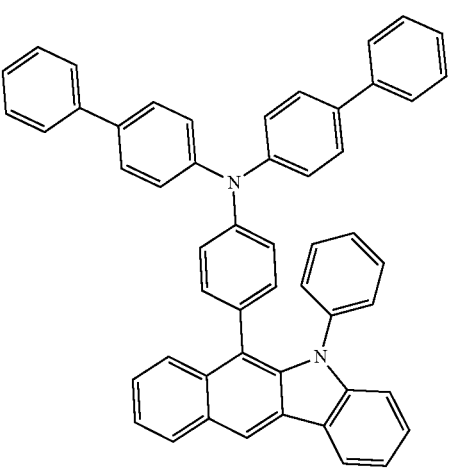
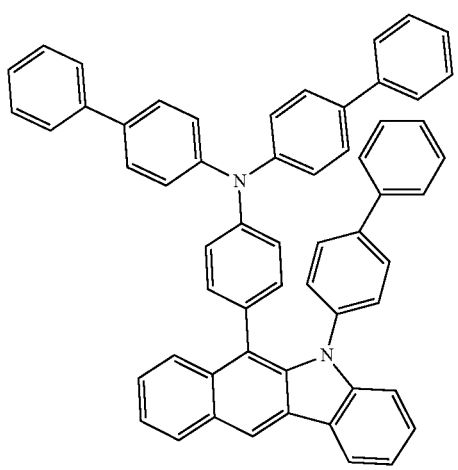
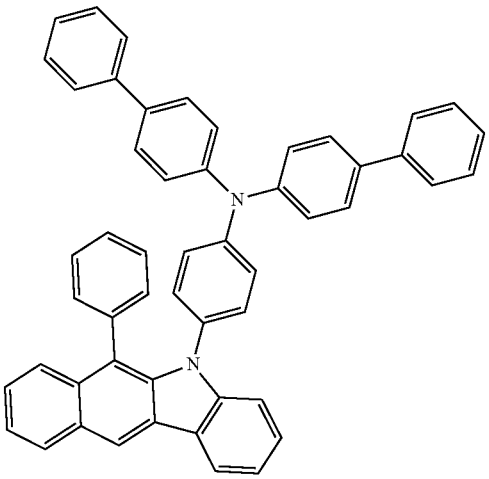

209
-continued
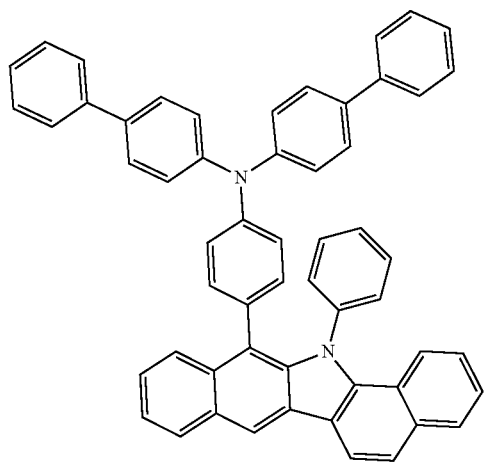
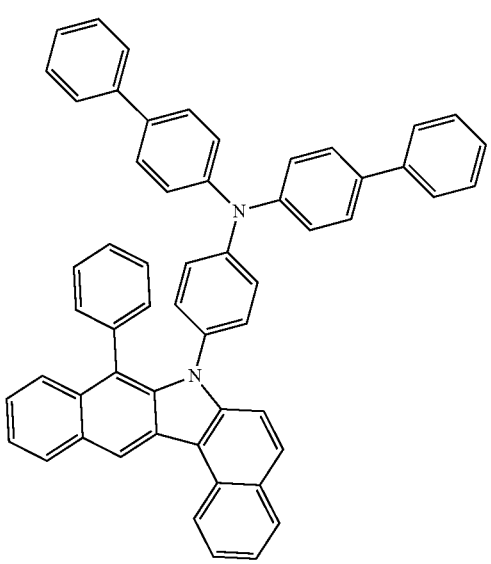
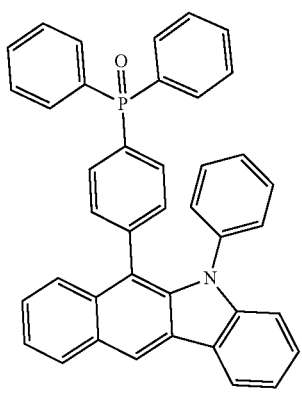
210
-continued
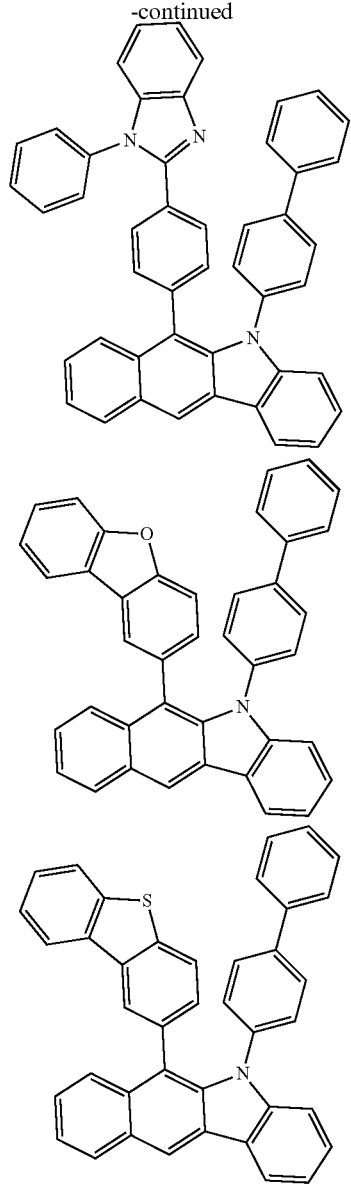
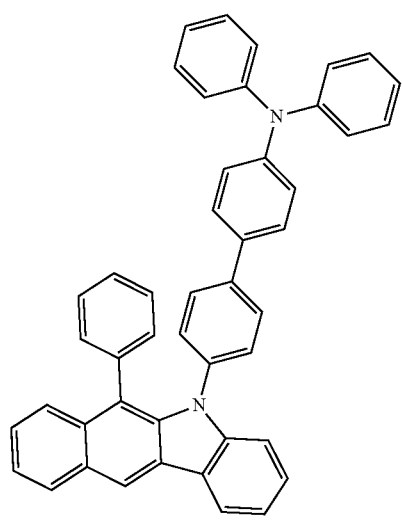

211
-continued
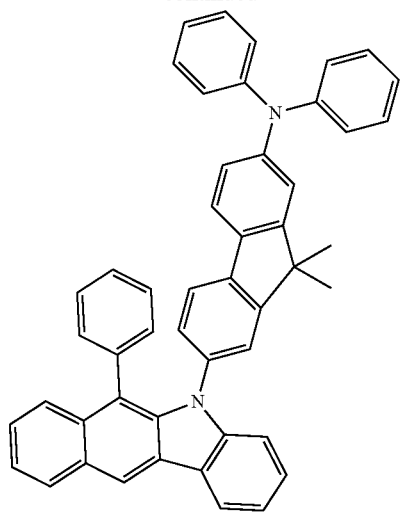
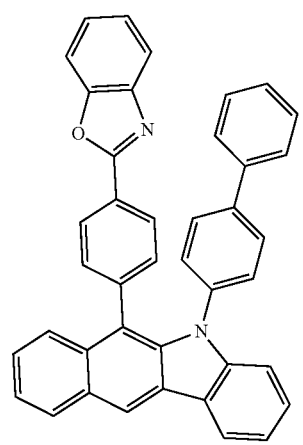
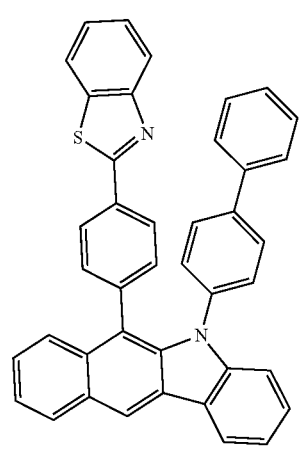
212
-continued
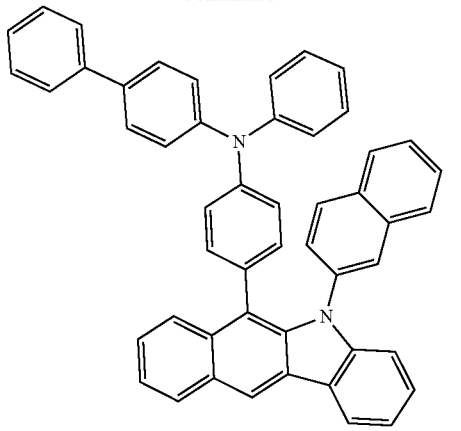

213
-continued
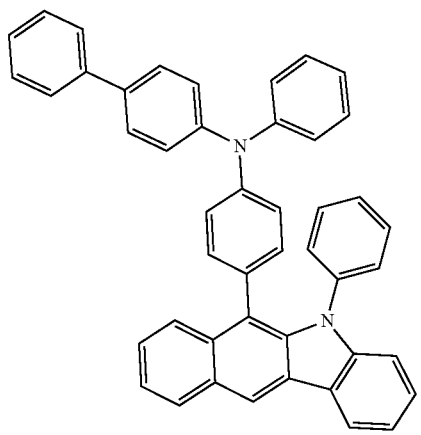
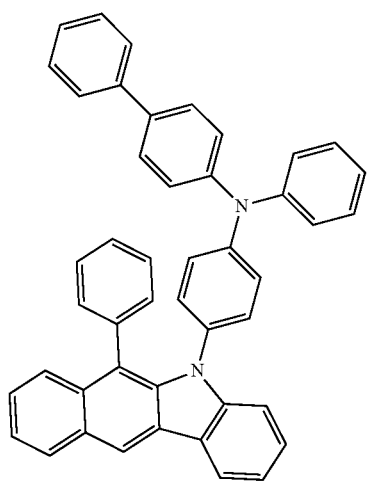
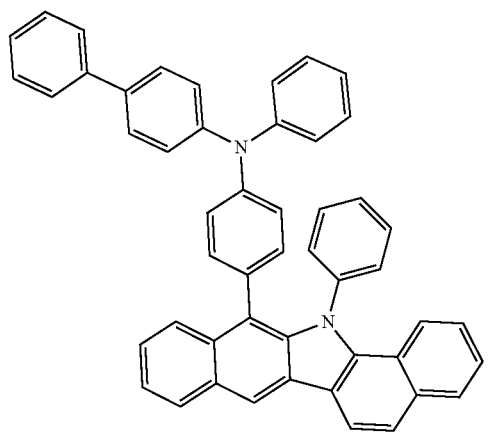
214
-continued
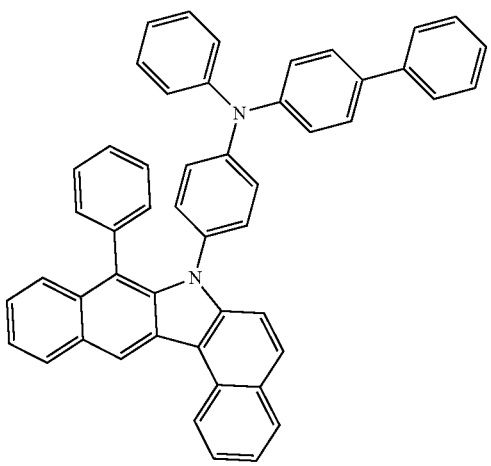
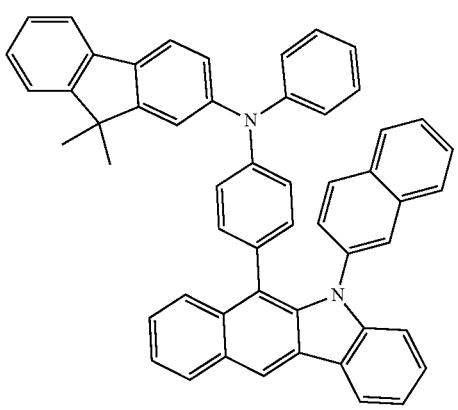
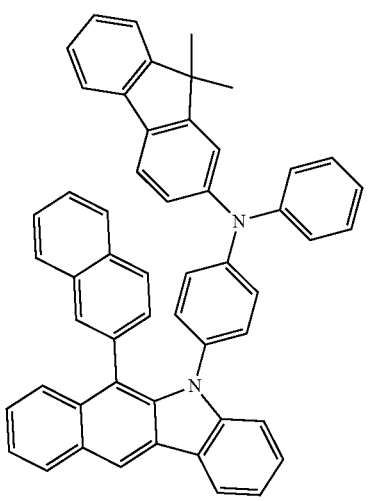

215
-continued
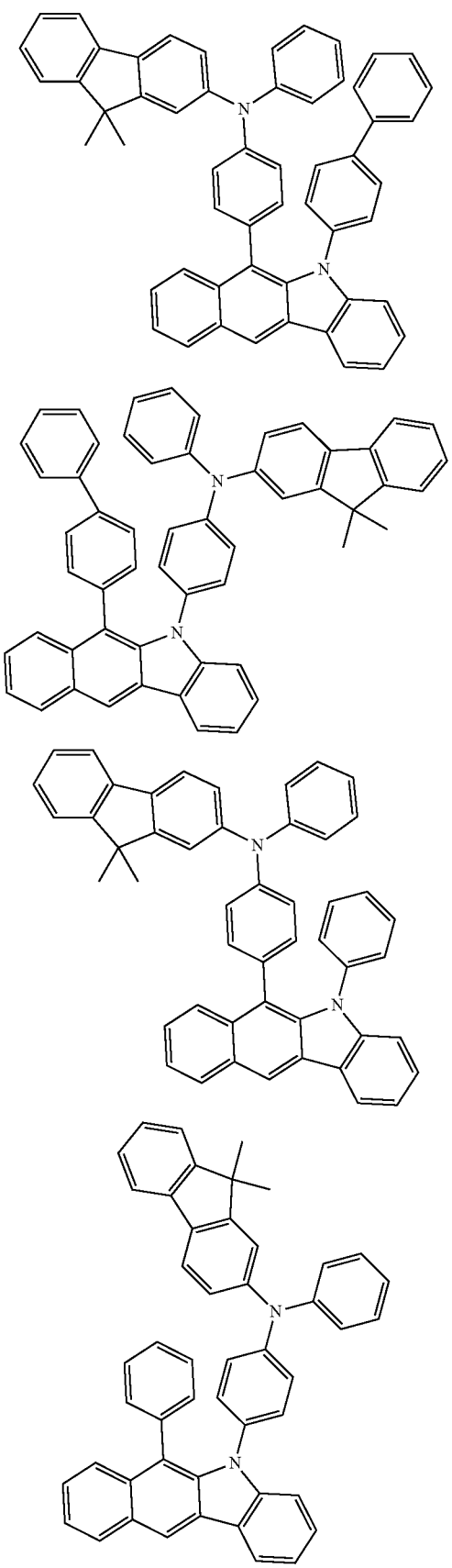
216
-continued
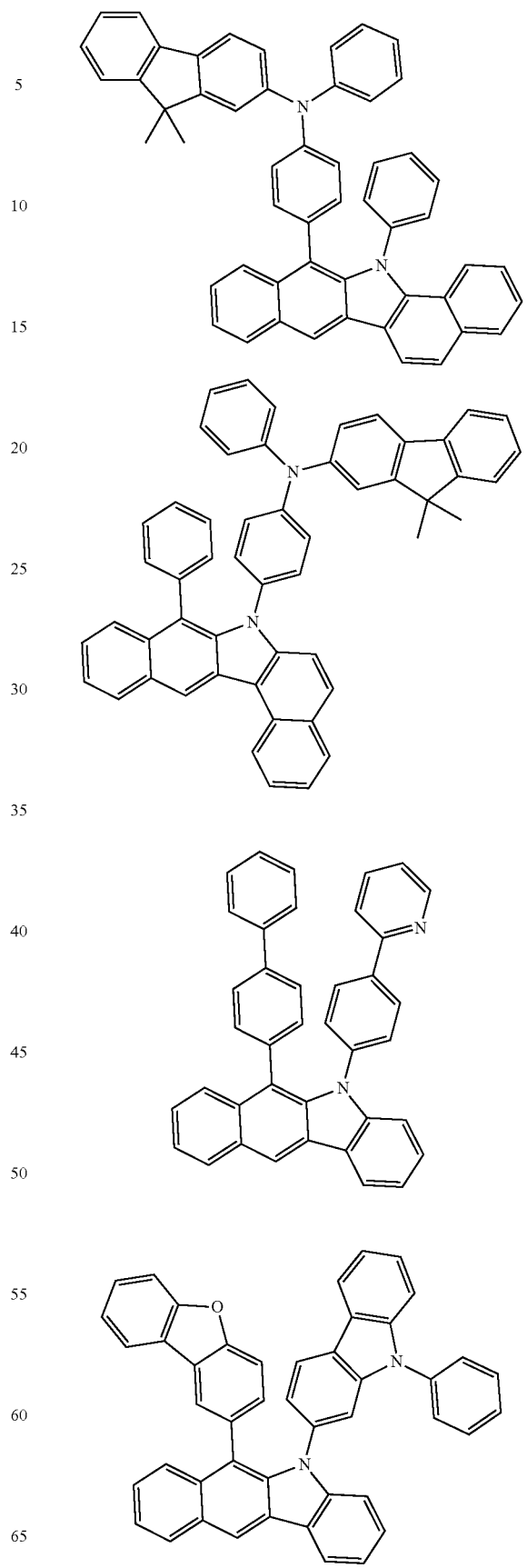

217
-continued
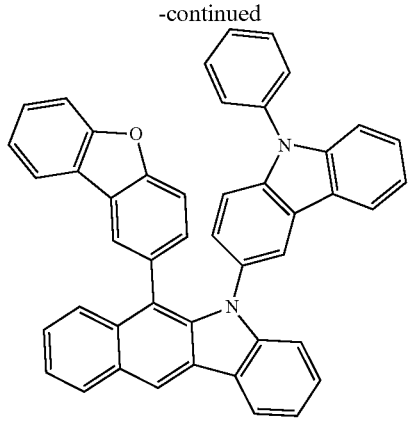
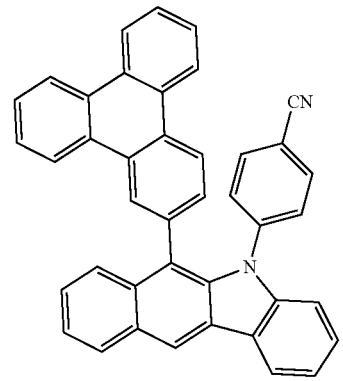
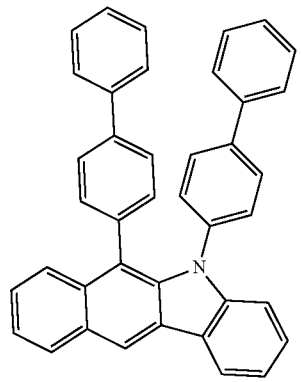
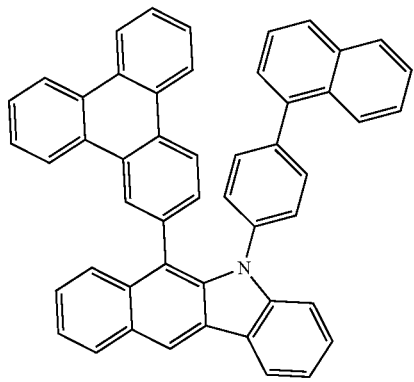
218
-continued
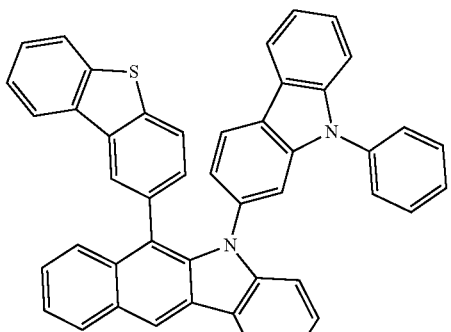
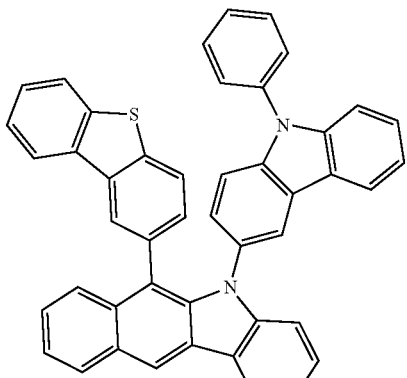
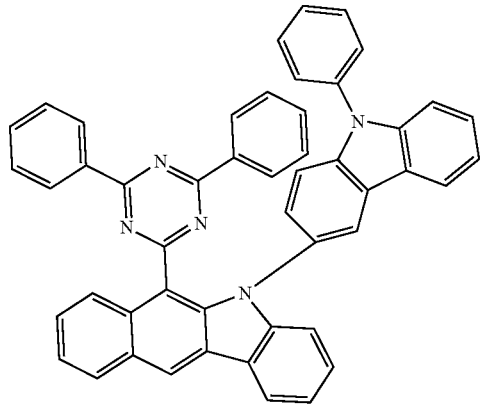
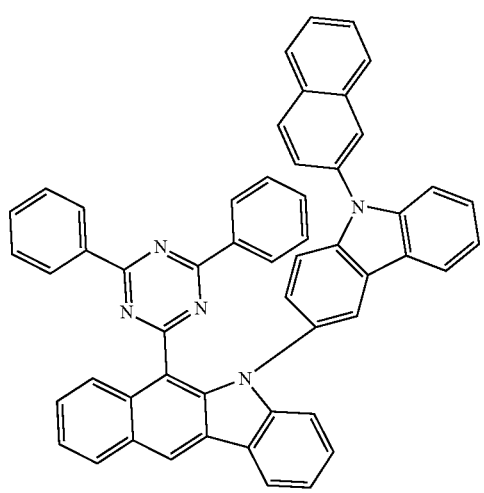

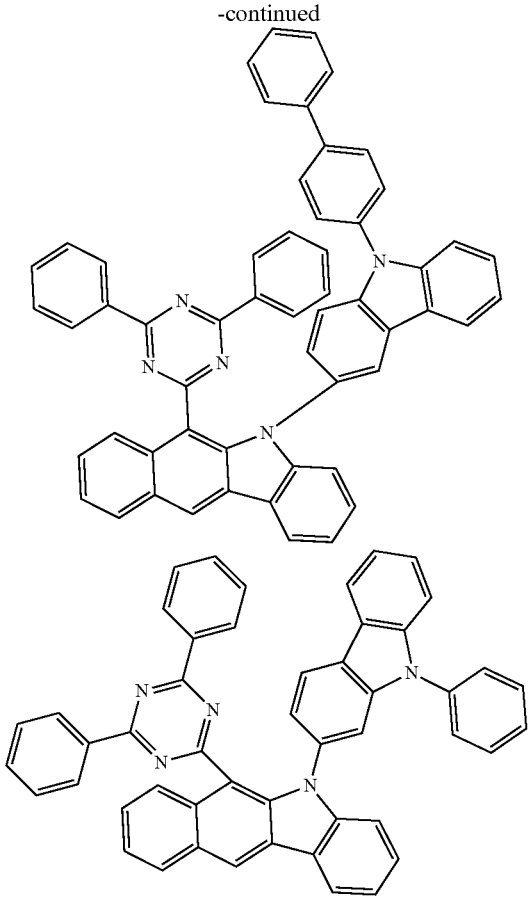
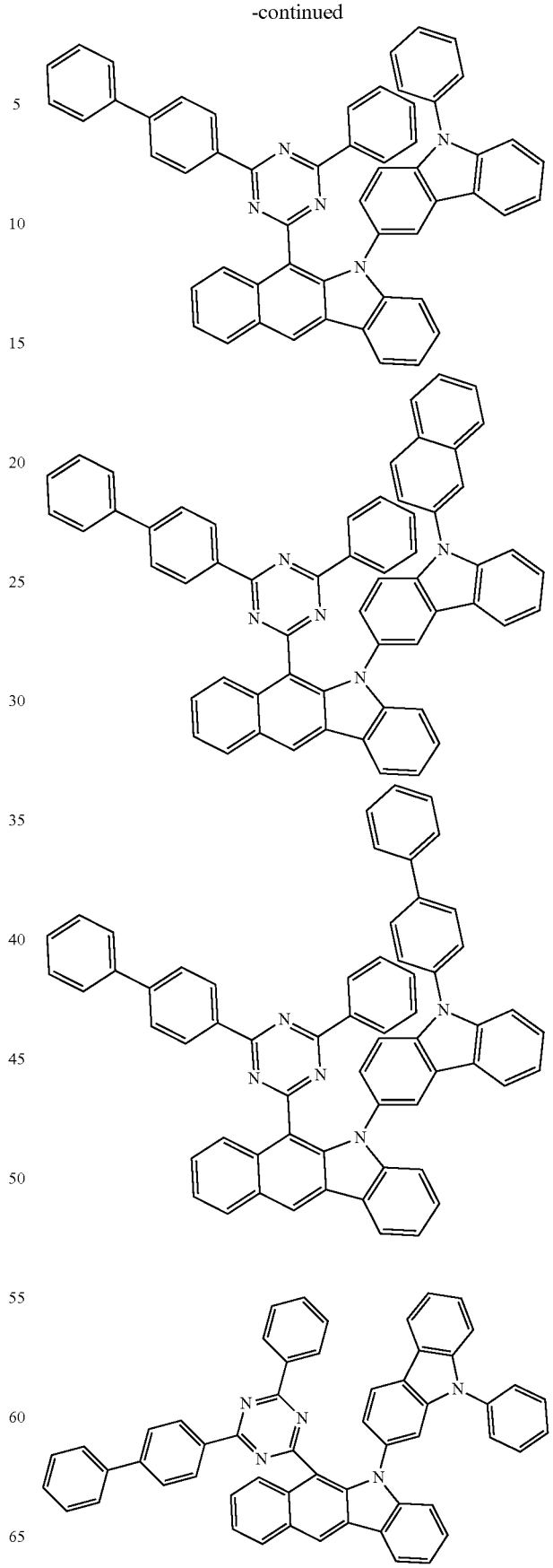

221
-continued
222
-continued
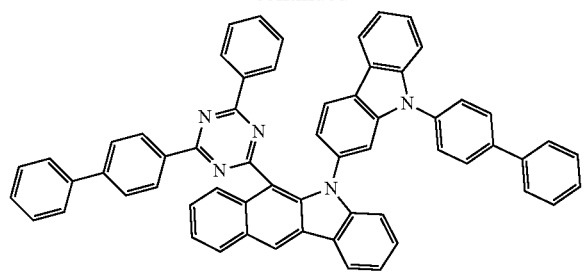
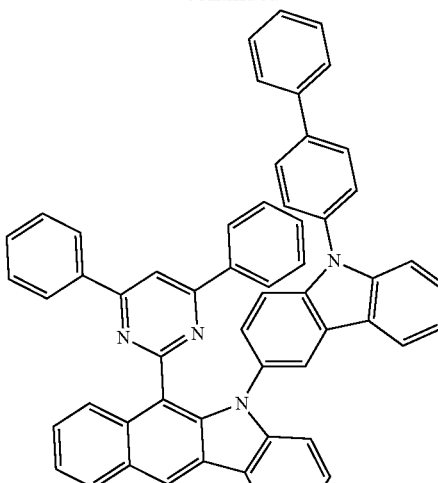
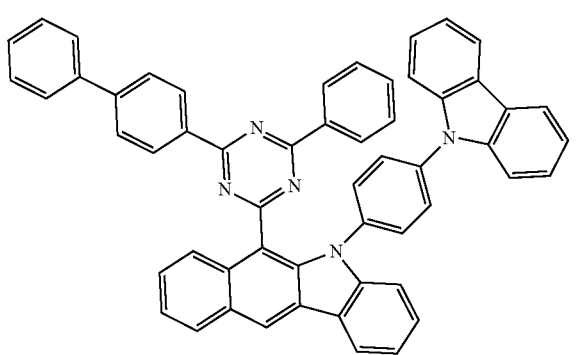
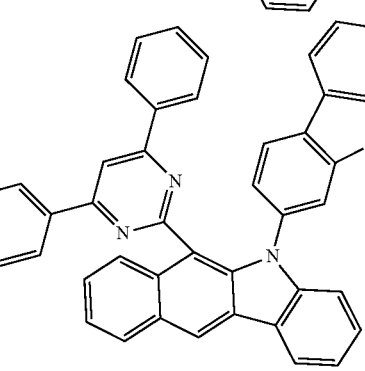
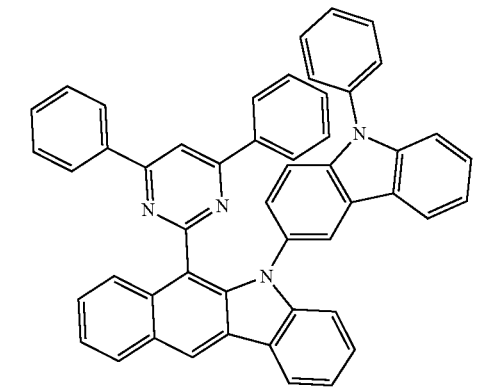
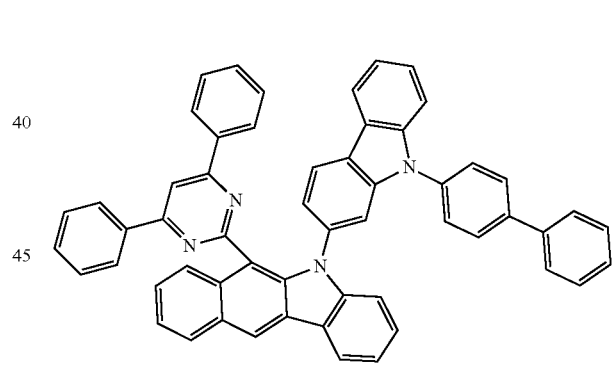
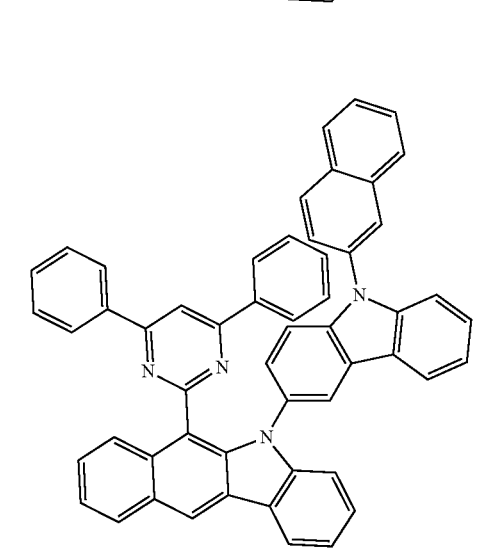
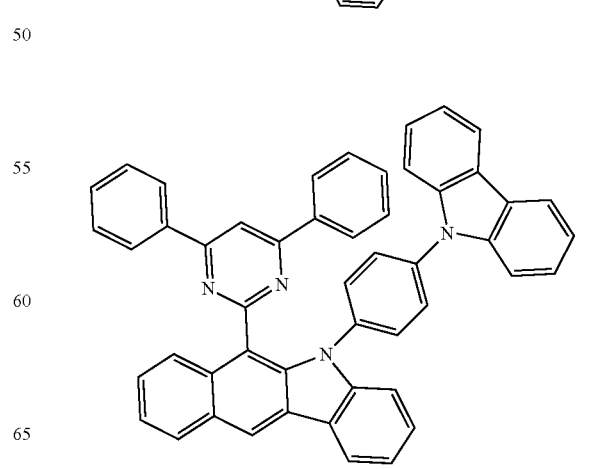

223
-continued
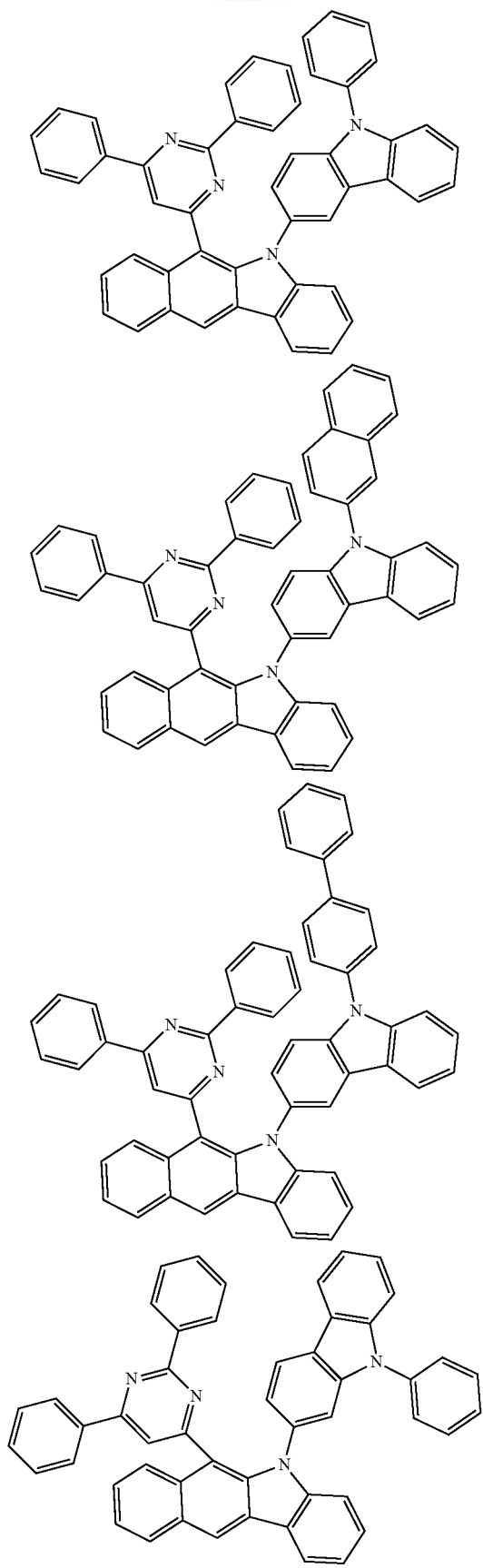
224
-continued
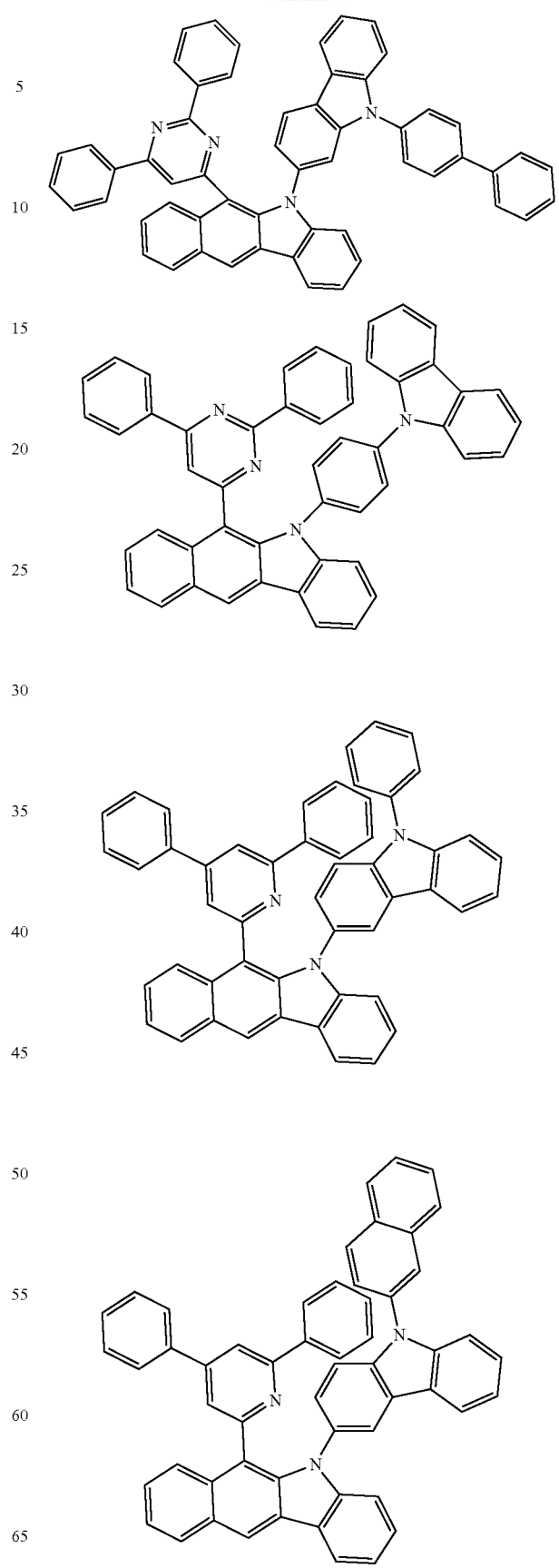

225
-continued
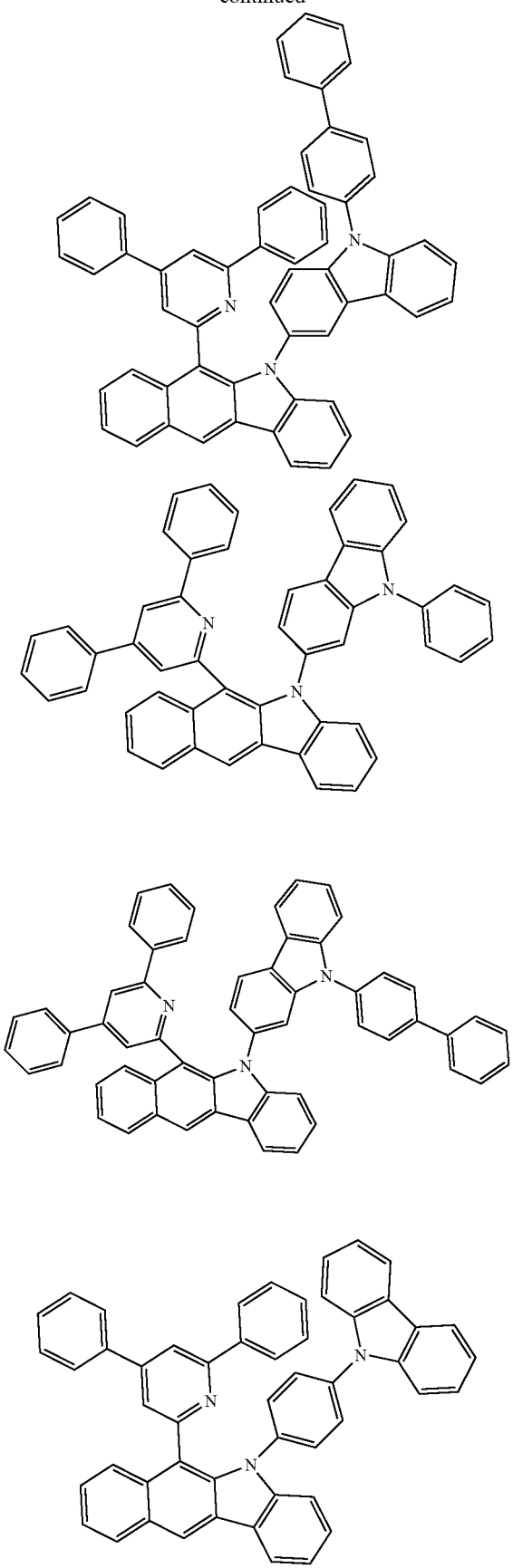
226
-continued
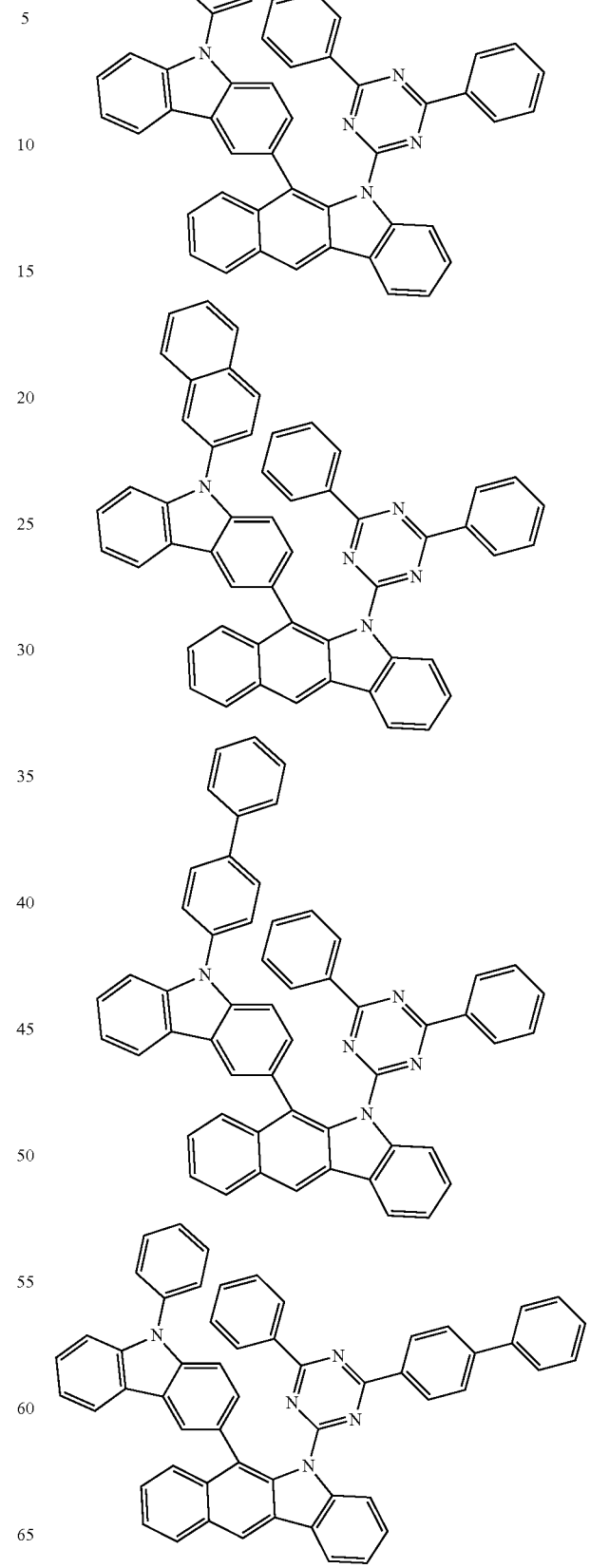

227
-continued
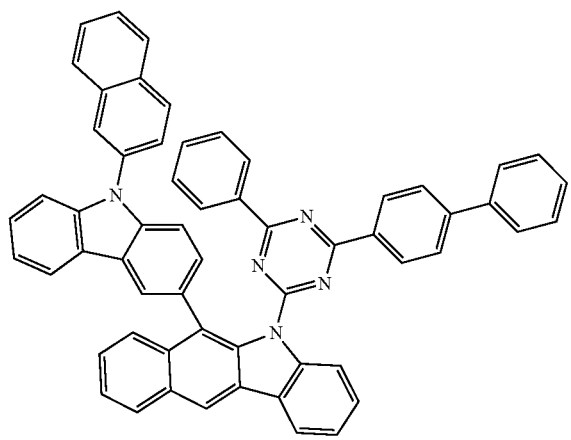
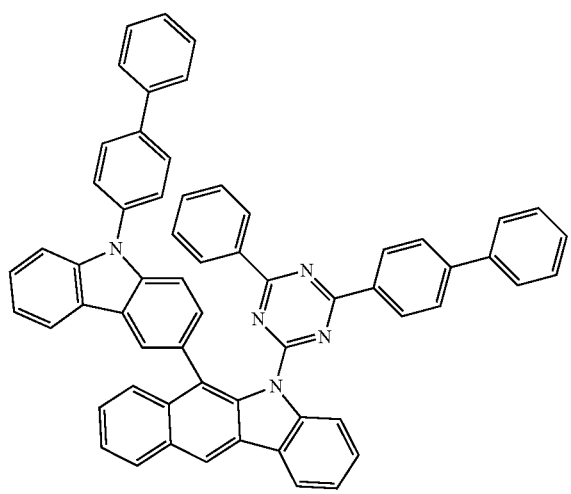
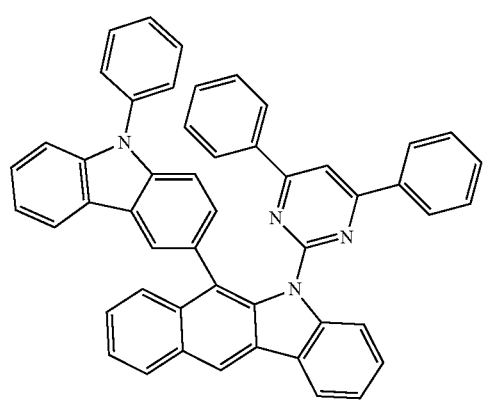
228
-continued
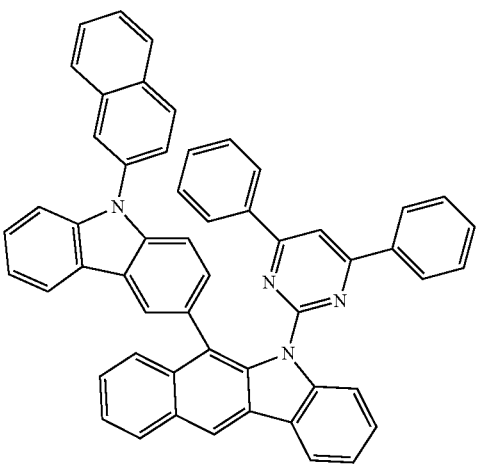
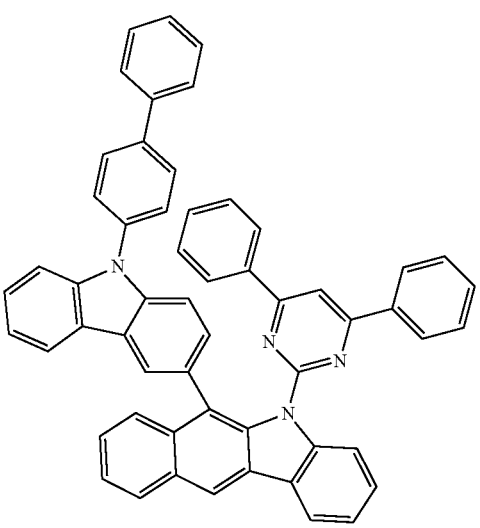
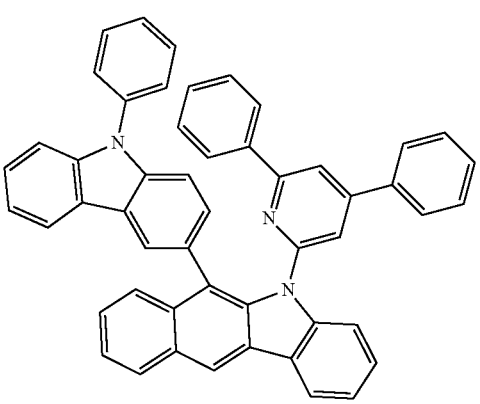

229
-continued
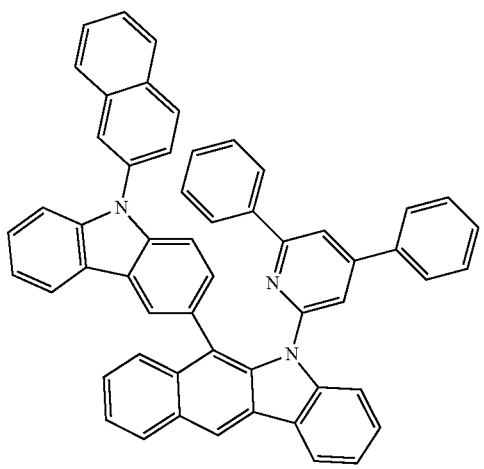
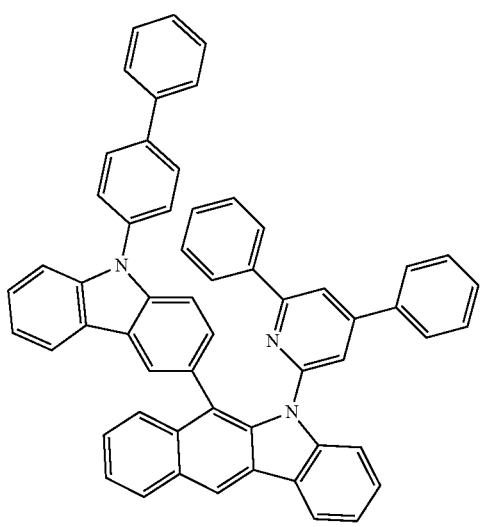
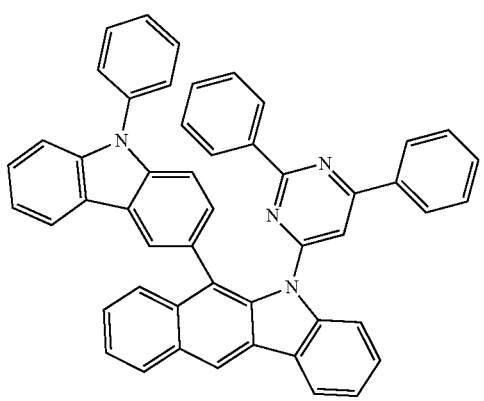
230
-continued
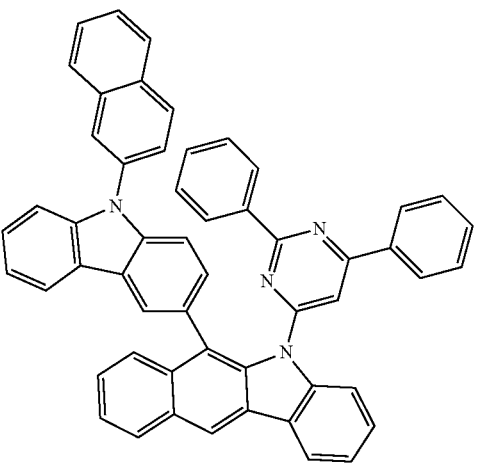
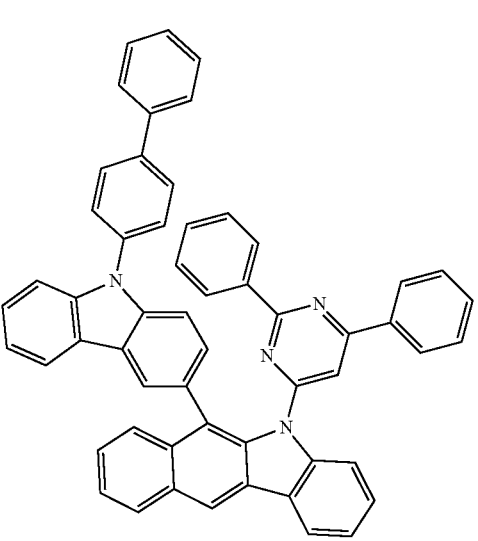
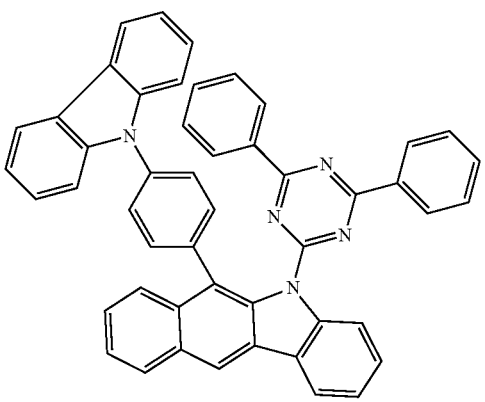

231
-continued
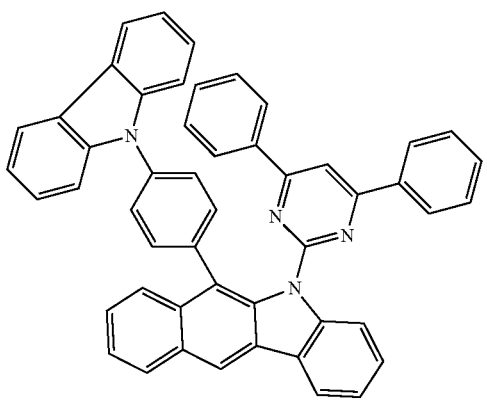
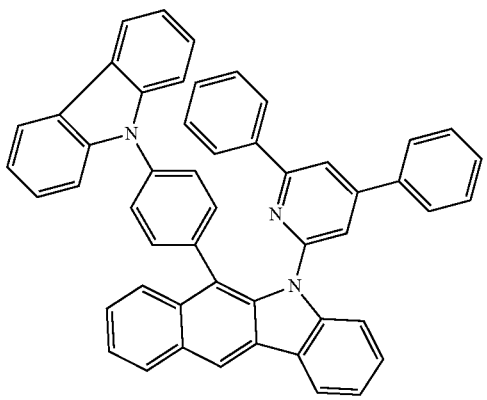
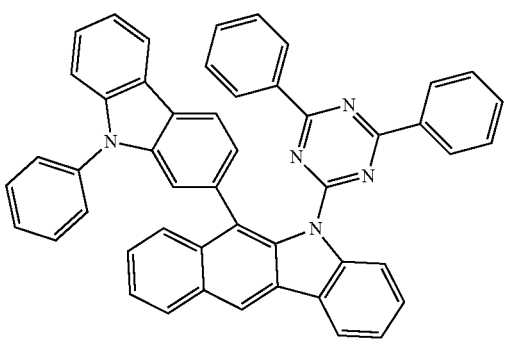
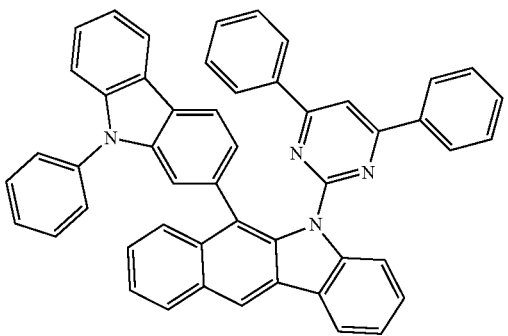
232
-continued
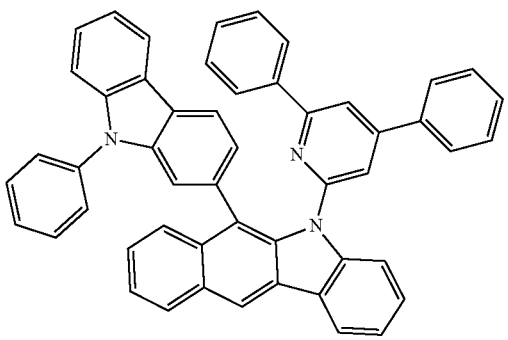
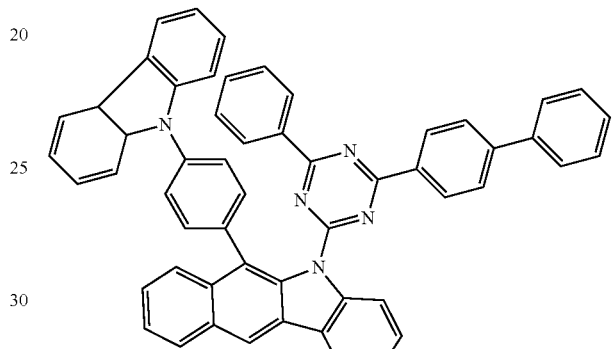
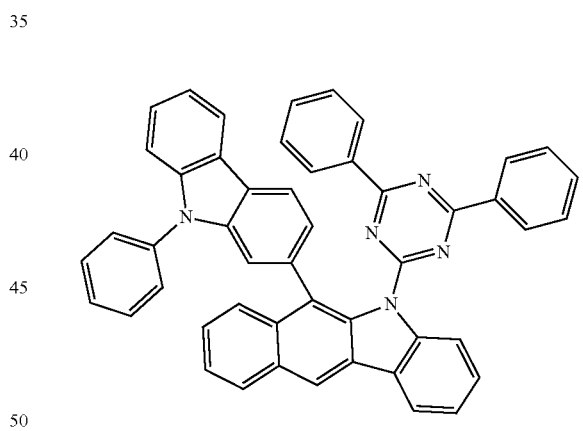
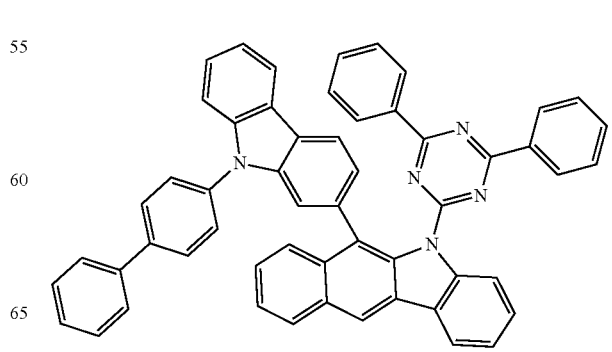

233
-continued
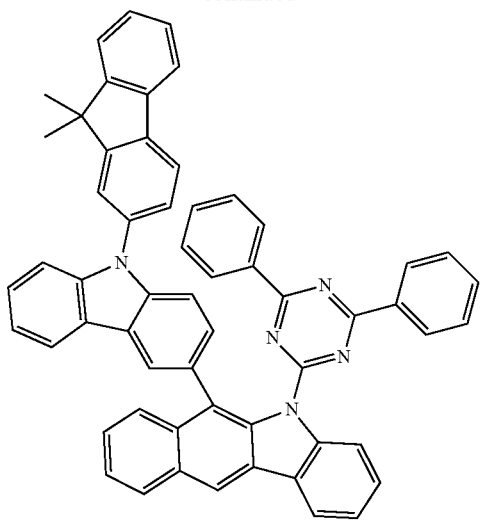
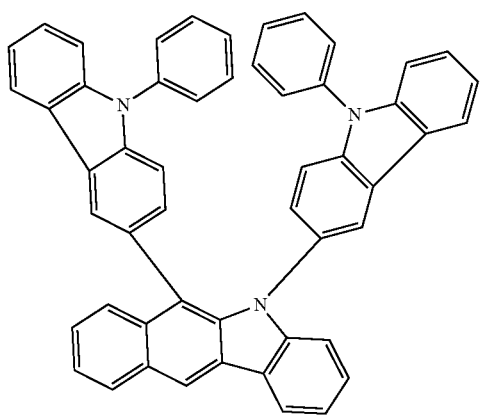
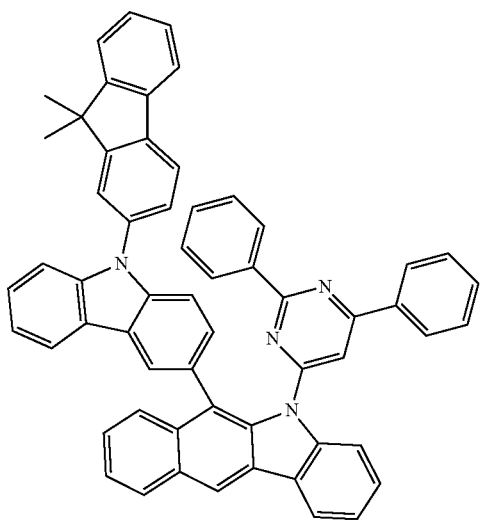
234
-continued
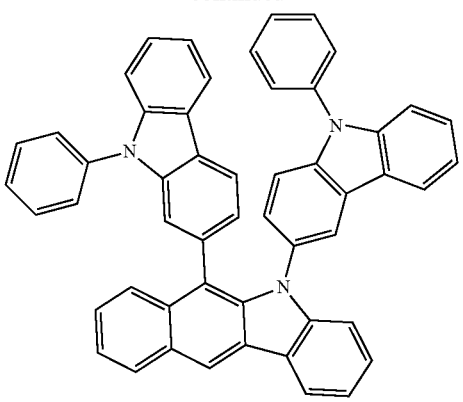
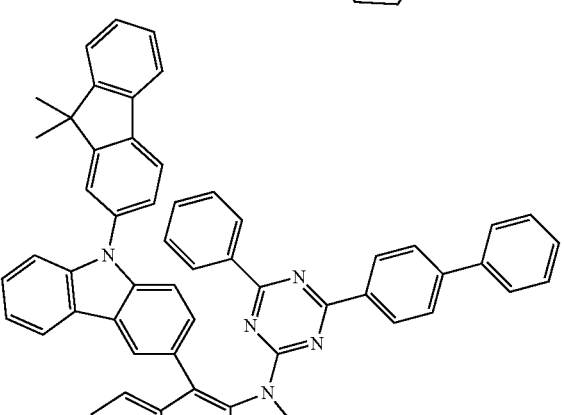
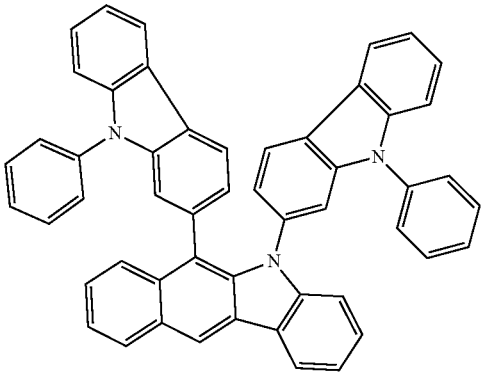
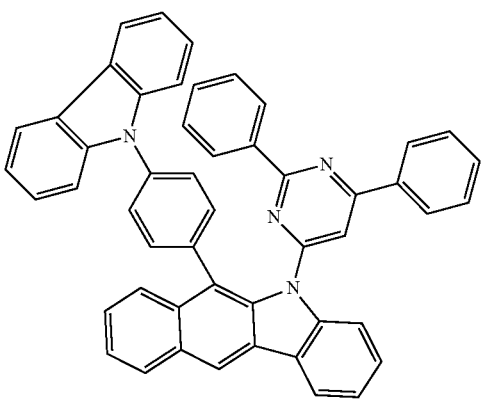

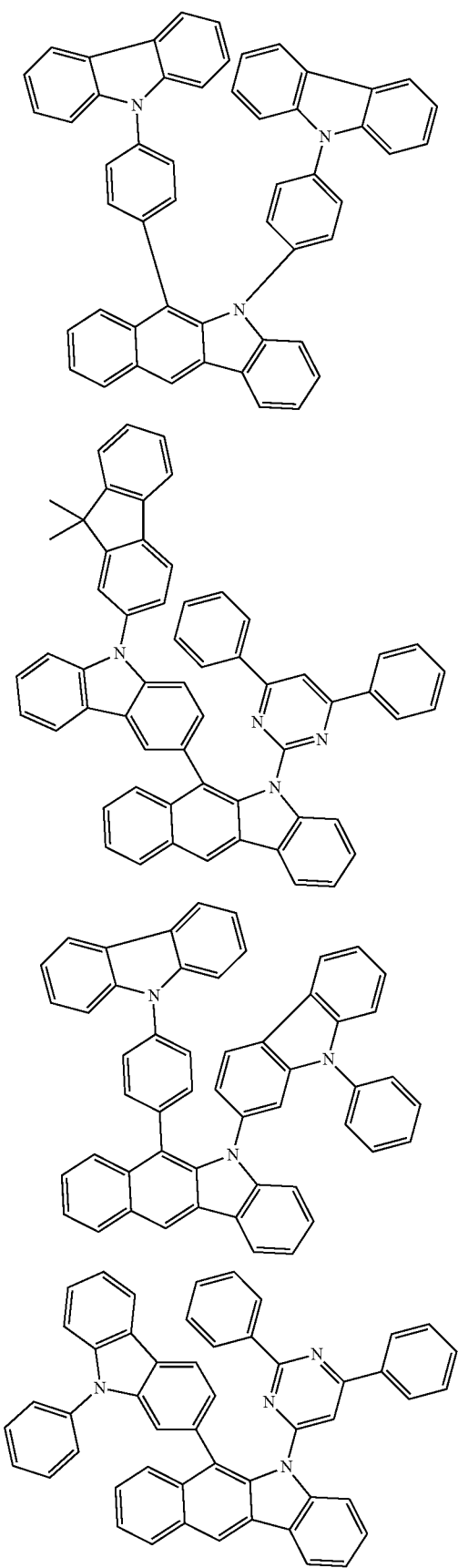
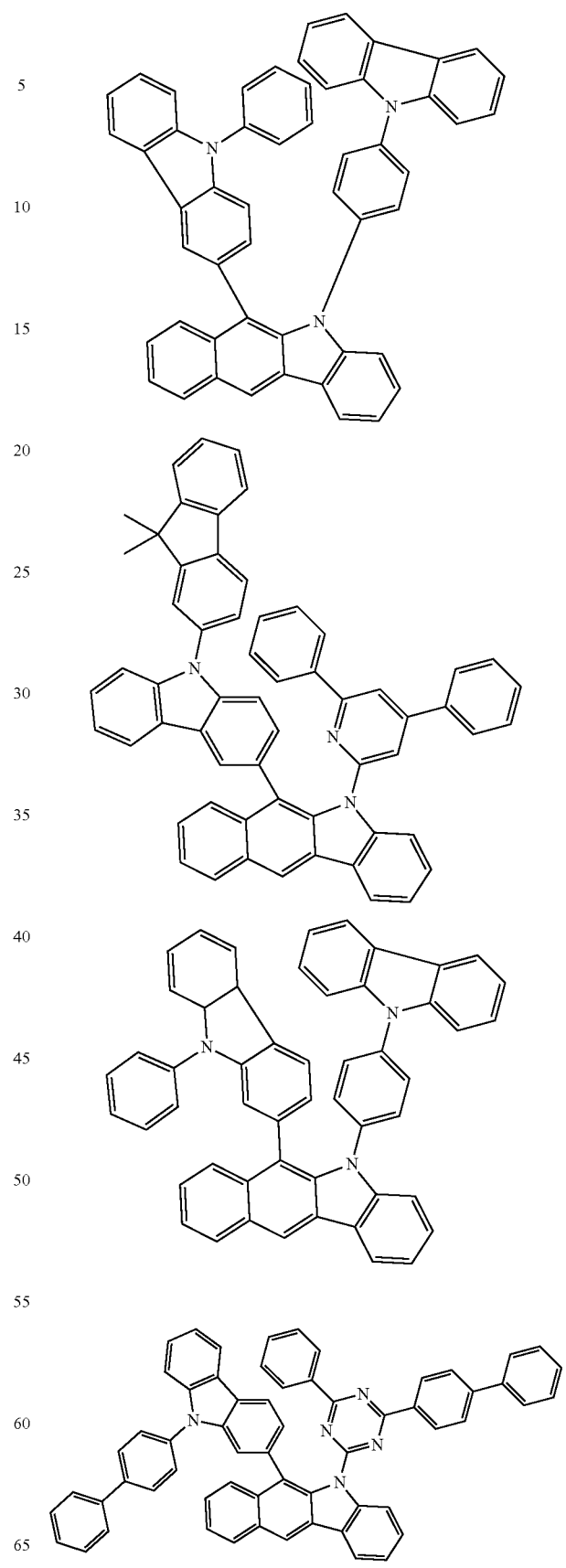

237
-continued
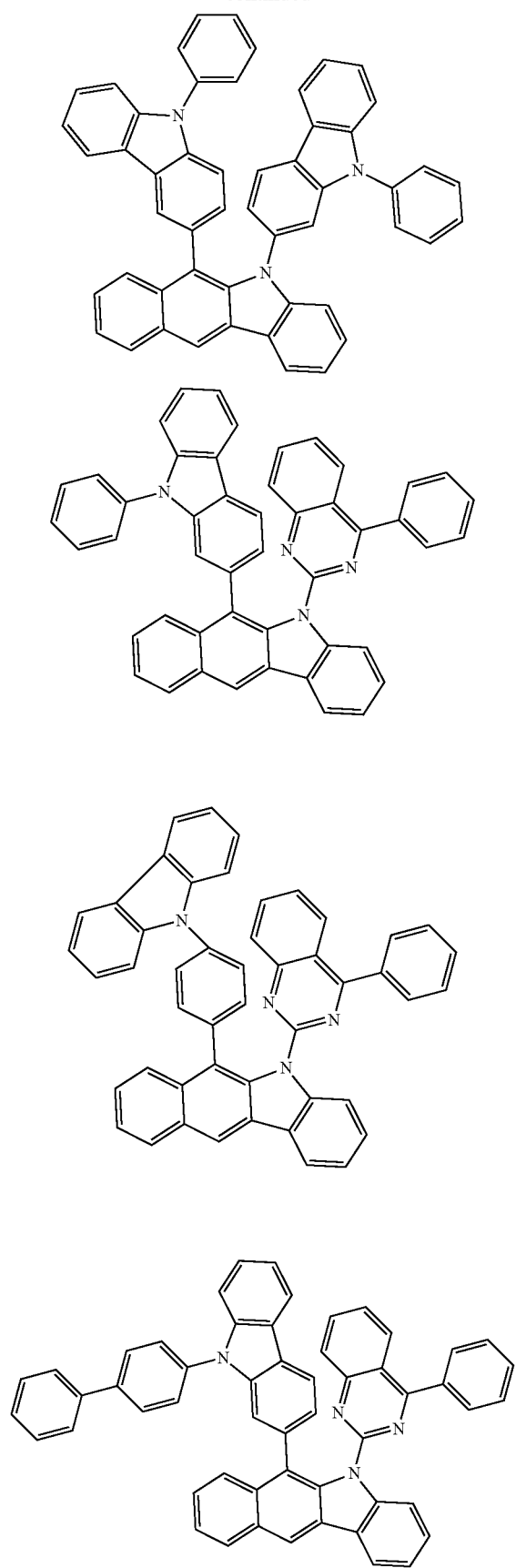
238
-continued
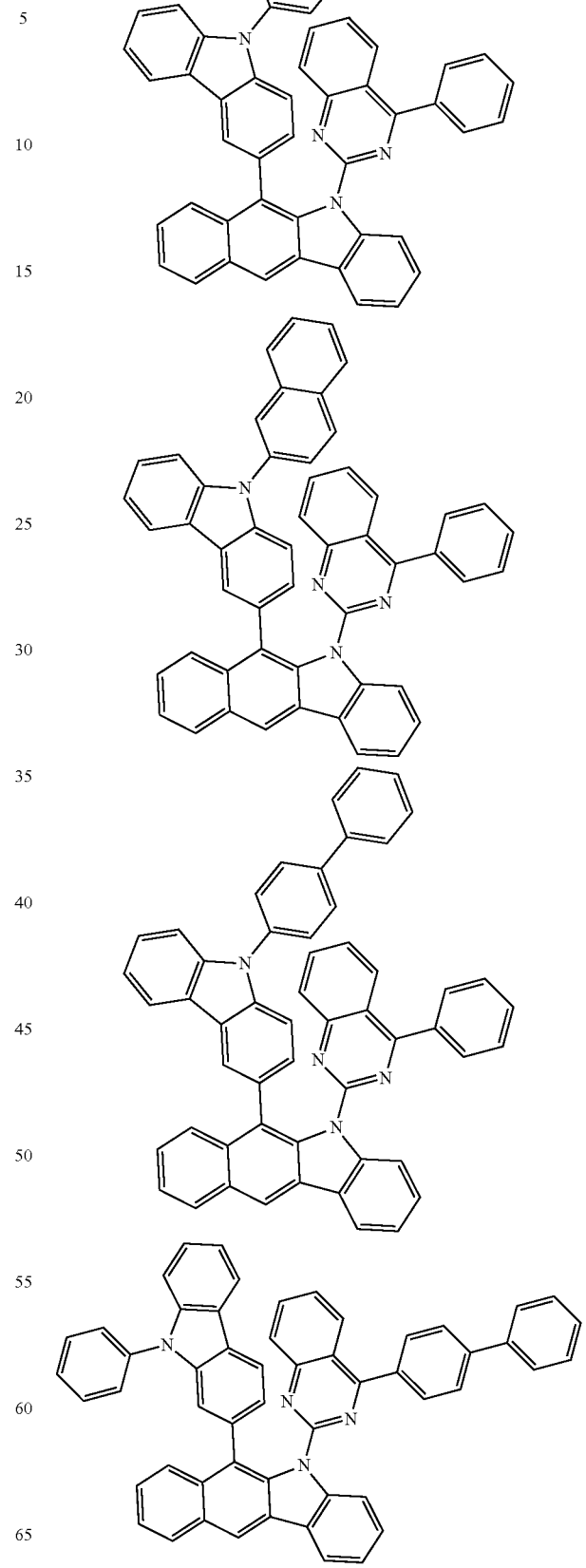

239
-continued
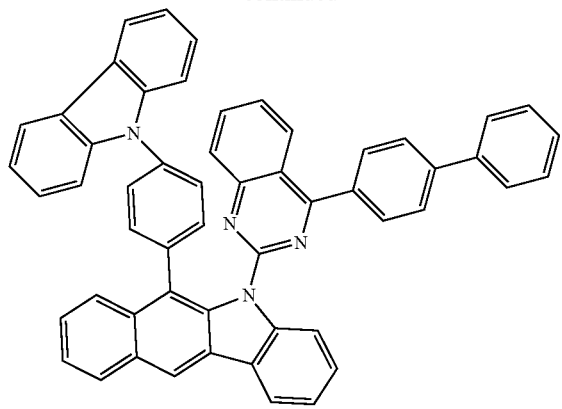
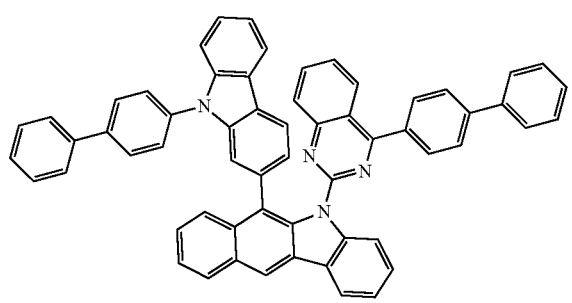
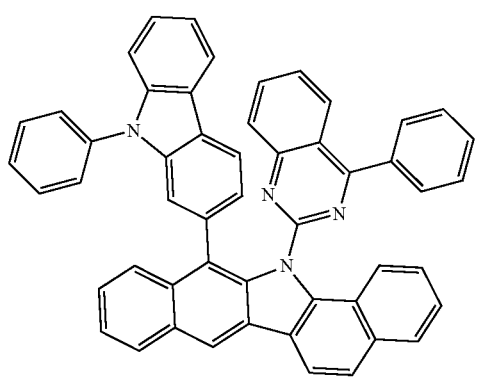
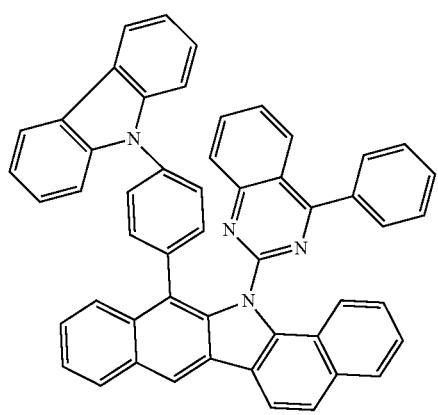
240
-continued
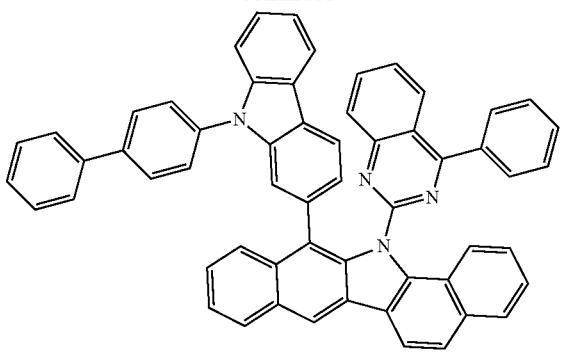
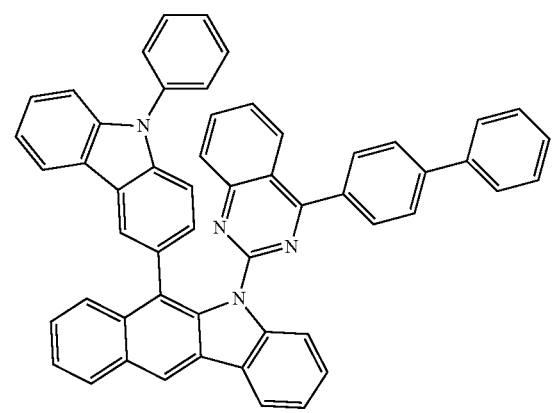
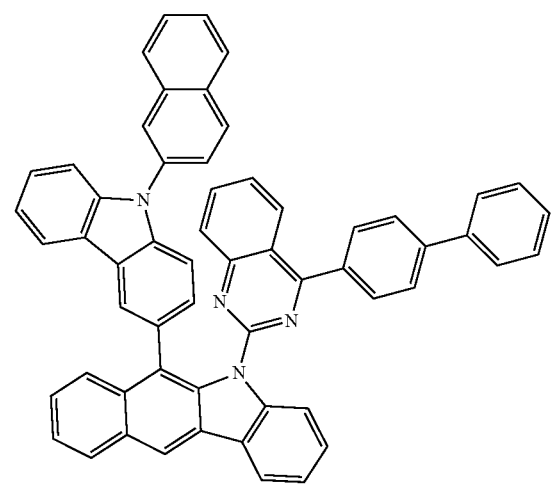

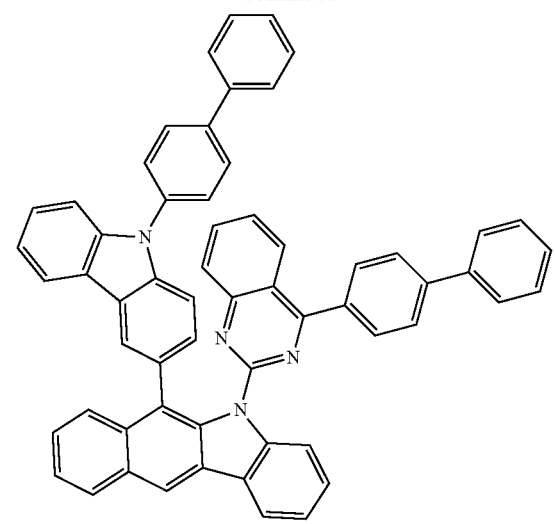
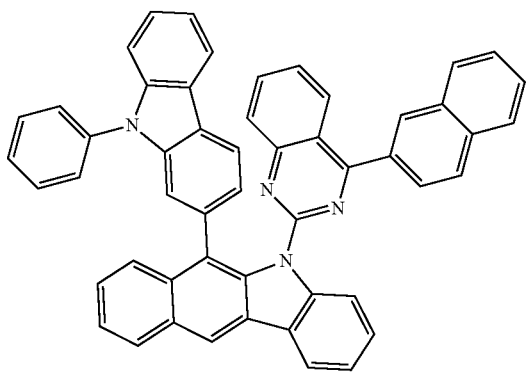
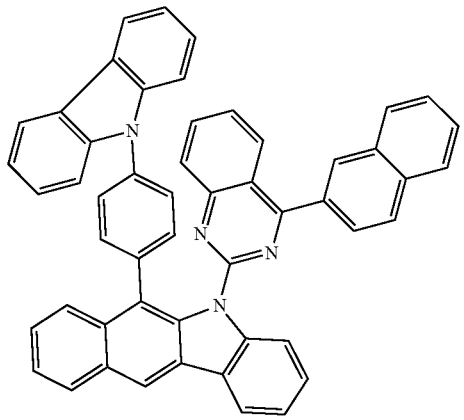
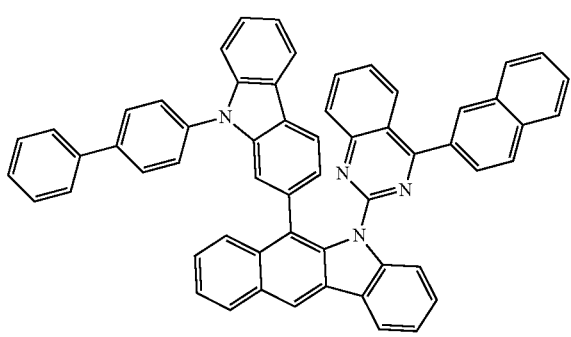
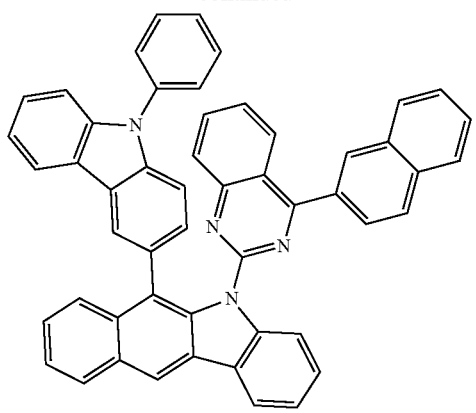
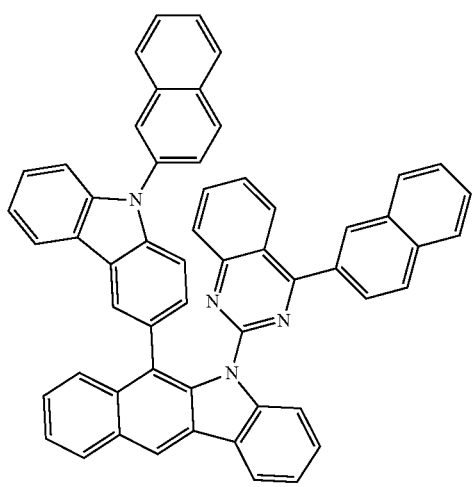
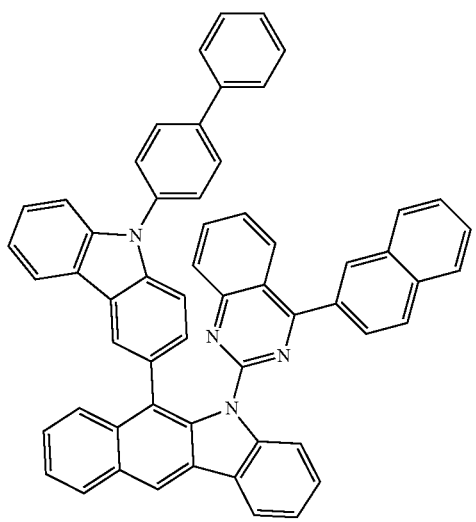

243
-continued
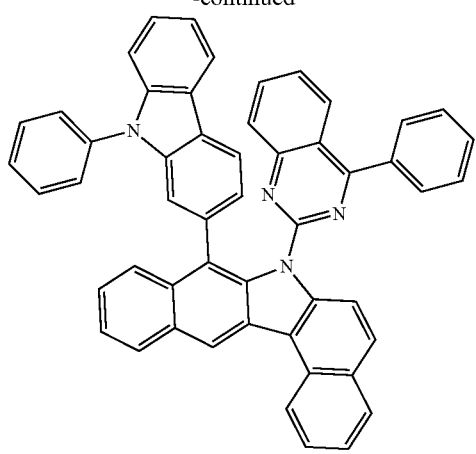
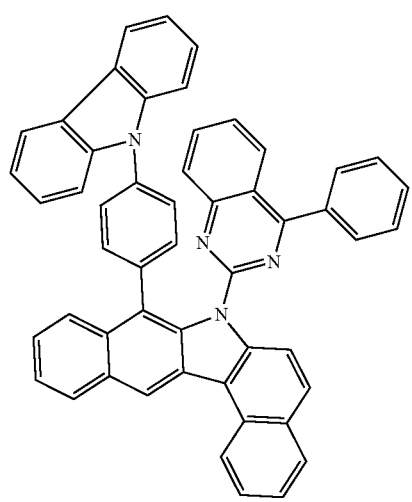
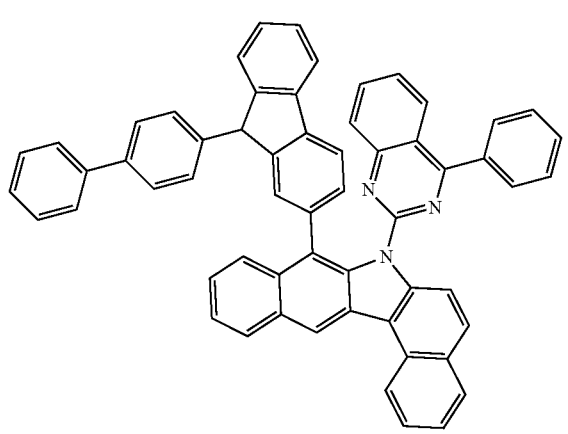
244
-continued
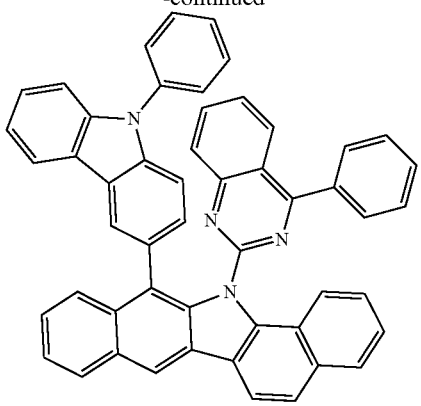
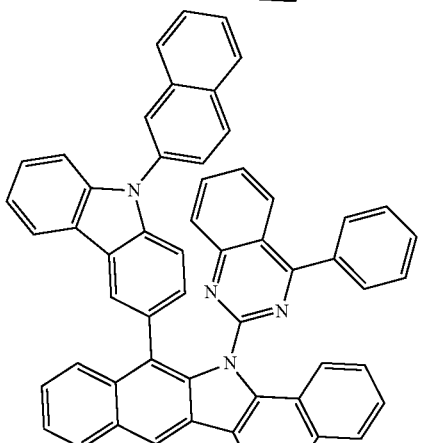
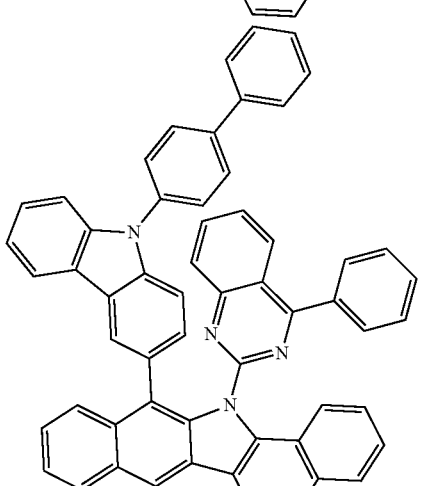
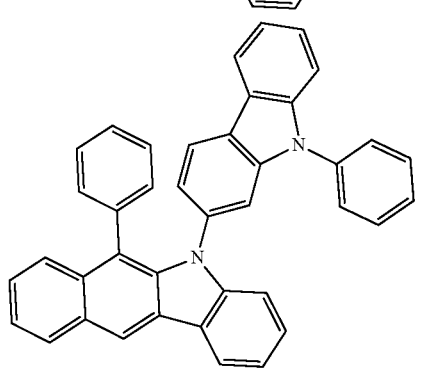

245
-continued
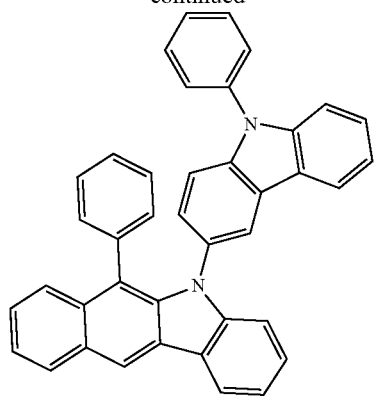
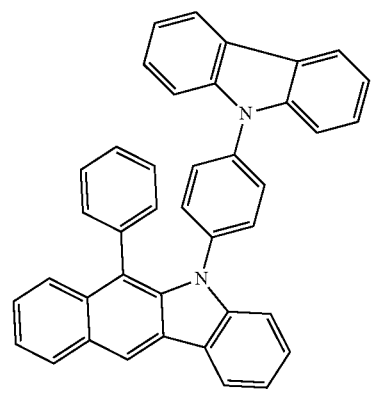
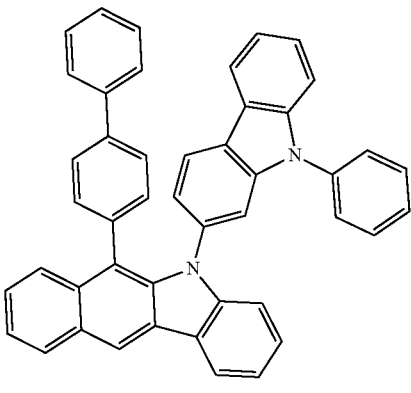
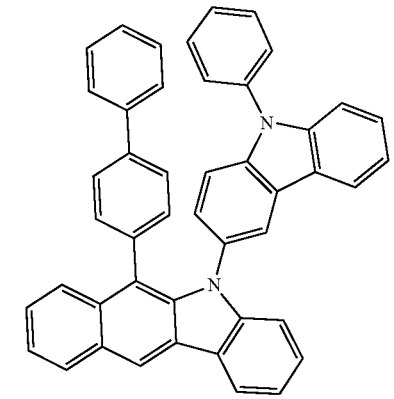
246
-continued
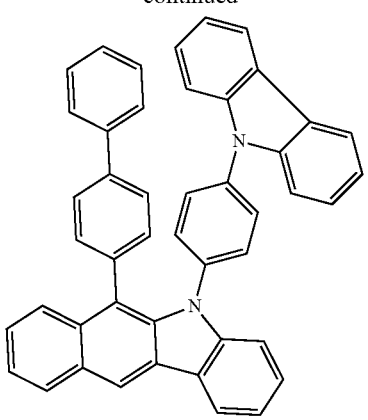
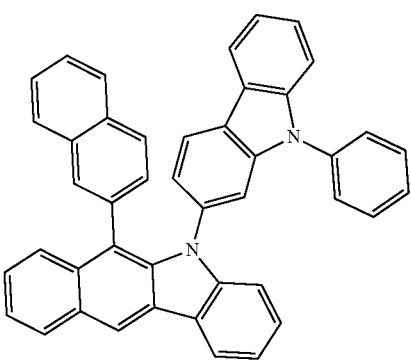
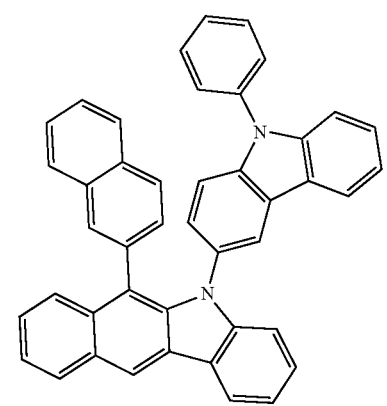
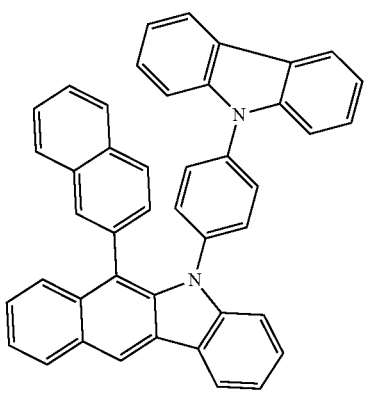

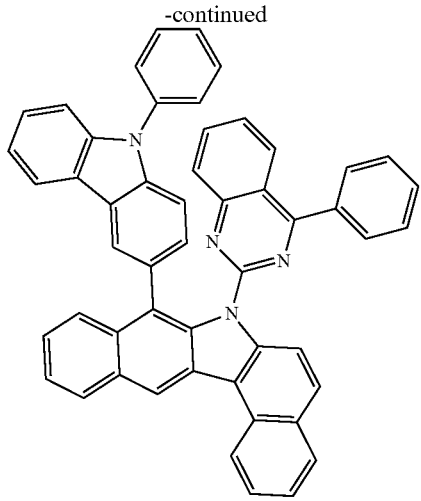
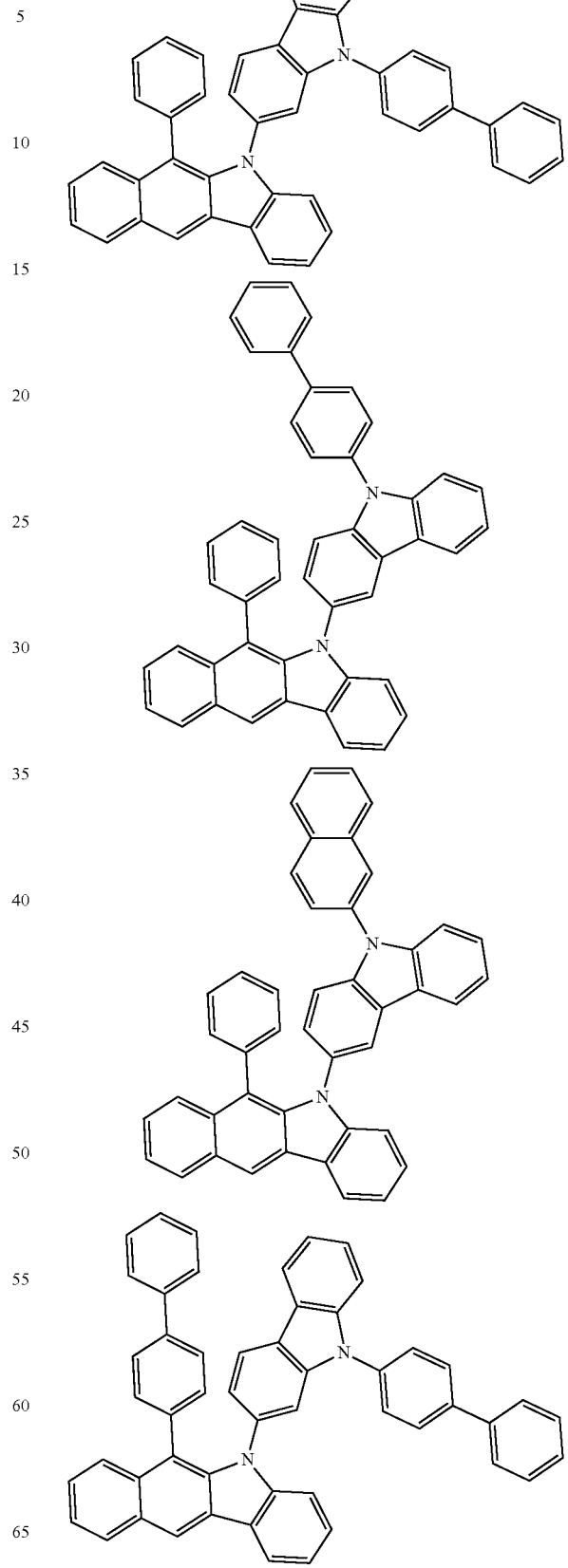

249
-continued
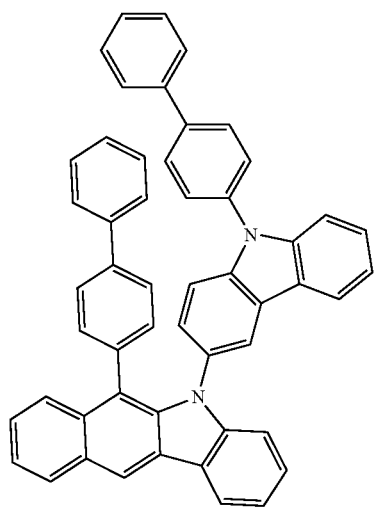
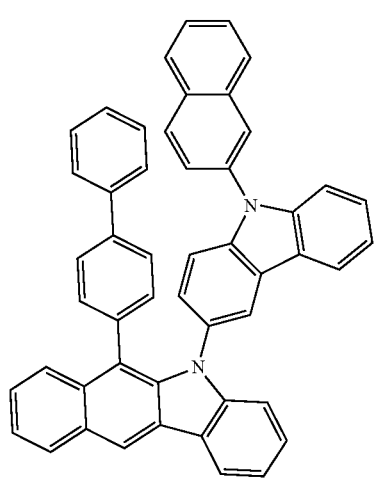
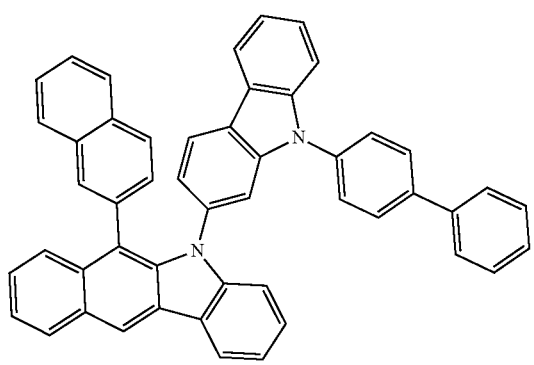
250
-continued
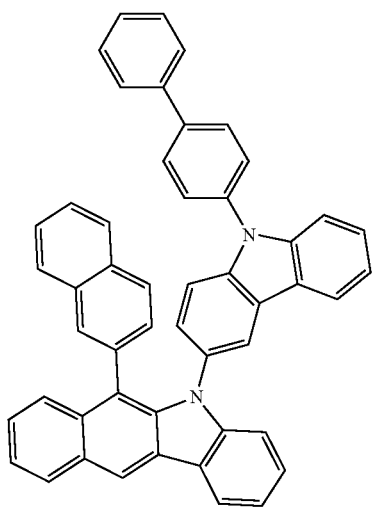
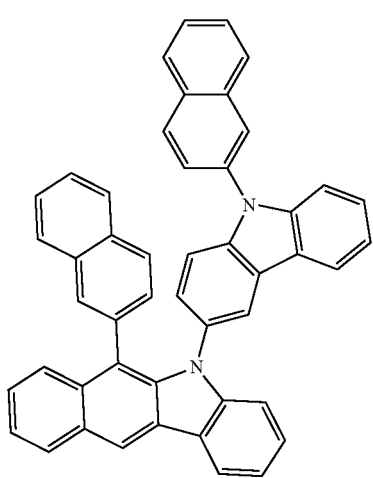
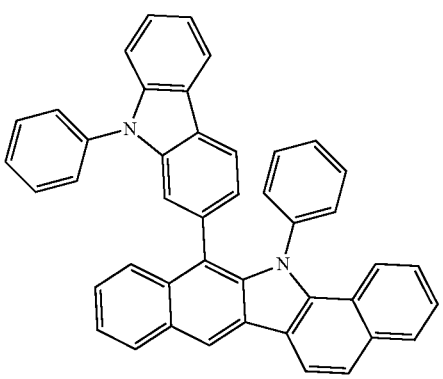

251
-continued
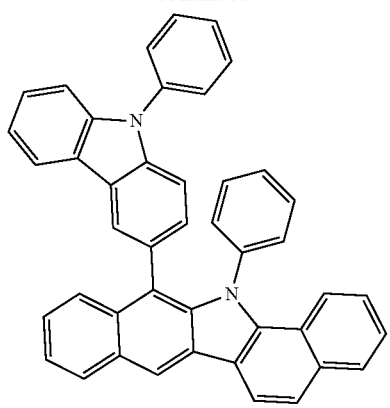
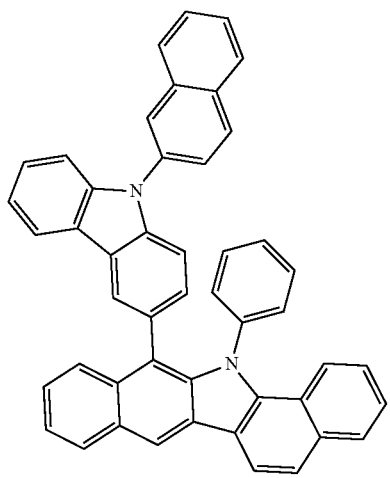
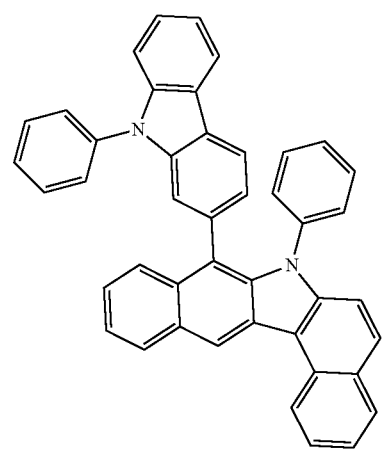
252
-continued
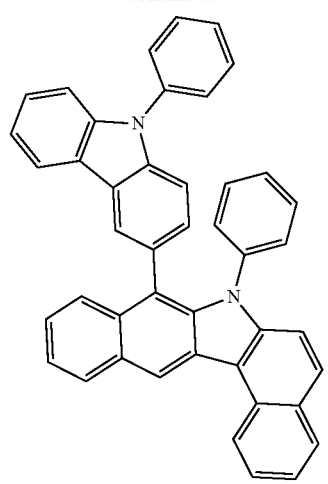
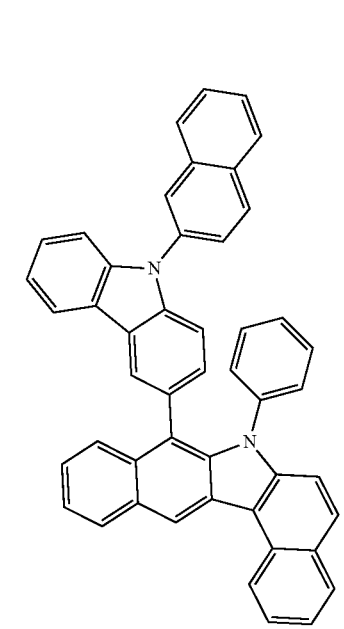
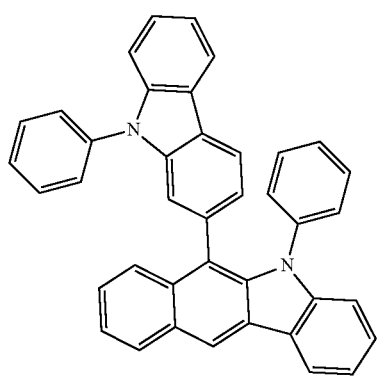

-continued
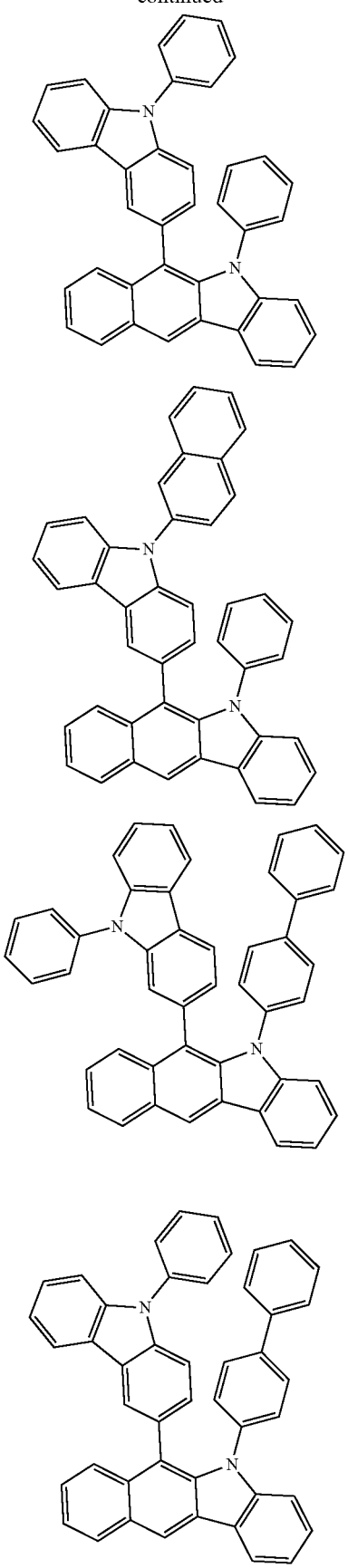
-continued
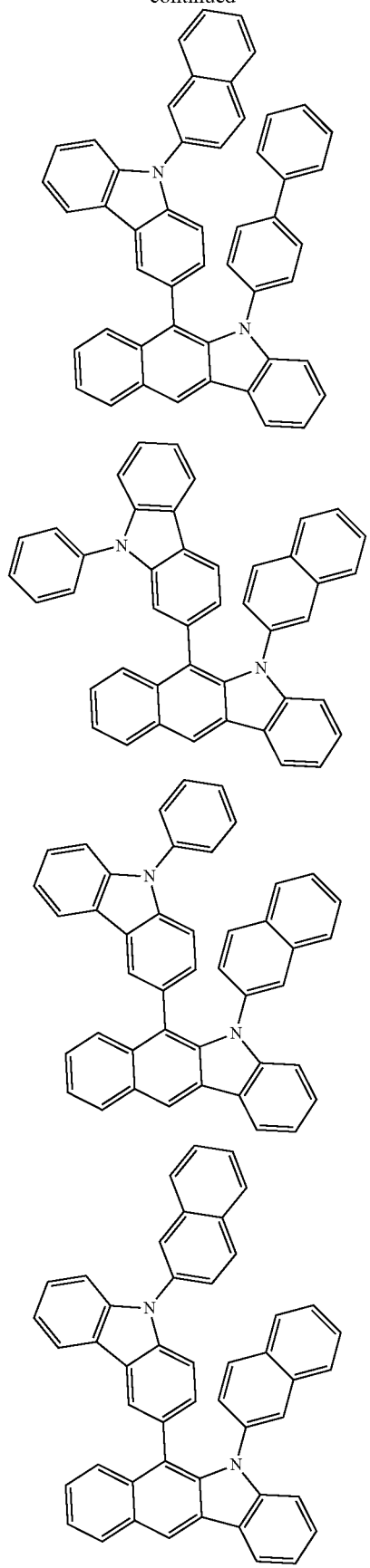

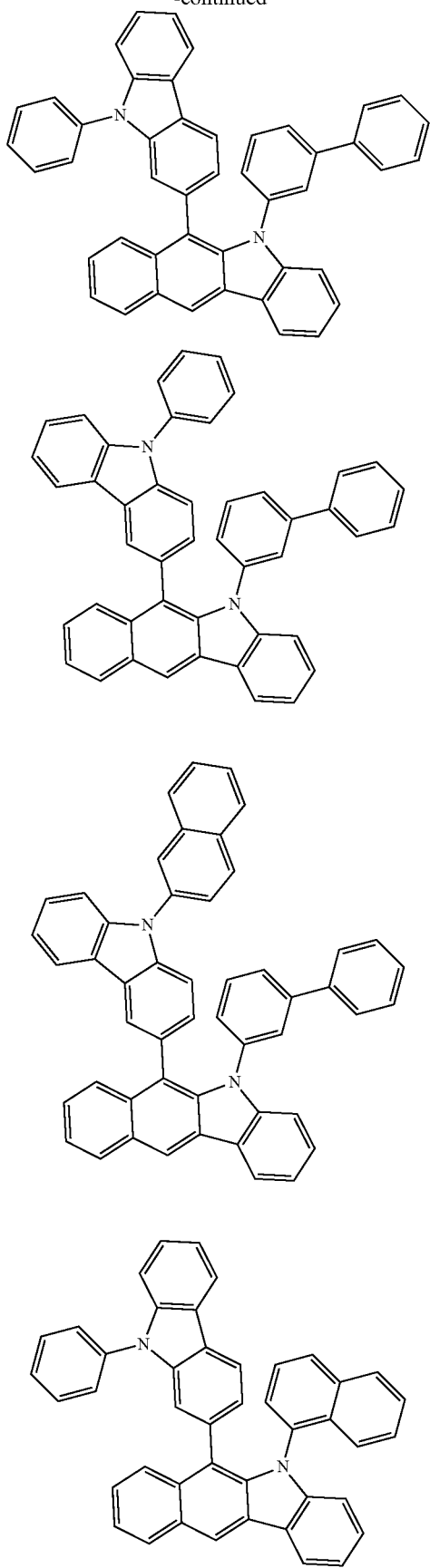
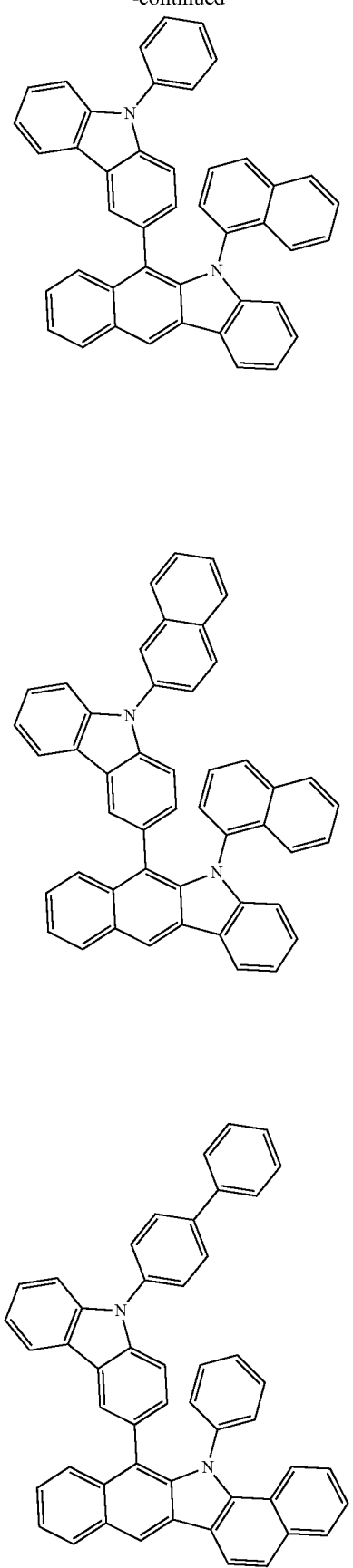

257
-continued
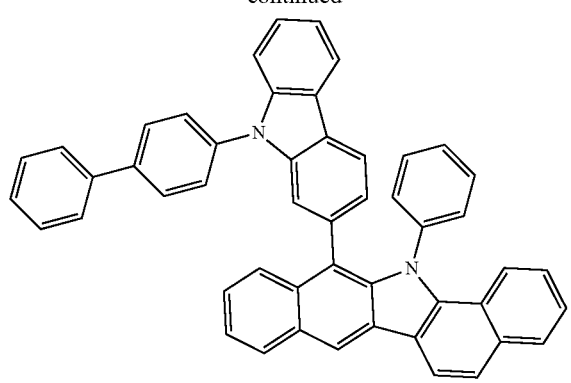
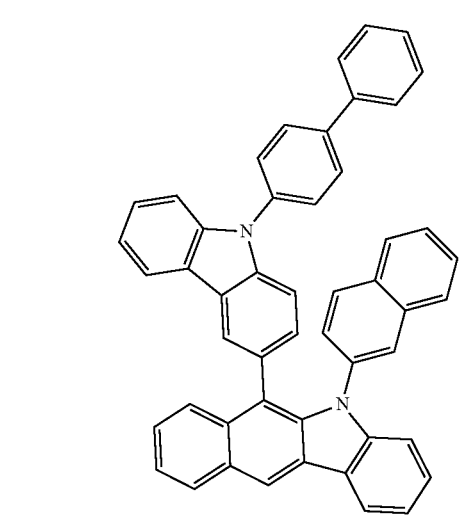
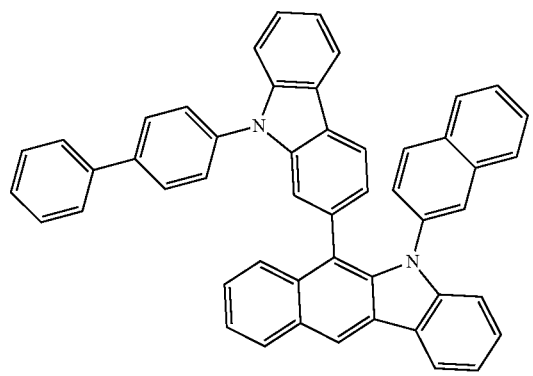
258
-continued
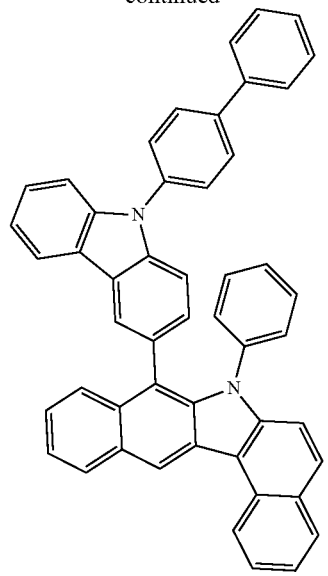
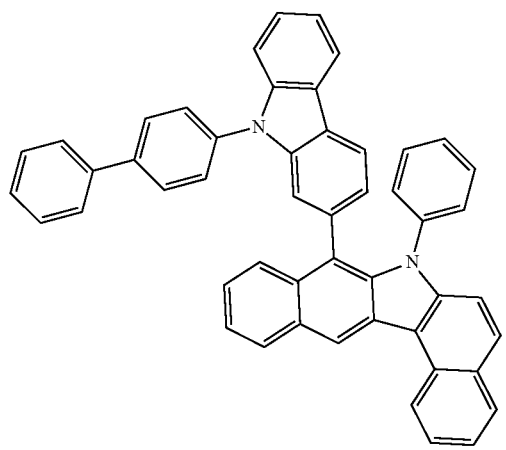
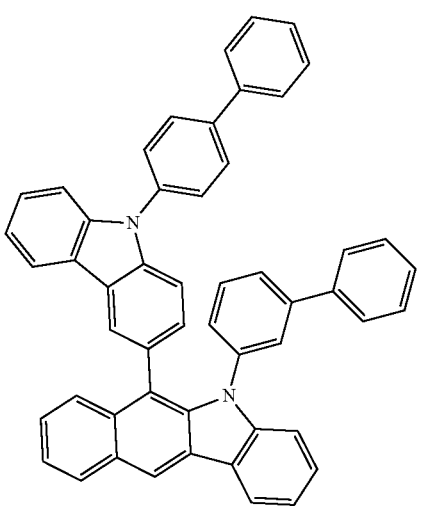

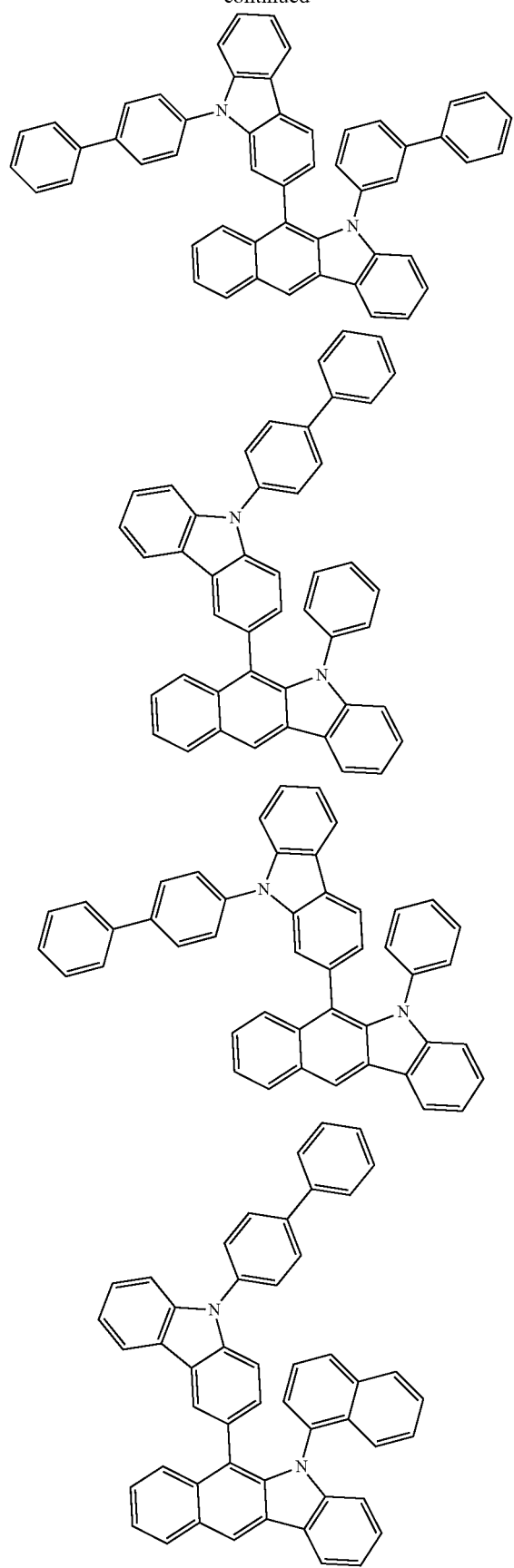
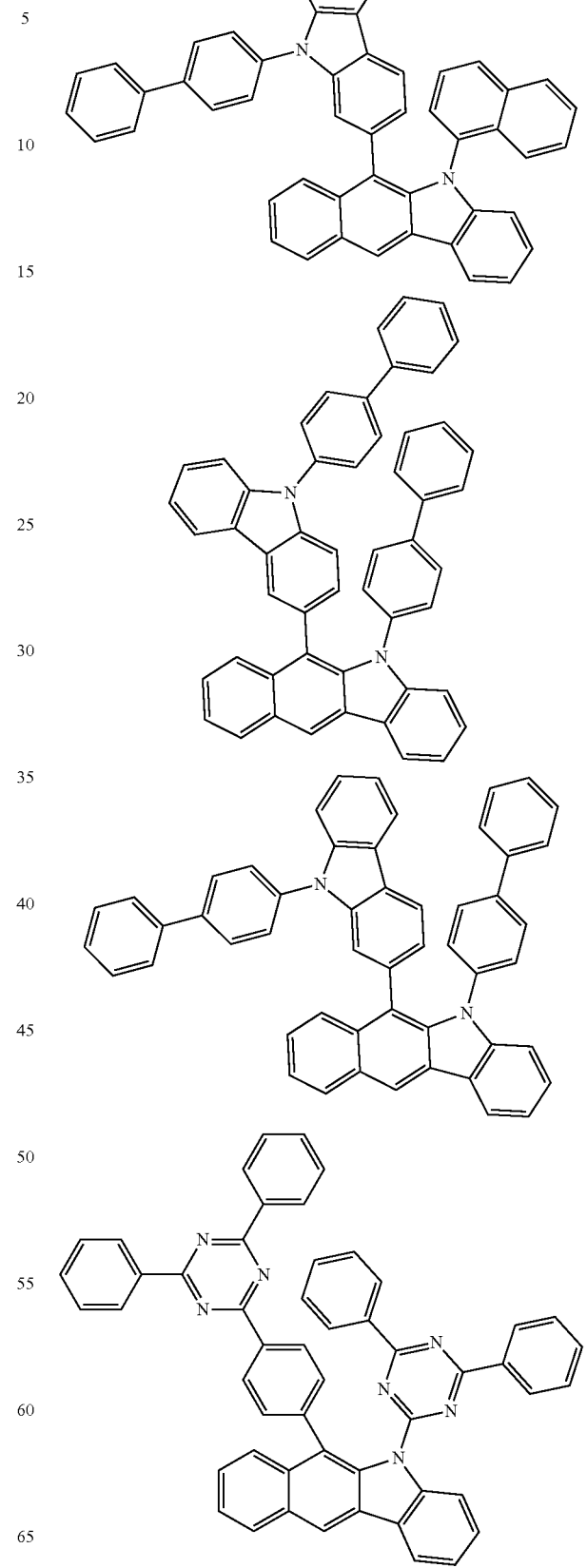

261
-continued
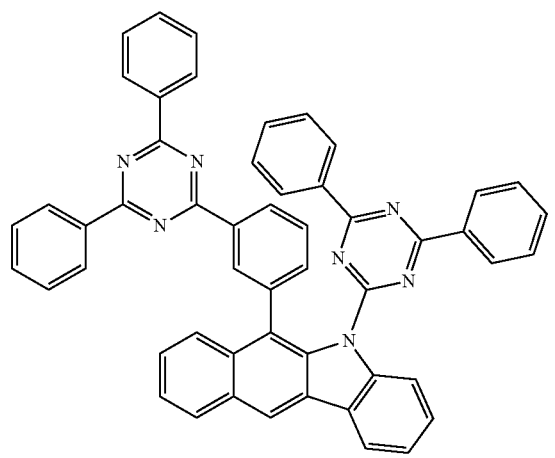
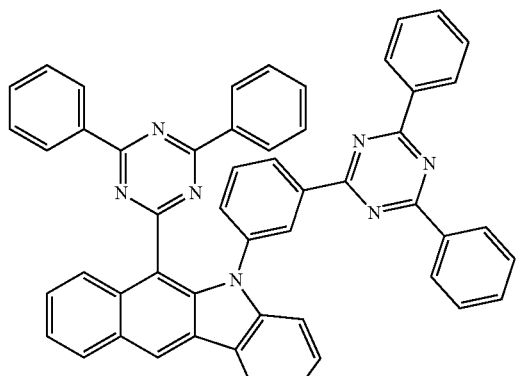
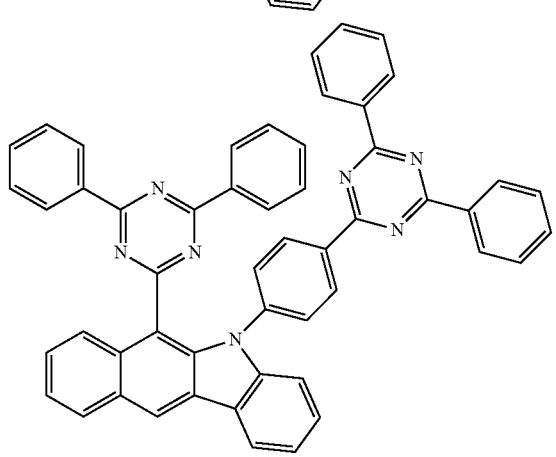
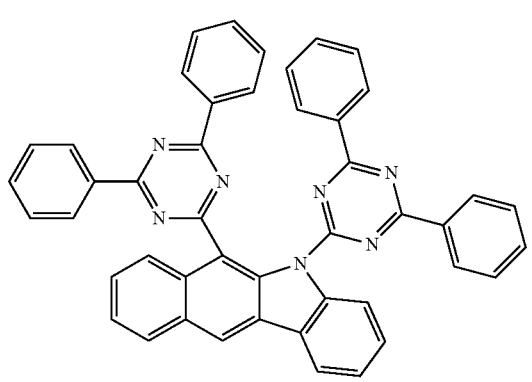
262
-continued
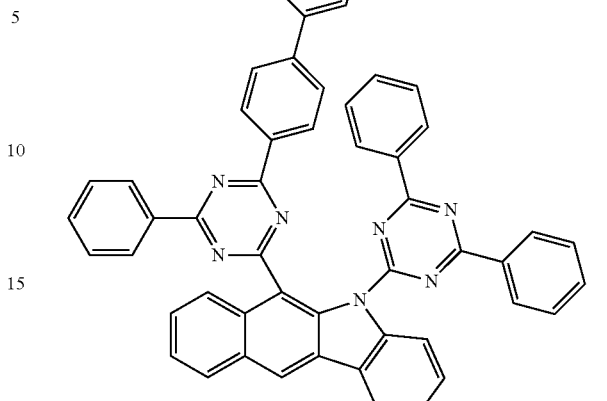
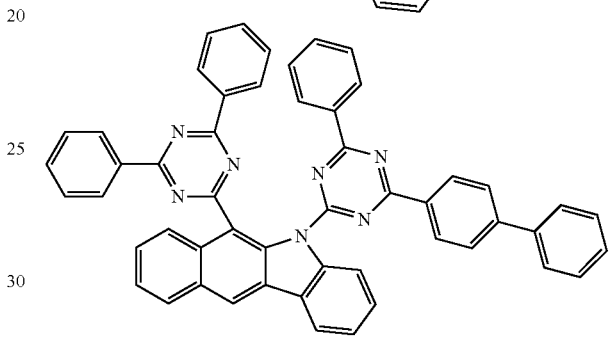
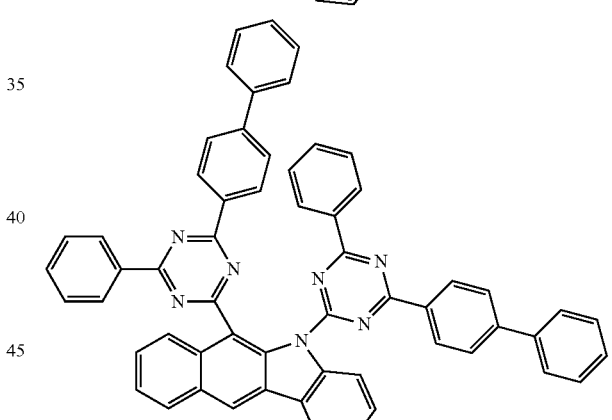
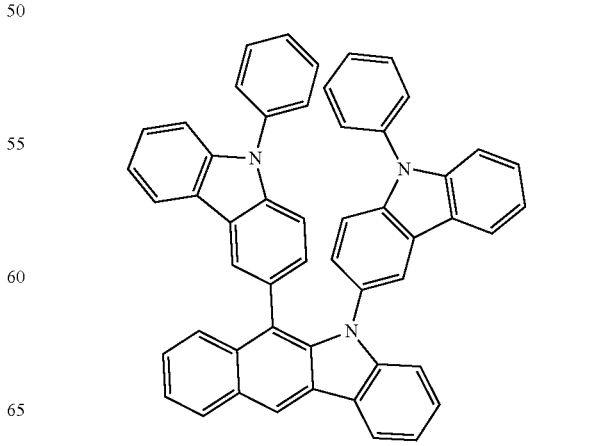

263
-continued
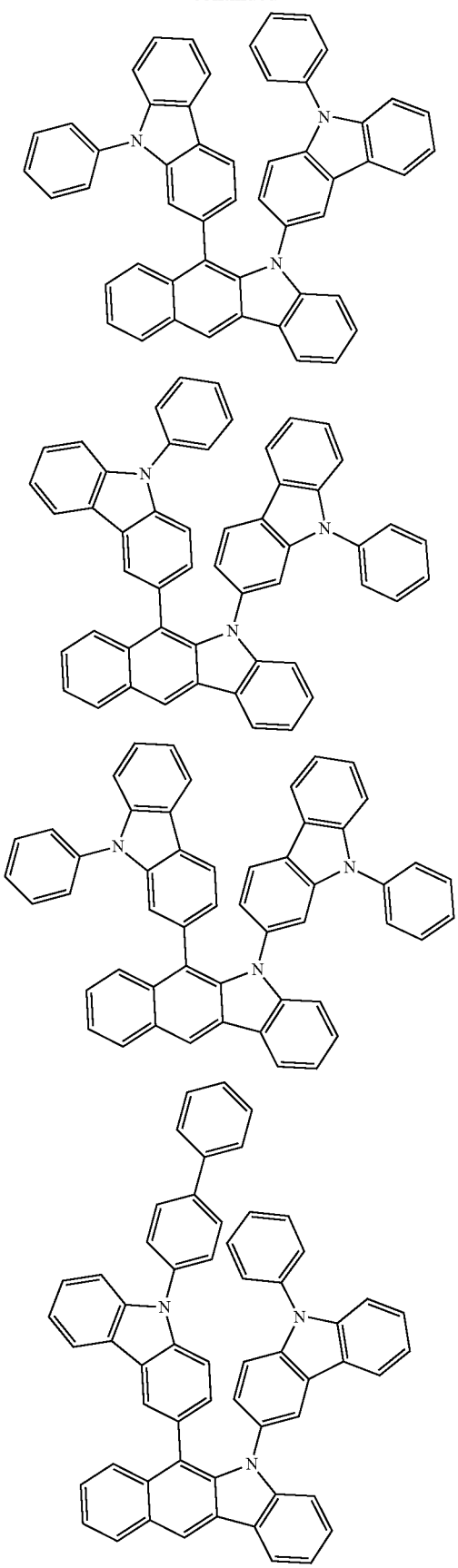
264
-continued
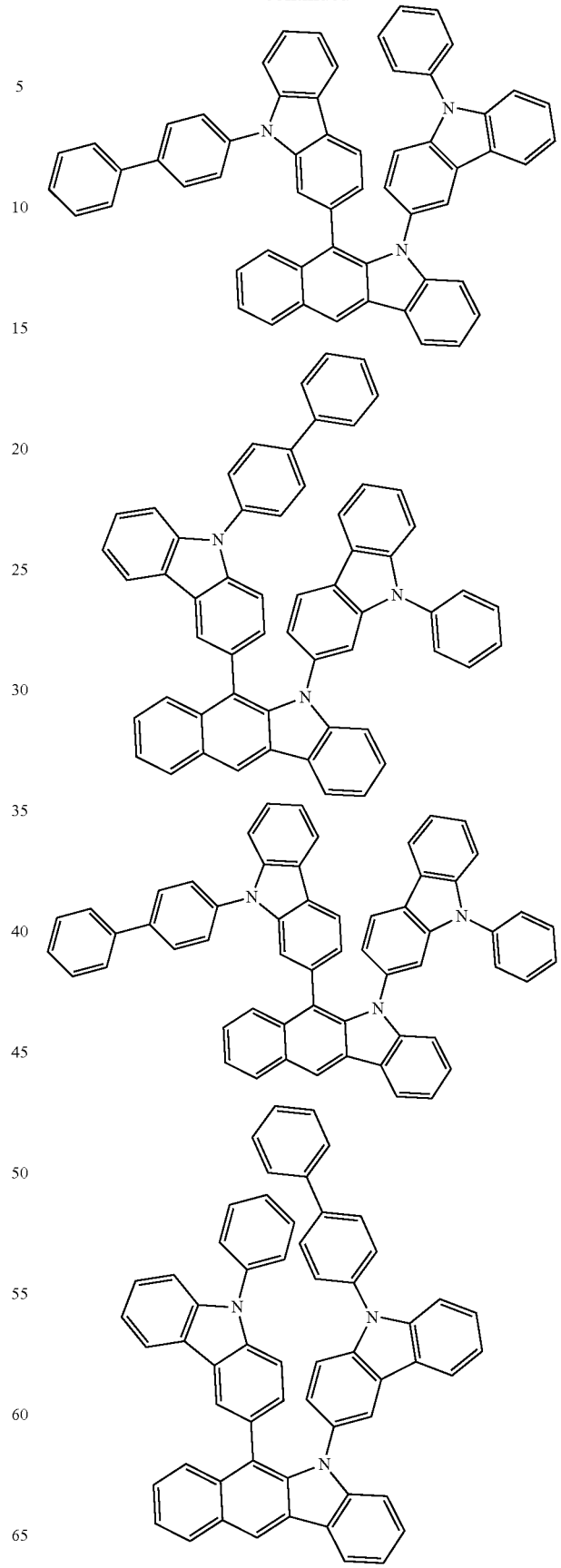

265
-continued
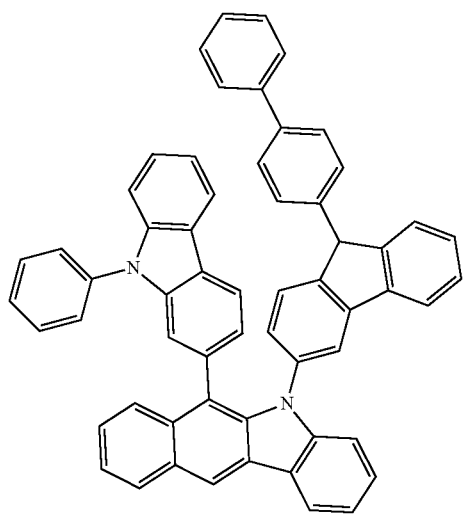
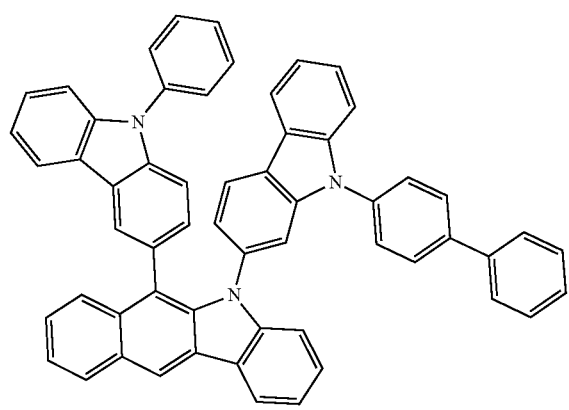
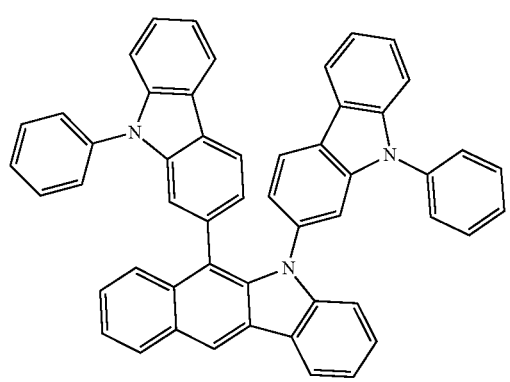
266
-continued
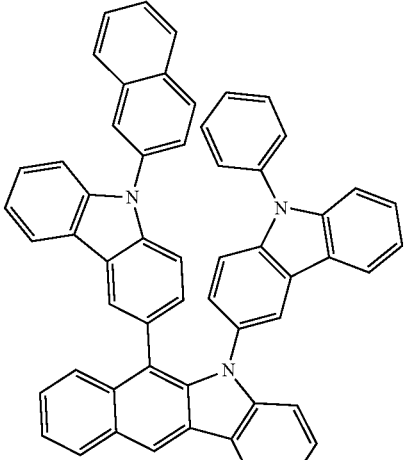
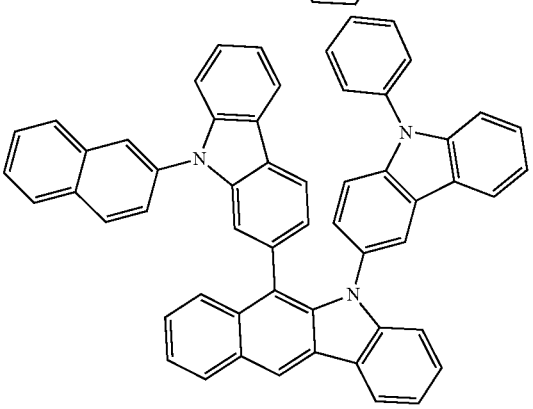
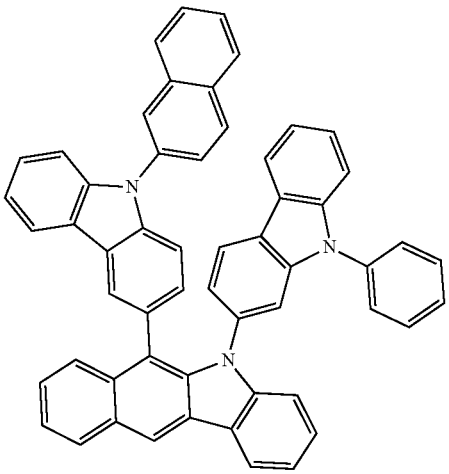
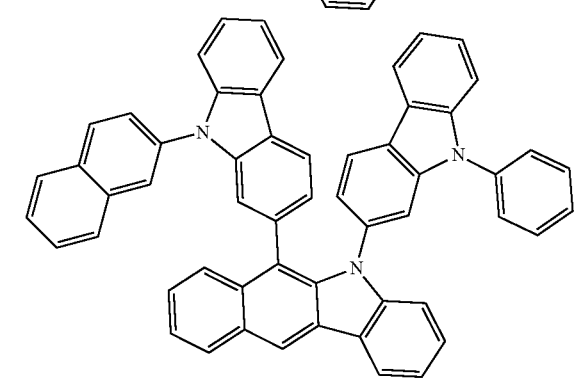

267
-continued
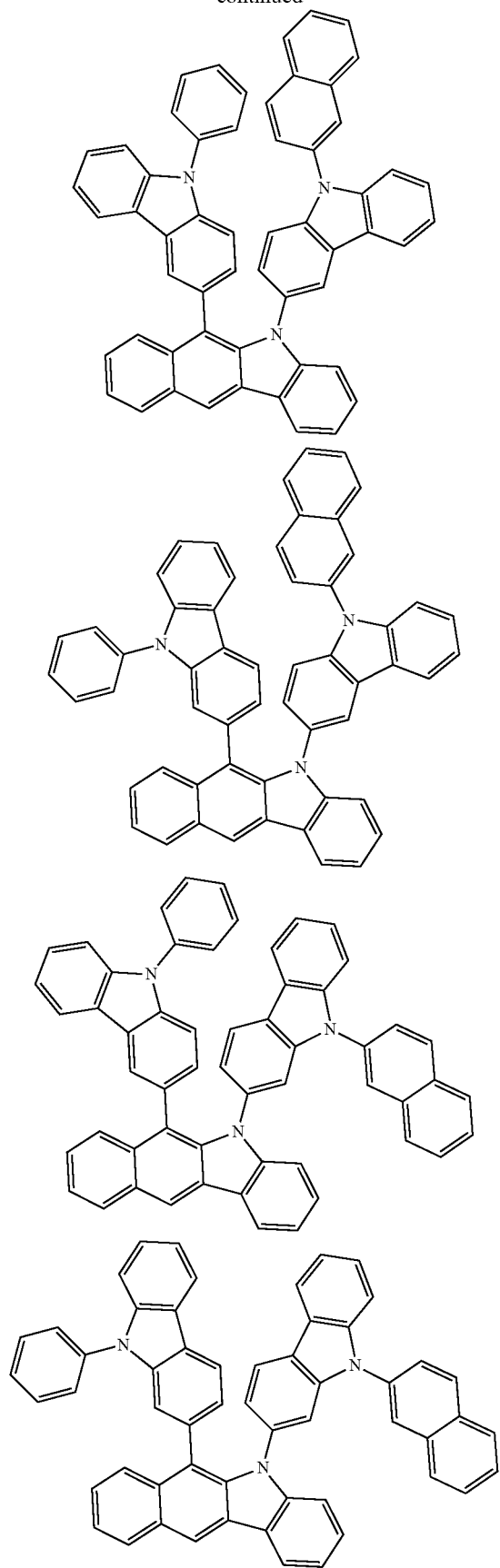
268
-continued
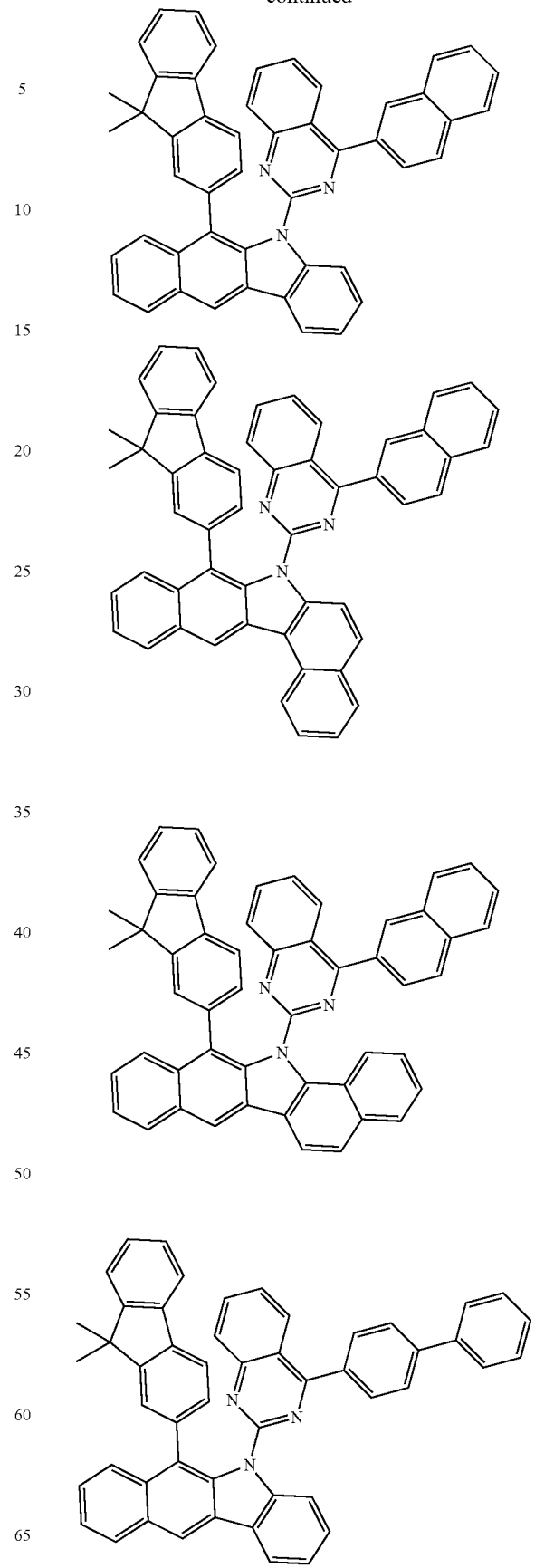

269
-continued
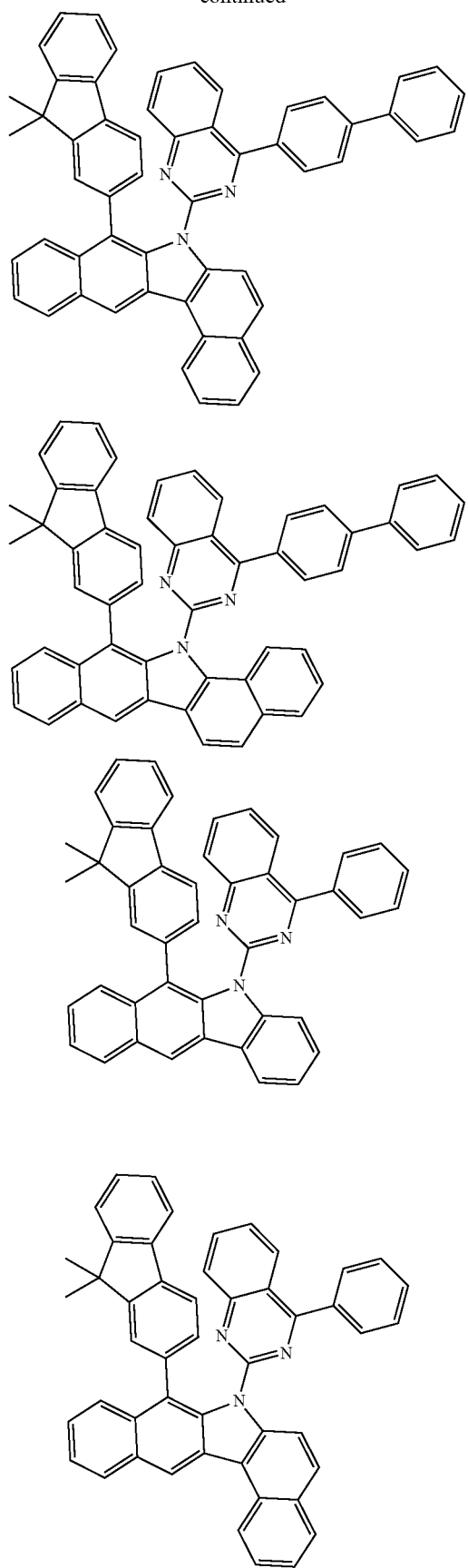
270
-continued
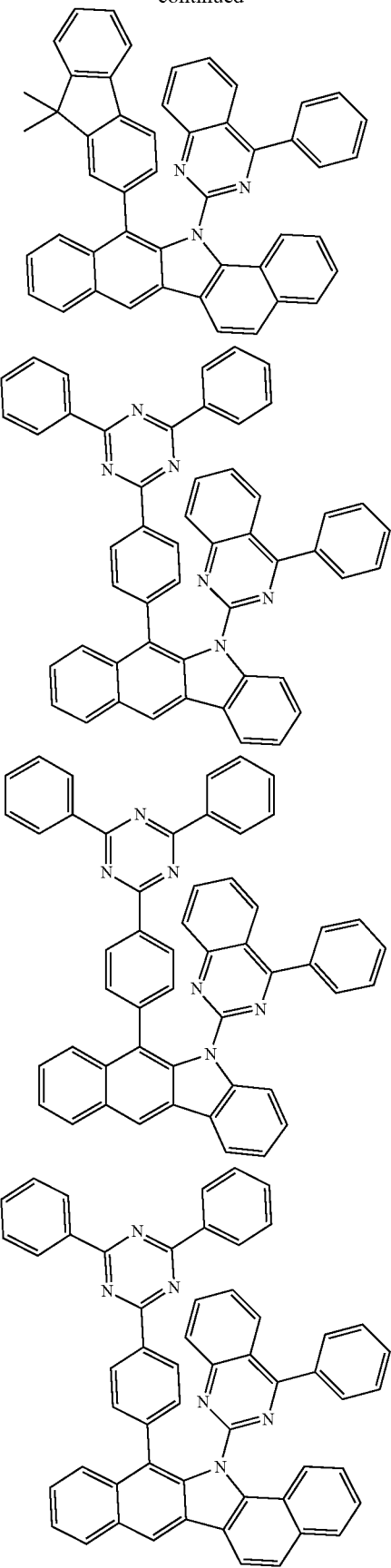

271
-continued
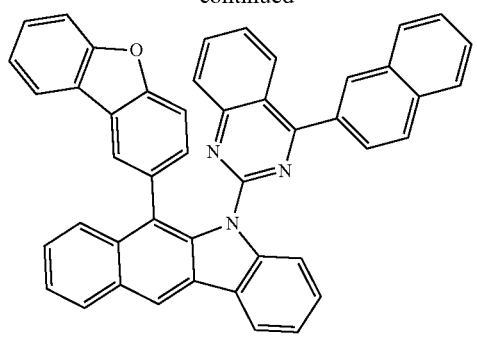
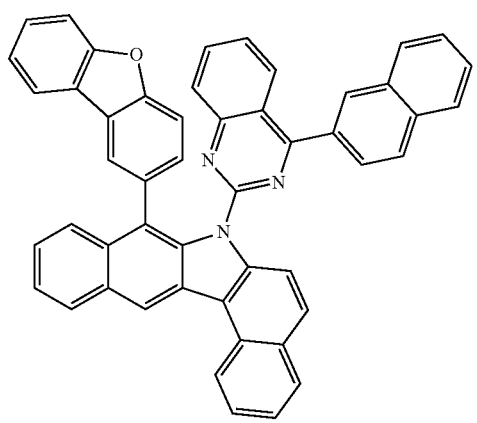
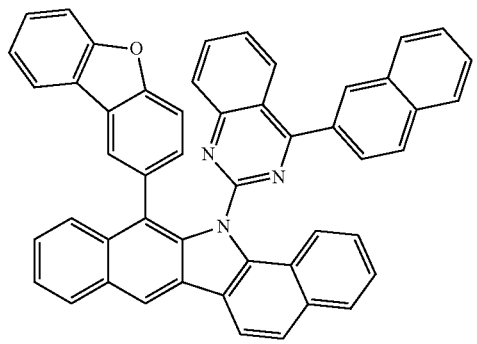
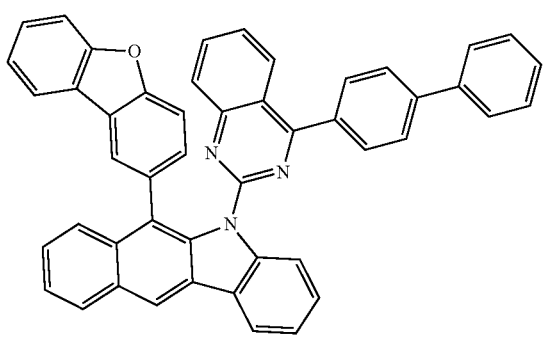
272
-continued
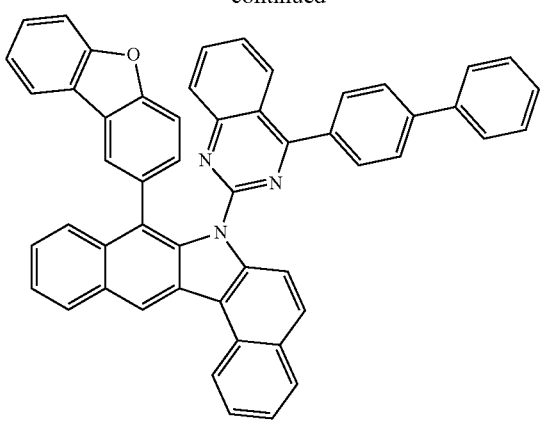
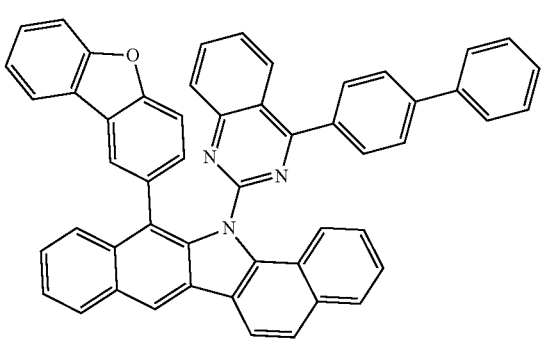
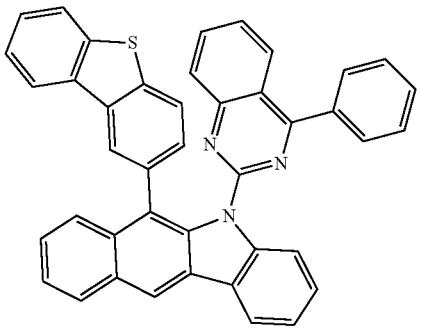
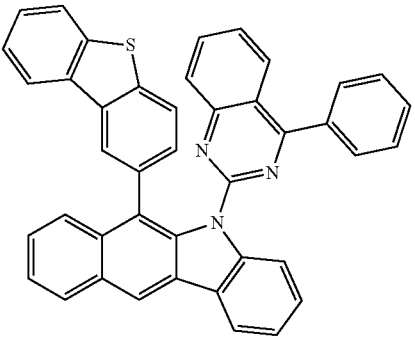

273
-continued
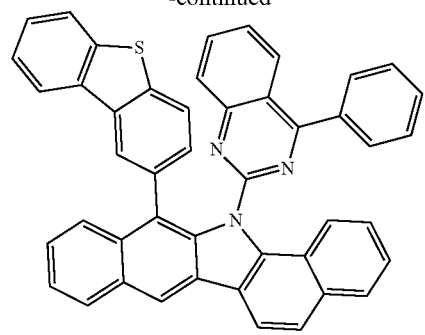
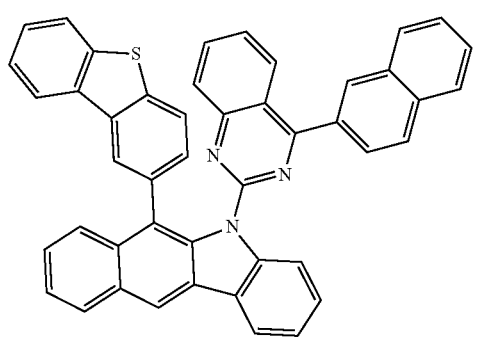
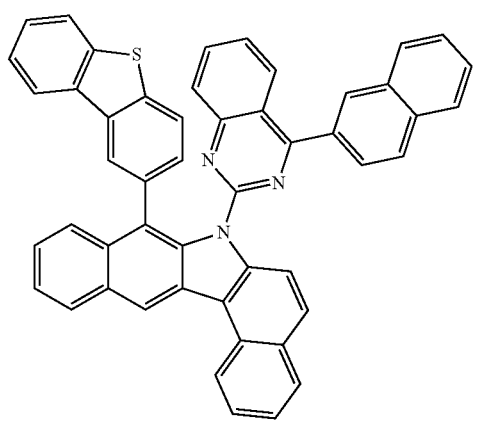
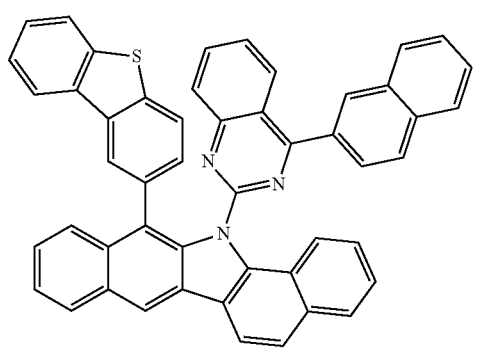
274
-continued
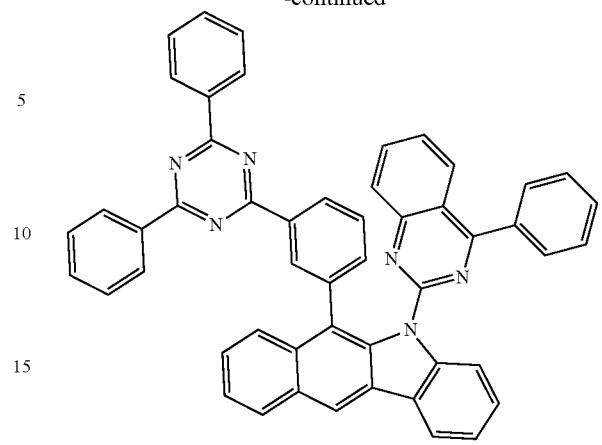
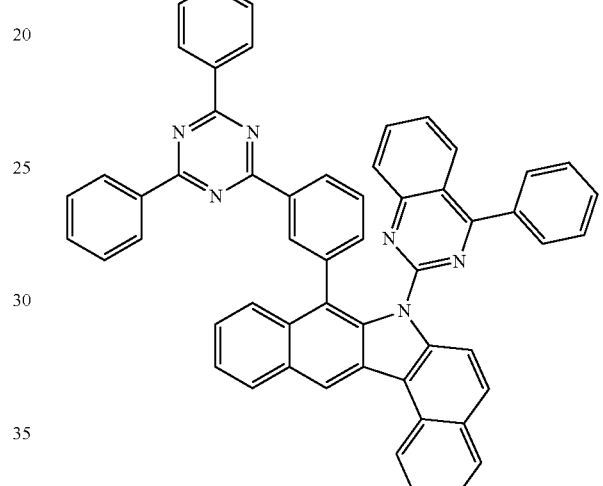
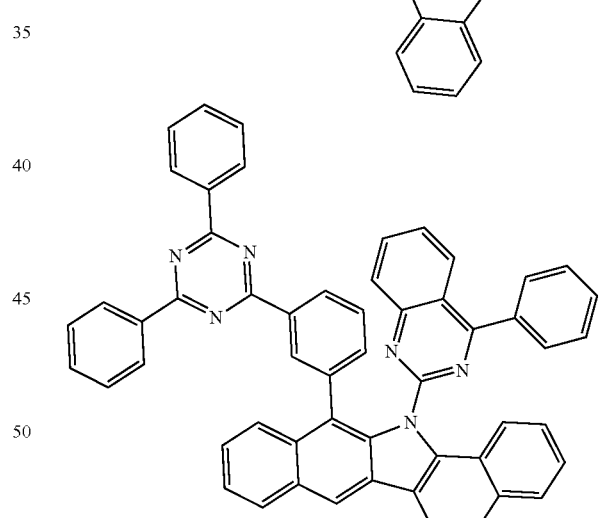
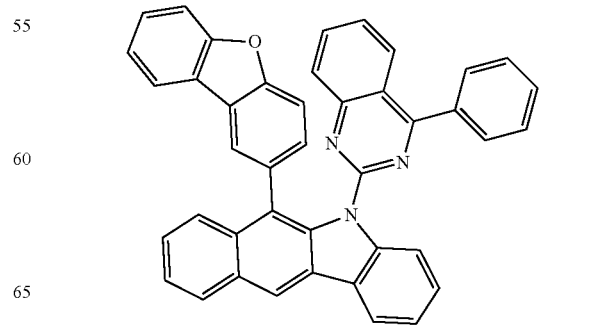

275
-continued
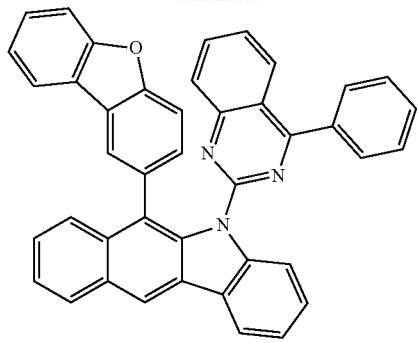
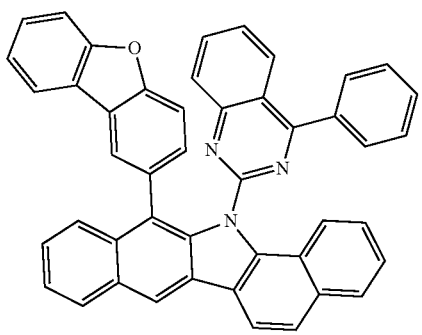
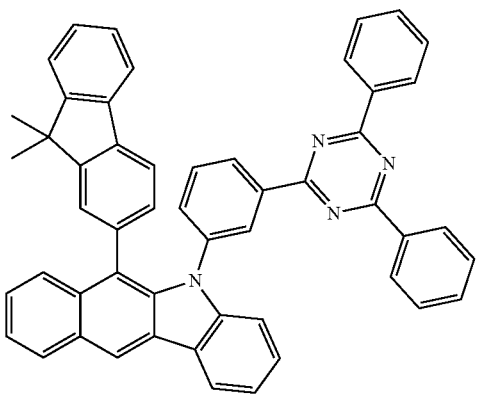
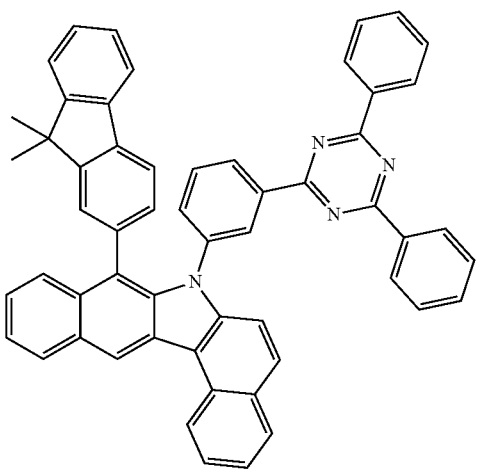
276
-continued
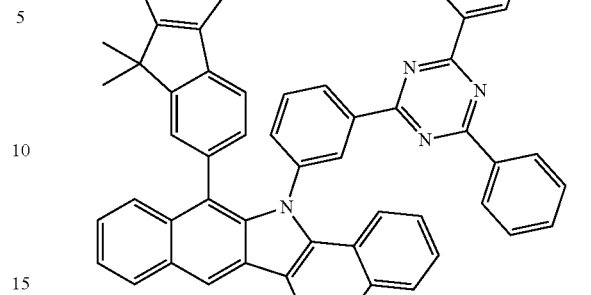
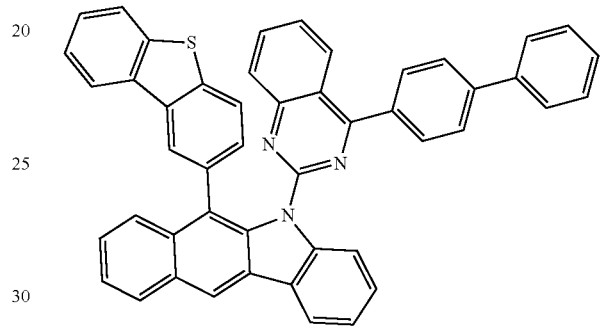
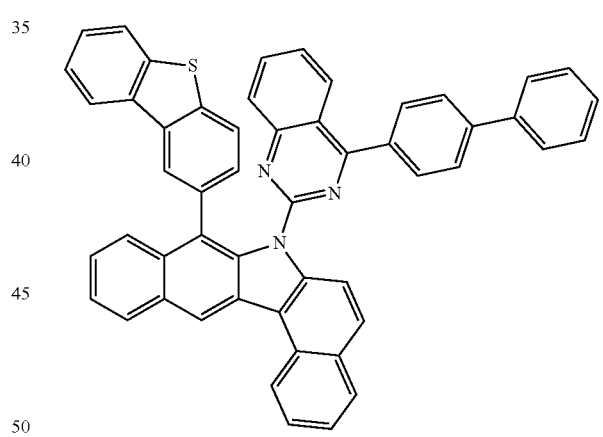
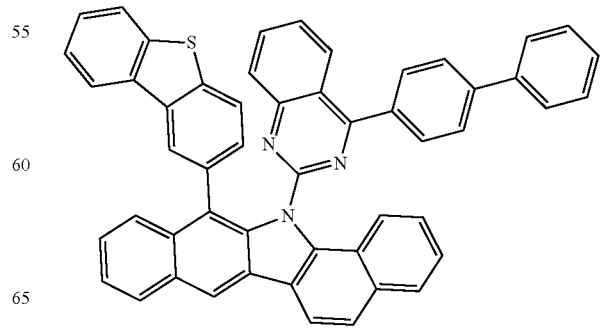

277
-continued
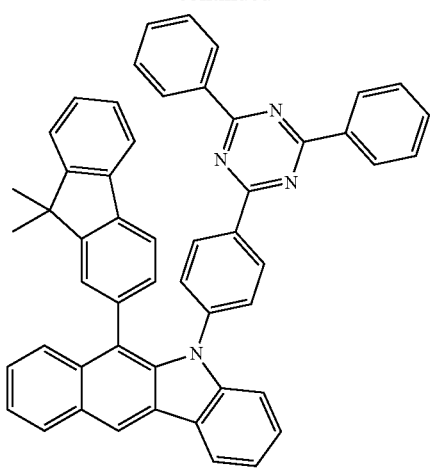
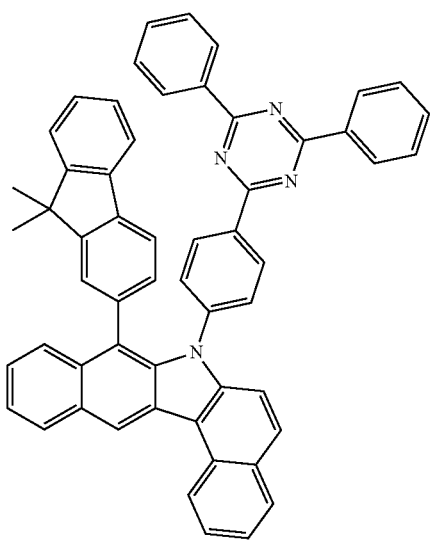
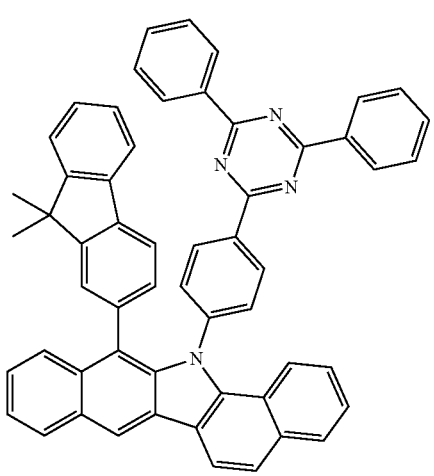
278
-continued
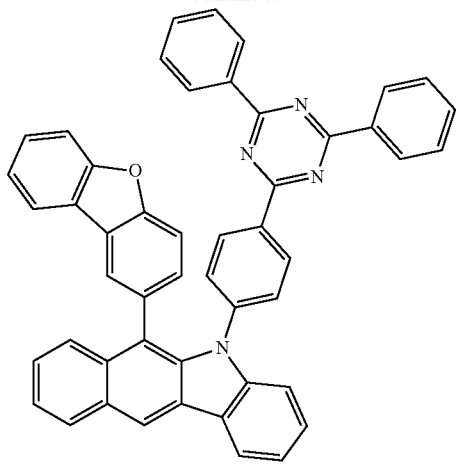
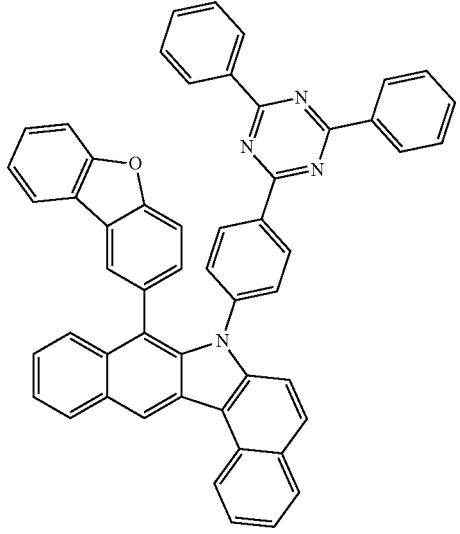
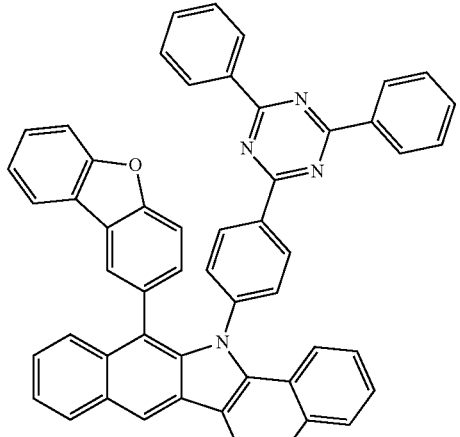

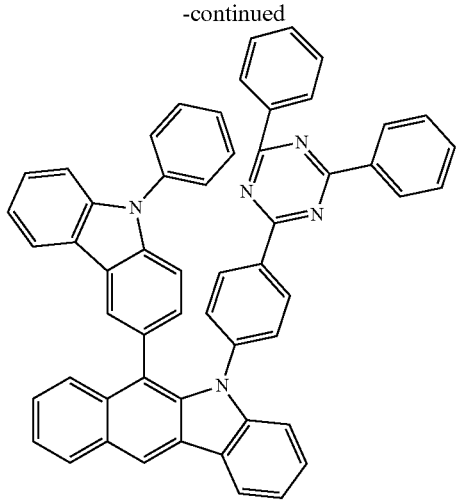
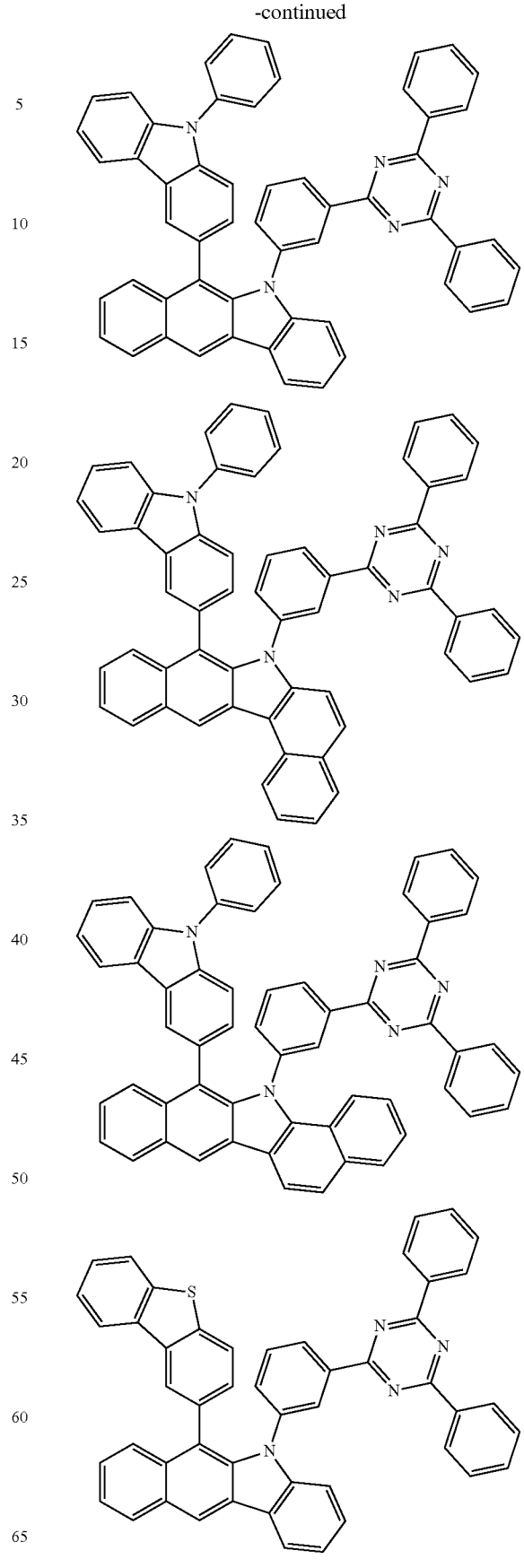

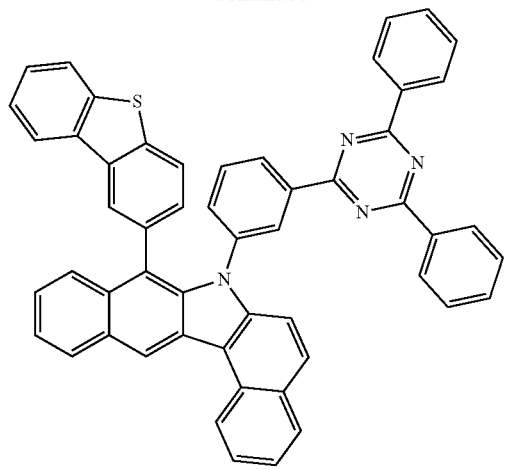
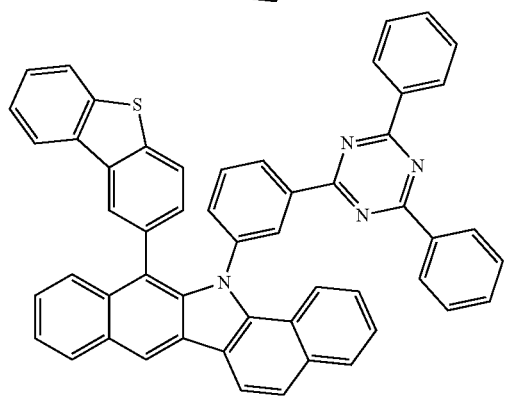
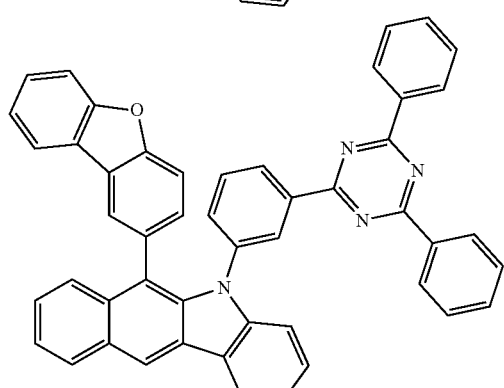
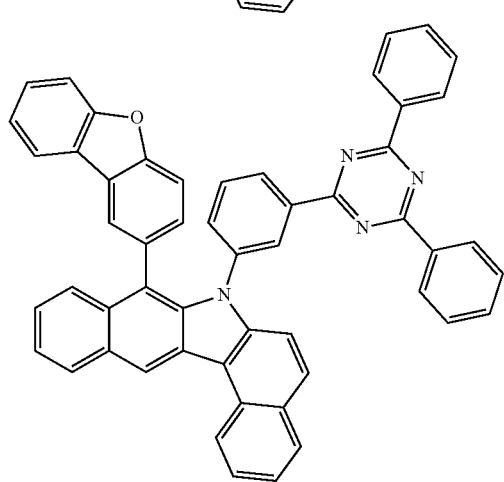
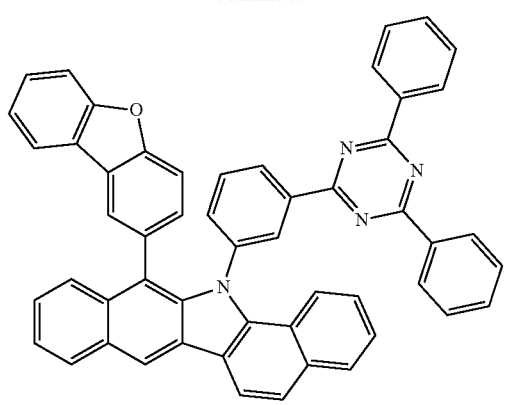
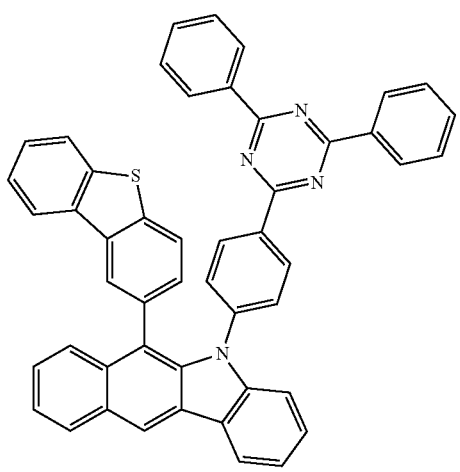
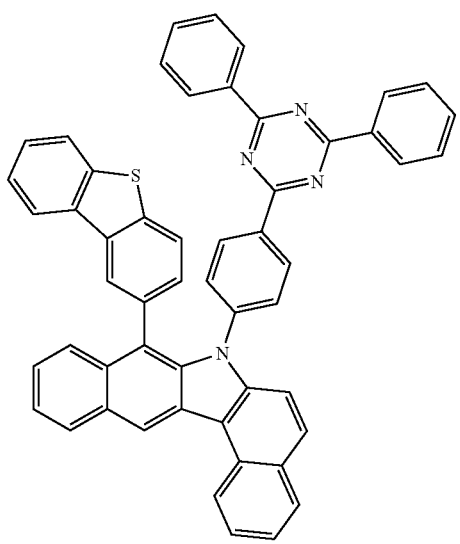

283
-continued
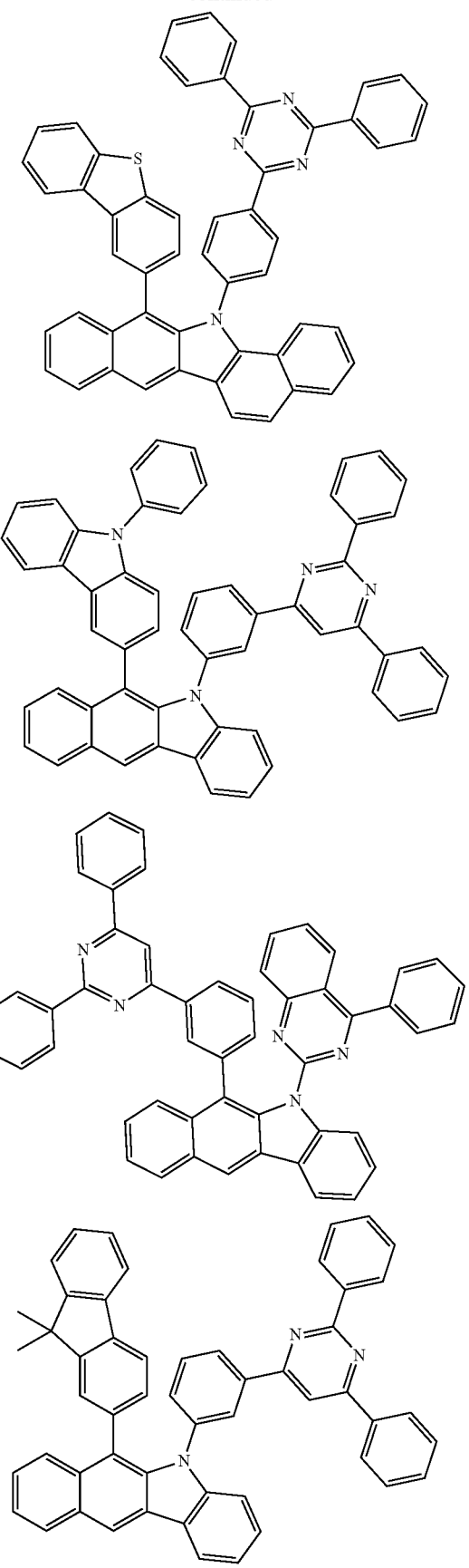
284
-continued
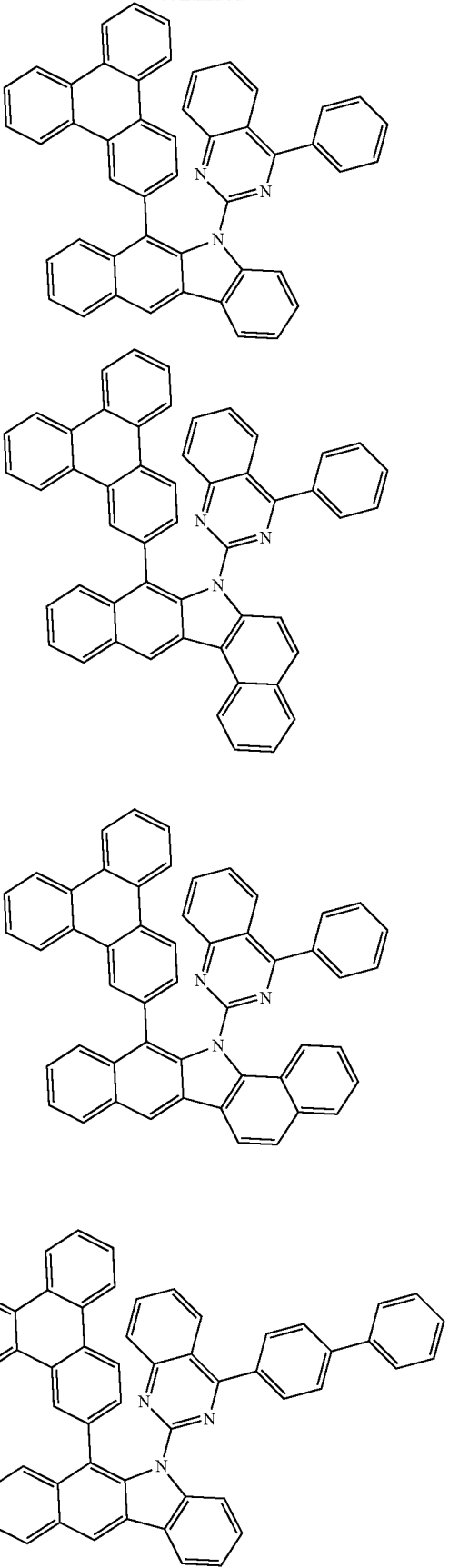

285
-continued
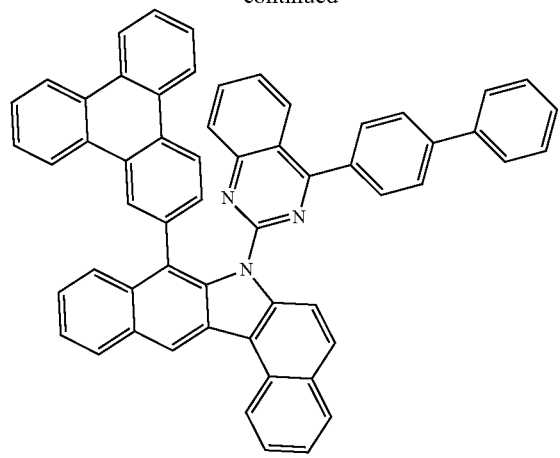
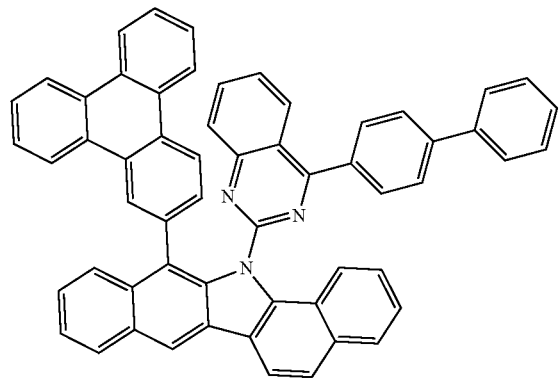
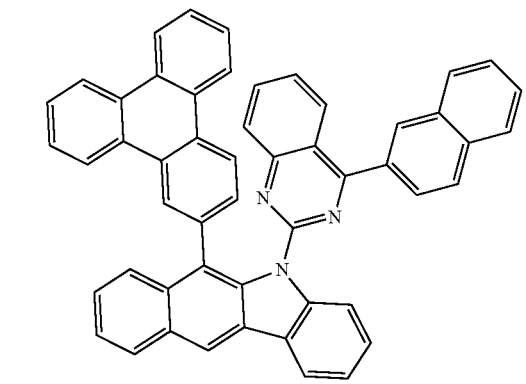
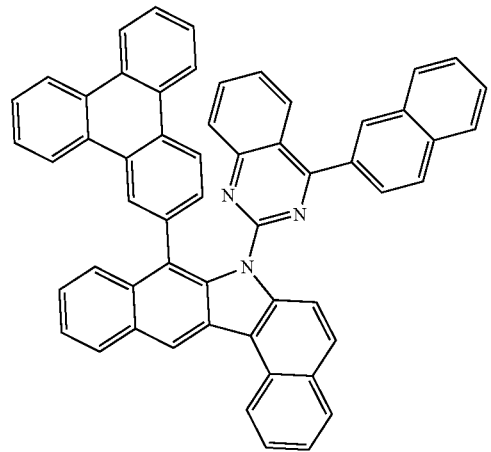
286
-continued
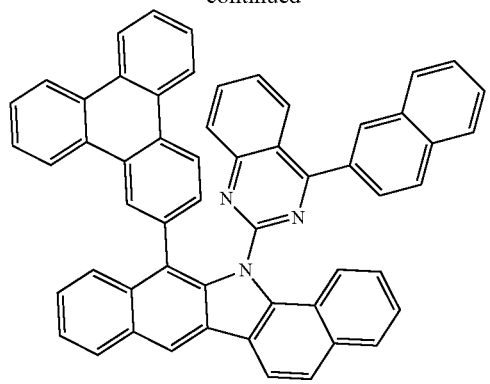
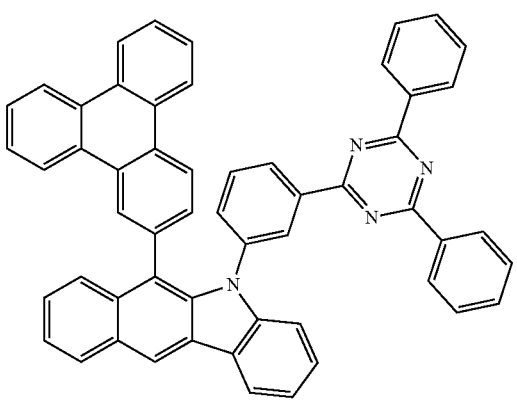
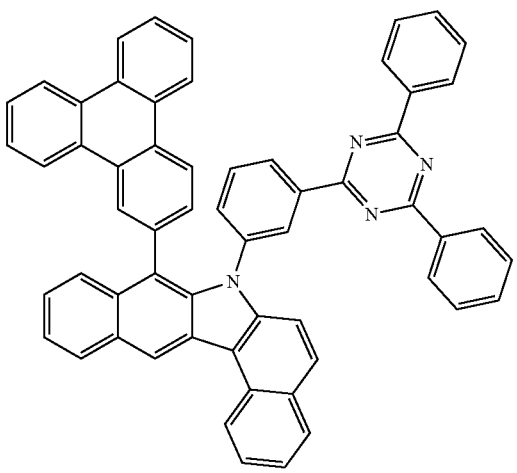
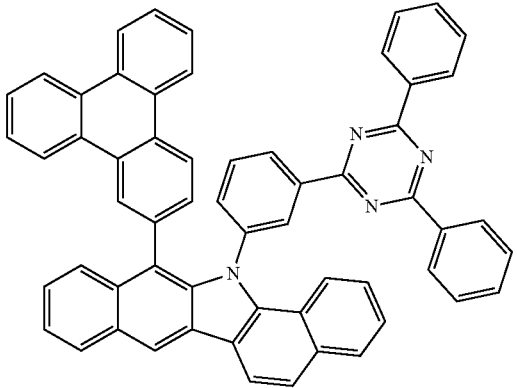

287
-continued
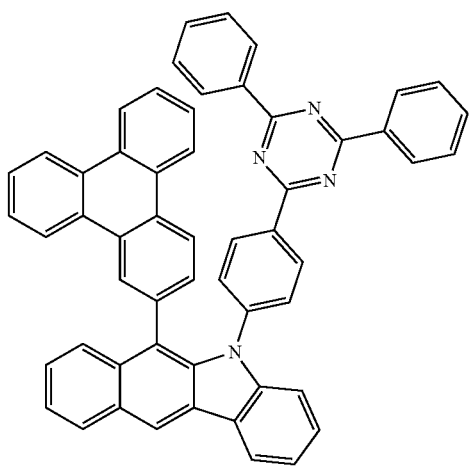
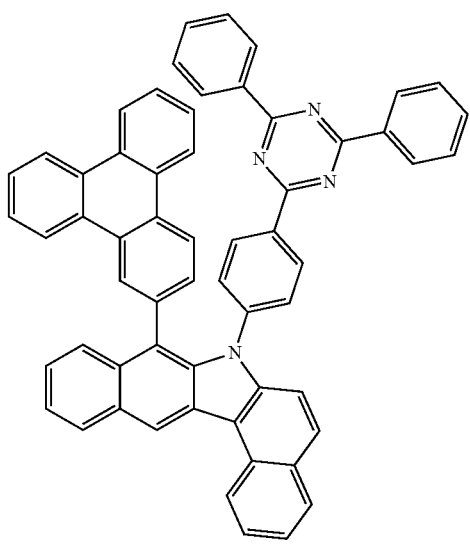
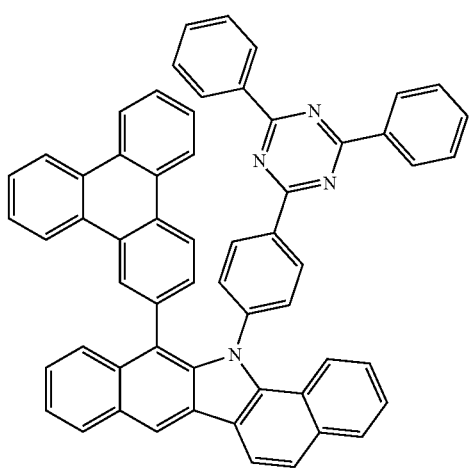
288
-continued
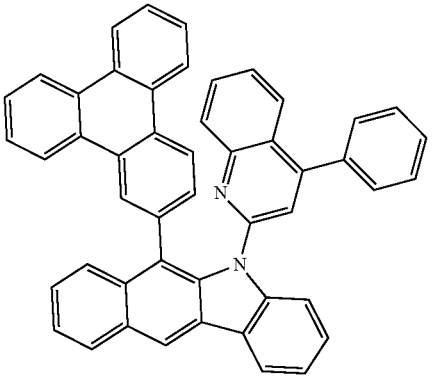
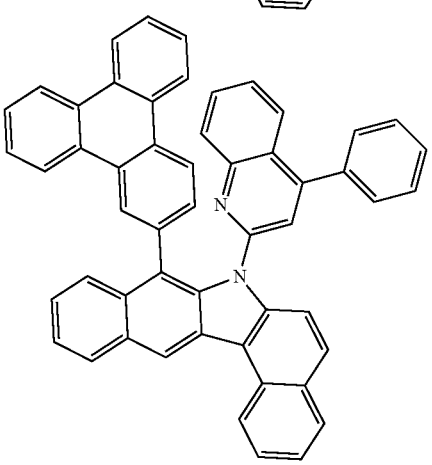
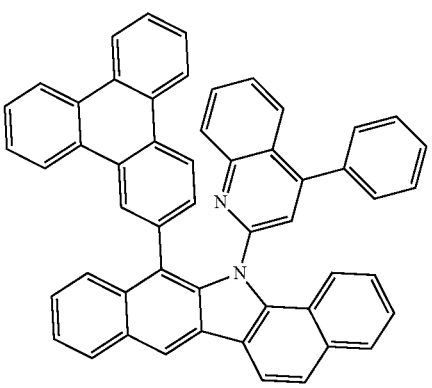
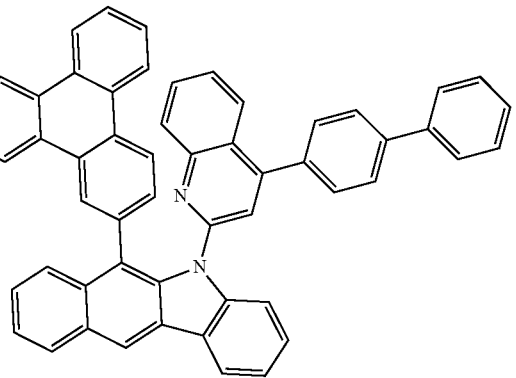

289
-continued
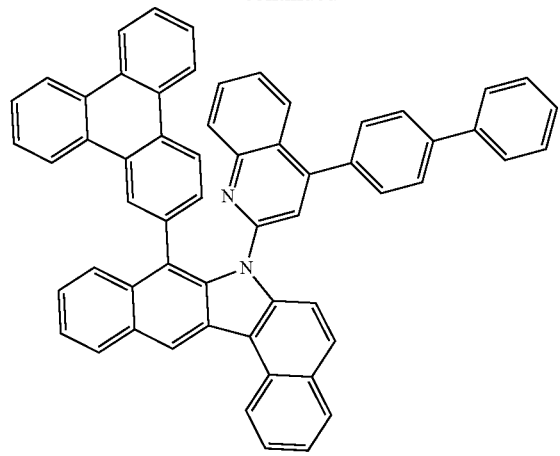
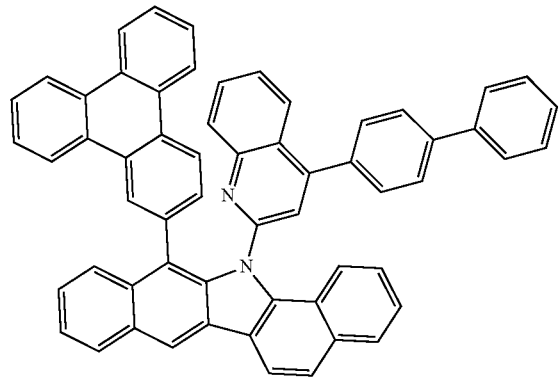
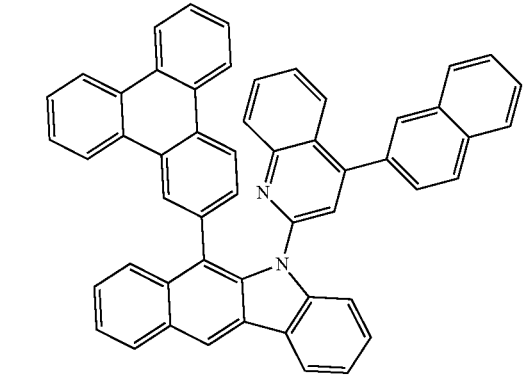
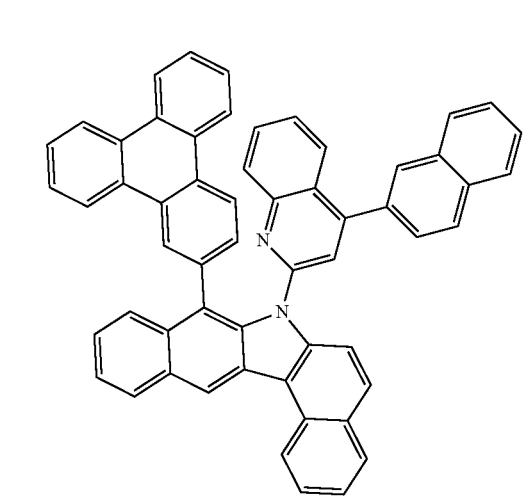
290
-continued
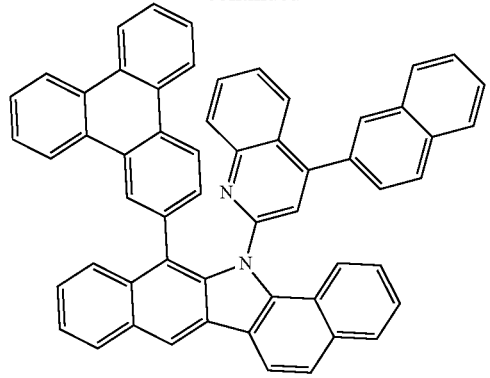
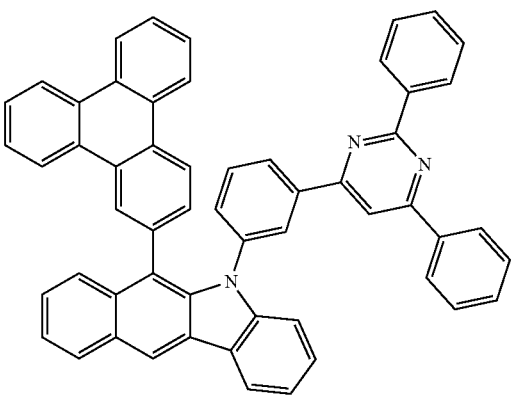
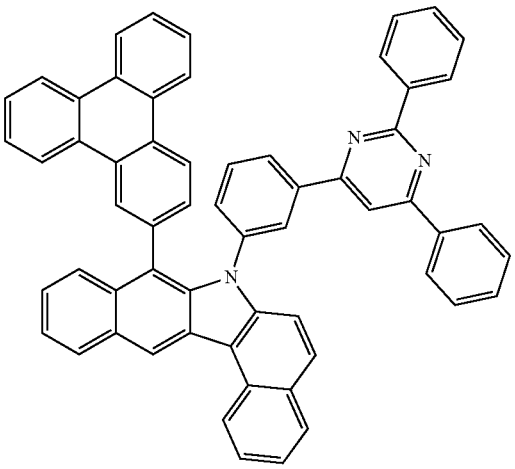
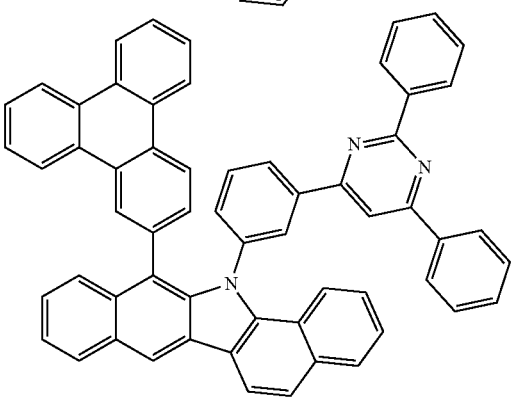

-continued

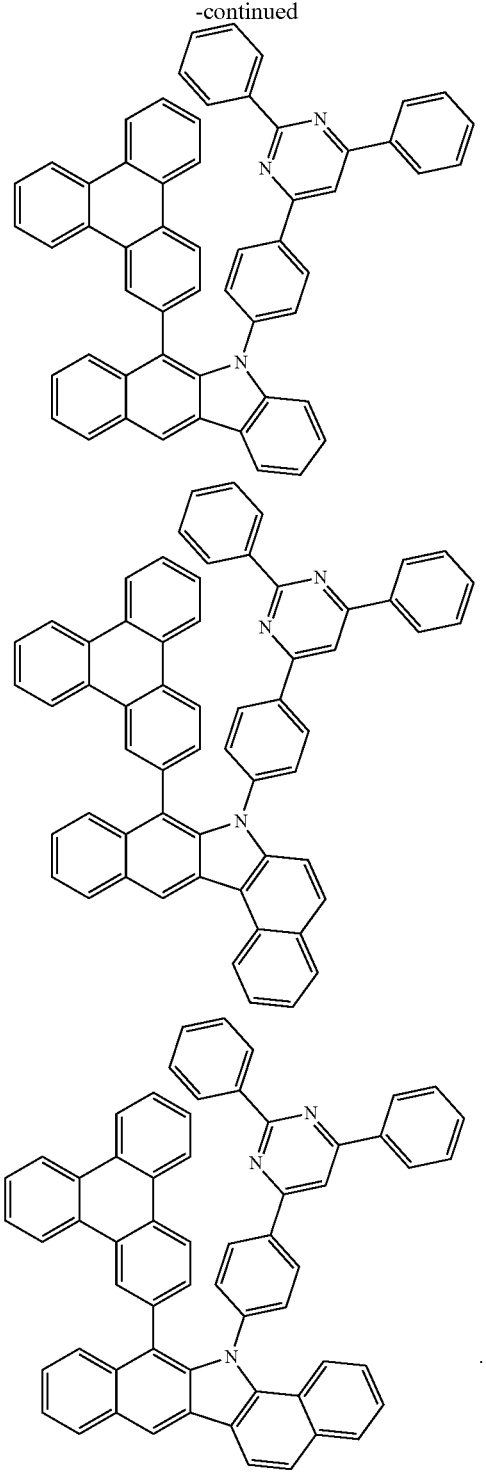

7. An organic light emitting device comprising:
a first electrode;
a second electrode provided opposite to the first electrode; and
one or more organic material layers provided between the first electrode and the second electrode,
wherein one or more layers of the organic material layers include the hetero-cyclic compound of claim 1.

8. The organic light emitting device of claim 7, wherein the organic material layer includes a hole transfer layer, and the hole transfer layer includes the hetero-cyclic compound.

9. The organic light emitting device of claim 7, wherein the organic material layer includes an electron blocking layer, and the electron blocking layer includes the hetero-cyclic compound.

10. The organic light emitting device of claim 7, wherein the organic material layer includes a light emitting layer, and the light emitting layer includes the hetero-cyclic compound.

11. The organic light emitting device of claim 7, wherein the organic material layer includes a light emitting layer, and the light emitting layer includes the hetero-cyclic compound as a host of the light emitting layer.

12. The organic light emitting device of claim 7, wherein the organic material layer includes a light emitting layer, and the light emitting layer includes the hetero-cyclic compound as a dopant of the light emitting layer.

13. The organic light emitting device of claim 7, wherein the organic material layer includes a hole blocking layer, and the hole blocking layer includes the hetero-cyclic compound.

14. The organic light emitting device of claim 7, wherein the organic material layer includes an electron injection layer, and the electron injection layer includes the hetero-cyclic compound.

15. The organic light emitting device of claim 7, wherein the organic material layer includes an electron transfer layer, and the electron transfer layer includes the hetero-cyclic compound.

16. The organic light emitting device of claim 7, wherein the organic material layer includes a light emitting layer, and the light emitting layer includes a compound represented by the following Chemical Formula 1-A:

[Chemical Formula 1-A]

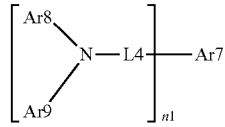

wherein, in Chemical Formula 1-A,
n1 is an integer of 1 or greater;
Ar7 is a substituted or unsubstituted monovalent or higher benzofluorene group; a substituted or unsubstituted monovalent or higher fluoranthene group; a substituted or unsubstituted monovalent or higher pyrene group; or a substituted or unsubstituted monovalent or higher chrysene group;
L4 is a direct bond; a substituted or unsubstituted arylene group; or a substituted or unsubstituted heteroarylene group;
Ar8 and Ar9 are the same as or different from each other, and each independently a substituted or unsubstituted aryl group; a substituted or unsubstituted silyl group; a substituted or unsubstituted germanium group; a substituted or unsubstituted alkyl group; a substituted or unsubstituted arylalkyl group; or a substituted or unsubstituted heteroaryl group, or bond to each other to form a substituted or unsubstituted ring; and
when n1 is 2 or greater, structures in the 2 or more parentheses are the same as or different from each other.

17. The organic light emitting device of claim 16, wherein L4 is a direct bond, Ar7 is a divalent pyrene group, Ar8 and Ar9 are the same as or different from each other and each independently an aryl group unsubstituted or substituted with a germanium group substituted with an alkyl group, and n1 is 2.

18. The organic light emitting device of claim 7, wherein the organic material layer includes a light emitting layer, and the light emitting layer includes a compound represented by the following Chemical Formula 2-A:

[Chemical Formula 2-A]

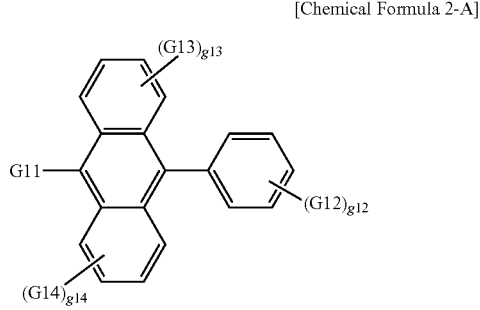

wherein, in Chemical Formula 2-A,

G11 is a phenyl group, a 1-naphthyl group, a 2-naphthyl group, a 1-anthryl group, a 2-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 3-methyl-2-naphthyl group, a 4-methyl-1-naphthyl group, or the following chemical formula

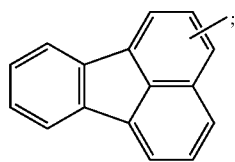

G12 is a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, an o-tolyl group, a m-tolyl group, a p-tolyl group, a p-t-butylphenyl group, a p-(2-phenylpropyl) phenyl group, a 3-methyl-2-naphthyl group, a 4-methyl-1-naphthyl group, a 4-methyl-1-anthryl group, a 4'-methylbiphenylyl group, a 4"-t-butyl-p-terphenyl-4-yl group or a 3-fluoranthenyl group;

G13 and G14 are the same as or different from each other, and each independently hydrogen; a substituted or unsubstituted alkyl group; a substituted or unsubstituted alkoxy group; a substituted or unsubstituted aryl group; or a substituted or unsubstituted heteroaryl group;

g12 is an integer of 1 to 5;

g13 and g14 are each an integer of 1 to 4; and when g12 to g14 are each 2 or greater, structures in the 2 or more parentheses are the same as or different from each other.

19. The organic light emitting device of claim 18, wherein G11 is a 1-naphthyl group, and G12 is a 2-naphthyl group.

20. The organic light emitting device of claim 16, wherein the light emitting layer includes a compound represented by the following Chemical Formula 2-A:

[Chemical Formula 2-A]

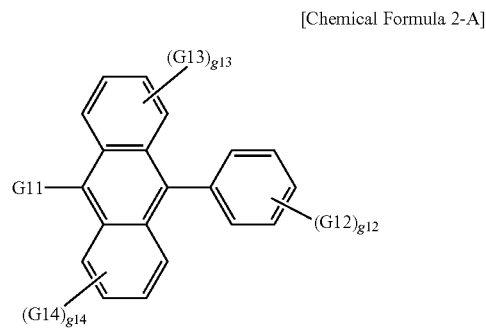

wherein, in Chemical Formula 2-A,

G11 is a phenyl group, a 1-naphthyl group, a 2-naphthyl group, a 1-anthryl group, a 2-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 3-methyl-2-naphthyl group, a 4-methyl-1-naphthyl group, or the following chemical formula

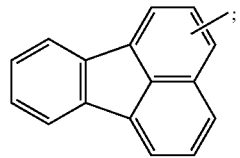

G12 is a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, an o-tolyl group, a m-tolyl group, a p-tolyl group, a p-t-butylphenyl group, a p-(2-phenylpropyl) phenyl group, a 3-methyl-2-naphthyl group, a 4-methyl-1-naphthyl group, a 4-methyl-1-anthryl group, a 4'-methylbiphenylyl group, a 4"-t-butyl-p-terphenyl-4-yl group or a 3-fluoranthenyl group;

G13 and G14 are the same as or different from each other, and each independently hydrogen; a substituted or unsubstituted alkyl group; a substituted or unsubstituted alkoxy group; a substituted or unsubstituted aryl group; or a substituted or unsubstituted heteroaryl group;

g12 is an integer of 1 to 5;

g13 and g14 are each an integer of 1 to 4; and when g12 to g14 are each 2 or greater, structures in the 2 or more parentheses are the same as or different from each other.

\* \* \* \* \*